(12) United States Patent
Heston et al.

(10) Patent No.: US 7,399,461 B2
(45) Date of Patent: Jul. 15, 2008

(54) PROSTATE-SPECIFIC MEMBRANE ANTIGEN AND USES THEREOF

(75) Inventors: Warren D. W. Heston, Chagrin Falls, OH (US); Ouathek Ouerfelli, New York, NY (US); John Pinto, East Norwalk, CT (US)

(73) Assignee: Sloan-Kettering Institute For Cancer Research, New York, NY (US)

( * ) Notice: Subject to any disclaimer, the term of this patent is extended or adjusted under 35 U.S.C. 154(b) by 414 days.

(21) Appl. No.: 10/614,625

(22) Filed: Jul. 2, 2003

(65) Prior Publication Data

US 2004/0198657 A1 Oct. 7, 2004

Related U.S. Application Data

(63) Continuation-in-part of application No. 10/433,694, filed on Oct. 21, 2003, now abandoned, and a continuation of application No. 08/705,477, filed on Aug. 29, 1996, now Pat. No. 6,569,432, and a continuation-in-part of application No. PCT/US96/02424, filed on Feb. 23, 1996, which is a continuation-in-part of application No. 08/466,381, filed on Jun. 6, 1995, now Pat. No. 6,953,668, and a continuation-in-part of application No. 08/470,735, filed on Jun. 6, 1995, now Pat. No. 7,105,159, which is a continuation of application No. 08/394,152, filed on Feb. 24, 1995, now Pat. No. 5,935,818.

(51) Int. Cl.
*A61K 47/22* (2006.01)
(52) U.S. Cl. .................................... 424/9.44
(58) Field of Classification Search ........................ None
See application file for complete search history.

(56) References Cited

U.S. PATENT DOCUMENTS

| | | | |
|---|---|---|---|
| 4,554,101 A | 11/1985 | Hopp | |
| 4,569,794 A | 2/1986 | Smith et al. | |
| 4,939,240 A | 7/1990 | Chu et al. | |
| 5,153,118 A | 10/1992 | Wright et al. | |
| 5,162,504 A | 11/1992 | Horoszewicz | |
| 5,538,866 A | 7/1996 | Israeli et al. | |
| 5,672,592 A | 9/1997 | Jackson et al. | |
| 5,773,292 A | 6/1998 | Bander | |
| 5,795,877 A | 8/1998 | Jackson et al. | |
| 5,804,602 A | 9/1998 | Slusher et al. | |
| 5,852,167 A | 12/1998 | Kay et al. | |
| 5,855,866 A | 1/1999 | Thorpe et al. | |
| 5,863,536 A | 1/1999 | Jackson et al. | |
| 5,880,112 A | 3/1999 | Jackson et al. | |
| 5,902,817 A | 5/1999 | Jackson et al. | |
| 5,935,818 A | 8/1999 | Israeli et al. | |
| 5,939,258 A | 8/1999 | Croce et al. | |
| 5,962,521 A | 10/1999 | Jackson et al. | |
| 5,968,915 A | 10/1999 | Jackson et al. | |
| 5,981,209 A | 11/1999 | Slusher et al. | |
| 6,011,021 A | 1/2000 | Slusher et al. | |
| 6,017,903 A | 1/2000 | Slusher et al. | |
| 6,025,344 A | 2/2000 | Jackson et al. | |
| 6,025,345 A | 2/2000 | Jackson et al. | |
| 6,046,180 A | 4/2000 | Jackson et al. | |
| 6,051,230 A | 4/2000 | Thorpe et al. | |
| 6,054,444 A | 4/2000 | Jackson et al. | |
| 6,103,463 A | 8/2000 | Chetverin et al. | |
| 6,107,090 A | 8/2000 | Bander | |
| 6,121,252 A | 9/2000 | Jackson et al. | |
| 6,136,311 A | 10/2000 | Bander | |
| 6,150,508 A | 11/2000 | Murphy et al. | |
| 6,271,245 B1 | 8/2001 | Jackson et al. | |
| 6,288,046 B1 | 9/2001 | Jackson et al. | |
| 6,348,464 B1 | 2/2002 | Jackson et al. | |
| 6,372,726 B1 | 4/2002 | Slusher et al. | |
| 6,384,022 B1 | 5/2002 | Jackson et al. | |
| 6,395,718 B1 | 5/2002 | Slusher et al. | |
| 6,413,948 B1 | 7/2002 | Slusher et al. | |
| 6,452,044 B2 | 9/2002 | Jackson et al. | |
| 6,458,775 B1 | 10/2002 | Jackson et al. | |
| 6,479,471 B1 | 11/2002 | Jackson et al. | |
| 6,569,432 B1 | 5/2003 | Israeli et al. | |
| 6,586,623 B2 | 7/2003 | Tsukamoto et al. | |
| 6,649,163 B1 | 11/2003 | Bander | |
| 6,953,668 B1 | 10/2005 | Israeli et al. | |
| 7,037,647 B1 | 5/2006 | Israeli et al. | |

(Continued)

FOREIGN PATENT DOCUMENTS

EP 0173951 12/1986

(Continued)

OTHER PUBLICATIONS

Serval et al. J Neurochem. 1990; 55: 39-46.*

(Continued)

*Primary Examiner*—Elizabeth C. Kemmerer
*Assistant Examiner*—Christina Borgeest
(74) *Attorney, Agent, or Firm*—John P. White; Cooper & Dunham LLP

(57) ABSTRACT

This invention provides a method of administering methotrexate triglutamate (MTXglu3), an inhibitor of the neurocarboxypeptidase activity of prostate specific membrane antigen, to a subject so as to inhibit release of glutamate by N-acetylaspartylglutamic acid (NAAG) hydrolysis in the subject.

1 Claim, 102 Drawing Sheets

U.S. PATENT DOCUMENTS

| | | | |
|---|---|---|---|
| 7,070,782 | B1 | 7/2006 | Israeli et al. |
| 7,105,159 | B1 | 9/2006 | Israeli et al. |
| 2001/0044459 | A1 | 11/2001 | Jackson et al. |
| 2002/0013295 | A1 | 1/2002 | Slusher et al. |
| 2002/0015704 | A1 | 2/2002 | Bander |
| 2002/0019430 | A1 | 2/2002 | Jackson et al. |
| 2002/0037289 | A1 | 3/2002 | Thorpe et al. |
| 2002/0151503 | A1 | 10/2002 | Slusher et al. |
| 2003/0003101 | A1 | 1/2003 | Bander |
| 2003/0007974 | A1 | 1/2003 | Nanus et al. |
| 2003/0017965 | A1 | 1/2003 | Slusher et al. |
| 2003/0031673 | A1 | 2/2003 | Bander |
| 2003/0064912 | A1 | 4/2003 | Slusher et al. |
| 2003/0083374 | A1 | 5/2003 | Jackson et al. |
| 2003/0105088 | A1 | 6/2003 | Tsukamoto et al. |
| 2003/0185832 | A1 | 10/2003 | Thorpe et al. |
| 2003/0216468 | A1 | 11/2003 | Tsukamoto et al. |
| 2004/0001846 | A1 | 1/2004 | Israeli et al. |
| 2004/0024188 | A1 | 2/2004 | Murphy et al. |
| 2004/0120958 | A1 | 6/2004 | Bander et al. |
| 2004/0213791 | A1 | 10/2004 | Bander et al. |
| 2006/0177450 | A1 | 8/2006 | Israeli et al. |

FOREIGN PATENT DOCUMENTS

| | | |
|---|---|---|
| EP | 1 306 095 | 5/2003 |
| WO | WO 93/17715 | 9/1993 |
| WO | WO 95/04548 | 2/1995 |
| WO | WO 97/48409 | 12/1997 |
| WO | WO 98/03873 | 1/1998 |
| WO | WO 98/53812 | 12/1998 |
| WO | WO 00/01668 | 1/2000 |
| WO | WO 00/38785 | 7/2000 |
| WO | WO 01/009192 | 2/2001 |
| WO | WO 03/064606 | 8/2003 |
| WO | WO 2004/098535 | 11/2004 |

OTHER PUBLICATIONS

Stauch et al. Neurosci Lett. 1989; 100: 295-300.*

Curt et al. J Clin Invest. 1985; 76: 1323-9.*

Communication Pursuant To Article 96(2) EPC issued Feb. 8, 2005 in connection with related European Patent Application No. 94 90 0538.3; and.

Communication Pursuant To Article 115(2) EPC issued Mar. 17, 2005 in connection with related European Patent Application No. 94 90 0538.3.

Carter, RE, et al., "Prostate-specific membrane antigen is a hydrolase with substrate and pharmacologic characteristics of a neuropeptidase," *Proc. Natl. Acad. Sci. USA*, 93: 749-53. (1996) (Exhibit 1).

Halsted, CH, et al., "Folylpoly-γ-glutamate Carboxypeptidase from Pig Jejunum. Molecular Characterization and Relation to Glutamate Carboxypeptidase II," *J. Biol. Chem.*, 273(32): 20417-24. (1998) (Exhibit 2).

Slusher, BS, et al., "Rat brain N-acetylated alpha-linked acidic dipeptidase activity. Purification and immunologic characterization," *J. Biol. Chem.*, 265(34): 21297-301. (1990) (Exhibit 3).

Wang, TT, et al., "Intracellular pteroylpolyglutamate hydrolase from human jejunal mucosa. Isolation and characterization," *J. Biol. Chem.*, 261(29): 13551-5. (1986) (Exhibit 4).

Abdel-Nabi, H., Wright, G.L., Gulfo, J.V., Petrylak, D.P., Neal, C.E. et al. (1992) Monoclonal Antibodies and Radioimmunoconjugates in the Diagnosis and Treatment of Prostate Cancer, *Semin. Urol.* 10: 45-54.

Axelrod, H.R. et al. (1992) Preclinical results and human immunohistochemical studies with $^{90}$Y-CYT-356. A new prostate cancer therapeutic agent, *Abstract 596. AUA 87th Annual Meeting*, May 10-14, 1992, Washingon, D.C.

Carter, B.H. and Coffey, D.S. (1990) The Prostate: An Increasing Medical Problem, *The Prostate* 16: 39-48.

Chang, C.S., Kokontis, J. and Liao, S.T. (1988) Structural Analysis of Complementary DNA and Amino Acid Sequences of Human and Rat Androgen Receptors, *Proc. Natl. Acad. Sci. USA* 85: 7211-7215.

Corr, J.G. et al. (1994) Prostate Specific Membrane Antigen (PSM) Expression in Orthotopically Implanted Human Procstate Cancer Cells in Nude Mice Slows Tumor Growth and Metastatic Potential, *J. Urol.* 151: 492A.

Culver, K.W., Ram, Z., Wallbridge, S., Ishii, H., Oldfield, E.H. and Blaese, R.M. (1992) In Vivo Gene Transfer with Retroviral Vector-Producer Cells for Treatment of Experimental Brain Tumors, *Science* 256: 1150-1552.

Decensi, A., Guarneri, D., Paoletti, M.C., Lalanne, J.M., Merlo, F. and Boccardo, F. (1991) Phase II Study of the Pure Non-steriodal Antiandrogen Nilutamide in Prostatic Cancer, *Eur. J. Cancer* 27: 1100-1104.

Faber, P.W., van Rooji, H.C., van der Korput, H.A., Baarends, W.M., Brinkmann, A.O., Grootegoed, J.A. and Trapman, J. (1991) Characterization of the Human Androgen Transcription Unit, *J. Biol. Chem.* 266: 10743-10749.

Feng, Q. et al. (1991) Purification and Biochemical Characterization of the 7E11-C5 Prostate Carcinoma-Associated Antigen, *Proc. Am. Assoc. Cancer Res.* 32: 239.

Fey, M.F., Kulozik, A.E., Hansen-Hagge, T.E. and Tobler, A. (1991) The Poymerase Chain Reaction: A New Tool for the Detection of Minimal Residual Disease in Haematological Malignancies, *Eur. J. Cancer* 27: 89-94.

Henttu, P. and Vihko, P. (1989) cDNA Coding for the Entire Human Prostate Specific Antigen Shows High Homologies to the Human Tissue Kallikrein Genes, *Biochem. Biophys. Res. Commun.* 160: 903-910.

Horoszewicz, J.S., Kawinski, E. and Murphy, G.P. (1987) Monoclonal Antibodies to a New Antigen Marker in Epithelial Prostatic Cells and Serum of Prostatic Cancer Patients, *AntiCancer Res.* 7: 927-936.

Huber, B.E., Richards, C.A. and Krenitsky, T.A. (1991) Retroviral-mediated Gene Therapy for the Treatment of Hepatocellular Carcinoma: An Innovative Approach for Cancer Therapy, *Proc. Natl. Acad. Sci. USA* 88:8039-8043.

Israeli, R.S. et al., (1992) Purification and Molecular Cloning of a New Prostate-Specific Antigen, *Cancer Res.* 33: 356.

Israeli, R.S., Powell, C.T., Fair, W.R. and Heston, W.D. (1993) Molecular Cloning of a Complementary DNA Encoding a Prostate-specific Membrane Antigen, *Cancer Res.* 53: 227-230.

Israeli, R.S. et al. (1993) Molecular Cloning and Characterization of a Prostate-Specific Membrane Antigen, *J. Urol.* 149: 471A.

Israeli, R.S. et al. (1993) Characterization of the Prostate-Specific Membrane Antigen (PSM), *Proc. Am. Assoc. Cancer Res.* 34: 255.

Israeli, R.S., Powell, C.T., Corr, J.G., Fair, W.R. and Heston, W.D. (1994) Expression of the Prostate Specific Membrane Antigen, *Cancer Res.* 54: 1807-1811.

Israeli, R.S., Miller, W.H. Jr., Su, S.L., Powell, C.T., Fair, W.R. et al. (1994) Sensitive Nested Reverse Transcription Polymerase Chain Reaction Detection of Circulating Prostatic Tumor Cells: Comparison of Prostate-specific Membrane Antigen and Prostate-.

Israeli, R.S. et al. (1994) Localization of the Prostate Specific Membrane Antigen (PSM) to the Putative Metastasis-Suppressor Region on Human Chromosome 11, *J. Urol.* 151:252A.

Israeli, R.S. et al., (1994) Sensitive Detection of Prostatic Hematogenous Micro-Metastases Using Prostate Specific Antigen (PSA) And Prostate Specific Membrane Antigen (PSM) Derived Primers in the Polymerase Chain Reaction (PCR), *J. Urol.* 151: 373A.

Israeli, R.S. et al. (1994) Localization of the Prostate Specific Membrane Antigen (PSM) to the Putative Metastasis-Suppressor Region on Human Chromosome 11, *Proc. Am. Assoc. Cancer Res.* 35: 271.

Keer, H.N., Kozlowski, J.M., Tsai, Y.C., Lee, C., McEwan, R.N. and Grayhack, J.T. (1990) Elevated Transferrin Receptor Content in Human Prostate Cancer Cell Lines Assessed In Vitro and In Vivo, *J. Urol.* 143:381-385.

Lopes, A. D. et al. (1993) Immunohistochemical and Pharmacokinetic Characterization of the Site-specific Immunoconjugate CYT-356 Derived from Antiprostate Monoclonal Antibody, *Cancer Res.* 50: 6423-6429.

Lubahn, D.B., Brown, T.R., Simental, J.A., Higgs, H.N., Migeon, C.J., Wilson, E.M. and French, F.S. (1989) Sequence of the Intron/exon Junctions of the Coding Region of the Human Androgen Receptor Gene and Identification of a Point Mutation in a family with Complete Androgen Insensitivity, *Proc. Natl. Acad. Sci. USA* 86: 9534-9538.

Lundwall, A, and Lilja, H. (1987) Molecular Cloning of Human Prostate Specific Antigen cDNA, *FEBS Lettr*. 214: 317-322.

Mukhopadhyay, T., Tainsky, M., Cavender, A.C. and Roth, J.A. (1991) Specific Inhibition of K-ras Expression and Tumorigenicity of Lung Cancer Cells by Antisense RNA[1], *Cancer Res*. 51: 1744-1748.

Riegman, P.H.J. et al. (1989) The Prostate-Specific Antigen Gene and the Human Glandular Kallikrein-1 Gene are Tandemly Located on Chromosome 19, *FEBS Lettr*. 247: 123-126.

Sharief, F.S., Lee, H., Leuderman, M.M., Lundwall, A., Deaven, L.L., Lee, C.L. and Li, S.S. (1989) Human prostatic acid phosphatase: cDNA cloning, gene mapping and protein sequence homology with lysosomal acid phosphatase. *Biochem. Biophys. Res. Commun*. 160: 79-86.

Solin, T., Kontturi, M., Pohlmann, R. and Vihko, P. (1990) Gene Expression and Prostate Specificity of Human Prostatic Acid Phosphatase (PAP): Evaluation By RNA Blot Analuses, *Biochem. Biophys. Acta* 1048: 72-77.

Su, S.L., et al. (1994) Sensitive Detection of Prostatic Hematogenous Micrometastases Using Prostate Specific Antigen (PSA) and Prostate Specific Membrane Antigen (PSM) Derived Parameters in the Polymerase Chain Reaction, *Proc. Am. Assoc. Cancer Res*. 35: 271.

Troyer, John K. (1994) Biochemical Characterization and Mapping of the 7E11-C5.3 Epitope of the Prostate Specific Membrane Antigen (PSMA), *Basic and Clinical Aspects of Prostate Cancer: Abstract C38*.

Vihko, P., Virkkunen, P., Henttu, P., Roiko, K., Solin, T. and Huhtala, M.L. (1988) Molecular Cloning and Sequence Analysis of cDNA Encoding Human Prostatic Acid Phosphatase, *FEBS Lettr*. 236: 275-281.

Vile, R.G. and Hart, I.R. (1993) In Vitro and In Vivo Targeting of Gene Expression to Melanoma Cells, *Cancer Res*. 53: 962-967.

Waibel, R. et al. (1990) Therapy of Small Cell Lung Cancer Xenografts in a Nude Mouse model: Evaluation of Radioimmunotherapy and Immunotoxin Therapy, *Antibody Immunoconjugates and Radiopharmaceuticals* 34: 54.

Watt, K.W.K. et al. (1986) Human Prostate-Specific Antigen: Structural and Functional Similarity with Serine Proteases, *Proc. Natl. Acad. Sci. USA* 83: 3166-3170.

Wright, Jr., G.L., Feng, Q., Beckett, M.L., Lopes, D. and Gilman, S.C. (1990) Characterization of a new prostate carcinoma-associated marker: 7E11-C5. *Antibody, and Immunoconjugates and Radiopharmaceuticals* 3: 89 (Abstract 193).

Young, R.A. and Davis, R.W. (1983) Efficient Isolation of Genes by Using Antibody Probes, *Proc. Natl. Acad. Sci. USA* 80: 1194-1198.

Su, S.L., Huang, I.P., Fair, W.R., Powell, C.T. and Heston, W.D. (1995) *Cancer Res*., 55: 1441-1443.

Bowie, J.U., Reidhaar-Olston, J.F., Lim, W.A. and Sauer, R.T. (1990) Deciphering the Message in Protein Sequences: Tolerance to Amino Acid Substitutions, *Science* 147: 1306-1310.

Kumar, V., Urban, J.L., Horvath, S.J. and Hood, L. (1990) Amino Acid Variations at a Single Residue in an Autoimmune Peptide Profoundly Affect Its Properties: T-Cell Activation, Major Histocompatibility Complex Binding, and Ability to Block Experimental Allergic Encephalomyelitis, *Proc. Natl. Acad. Sci. USA* 87: 1337-1341.

Lazar, E., Watanabe, S., Dalton, S. and Sporn, M.B. (1988) Transforming Growth Factor α: Mutation of Aspartic Acid 47 and Leucine 48 Results in Different Biological Activities, *Mol. Cell Biol*. 8: 1247-1252.

Gately, M.K., Wolitzky, A.G., Quinn, P.M. and Chizzonite, R. (1992) "Regulation of Human Cytololytic Lymphocyte Responses by Interleukin-12", *Cell. Immunol*. 143: 127-142.

Paul, W.E. (1989) *Fundamental Immunology*, Raven Press, pp. 628-629, 647-651; Paul, W.E. (1989) *Fundamental Immunology*, Raven Press, pp. 629-629, 647-651.

Rose, N.R. et al. (1986) *Manual of Clinical Laboratory Immunology*, American Society for Microbiology, 89-109.

Rossi, M. C. and Zetter, B.R. (1992) Selective Stimulation of Prostatic Carcinoma Cell Proliferation by Transferrin, *Proc. Natl. Acad. Sci. USA* 89: 6197-6201.

Sambrook, J., Fritsch, E.F. and Maniatis, T. (1989) *Molecular Cloning, A Laboratory Manual*, Cold Spring Harbor Laboratory Press, 16.1-16.81.

Schneider, C., Owen, M.J., Banville, D. and Williams, J. G. (1984) Primary Structure of Human Transferrin Receptor Deduced from the mRNA sequence, *Nature* 311: 675-678.

Stites, D.P. et al. (1991) *Basic and Clinical Immunology*, Appleton & Lange, 229-251.

Tortora, G.J. et al. (1989) *Microbiology, An Introduction*, Benjamin/Cummings Publishing Co., 423-426, 471.

Elgamal et al., (2000), Abstract, *Semin. Surg. Oncol*, 18:10-6.

Abraham et al., (1990), Folate Analogues. 33. Synthesis of folate and antifolate poly-gamma-glutamates by [(9-fluorenylmethoxy)oxy] carbonyl chemistry and biological evaluation of certain methotrexate polyglutamate polylysine conjugates as inhibitors of the growth of H35 hepatoma cells, *J. Med. Chem*., 33(2):711-717.

Whitehead et al., (1992), Accumulation of high levels of methotrexate polyglutamates in lymphoblasts from children with hyperdiploid (>50 chromosomes) B-Lineage acute lymphoblastic leukemia: a pediatric oncology group study, *Blood* 80(5):1316-1323.

Ghosh Arundhati et al., (2005), Novel role of prostate-Specific membrane antigen in suppressing prostate cancer invasiveness, *Cancer Research*, 65(3):727-731.

Tasch et al., (2001), A unique folate hydrolase, prostate-specific membrane antigen (PSMA): a target for immunotherapy?, *Crit. Rev. in Immunol*., 21(1-3):249-261.

Heston, W., (1996), Bedeuteng des prostataspezifischen membranantigens (PSMA), *Urologe Ausgabe A*, 35(5):400-407.

English language translation of Heston, W., (1996), Bedeuteng des prostataspezifischen membranantigens (PSMA), *Urologe Ausgabe A*, 35(5):400-407.

Extended Search Report and European Search Opinion issued Mar. 28, 2007 in connection with European Application No. 06002339.7.

Bell, G.I., et al., "cDNA Sequence Coding For Human Kidney Catalase," *Nucelic Acids Research*, 14(13):5561-2(1986).

Garcia, G., et al., "Selenoprotein A Component Of The Glycine Reductase Complex From *Clostridium purinolyticum*: Nuceleotide Sequence Of The Gene Shows That Selenocysteine Is Encoded By UGA," *J. Bacteriol*., 173(6):2093-2098 (Mar. 1991).

Harlow, E., et al., *Antibodies: A Laboratory Manual*, Cold Springs Harbor, p. 76 (1988).

Hartnett, C., et al., "DNA Sequences Of Genes Encoding *Acinetobacter calcoaceticus* Protcatechuate 3,4-Dioxygenase: Evidence Indicating Shuffling Of Genes And Of DNA Sequences Within Genes During Their Evolutionary Divergence," *J. Bacteriology*, 172(2):956-966 (Feb. 1990).

Holmes, Eric H., "PSMA Specific Antibodies And Their Diagnostic And Therapeutic Use," *Exp. Opin. On Invest. Drugs*, 10(3):511-519 (2001).

Palm, P., et al., "Complete Nucleotide Sequence Of The Virus SSV1 Of The Archaebacterium *Sulfolobus shibatae*," *Virology*, 185:242-250 (1991).

Ramakrishnan, V., et al., "Cloning, Sequencing And Overexpressing Of Genes For Ribosomal Proteins From *Bacillus Stearothermophilus*," *J. Niol. Chem*., 266(2):880-885 (1991).

Schiefer-Ullrich, H., et al., "Comparative Studies On Physiology And Taxonomy Of Obligately Purinolytic Closteridia," *Arch. Microbiol*., 138:345-353 (1984).

Sulavik, M.C., et al., "Idetification Of A Gene, *rgg*,Which Regulates Expression Of Glucosyltransferase And Influences the Spp Phenotype Of *Streptococcus gordonii* Challis," *J. Bacteriology*, 174(11):3577-3586 (1992); and Communication Pursuant To Article 115(2) EPC issued Aug. 30, 2004 in connection with related European Patent Application No. 94 90 0538.3.

Murphy, GP, (1996) Measurement of Prostate Specific Membrane Antigen in the Serum with New Antibody, Prostate, (1996) 28 (4) : 266-271.

Tino, WT, (2000) Isolation and Characterization of Monoclonal Antibodies Specific for Protein Conformational Epitopes Present in Prostate-Specific Membrane Antigen (PSMA), Hybridoma, 19 (3):249-257.

U.S. Appl. No. 11/480,319, filed on Jun. 30, 2006, Israeli et al.

Chandler et al., (1986) Pteroylpolyglutamate Hydrolase from Humna Jejunal Brush Borders, J. Biol. Chem., 261(2)928-933.

Silver, D.A. et al., Prostate-Specific Membrane Antigen Expression in Normal and Malignant Human Tissues, Clin. Cancer Res. (1997) 3:81-85.

Chang, S.S. et al., Five Different Anti-Prostate-Specific membrane Antigen (PSMA) Antibodies Confirm PSMA Expression in Tumor-Associated Neovasculature, Cancer Res. (1999) 59:3192-3198.

Lerner, R.A., Antibodies of Predetermined Specificity in Biology and Medicine, (1984) Advances in Immunology 36:1-44.

Brinkmann, U. et al., A Recombinant Immunotoxin Containing A Disulfide-Stabilized Fv Fragment, PNAS, 60(16):7538-7542 (1993).

Communication of a Notice of Oppositions mailed Jul. 18, 2007 in connection with related European Application No. 94900538.3, now European Patent No. 668777 granted Oct. 11, 2006, as well as (A) opposition documents filed by BZL Biologics LLC including (1) a Notice of Opposition Form 2300 filed by BZL Biologics LLC; and (2) Statement of Grounds for Opposition and copies of references cited in the Grounds for Opposition ((i) EP 066877; (ii) WO94/09820; (iii) Holmes et al., 2001, Expert Opinion on Investigational Drugs, 10 (3):544-519; and (iv) Schulke et al., 2003, PNAS, 100(22):1259012595) and (B) opposition documents filed by Northwest Bio Therapeutics Inc. including a Notice of Opposition form 2300 from Northwest Bio Therapeutics Inc.; and (2) Statement of Grounds for Opposition including a list of documents D1 through D36 (D1 through D28, D30-D32 and D36 of which are of record in the subject application; D26 being part of Exhibit 12 - *Communication Pursuant To Article 96 (2) EPC, issued Feb. 8, 2005 in connection with related European Patent Application No. 94 90 0538.3*- of the Supplemental Information Disclosure Statement filed Apr. 4, 2005 in connection with the above-identified application), copies of D28 through D36 of which are enclosed (D28 - Horoszewicz J. et al., 1987, Anticancer Research 7:927-936; D29 - Horoszewicz J. et al., 1983, Cancer Research 43:1809-1818; D30 - Wright et al. (1990), Antibody, Immunoconjugates and Radiopharmaceuticals 3:39 (Abst#193); D31 - Axelrod et al., 1992, AUA 87th Annual Meeting, Abstract 596; D32 - Israeli et al., (1992), Proc. 83rd Ann. Meeting of the American Association for Cancer, 33:356 (Abstract); D33 - Declaration in the name of Julius S. Horoszewicz; D34 - Declaration in the name of John D. Rodwell; D35 - Declaration in the name of Paul Kaladas; D36 - U.S. Appl. No. 5,162504, issued Nov. 10, 1992, Horoszewicz et al.)

* cited by examiner

FIGURE 7

| CELL LINE/TYPE | 11p11.2-13 REGION | METASTATIC | PSM RNA DETECTED | PSM DNA DETECTED |
|---|---|---|---|---|
| LNCap | | | + + | ND |
| HUMAN PROSTATE | | | + + | ND |
| A9 (FIBROSARCOMA) | NO | NO | − | − |
| A9(11) (A9+HUM. 11) | YES | NO | − | REPEAT |
| AT6.1 (RAT PROSTATE) | NO | YES | − | − |
| AT6.1-11-c11 | YES | NO | + | + + |
| AT6.1-11-c12 | NO | YES | − | − |
| R1564 (RAT MAMMARY) | NO | YES | − | − |
| R1564-11-c14 | YES | YES | − | + |
| R1564-11-c15 | YES | YES | − | REPEAT |
| R1564-11-c16 | YES | YES | − | ND |
| R1564-11-c12 | YES | YES | ND | + |

FIGURE 14

| Patient | Stage | Treatment | PSA | PAP | PSA-PCR | PSM-PCR |
|---|---|---|---|---|---|---|
| 1 | T2NxMo | None | 8.9 | 0.7 | − | + |
| 2 | T2NoMo | RRP 7/93 | 6.1 | − | − | + |
| 3 | T2CNoMo | PLND 5/93 | 4.5 | 0.1 | − | + |
| 4 | T2BNoMo | RRP 3/92 | NMA | 0.4 | − | + |
| 5 | T3NxMo | Proscar + Flutamide | 51.3 | 1.0 | − | + |
| 6 | Recur T3 | I-125 1986 | 54.7 | 1.4 | − | + |
| 7 | T3ANoMo | RRP 10/92 | NMA | 0.3 | − | + |
| 8 | T3NxMo | XRT 1987 | 7.5 | 0.1 | − | − |
| 9 | T3NxMo | Proscar + Flutamide | 35.4 | 0.7 | − | − |
| 10 | D2 | S/P XRT Flutamide +Emcyt | 311 | 4.5 | + | + |
| 11 | D2 | RRP 4/91 Lupron 10/92 Velban + Emcyt 12/92 | 1534 | 1.4 | + | + |
| 12 | T2NoMo | RRP 8/91 | NMA | 0.5 | − | + |
| 13 | T3NoMo | RRP 1/88 Lupron + Flutamide 5/92 | 0.1 | 0.3 | − | − |
| 14 | D1 | PLND 1989 XRT 1989 | 1.6 | 0.4 | − | − |
| 15 | D1 | Proscar + Flutamide | 20.8 | 0.5 | − | − |
| 16 | T2CNoMo | RRP 4/92 | 0.1 | 0.3 | − | − |

FIGURE 15A

```
            10         20         30         40         50         60
             |          |          |          |          |          |
  1 GCGCCTTAAA AAAAAAAAAC TTTCTTGGAA AATGTCCAGC TCTTGCTTAA ATATAAAAAT
    CGCGGAATTT TTTTTTTTTG AAAGAACCTT TTACAGGTCG AGAACGAATT TATATTTTTA

61 GAAAGGAAGA AAGAGACTCT CCTCTCTCCA CTCCTATAAT TATGAGGAAC TTTTATTCAA
    CTTTCCTTCT TTCTCTGAGA GGAGAGAGGT GAGGATATTA ATACTCCTTG AAAATAAGTT

121 CTCTGAAATT CTATACAATC TCTACAATAC TCTACTGAAT AAAAGCAGAG CAGAAAAAGC
    GAGACTTTAA GATATGTTAG AGATGTTATG AGATGACTTA TTTTCGTCTC GTCTTTTTCG

181 TGCGCTTTTT TTCCATAGTC GGGAATGCTT GTCATCAGTG TAAATCACCA CCGCGCCCTT
    ACGCGAAAAA AAGGTATCAG CCCTTACGAA CAGTAGTCAC ATTTAGTGGT GGCGCGGGAA

241 TTTCCTAAAG AATATTATTG TTATTAATAA ACATGTAGGG TATTATCCTC CACTTACATT
    AAAGGATTTC TTATAATAAC AATAATTATT TGTACATCCC ATAATAGGAG GTGAATGTAA

301 ACAAAACCAT TTTTTAAAGC CGGGCGTGGT GGCTCACGCC TGTAATCCCA GCACTTTGGG
    TGTTTTGGTA AAAAATTTCG GCCCGCACCA CCGAGTGCGG ACATTAGGGT CGTGAAACCC

361 AGGCCCAGAC AGGCGGATCA CGAAGTCGAG AAATCGAGAC CATCCTGGCC AACATGGTGA
    TCCGGGTCTG TCCGCCTAGT GCTTCAGCTC TTTAGCTCTG GTAGGACCGG TTGTACCACT

421 AACCCCATCT CTACTAAAAA TACAAAAATT AGCTGGGCGT GGTGGCGGGC TCCTGTAGTC
    TTGGGGTAGA GATGATTTTT ATGTTTTTAA TCGACCCGCA CCACCGCCCG AGGACATCAG

481 CCAGCTACTC AGGAGGCTGA GGCAGGAGAA TCGCTTGAAC CGGGGAGGCG GAGGTTGCAG
    GGTCGATGAG TCCTCCGACT CCGTCCTCTT AGCGAACTTG GCCCCTCCGC CTCCAACGTC

541 TCAGCCAAGA TAGCGCCACT GCACTGGAGC CTGGTGACAG AGTGAGACTC CCTCAAGAAA
    AGTCGGTTCT ATCGCGGTGA CGTGACCTCG GACCACTGTC TCACTCTGAG GGAGTTCTTT

601 GAAAGGAAGG GAAGGGAAAG GGAAGGAAGG GGAGGGGAAG GGAGGGGAGG GGAGGGGAGG
    CTTTCCTTCC CTTCCCTTTC CCTTCCTTCC CCTCCCCTTC CCTCCCCTCC CCTCCCCTCC

661 AAAGAAAAGA ATACTGGAAC TTGTTGAAGG CAGAGACTTT ATTTTCATAT CCCGGCTATG
    TTTCTTTTCT TATGACCTTG AACAACTTCC GTCTCTGAAA TAAAAGTATA GGGCCGATAC

721 TCTGGCTACT GTCTTACGTA ATAGATATAA AATCAATCTT GGTTGGATTA ACCAGAAGAA
    AGACCGATGA CAGAATGCAT TATCTATATT TTAGTTAGAA CCAACCTAAT TGGTCTTCTT
```

FIGURE 15B

```
 781 TGAGAAGATA TATTCTGGTA AGTTGAATAC TTAGCACCCA GGGGTAATCA GCTTGGACAG
     ACTCTTCTAT ATAAGACCAT TCAACTTATG AATCGTGGGT CCCCATTAGT CGAACCTGTC

841 GACCAGGTCC AAAGACTGTT AAGAGTCTTC TGACTCCAAA CTCAGTGCTC CCTCCAGTGC
     CTGGTCCAGG TTTCTGACAA TTCTCAGAAG ACTGAGGTTT GAGTCACGAG GGAGGTCACG

901 CACAAGCAAA CTCCATAAAG GTATCCTGTG CTGAATAGAG ACTGTAGAGT GGTACAAAGT
     GTGTTCGTTT GAGGTATTTC CATAGGACAC GACTTATCTC TGACATCTCA CCATGTTTCA

961 AAGACAGACA TTATATTAAG TCTTAGCTTT GTGACTTCGA ATGACTTACC TAATCTAGCT
     TTCTGTCTGT AATATAATTC AGAATCGAAA CACTGAAGCT TACTGAATGG ATTAGATCGA

1021 AAATTTCAGT TTTACCATGT GTAAATCAGG AAGAGTAATA GAACAAACCT TGAAGGGTCC
     TTTAAAGTCA AAATGGTACA CATTTAGTCC TTCTCATTAT CTTGTTTGGA ACTTCCCAGG

1081 CAATGGTGAT TAAATGAGGT GATCTACATA ACATGCATCA CTCATAATAA GTGCTCTTTA
     GTTACCACTA ATTTACTCCA CTACATGTAT TGTACGTAGT GAGTATTATT CACGAGAAAT

1141 AATATTAGTC ACTATTATTA GCCATCTCTG ATTAGATTTG ACAATAGGAA CATTAGGAAA
     TTATAATCAG TGATAATAAT CGGTAGAGAC TAATCTAAAC TGTTATCCTT GTAATCCTTT

1201 GATATAGTAC ATTCAGGATT TTGTTAGAAA GAGATGAAGA AATTCCCTTC CTTCCTGCCC
     CTATATCATG TAAGTCCTAA AACAATCTTT CTCTACTTCT TTAAGGGAAG GAAGGACGGG

1261 TAGGTCATCT AGGAGTTGTC ATGGTTCATT GTTGACAAAT TAATTTTCCC AAATTTTTCA
     ATCCAGTAGA TCCTCAACAG TACCAAGTAA CAACTGTTTA ATTAAAAGGG TTTAAAAAGT

1321 CTTTGCTCAG AAAGTCTACA TCGAAGCACC CAAGACTGTA CAATCTAGTC CATCTTTTTC
     GAAACGAGTC TTTCAGATGT AGCTTCGTGG GTTCTGACAT GTTAGATCAG GTAGAAAAG

1381 CACTTAACTC ATACTGTGCT CTCCCTTTCT CAAAGCAAAC TGTTTGCTAT TCCTTGAATA
     GTGAATTGAG TATGACACGA GAGGGAAAGA GTTTCGTTTG ACAAACGATA AGGAACTTAT

1441 CACTCTGAGT TTTCTGCCTT TGCCTACTCA GCTGGCCCAT GGCCCCTAAT GTTTCTTCTC
     GTGAGACTCA AAAGACGGAA ACGGATGAGT CGACCGGGTA CCGGGGATTA CAAAGAAGAG

1501 ATCTCCACTG GGTCAAATCC TACCTGTACC TTATGGTTCT GTTAAAAGCA GTGCTTCCAT
     TAGAGGTGAC CCAGTTTAGG ATGGACATGG AATACCAAGA CAATTTTCGT CACGAAGGTA

1561 AAAGTACTCC TAGCAAATGC ACGGCCTCTC TCACGGATTA TAAGAACACA GTTTATTTTA
     TTTCATGAGG ATCGTTTACG TGCCGGAGAG AGTGCCTAAT ATTCTTGTGT CAAATAAAAT

1621 TAAAGCATGT AGCTATTCTC TCCCTCGAAA TACGATTATT ATTATTAAGA ATTTATAGCA
     ATTTCGTACA TCGATAAGAG AGGGAGCTTT ATGCTAATAA TAATAATTCT TAAATATCGT

1681 GGGATATAAT TTTGTATGAT GATTCTTCTG GTTAATCCAA CCAAGATTGA TTTTATATCT
     CCCTATATTA AAACATACTA CTAAGAAGAC CAATTAGGTT GGTTCTAACT AAAATATAGA

1741 ATTACGTAAG ACAGTAGCCA GACATAGCCG GGATATGAAA ATAAAGTCTC TGCCTTCAAC
     TAATGCATTC TGTCATCGGT CTGTATCGGC CCTATACTTT TATTTCAGAG ACGGAAGTTG

1801 AAGTTCCAGT ATTCTTTTCT TTCCTCCCCT CCCTCCCCT CCCTTCCCCT CCCCTTCCTT
     TTCAAGGTCA TAAGAAAAGA AAGGAGGGGA GGGAGGGA GGGAAGGGGA GGGGAAGGAA

1861 CCCTTTCCCT TCCCTTCCTT TCTTTCTTGA GGGAGTCTCA CTCTGTCACC AGGCTCCAGT
     GGGAAAGGGA AGGGAAGGAA AGAAAGAACT CCCTCAGAGT GAGACAGTGG TCCGAGGTCA
```

FIGURE 15C

```
1921 GCAGTGGCGC TATCTTGGCT GACTGCAACC TCCGCCTCCC CGGTTCAAGC GATTCTCCTG
     CGTCACCGCG ATAGAACCGA CTGACGTTGG AGGCGGAGGG GCCAAGTTCG CTAAGAGGAC

1981 CCTCAGCCTC CTGAGTAGCT GGGACTACAG GAGCCCGCCA CCACGCCCAG CTAATTTTTG
     GGAGTCGGAG GACTCATCGA CCCTGATGTC CTCGGGCGGT GGTGCGGGTC GATTAAAAAC

2041 TATTTTTAGT AGAGATGGGG TTTCACCATG TTGGCCAGGA TGGTCTCGAT TTCTCGACTT
     ATAAAAATCA TCTCTACCCC AAAGTGGTAC AACCGGTCCT ACCAGAGCTA AAGAGCTGAA

2101 CGTGATCCGC CTGTCTGGGC CTCCCAAAGT GCTGGGATTA CAGGCGTGAG CCACCACGCC
     GCACTAGGCG GACAGACCCG GAGGGTTTCA CGACCCTAAT GTCCGCACTC GGTGGTGCGG

2161 CGGCTTTAAA AAATGGTTTT GTAATGTAAG TGGAGGATAA TACCCTACAT GTTTATTAAT
     GCCGAAATTT TTTACCAAAA CATTACATTC ACCTCCTATT ATGGGATGTA CAAATAATTA

2221 AACAATAATA TTCTTTAGGA AAAAGGGCGC GGTGGTGATT TACACTGATG ACAAGCATTC
     TTGTTATTAT AAGAAATCCT TTTTCCCGCG CCACCACTAA ATGTGACTAC TGTTCGTAAG

2281 CCGACTATGG AAAAAAAGCG CAGCTTTTTC TGCTCTGCTT TTATTCAGTA GAGTATTGTA
     GGCTGATACC TTTTTTTCGC GTCGAAAAAG ACGAGACGAA AATAAGTCAT CTCATAACAT

2341 GAGATTGTAT AGAATTTCAG AGTGAATAA AAGTTCCTCA TAATTATAGG AGTGGAGAGA
     CTCTAACATA TCTTAAAGTC TCAACTTATT TTCAAGGAGT ATTAATATCC TCACCTCTCT

2401 GGAGAGTCTC TTTCTTCCTT TCATTTTTAT ATTTAAGCAA GAGCTGGACA TTTTCCAAGA
     CCTCTCAGAG AAAGAAGGAA AGTAAAAATA TAAATTCGTT CTCGACCTGT AAAAGGTTCT

2461 AAGTTTTTTT TTTTTAAGGC GCCTCTCAAA AGGGGCCGGA TTTCCTTCTC CTGGAGGCAG
     TTCAAAAAAA AAAAATTCCG CGGAGAGTTT TCCCCGGCCT AAAGGAAGAG GACCTCCGTC

2521 ATGTTGCCTC TCTCTCTCGC TCGGATTGGT TCAGTGCACT CTAGAAACAC TGCTGTGGTG
     TACAACGGAG AGAGAGAGCG AGCCTAACCA AGTCACGTGA GATCTTTGTG ACGACACCAC

2581 GAGAAACTGG ACCCCAGGTC TGGAGCGAAT TCCAGCCTGC AGGGCTGATA AGCGAGGCAT
     CTCTTTGACC TGGGGTCCAG ACCTCGCTTA AGGTCGGACG TCCCGACTAT TCGCTCCGTA

2641 TAGTGAGATT GAGAGAGACT TTACCCCGCC GTGGTGGTTG GAGGGCGCGC AGTAGAGCAG
     ATCACTCTAA CTCTCTCTGA AATGGGGCGG CACCACCAAC CTCCCGCGCG TCATCTCGTC

2701 CAGCACAGGC CCGGGTCCCG GGAGGCCGGC TCTGCTCGCG CCGAGATGTG GAATCTCCTT
     GTCGTGTCCG CGCCCAGGGC CCTCCGGCCG AGACGAGCGC GGCTCTACAC CTTAGAGGAA

2761 CACGAAACCG ACTCGGCTGT GGCCACCGCC CGCCGCCCGC GCTGGCTGTG CGCTGGGGCG
     GTGCTTTGGC TGAGCCGACA CCGGTGGCGC GCGGCGGGCG CGACCGACAC GCGACCCCGC

2821 CTGGTGCTGG CGGGTGGCTT CTTTCTCCTC GGCTTCCTCT TCGGTAGGGG GGCGCCTCGC
     GACCACGACC GCCCACCGAA GAAAGAGGAG CCGAAGGAGA AGCCATCCCC CCGCGGAGCG

2881 GGAGCAAACC TCGGAGTCTT CCCCGTGGTG CCGCGGTGCT GGGACTCGCG GGTCAGCTGC
     CCTCGTTTGG AGCCTCAGAA GGGGCACCAC GGCGCCACGA CCCTGAGCGC CCAGTCGACG

2941 CGAGTGGGAT CCTGTTGCTG GTCTTCCCCA GGGGCGGCGA TTAGGGTCGG GGTAATGTGG
     GCTCACCCTA GGACAACGAC CAGAAGGGGT CCCCGCCGCT AATCCCAGCC CCATTACACC

3001 GGTGAGCACC CCTCGAG
     CCACTCGTGG GGAGCTC
```

*FIGURE 15D*

```
- 2401  GGAGAGTCTC TTTCTTCCTT TCATTTTTAT ATTTAAGCAA GAGCTGGACA TTTTCCAAGA
        CCTCTCAGAG AAAGAAGGAA AGTAAAAATA TAAATTCGTT CTCGACCTGT AAAAGGTTCT

- 2461  AAGTTTTTTT TTTTTAAGGC GCCTCTCAAA AGGGGCCGGA TTTCCTTCTC CTGGAGGCAG
        TTCAAAAAAA AAAAATTCCG CGGAGAGTTT CCCCGGCCT AAAGGAAGAG GACCTCCGTC

- 2521  ATGTTGCCTC TCTCTCTCGC TCGGATTGGT TCAGTGCACT CTAGAAACAC TGCTGTGGTG
        TACAACGGAG AGAGAGAGCG AGCCTAACCA AGTCACGTGA GATCTTTGTG ACGACACCAC

- 2581  GAGAAACTGG ACCCCAGGTC TGGAGCGAAT TCCAGCCTGC AGGGCTGATA AGCGAGGCAT
        CTCTTTGACC TGGGGTCCAG ACCTCGCTTA AGGTCGGACG TCCCGACTAT TCGCTCCGTA

- 2641  TAGTGAGATT GAGAGAGACT TTACCCCGCC GTGGTGGTTG GAGGGCGCGC AGTAGAGCAG
        ATCACTCTAA CTCTCTCTGA AATGGGGCGG CACCACCAAC CTCCCGCGCG TCATCTCGTC

- 2701  CAGCACAGGC GCGGGTCCCG GGAGGCCGGC TCTGCTCGCG CCGAGATGTG GAATCTCCTT
        GTCGTGTCCG CGCCCAGGGC CCTCCGGCCG AGACGAGCGC GGCTCTACAC CTTAGAGGAA

- 2761  CACGAAACCG ACTCGGCTGT GGCCACCGCG CGCCGCCCGC GCTGGCTGTG CGCTGGGGCG
        GTGCTTTGGC TGAGCCGACA CCGGTGGCGC GCGGCGGGCG CGACCGACAC GCGACCCCGC

- 2821  CTGGTGCTGG CGGGTGGCTT CTTTCTCCTC GGCTTCCTCT TCGGTAGGGG GGCGCCTCGC
        GACCACGACC GCCCACCGAA GAAAGAGGAG CCGAAGGAGA AGCCATCCCC CCGCGGAGCG

- 2881  GGAGCAAACC TCGGAGTCTT CCCCGTGGTG CCGCGGTGCT GGGACTCGCG GGTCAGCTGC
        CCTCGTTTGG AGCCTCAGAA GGGGCACCAC GGCGCCACGA CCCTGAGCGC CCAGTCGACG

- 2941  CGAGTGGGAT CCTGTTGCTG GTCTTCCCCA GGGGCGGCGA TTAGGGTCGG GGTAATGTGG
        GCTCACCCTA GGACAACGAC CAGAAGGGGT CCCCGCCGCT AATCCCAGCC CCATTACACC

- 3001  GGTGAGCACC CCTCGAG
        CCACTCGTGG GGAGCTC
```

FIGURE 16

Potential binding sites on the PSM promoter*

| Site | Seq | **Location | #nt matched |
|---|---|---|---|
| AP1 | TKAGTCA | -1145 | 7/7 |
| E2-RS | ACCNNNNNNGGT | -1940 | 12/12 |
|  |  | -1951 | 12/12 |
| GHF | NNNTAAATNNN | -580 | 11/11 |
|  |  | -753 | 11/11 |
|  |  | -1340 | 11/11 |
|  |  | -1882 | 11/11 |
|  |  | -1930 | 11/11 |
|  |  | -1979 | 11/11 |
|  |  | -2001 | 11/11 |
|  |  | -2334 | 11/11 |
|  |  | -2374 | 11/11 |
|  |  | -2591 | 11/11 |
|  |  | -2620 | 11/11 |
|  |  | -2686 | 11/11 |
| JVC repeat | GGGNGGRR | -1165 | 8/8 |
|  |  | -1175 | 8/8 |
|  |  | -1180 | 8/8 |
|  |  | -1185 | 8/8 |
|  |  | -1190 | 8/8 |
| NFkB | GGGRHTYYHC | -961 | 10/10 |
| uteroglobi | RYYWSGTG | -250 | 8/8 |
|  |  | -921 | 8/8 |
|  |  | -1104 | 8/8 |
| IFN | AAWAANGAAAGGR | 590 | 13/13 | Cell 41:509 (1985) |

FIGURE 18

```
                                                            CTCAAAAGGGGCCGGATTTCCT
TCT TGGAGGCAGATGTTGCCCTCTCTCTCGCTCGGATTGGTTCAGTGCACTCTAGAAACACTGCTGTGGTGGAGAAACT
GGACCCCGAGGTCTGGAGGCGAATTCCAGCCTGCAGGGCTGATAAGCGAGGCATTAGTGAGATTGAGAGAGACTTTACCC
CGCGGTGGTTGGAGGGGCGGCAGTAGAGCAGCAGCACAGGCGGGGAGGTCCCGGGAGGCCGGCTCTGCTCGCGGCCGAG
```

ATG TGG AAT CTC CTT CAC GAA ACC GAC TCG GCT GTG GCC ACC GCG CGC CCG CGC TGG CTG
Met Trp Asn Leu Leu His Glu Thr Asp Ser Ala Val Ala Ala Arg Arg Pro Arg [Trp Leu]

TGC GCT GGG GCG CTG GTG CTG GCG GGT GGC TTC TTT CTC CTC GGC TTC CTC TTC GGA TGG TTT
Cys Ala Gly Ala Leu Val Leu Ala Gly Gly Phe Phe Leu Leu Gly Phe Leu Phe Gly Trp Phe

ATA AAA TCC TCC AAT GAA GCT ACT AAC ATT ACT CCA AAG CAT AAT ATG AAA GCA TTT TTG GAT GAA
[Ile] Lys Ser Ser Asn Glu Ala Thr Asn Ile Thr Pro Lys His Asn Met Lys Ala Phe Leu Asp Glu
                                                              *

TGG AAA GCT GAG AAC ATC AAG AAG TTC TTA TAT AAT TTT ACA CAG ATA CCA CAT TTA GCA GGA ACA
Trp Lys Ala Glu Asn Ile Lys Lys Phe Leu Tyr Asn Phe Thr Gln Ile Pro His Leu Ala Gly Thr

Leu Lys Ala Glu Asn Ile Lys Lys Phe Leu Tyr Asn Phe Thr Gln Ile Pro His Leu Ala Gly Thr

FIGURE 28

| TISSUE/CELL LINE | CANCER CELL TYPE | ¹PSM DNA | ²PSM RNA |
|---|---|---|---|
| HUMAN PROSTATE | N.A. | + | + |
| HUMAN MAMMARY | N.A. | + | - |
| AT6.1 | RAT PROSTATIC ADENOCARCINOMA | - | - |
| AT6.1-11-CL1 | " | + | + |
| AT6.1-11-CL2 | " | - | - |
| R1564 | RAT MAMMARY ADENOCARCINOMA | - | - |
| R1564-11-CL2 | " | + | - |
| R1564-11-CL4 | " | + | - |
| R1564-11-CL5 | " | + | - |
| R1564-11-CL6 | " | + | - |
| A9 | MOUSE FIBROSARCOMA | - | - |
| A9(11) | " | + | - |

Prostate Specific Promoter: Cytosine Deaminase Chimera

FIGURE 32A

```
            10         20         30         40         50         60
             |          |          |          |          |          |
  1 AAGGGTGCTC CTTAGGCTGA ATGCTTGCAG ACAGGATGCT TGGTTACAGA TGGGCTGTGA
    TTCCCACGAG GAATCCGACT TACGAACGTC TGTCCTACGA ACCAATGTCT ACCCGACACT

61 CTCGAGTGGA GTTTTATAAG GGTGCTCCTT AGGCTGAATG CTTGCAGACA GGATGCTTGG
    GAGCTCACCT CAAAATATTC CCACGAGGAA TCCGACTTAC GAACGTCTGT CCTACGAACC

121 TTACAGATGG GCTGTGAGCT GGGTGCTTGT AAGAGGATGC TTGGGTGCTA AGTGAGCCAT
    AATGTCTACC CGACACTCGA CCCACGAACA TTCTCCTACG AACCCACGAT TCACTCGGTA

181 TTGCAGTTGA CCCTATTCTT GGAACATTCA TTCCCCTCTA CCCCTGTTTC TGTTCCTGCC
    AACGTCAACT GGGATAAGAA CCTTGTAAGT AAGGGGAGAT GGGGACAAAG ACAAGGACGG

241 AGCTAAGCCC ATTTTTCATT TTTCTTTTAA CTCCTTAGCG CTCCGCAAAA CTTAATCAAT
    TCGATTCGGG TAAAAAGTAA AAAGAAAATT GAGGAATCGC GAGGCGTTTT GAATTAGTTA

301 TTCTTTAAAC CTCAGTTTTC TTATCTGTAA AAGGTAAATA ATAATACAGG GTGCAACAGA
    AAGAAATTTG GAGTCAAAAG AATAGACATT TTCCATTTAT TATTATGTCC CACGTTGTCT

361 AAAATCTAGT GTGGTTTACA TAATCACCTG TTAGAGATTT TAAATTATTT CAGGATAAGT
    TTTTAGATCA CACCAAATGT ATTAGTGGAC AATCTCTAAA ATTTAATAAA GTCCTATTCA

421 CATGATAATT AAATGAAATA ATGCACATAA AGCACATAGT GTGGTGTCCT CCATATAGAA
    GTACTATTAA TTTACTTTAT TACGTGTATT TCGTGTATCA CACCACAGGA GGTATATCTT

481 AATGCTCAGT ATATTGGTTA TTAACTACTT GTTGAAGGTT TATCTTCTCC ACTAAACTGT
    TTACGAGTCA TATAACCAAT AATTGATGAA CAACTTCCAA ATAGAAGAGG TGATTTGACA

541 AAGTTCCACA AGCCTTACAA TATGTGACAG ATATTCATTC ATTGTCTGAA TTCTTCAAAT
    TTCAAGGTGT TCGGAATGTT ATACACTGTC TATAAGTAAG TAACAGACTT AAGAAGTTTA

601 ACATCCTCTT CACCATAGCG TCTTATTAAT TGAATTATTA ATTGAATAAA TTCTATTGTT
    TGTAGGAGAA GTGGTATCGC AGAATAATTA ACTTAATAAT TAACTTATTT AAGATAACAA

661 CAAAAATCAC TTTTATATTT AACTGAAATT TGCTTACTTA TAATCACATC TAACCTTCAA
    GTTTTTAGTG AAAATATAAA TTGACTTTAA ACGAATGAAT ATTAGTGTAG ATTGGAAGTT

721 AGAAAACACA TTAACCAACT GTACTGGGTA ATGTTACTGG GTGATCCCAC GTTTTACAAA
    TCTTTTGTGT AATTGGTTGA CATGACCCAT TACAATGACC CACTAGGGTG CAAAATGTTT
```

FIGURE 32B

```
 781 TGAGAAGATA TATTCTGGTA AGTTGAATAC TTAGCACCCA GGGGTAATCA GCTTGGACAG
     ACTCTTCTAT ATAAGACCAT TCAACTTATG AATCGTGGGT CCCCATTAGT CGAACCTGTC

841 GACCAGGTCC AAAGACTGTT AAGAGTCTTC TGACTCCAAA CTCAGTGCTC CCTCCAGTGC
     CTGGTCCAGG TTTCTGACAA TTCTCAGAAG ACTGAGGTTT GAGTCACGAG GGAGGTCACG

901 CACAAGCAAA CTCCATAAAG GTATCCTGTG CTGAATAGAG ACTGTAGAGT GGTACAAAGT
     GTGTTCGTTT GAGGTATTTC CATAGGACAC GACTTATCTC TGACATCTCA CCATGTTTCA

961 AAGACAGACA TTATATTAAG TCTTAGCTTT GTGACTTCGA ATGACTTACC TAATCTAGCT
     TTCTGTCTGT AATATAATTC AGAATCGAAA CACTGAAGCT TACTGAATGG ATTAGATCGA

1021 AAATTTCAGT TTTACCATGT GTAAATCAGG AAGAGTAATA GAACAAACCT TGAAGGGTCC
     TTTAAAGTCA AAATGGTACA CATTTAGTCC TTCTCATTAT CTTGTTTGGA ACTTCCCAGG

1081 CAATGGTGAT TAAATGAGGT GATGTACATA ACATGCATCA CTCATAATAA GTGCTCTTTA
     GTTACCACTA ATTTACTCCA CTACATGTAT TGTACGTAGT GAGTATTATT CACGAGAAAT

1141 AATATTAGTC ACTATTATTA GCCATCTCTG ATTAGATTTG ACAATAGGAA CATTAGGAAA
     TTATAATCAG TGATAATAAT CGGTAGAGAC TAATCTAAAC TGTTATCCTT GTAATCCTTT

1201 GATATAGTAC ATTCAGGATT TTGTTAGAAA GAGATGAAGA AATTCCCTTC CTTCCTGCCC
     CTATATCATG TAAGTCCTAA AACAATCTTT CTCTACTTCT TTAAGGGAAG GAAGGACGGG

1261 TAGGTCATCT AGGAGTTGTC ATGGTTCATT GTTGACAAAT TAATTTTCCC AAATTTTTCA
     ATCCAGTAGA TCCTCAACAG TACCAAGTAA CAACTGTTTA ATTAAAAGGG TTTAAAAAGT

1321 CTTTGCTCAG AAAGTCTACA TCGAAGCACC CAAGACTGTA CAATCTAGTC CATCTTTTTC
     GAAACGAGTC TTTCAGATGT AGCTTCGTGG GTTCTGACAT GTTAGATCAG GTAGAAAAAG

1381 CACTTAACTC ATACTGTGCT CTCCCTTTCT CAAAGCAAAC TGTTTGCTAT TCCTTGAATA
     GTGAATTGAG TATGACACGA GAGGGAAAGA GTTTCGTTTG ACAAACGATA AGGAACTTAT

1441 CACTCTGAGT TTTCTGCCTT TGCCTACTCA GCTGGCCCAT GGCCCCTAAT GTTTCTTCTC
     GTGAGACTCA AAAGACGGAA ACGGATGAGT CGACCGGGTA CCGGGGATTA CAAAGAAGAG

1501 ATCTCCACTG GGTCAAATCC TACCTGTACC TTATGGTTCT GTTAAAAGCA GTGCTTCCAT
     TAGAGGTGAC CCAGTTTAGG ATGGACATGG AATACCAAGA CAATTTTCGT CACGAAGGTA

1561 AAAGTACTCC TAGCAAATGC ACGGCCTCTC TCACGGATTA TAAGAACACA GTTTATTTTA
```

FIGURE 32C

```
      TTTCATGAGG ATCGTTTACG TGCCGGAGAG AGTGCCTAAT ATTCTTGTGT CAAATAAAAT

1621  TAAAGCATGT AGCTATTCTC TCCCTCGAAA TACGATTATT ATTATTAAGA ATTTATAGCA
      ATTTCGTACA TCGATAAGAG AGGGAGCTTT ATGCTAATAA TAATAATTCT TAAATATCGT

1681  GGGATATAAT TTTGTATGAT GATTCTTCTG GTTAATCCAA CCAAGATTGA TTTTATATCT
      CCCTATATTA AAACATACTA CTAAGAAGAC CAATTAGGTT GGTTCTAACT AAAATATAGA

1741  ATTACGTAAG ACAGTAGCCA GACATAGCCG GGATATGAAA ATAAAGTCTC TGCCTTCAAC
      TAATGCATTC TGTCATCGGT CTGTATCGGC CCTATACTTT TATTTCAGAG ACGGAAGTTG

1801  AAGTTCCAGT ATTCTTTTCT TTCCTCCCCT CCCCTCCCCT CCCTTCCCCT CCCCTTCCTT
      TTCAAGGTCA TAAGAAAAGA AAGGAGGGGA GGGGAGGGGA GGGAAGGGGA GGGGAAGGAA

1861  CCCTTTCCCT TCCCTTCCTT TCTTTCTTGA GGGAGTCTCA CTCTGTCACC AGGCTCCAGT
      GGGAAAGGGA AGGGAAGGAA AGAAAGAACT CCCTCAGAGT GAGACAGTGG TCCGAGGTCA

1921  GCAGTGGCGC TATCTTGGCT GACTGCAACC TCCGCCTCCC CGGTTCAAGC GATTCTCCTG
      CGTCACCGCG ATAGAACCGA CTGACGTTGG AGGCGGAGGG GCCAAGTTCG CTAAGAGGAC

1981  CCTCAGCCTC CTGAGTAGCT GGGACTACAG GAGCCCGCCA CCACGCCCAG CTAATTTTTG
      GGAGTCGGAG GACTCATCGA CCCTGATGTC CTCGGGCGGT GGTGCGGGTC GATTAAAAAC

2041  TATTTTTAGT AGAGATGGGG TTTCACCATG TTGGCCAGGA TGGTCTCGAT TTCTCGACTT
      ATAAAAATCA TCTCTACCCC AAAGTGGTAC AACCGGTCCT ACCAGAGCTA AAGAGCTGAA

2101  CGTGATCCGC CTGTCTGGGC CTCCCAAAGT GCTGGGATTA CAGGCGTGAG CCACCACGCC
      GCACTAGGCG GACAGACCCG GAGGGTTTCA CGACCCTAAT GTCCGCACTC GGTGGTGCGG

2161  CGGCTTTAAA AAATGGTTTT GTAATGTAAG TGGAGGATAA TACCCTACAT GTTTATTAAT
      GCCGAAATTT TTTACCAAAA CATTACATTC ACCTCCTATT ATGGGATGTA CAAATAATTA

2221  AACAATAATA TTCTTTAGGA AAAAGGGCGC GGTGGTGATT TACACTGATG ACAAGCATTC
      TTGTTATTAT AAGAAATCCT TTTTCCCGCG CCACCACTAA ATGTGACTAC TGTTCGTAAG

2281  CCGACTATGG AAAAAAAGCG CAGCTTTTTC TGCTCTGCTT TTATTCAGTA GAGTATTGTA
      GGCTGATACC TTTTTTTCGC GTCGAAAAAG ACGAGACGAA AATAAGTCAT CTCATAACAT

2341  GAGATTGTAT AGAATTTCAG AGTTGAATAA AAGTTCCTCA TAATTATAGG AGTGGAGAGA
      CTCTAACATA TCTTAAAGTC TCAACTTATT TTCAAGGAGT ATTAATATCC TCACCTCTCT
```

FIGURE 33
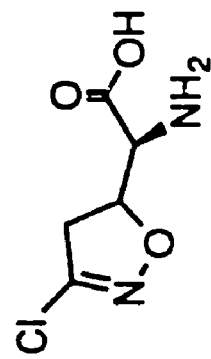
Acivicin
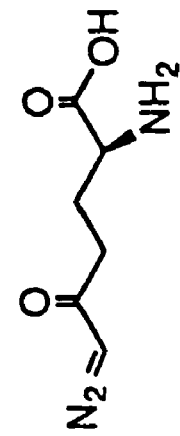
6-diazo-5-oxo-norleucine, DON
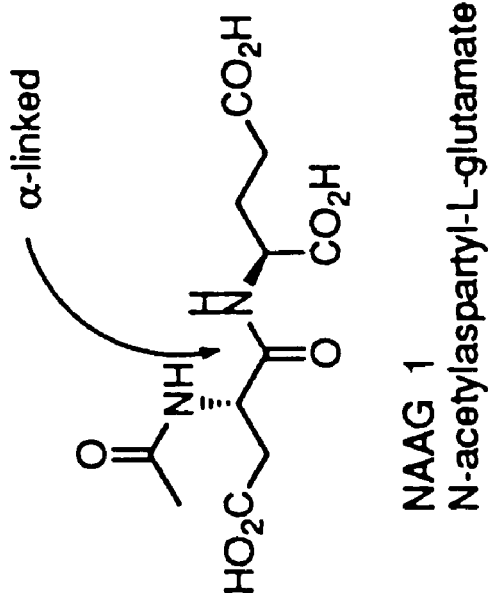
NAAG 1
N-acetylaspartyl-L-glutamate
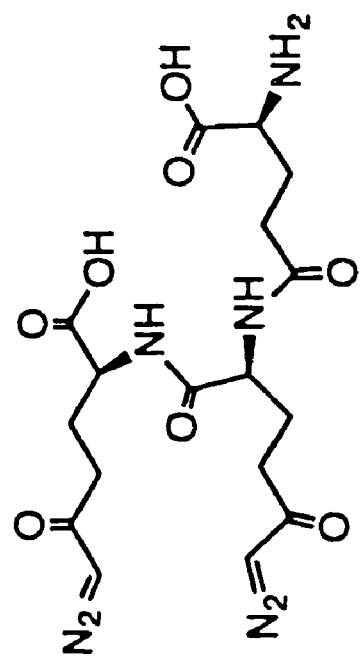
Azotomycin, becomes active by in vivo conversion to DON

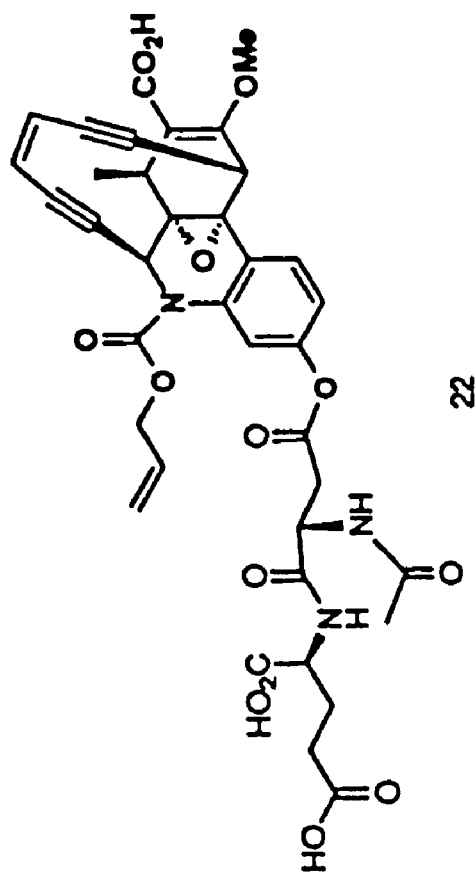
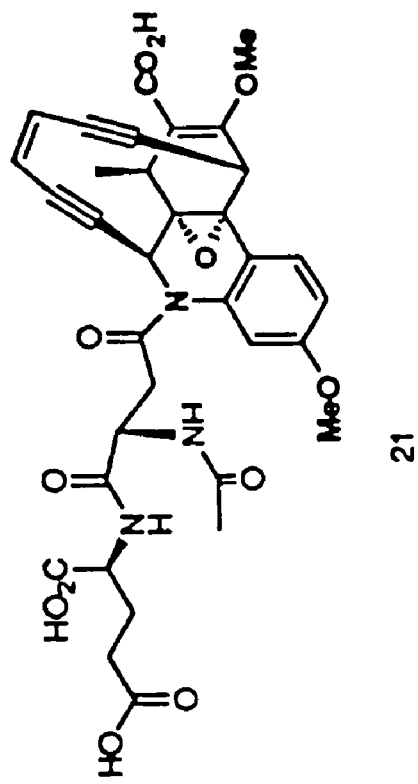
*FIGURE 40*

FIGURE 42
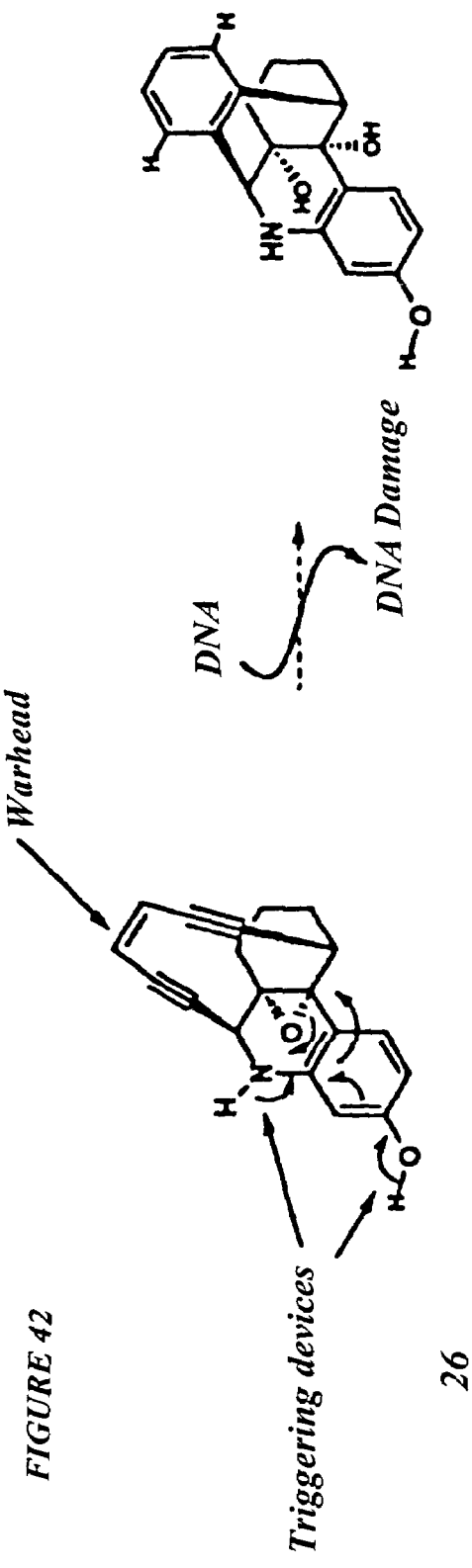
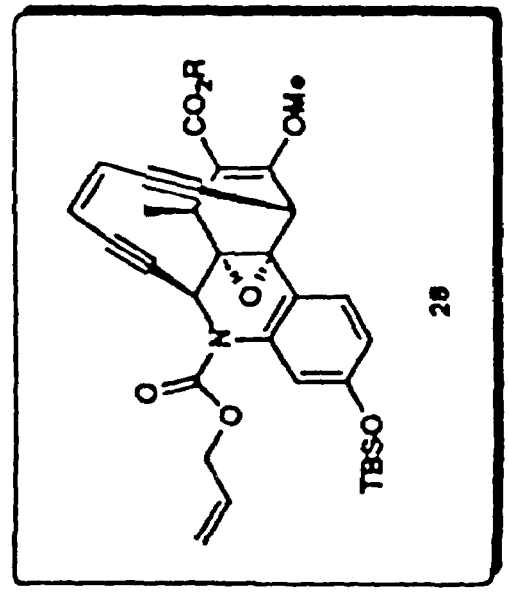
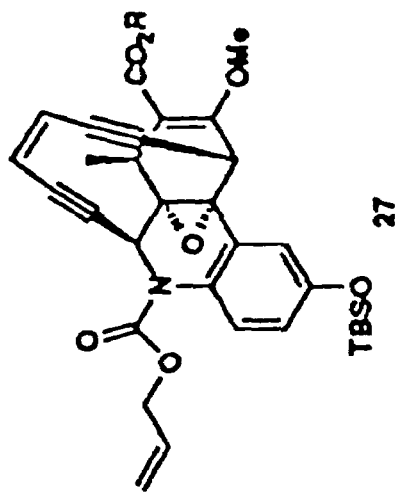
active at the nano to picomolar levels in different cell lines readily rearranges when one or both triggering devices are deprotected

FIGURE 46A

```
           10         20         30         40         50         60
           |          |          |          |          |          |
  1  TAGGGGGGCG CCTCGCGGAG AAACCTCGGA GTCTTCCCCG TGGTGCCGCG GTGCTGGGAC
     ATCCCCCCGC GGAGCGCCTC TTTGGAGCCT CAGAAGGGGC ACCACGCGC CACGACCCTG

61  TCGCGGGTCA GCTGCCCAGT GGGATCCTGT TGCTGGTCTT CCCCAGGGGC GGGGATTAGG
     AGCGCCCAGT CGACGGGTCA CCCTAGGACA ACGACCAGAA GGGGTCCCCG CCGCTAATCC

121  GTCGGGGTAA TGTGGGGTGA GCACCCCTCG AGTTAGGAGG AGGGTAGCTG GGAAGGGTGC
     CAGCCCCATT ACACCCCACT CGTGGGGAGC TCAATCCTCC TCCCATCGAC CCTTGCCACG

181  AGGGCTGAGT TCTCGACAAG CTGCTGGTAG GACAGTCACT CAGGTTGAGG GTAGAACTGA
     TCCCGACTCA AGAGCTGTTC GACGACCATC CTGTCAGTGA GTCCAACTCC CATCTTGACT

241  GAGAACCTGA AACTGGGCGT AGGAAGGTTC CAAGTGCTGG AGCCCTGCAA GACAGAGGAA
     CTCTTGGACT TTGACCCGCA TCCTTCCAAG GTTCACGACC TCGGGACGTT CTGTCTCCTT

301  GTTTTTTTT TGCTTTTGTT TTGTTTTGTT TTGTTTTGTT TTGTTTGTTG TGTTTGTTTG
     CAAAAAAAAA ACGAAAACAA AACAAAACAA AACAAAACAA AACAAACAAC ACAAACAAAC

361  TTTTTTTACC TCTCTGTGCA TTCTTTCTTC CTTGGAAGTA ACAGAGCCAA GCTTGGGAAC
     AAAAAAATGG AGAGACACGT AAGAAGAAG GAACCTTCAT TGTCTCCGTT CGAACCCTTG

421  TGTGTGAACC AGGTCAGCAA TCTGCACAGG TCTTTACCAG CGGTCTTTT GCTGTTTTTC
     ACACACTTGG TCCAGTCGTT AGACCTGTCC AGAAATGGTC GCCCAGAAAA CGACAAAAG

481  CTGGGTACTG ATTTGCAGAC TTGATCCAAC TTTCTAAGAA AAGCAGAACC ACACAGGCAA
     GACCCATGAC TAAACGTCTG AACTAGGTTG AAAGATTCTT TTCGTCTTGG TGTGTCCGTT

541  GCTCAGACTC TTTTATTAAA TTCCAGTTTT GACTTTGCCA CTTCTTAGTG GCCTTGAACA
     CGAGTCTGAG AAAATAATTT AAGGTCAAAA CTGAAACGGT GAAGAATCAC CGGAACTTGT
```

*FIGURE 46B*

```
501  AGTTACCGAC TCCCTCTCAG CGTTAGTTAC CCTATTTTAT GATGAGGATA ATATTATCTG
     TCAATGGCTG AGGGAGAGTC GCAATCAATG GGATAAAATA CTACTCCTAT TATAATAGAC

561  CAAATTATTG GTAATAGTAA ATAATATAGC ATGTAAATCT CCTAGCACAG TACTGGGATT
     GTTTAATAAC CATTATCATT TATTATATCG TACATTTAGA GGATCGTGTC ATGACCCTAA

721  TTCCCCACTT TATTTCTTCT TTTACCAAGA TACTCCTCAT TGGACTTTAA TACACAGGAC
     AAGCGGTGAA ATAAAGAAGA AAATGGTTCT ATGAGGAGTA ACCTGAAATT ATGTGTCCTG

781  TAGTCTAAGG TATCACCAGG TAGTCCACTC CTGCTCGGAA TTCTTGACCC TCTTTCGGGA
     ATCAGATTCC ATAGTGGTCC ATCAGGTGAG GACGAGCCTT AAGAACTGGG AGAAAGCCCT

841  TTTAGAAGAA TAGGGCATGG ACCAGATGGG TTTAAACAAA TTCAATATCT TCCACTAGCT
     AAATCTTCTT ATCCCGTACC TGGTCTACCC AAATTTGTTT AAGTTATAGA AGGTGATCGA

901  TCACCTTGGG GTTGTTAAAA GATTTTTGAA CCACACACTG TGCTCATAAC AATCTTCATC
     AGTGGAACCC CAACAATTTT CTAAAAACTT GGTGTGTGAC ACGAGTATTG TTAGAAGTAG

961  TCTTAAAAGG ATTTTATTCT TCCTGGTATT GCCCTCACTC TCATCCCTGT ATTCCGTGCT
     AGAATTTTCC TAAAATAAGA AGGACCATAA CGGGAGTGAG AGTAGGGACA TAAGGCACGA
```

FIGURE 46C

```
1021 CAGTGGCTGA CACAGAAGAG TTCTTTATTG ATGTCCGCCC CCCACCCACT AGGATTCTCT
     GTCACCGACT GTGTCTTCTC AAGAAATAAC TACAGGCGGG GGGTGGGTGA TCCTAAGAGA

1081 GCTCTCCCCT CCCCCTACAG GCCTCCATCC TCTTCATTTT GTTCATTTTT CAGATCTCAG
     CGAGAGGGGA GGGGGATGTC CGGAGGTAGG AGAAGTAGGA CAAGTAAAAA GTCTAGAGTC

1141 TTCAAGCATC TGTCCTCAG TGTGGTGTTT CCTGATCCCT GTTGCGTTCC CACTCTAATC CAAGTCTTTC
     AAGTTCGTAG AGCAGGAGTC ACACCACAAA GGACTAGGGA CAACGCAGG GTGAGATTAG GTTCAGAAAG

1201 TGTTTTATGC ACAGGTGGAA TCTTATTTCC TTGTATGCAT GCGATTAAGA AATCATGTAT TTTAATATGC
     ACAAAATACG TGTCCACCTT AGAATAAAGG AACATACGTA CGCTAATTCT TTAGTACATA AAATTATACG

1261 ATGTATATAT GTATCTGCAT TTGTATGCAT GCGATTAAGA ACTAGAATAA TTAATAATTG
     TACATATATA CATACACGTA AACATACGTA CGCTAATTCT TGATCTTATT AATTATTAAC

1321 GAAAGCTCCA TGACTGCAGG TTGGGACTA ATTTGTAAC TACTTTATTC CCAGATCCTG
     CTTTCGAGGT ACTGACGTCC AACCCCTGAT TAAACATTG ATGAAATAAG GGTCTAGGAC

1381 TAATTTCTCT AAATAACCC TGGAATCTTG CCTTATCTCC TTCAGGTTAA AAGCCAACTG
     ATTAAAGAGA TTTATTTGGG ACCTTAGAAC GGAATAGAGG AAGTCCAATT TTCGGTTGAC

1441 CAAGTCTAA TGACTGCAGG ATCTAGCTAT CCATTGTTTC TGGCCGCCTA TGCGTGCACT
     GTTCCAGATT ACTGACGTCC TAGATCGATA GGTAACAAAG ACCGGCGGAT ACGCACGTGA

1501 GGGTGTCTGG CAGAGAGGCT GGGTAAATTG TAGTTTCATT GTAGCTGTCT GACTTGGATT
     CCCACAGACC GTCTCTCCGA CCCATTTAAC ATCAAAGTAA CATCGACAGA CTGAACCTAA

1561 TCTCACGCCT ACTTCACTGG AAACGCAAAC AATTTCCTTC TCTCACACCA TTTGTTTTA GTTTCAGAAT
     AGAGTGCGGA TGAAGTGACC TTTGCGTTTG TTAAGGAAG AGAGTGTCGT AAACAAAT CAAAGTCTTA

1621 CAGAGCAAAT TAGAAGTCTG AATTTCCTTC AACACTTGGA AATAATTAT TTATTGAAA
     GTCTCGTTTA ATCTTCAGAC TTAAGGAAG TTGTGAACCT TTATTAAATA AATAACTT

1681 TATATTCATA ATTAATTCGT TATAAAATG TATTAAATGC TTATTGAGT CAGCAGAGGA
     ATATAAGTAT TAATTAAGCA ATATTTTAC ATAATTACG AATAACTCA GTCGTCTCCT
```

*FIGURE 46D*

```
1741  AGATAGAAAC TTTATGAAAG TAGAAGGTGG ATCTCCTTTT TGCCTTCATT TTCAGAACAT
      TCTATCTTTG AAATACTTTC ATCTTCCACC TAGAGGAAAA ACGGAAGTAA AAGTCTTGTA

1801  CTCGTTTACA CCCATTAGTT GAAACATTAA TGTCATTTTA TTTTCGTCCT GATTATCTCA
      GAGCAAATGT GGGTAATCAA CTTTGTAATT ACAGTAAAAT AAAGCAGGA CTATAGAGT

1861  TAAAACATTT CTTAGAATAA CAGCAATACC TATCATTGAA GTTGGATAAG AAATATTTTG
      ATTTTGTAAA GAATCTTATT GTCGTTATGG ATAGTAACTT CAACCTATTC TTTATAAAAC

1921  CAATTGGTTT GCAACTAAA CATGACTCTT TTTCAGTGAA AGTAGGCAAG
      GTTAACCAAA CGTTGAATTT GTACTGAGAA AAGTCACTT TCATCCGTTC

1981  AGAAATTAAA ATTCAGAAAT ATCCACCTA ATGTCAGAGG TAATATTGAT AATTTCTGTT
      TCTTTAATTT TAAGTCTTTA TAGAGTGGAT TACAGTCTCC ATTATAACTA TTAAACACAA

2041  TTACAAATAA TACATACAAC AATAAGTCCT AATAAGTCCT TCGTATCTCA
      AATGTTTATT ATGTATGTTG TTATTACTTT TTATTCAGGA TAGATATCCG AGCATAGAGT

2101  TGCCTATTTT TGGATGTATT TTTCA
      ACGGATAAAA ACCTACATAA AAAGT
```

FIGURE 47A

```
         10         20         30         40         50         60
         |          |          |          |          |          |
  1  TGAAAATAC ATCAAAATA GGCATGAGAT ACGAGCCTAT AGATAGGACT TATTTTTTAT
     ACTTTTTATG TAGTTTTTAT CCGTACTCTA TGCTCGGATA TCTATCCTGA ATAAAAATA

61  TATTGTTGTA TGTATTATTT GTAAACACA AATTATCAAT ATTACCTCTG ACATTAGGTG
     ATACAACAT ACATAATAAA CATTTGTGT TTAATAGTTA TAATGGAGAC TGTAATCCAC

121  AGATATTCTG AATTTTAATT TCTCTTGCCT ACTTTCACTG AAAAGAGTC ATGCAAACAG
     TCTATAAGAC TTAAAATTAA AGAGAACGGA TGAAAGTGAC TTTTTCTCAG TACGTTTGTC

181  ATTTTTAAGT TGCAAACCAA TTGCAAAATA TTTTTTTATC CAACTTCAAT GATAGGTATT
     TAAAAATTCA ACGTTTGGTT AACGTTTTAT AAAAAATAG GTTGAAGTTA CTATCCATAA

241  GCTGTTAATT CTAAGATATG CATTAATTGT TTCAACTAAT GGGTGTCAAA CGAGATGTTC
     CGACAATTAA GATTCTATAC GTAATTAACA AAGTTGATTA CCCACAGTTT GCTCTACAAG

301  TGAAAATGAA GGCAAAAAGG AGATCCACCT TCTACTTTCA TAAAGTTTCT ATCTTCCTCT
     ACTTTTACTT CCGTTTTTCC TCTAGGTGGA AGATGAAAGT ATTTCAAAGA TAGAAGGAGA

361  GCTGACTCAA ATAAGCATTT AATACATTTT ATAACGAATT AATTATGAAT ATATTTCAAA
     CGACTGAGTT TATTCGTAAA TTATGTAAAA TATTGCTTAA TTAATACTTA TATAAAGTTT

421  TAAATAAATT ATTTCCAAGT GTTGAAGGAA ATTCAGACTT CTAATTGCT CTGATTCTGA
     ATTTATTTAA TAAAGGTTCA CAACTTCCTT TAAGTCTGAA GATTAAACGA GACTAAGACT
```

FIGURE 47B

```
481  AACTAAAACA AATGCTCTGT GAGAGTTTGC GTTCCAGTG AAGTAGGCTG AGAAATCCAA
     TTGATTTTGT TTACGAGACA CTCTCAAACG CAAGGTCAC TTCATCGCAC TCTTTAGGTT

541  GTCAGAGACAGC TACATGAAAC TACATTACC AGCTCTCTGC CAGACACCAG TGCACGATAG
     CAGTCTGTCG ATGTACTTTG ATGTAATGG TCGAGAGACG GTCTGTGGTC ACGTGCTATC

601  CGCAGAACAT GTAGCTAGAT CTCAGTCATA GCTNNNNNNN NNNNNNNNNN AGACCTTGCA
     GCGTCTTGTA CATCGATCTA GAGTCAGTAT CGANNNNNNN NNNNNNNNNN TCTGGAACGT

661  CTTGGCTTTT AACCTGAAGG AGATAAGGCA GATTCCAGG GTTTATTTAG AGAAATTACA
     GAACCGAAAA TTGGACTTCC TCTATTCCGT TCTAAGGTCC CAAATAAATC TCTTTAATGT

721  GGATCTGGGA ATAAAGTAGT TACAAAATTA GTCCCCAACC AGCTTTCATG GAGCTTTCAA
     CCTAGACCCT TATTCATCA ATGTTTTAAT CAGGGGTTGG TCGAAAGTAC CTCGAAAGTT
```

FIGURE 47C

```
781  TTATTAATTA TTCTAGTTCT TAATCGCATG CATACAATGC ACATACATAT ATACATGCAT
     AATAATTAAT AAGATCAAGA ATTAGCGTAC GTATGTTACG TGTATGTATA TATGTACGTA

841  ATTAAATAC  ATGATTGGAC GCAAACGGAA ATAAGATTCC ACCTGTGCAT AAAACAGAAA
     TAATTTTATG TACTAACCTG CGTTTGCCTT TATTCTAAGG TGGACACGTA TTTTGTCTTT

901  GACTTGGTTA GAGTGAGGGA TCAGGAAACA CCACACTGAG GACGAGATGN NNNNNNNNNN
     CTGAACCAAT CTCACTCCCT AGTCCTTTGT GGTGTGACTC CTGCTCTACN NNNNNNNNNN

961  NTAGTGGCTG GGGGCGGGAC ATCAATAAAG AACTCTCTG  TGTCAGCCAC TGAGCACGGA
     NATCACCGAC CCCCGCCCTG TAGTTATTTC TTGAGAAGAC ACAGTCGGTG ACTCGTGCCT

1021 ATAAAGGGAT GAGAGTGAGG GCAANTACCA GAAGAATAAA ATCCTTTTAA GAGATGAAGA
     TATTTCCCTA CTCTCACTCC CGTTNATGGT CTTCTTATTT TAGGAAAATT CTCTACTTCT

1081 TTGTTATGAG CACAGTGTGT GGNTTCAAAA ATCTTTTAAC AACCCCAAGG TGAAGCTAGT
     AACAATACTC GTGTCACACA CCNAAGTTTT TAGAAAATTG TTGGGGTTCC ACTTCGATCA

1141 TGGAAGATAT TTGAATTTGT TTAAACCCAT CTGGTCCTAG CCCTATTCTT TGAATCCCGA
     ACCTTCTATA AACTTAAACA AATTTGGGTA GACCAGGATC GGGATAAGAA ACTTAGGGCT
```

*FIGURE 47D*

```
1201 AAGAGGGTCA AGAATTCCGA GCAGGAGTGG ACTACCTGGT GATACCTTAG ACTAGTCCTG
     TTCTCCCAGT TCTTAAGGCT CGTCCTCACC TGATGGACCA CTATGGAATC TGATCAGGAC

1261 TGTATTAAAG TCCAATGAGG AGTATCTTGG TAAAATAATA AATAAGTCC  CGAAATCCC
     ACATAATTTC AGTTACTCC  TCATAGAACC ATTTATTAT  TTATTCAGG  GCTTTAGGG

1321 AGTACTGTGC TAGGAGATTI ACATGCTATA TTATTACTA  TNNNNNNNNT AATTGCAGA
     TCATGACACG ATCCTCTAAA TGTACGATAT AATAAATGAT AINNNNNNNA TTAAACGTCT

1381 TAAATATTATC CTCATCATAA AATAGGGTAA CTAACGCTGA GAGGGACTCG GTAACTGTT
     ATTATAATAG GAGTAGTATT TTATCCCATT GATTGCGACT CTCCCTGAGC CATTGAACAA

1441 CAAGGCCACT AAGAAGTGGC AAAGTCAAAA CTGAATTTT  AATAAAGAG  TCTAGCTTGC
     GTTCCGGTGA TTCTTCACCG TTTCAGTTTT GACCTTAAA  TTATTTTCTC AGATCGAACG

1501 CTGTGTGGTT CTGCTTTTCT TAGAAAGTTG GANNAAGTCT CANATCAGTA CCCAGGAAAA
     GACACACCAA GACGAAAGA  ATCTTTCAAC CTNNTTCAGA GTNTAGTCAT GGGTCCTTTT

1561 ACAGCAAAAG ACCCGCTGGT AAAGACCTGT CCAGATTGCT GACCTGGTTC ACACANNTCC
```

*FIGURE 47E*

```
      TGTCGTTTC TGGGCGACCA TTTCTGGACA GGTCTAACGA CTGGACCAAG TGTGTNAGG
1621 AAGCTTGCCT CTGTTACTTC CAAGGAAGAA AGAATGCACA GAGAGGTAAA AAACAAACA
     TTCGAACGGA GACAATGAAG GTTCCTTCTT TCTTACGTGT CTCTCCATTT TTTGTTTGT
1681 AACCAAAACAA AACAAAACAA AACAAAAACAA AAGCAAAAAA AAACTTCCTC
     TTGGTTTTGTT TTGTTTTGTT TTGTTTTGTT TTCGTTTTTT TTTGAAGGAG
1741 TGTCTTGCAG GGCTCCAGCA CTTGGAACCT TCCTACGTCC TANTTTCAGG TTCTCTCAGT
     ACAGAACGTC CCGAGGTCGT GAACCTTGGA AGGATGCAGG ATNAAAGTCC AAGAGAGTCA
1801 TCTACCCTCA ACCTGAGTGA CTGTCCTACC AGCAGCTTGT CGAGAACTCA GCCCTGCACC
     AGATGGGAGT TGGACTCACT GACAGGATGG TCGTCGAACA GCTCTTGAGT CGGGACGTGG
1861 GTTCCCAGCT ACCCTCCTCC TAACTCGAGG GGTGCT
     CAAGGGTCGA TGGGAGGAGG ATTGAGCTCC CCACGA
```

FIGURE 48A

```
            10         20         30         40         50         60
            |          |          |          |          |          |
  1 GGATTCTGTT GAGCCCTAGG TCATTATGAT GTCCTGTGT CCTACCCAAA TAAGACTCAT
    CCTAAGACAA CTCGGGATCC AGTAATACTA CAGGACAACA GGATGGGTTT ATTCTGAGTA

61 CCCAACTACA TCTCAATAAT TAATGAAGAT GGAAATGAGG TAAAAATAA ATAATAAAT
    GGGTTGATGT AGAGTTATTA ATTACTTCTA CCTTTACTCC ATTTTTATT TATTATTTA

121 AAAGAACA TTCCCCCCCA TTTATTATTT TTTCAAATAC CTTCTATGAA ATATGTTCT
    TTTCTTTGT AAGGGGGGT AAATAATAAA AAAGTTTATG GAAGATACTT TATTACAAGA

181 ATCCCTCTCT AAATATTAAT AGAAATCAAT ATTATTGGAA CTGTGAATAC CTTTAATATC
    TAGGGAGAGA TTTATAATTA TCTTTAGTTA TAATAACCTT GACACTTATG GAAATTATAG

241 TCATTATCCG GTGTCAACTA CTTTCCTATG ATGTTGAGTT ACTGGGTTTA GAAGTCGGGA
    AGTAATAGGC CACAGTTGAT GAAAGCATAC TACAACTCAA TGACCCAAAT CTTCAGCCCT

301 AATAATGCTG TAAANNNNNN AGTTAGTCTA CACACCAATA TCAAATATGA TATACTTGTA
    TTATTACGAC ATTTNNNNNN TCAATCAGAT GTGTGGTTAT AGTTTATACT ATATGAACAT

361 AACTTCCAAG CATAAAAAGA GATACTTTAT AAAGAGGTT CTTTTTTCT TTTTTTTTT
    TTGGAGGTTC GTATTTTTCT CTATGAAATA TTTTCTCCAA GAAAAAAGA AAAAAAAAA
```

*FIGURE 48B*

```
421  TCCAGATGGA GTTCACTCC  TGTCAGGCAG GCNGAGTGCA GTGGTGCCAT CTGGCTCAC
     AGGTCTACCT CAAAGTGAGG ACAGTCCGTC CGNCTCACGT CACCACGGTA GAGCCGAGTG

481  TGCAACCTCC ACCTCCCATG TTCAAGGGAT TCTCCTTCCT CAGTCTCCTG AGTAGCTGGG
     ACGTTGGAGG TGGAGGGTAC AAGTTCCCTA AGAGGAAGGA GTCAGAGGAC TCATCGACCC

541  ATTACAGGTG TGCACCACCA CACCCAGCTA ATTTTTGTAT TTTTAATAGA GACAGGGTTT
     TAATGTCCAC ACGTGGTGGT GTGGGTCGAT TAAAACATA  AAAATTATCT CTGTCCCAAA

601  CATCGATGTT GGCCAGGCTA GTCTCGAACT CCTGACCTCT AGGTGATCCA CCCGCCTCAG
     GTAGCTACAA CCGGTCCGAT CAGAGCTTGA GGACTGGAGA TCCACTAGGT GGGCGGAGTC

661  CCTCCCAAAG TTGTAGAATT ACACGTGTGA GGCACTGCTC TGGCCAGGAG ATACATTTTT
     GGAGGGTTTC AACATCTTAA TGTGCACACT CCGTGACGAG ACCGGTCCTC TATGTAAAAA

721  GATAGGTTTA ATTTATAAAG ACACTGCACA GATTTGGACT TGCTGGAAAA TCACGATCCA
     CTATCCAAAT TAAATATTTC TGTGACGTGT CTAAACCTGA ACGACCCTTT AGTGCTAGGT
```

```
 781 GTATGCATTT GACCCAGCAA TTTTTATTGG TACTTAATGA TTATATCTCA ATTGATCAGG
     CATACGTAAA CTGGGTCGTT AAAATAACC ATGAATTACT AATATAGAGT TAACTAGTCC

841 TTGAACTCTG TGCGAAGAAT TTGTGTGTGG ACATTTGAGA GGACAGTTTG GAGGCAAGGT
     AACTTGAGAC ACGCTTCTTA AACACACACC TGTAAACTCT CCTGTCAAAC CTCCGTTCCA

901 ATTTAGTAG ATTTAAAGAA TTTGAATCTT GTTTGCAAGT ATATATGTGT ACTGAGAAAG
     TAAAATCATC TAAATTTCTT AAACTTAGAA CAAACGTTCA TATATACATA TGACTCTTTC

961 AGAAGACAAT GCAGATAAAT TGATATATT ATTATGATGT ATGTTCAATA TGAAAGATCA
     TCTTCTGTTA CGTCTATTA ACTATATATA TAATACTACA TACAAGTTAT ACTTCTAGT

1021 CAAAATATA CATACATNNA TCTTACTTAA CATACCTCAG TTTTAGAGCT ACCGTATCTA
     GTTTTATATT GTATGTANNT AGAATGAATT GTATGGAGTC AAATCTGGA TGGCATACAT

1081 GAAGAGTCCA TTTCTATTTA GGTAAGTTCC TTTAGTCCTT AAACCAGGAA TTATTACTGG GCACTCTTAA
     CTTCTCAGGT AAAGATAAAT CCATTCAAGG AAACCAGGAA AATAATGACC CGTAGAATT

1141 TTACATGTAG CTTGAATAT GTCCAGTTTG AGCAGTGAAC TGAAAATGTC ATGTGATTAA
     AATGTACATC GAACTTTATA CAGGTCAAAC TCGTCACTTG ACTTTTACAG TACACTAATT

1201 GTACATATAT AATTTTTTT CATAGTAGGT CAATAACCTC CTTTATTGA CTAATGAATC
     CATGTATATA TTAAAAAAA GTATCATCCA GTTATTGGAG GAAAATAACT GATTACTTAG

1261 ACTTCTCTAA TGATTATACG
     TCAAGAGATT ACTAATATGC
```

```
            10         20         30         40         50         60
            |          |          |          |          |          |
  1 AATCAAAATA AAACAGTTAA AGTTTGATTA CTATAATCAA ACACAAAAAA AATGAATATT
    TTAGTTTTAT TTTGTCAATT TCAAACTAAT GATATTAGTT TGTGTTTTTT TTACTTATAA

61 ATCTTTATG  TCAGTAGAGG GTGAATGAAT CCTTCAGGAT TTTGATGATA GTATCAGATA
    TAGAAAATAC AGTCATCTCC CACTTACTTA GGAAGTCCTA AAACTACTAT CATAGTCTAT

121 CCCAGCACTA TGCTAGAAGT TGTGAAGAAT TCACGAGATG AATAAATCAC AGATTCTGTC
    GGGTCGTGAT ACGATCTTCA ACACTTCTTA AGTGCTCTAC TTATTTAGTG TCTAAGACAG

181 CTCAAAATGG TTAGATCTAT TCAGGAAACA AAGCTAAAAA AACCCCACCA ATAACTAAAA
    GAGTTTTACC AATCTAGATA AGTCCTTTGT TTCGATTTTT TTGGGGTGGT TATTGATTTT

241 ATCAACCAAA TGAAAAACAA CAATCATAAA ATAAGTAAGT ACCTATAGAA AGAAAGCTC
    TAGTTGGTTT ACTTTTTGTT GTTAGTATTT TATTCATTCA TGGATATCTT TCTTTTCGAG

301 AGAGGAGGTA AAAGATAAC  TCTTCCAAAA GGAATACTAT ATACTGTAAA CTGTGTACTG
    TCTCCTCCAT TTTTCTATTG AGAAGGTTTT CCTTATGATA TATGACATTT GACACATGAC

361 ATAGAAGGAA GAATTAGAAA NNNNNNNNTG TAAGTGGCAT ACATACTAAG CTAGTGTGAA
    TATCTTCCTT CTTAATCTTT NNNNNNNNAC ATTCACCGTA TGTATGATTC GATCACACTT
```

FIGURE 49B

```
421  CACAAGCCTA AATATGTAGT TGCTTCACAG AAGGTTAGAA GTAAATTAAC CTCATGAATT
     GTGTTCGGAT TTATACATCA ACGAAGTGTC TTCCAATCTT CATTTAATTG GAGTACTTAA

481  TCTTGAGAGA ACTTGTAAGG ACTAAGCTTT CGATTTTGGA GAAAGATTTT AATACCAAAT
     AGAACTCTCT TGAACATTCC TGATTCGAAA GCTAAAACCT CTTTCTAAAA TTATGGTTTA

541  AAAAGTACC TTTGTTTGGT AATCTCAATC ATTATAATAG TGCTTAGATA ATACCTAGGA
     TTTTCATGG AAACAAACCA TTAGAGTTAG TAATATTATC ACGAATCTAT TATGGATCCT

601  ACAAATTAAA TATTAAATTT ACTTTAAAAA AAGTACATG ATTGGGGAAT CACAACTGGC
     TGTTTAATTT ATAATTTAAA TGAAATTTTT TTTCATGTAC TAACCCCTTA GTGTTGACCG

661  CTTACTAGAT TCTCTNNNNN NATATGCACT GAAAGAATG AAAACACTG AACCAAATAT
     GAATGATCTA AGAGANNNNN NTATACGTGA CTTTCTTAC TTTTGTGAC TGGTTTATA

721  NTGTTTTTT AAGTTAAAA TTAAATTGGA AAAAATAGT AAGGAATATC AGAAGCAAAA
     NACAAAAAA TTCAAATTTT AATTTAACCT TTTTTATCA TTCCTTATAG TCTTCGTTTT
```

FIGURE 49C

```
 781  AAATAAAATG AAAGCAAGAA TCCTCAGAGG TAGCACCAAA TTTGGCTTTG CTTAGATGAA
      TTTATTTTAC TTTCGTTCTT AGGAGTCTCC ATCGTGGTTT AAACCGAAAC GAATCTACCT

841  TCTATCAAAG CTATGGCCCA TGAAAGGAT  TCAGGAGTTA GTTTAAGCT  GGTTCACATA
      AGATAGTTTC GATACCGGGT ACTTTTCCTA AGTCCTCAAT CAAATTTCGA CCAAGTGTAT

901  ATGGAATCTA GCAGAGAGACT GTGCATAAAG GTGGTCTAAG AACAACAATA TCCTGACCAG
      TACCTTAGAT CGTCTCTGA  CACGTATTTC CACCAGATTC TTGTTGTTAT AGGACTGGTC

961  GTGAGGGGGC TCACNCTNAA TNCCAGCACT TTGGGAGCCC AAGGTGGGTG GATCACGAGG
      CACTCCCCCG AGTGNGANTT ANGGTCGTGA AACCCTCGGG TTCCACCCAC CTAGTGCTCC

1021  TCAGGAGTTT GAGACCAGCC TGACCAACAT GGTGAAACCG CGTCTCTACT AAAAATAGAA
      AGTCCTCAAA CTCTGGTCGG ACTGGTTGTA CCACTTTGGC GCAGAGATGA TTTTTATCTT

1081  AAATTAGCCG NGCCTACGTG CTTCTAATCC AAGCTTNNNN NNGCCACTGC ACTCCAGCCT
      TTTAATCGGC NCGGATGCAC GAAGATTAGG TTCGAANNNN NNCGGTGACG TGAGGTCGGA

1141  ATCACTTGAA CCCAGCATGC AAGCTTNNNN NNGCCACTGC ACTCCAGCCT AGGGTGCAAA
      TAGTGAACTT GGGTCGTACG TTCGAANNNN NNCGGTGACG TGAGGTCGGA TCCCACGTTT

1201  AAAAAAAAA ANGACACATT ACTCAGGTAA GGTAATCAAT AA
      TTTTTTTTT TNCTGTGTAA TGAGTCCATT CCATTAGTTA TT
```

FIGURE 50A

```
- AAGGTAAAAATTATCTCTTTTTTTCTCTCCCCCAATGTAAAAAGTTATAG -
  ||||||||||||||||||||||||||||||||||||||||||||||||||
- AAGGTAAAAATTATCTCTTTTTTTCTCTCCCCCAATGTAAAAAGTTATAG -

- TGGGTTTTACATGTGTAGAATCATTTTCTTAAAACTTTATGAATACCATT -
  ||||||||||||||||||||||||||||||||||||||||||||||||||
- TGGGTTTTACATGTGTAGAATCATTTTCTTAAAACTTTATGAATACCATT -

- ATTTTCTTGTATTCTGTGACATGCCCACCTTACAGAGAGGACACATTTAC -
  ||||||||||||||||||||||||||||||||||||||||||||||||||
- ATTTTCTTGTATTCTGTGACATGCCCACCTTACAGAGAGGACACATTTAC -

- TAGGTTATATCCCGGGGTTAAATTCGAGCATTGGAATTTGGCCAGTGTAG -
  ||||||||||||||||||||||||||||||||||||||||||||||||||
- TAGGTTATATCCCGGGGTTAAATTCGAGCATTGGAATTTGGCCAGTGTAG -

- ATGTTTAGAGTGAACAGAACAAATTTTTCTGTGCTTACAGGTTATGGCTG -
  ||||||||||||||||||||||||||||||||||||||||||||||||||
- ATGTTTAGAGTGAACAGAACAAATTTTTCTGTGCTTACAGGTTATGGCTG -

- TGGCCTACAAGAAGCATGCACTGGGTTTATTATTAACTTTCAGTATCTTT -
  ||||||||||||||||||||||||||||||||||||||||||||||||||
- TGGCCTACAAGAAGCATGCACTGGGTTTATTATTAACTTTCAGTATCTTT -

- GTTTAAATATTTTCTACAAAAATGTTTACTAAATTAAATTGTAGTATGA -
  ||||||||||||||||||||||||||||||||||||||||||||||||||
- GTTTAAATATTTTCTACAAAAATGTTTACTAAATTAAATTGTAGTATGA -

- ATTGTTATAAATAATGAGGGAAAACAATTTACACATAGCAAATTTAAAAA -
  ||||||||||||||||||||||||||||||||||||||||||||||||||
- ATTGTTATAAATAATGAGGGAAAACAATTTACACATAGCAAATTTAAAAA -

- TTACTGTCATTTGATTTGTTAATATATTTTCTCTTTAGTGGGAAATTAA -
  ||||||||||||||||||||||||||||||||||||||||||||||||||
- TTACTGTCATTTGATTTGTTAATATATTTTCTCTTTAGTGGGAAATTAA -

- ATTTTAAAAAATTCCCTTTCGACTGTAGAACAAATAGGAATTTGGCCTGT -
```

*FIGURE 50B*

```
ATTTAAAATTCCCTTCGACTGTAGAACAAATAGGAATTTGGCCTGT
GGGGTCTACTCTTGCTTATTATATTTGTAAGCTAGTGGTAGAAATAGCAAA
GGGGTCTACTCTTGCTTATTATATTTGTAAGCTAGTGGTAGAAATAGCAAA
TGCTCACTACCACTAATAAGAACATTTCTAAATCTGATGTTCTGAGGATT
TGCTCACTACCACTAATAAGAACATTTCTAAATCTGATGTTCTGAGGATT
TTTAGAGCTTATAGTAGCAAAAAGGGAAATTCTATCCGAGATGTC
TTTAGAGCTTATAGTAGCAAAAAGGGAAATTCTATCCGAGATGTC
CTTTGTTGTAGGCCTAATGAGAAAAGGTTGAAGATAAAGTTCTGGTACTC
CTTTGTTGTAGGCCTAATGAGAAAAGGTTGAAGATAAAGTTCTGGTACTC
ATTTAAGTGTAATATTGAAATTGATATTACCGAATCTGGAACCAAT
ATTTAAGTGTAATATTGAAATTGATATTACCGAATCTGGAACCAAT
TAAAATAAGGAAGAAGACACTGTGTTTCT
TAAAATAAGGAAGAAGACACTGTGTTTCT
```

FIGURE 51A

```
              10         20         30         40         50         60
              |          |          |          |          |          |
  1  AGAAACACA GTGTCTTTCT TTCCTTATTT TAAATTGGTT GTTCCAGATT CGGTAATATC
     TCTTTGTGT CACAGAAAGA AAGGAATAAA ATTTAACCAA CAAGGTCTAA GCCATTATAG

61  AATTTTCAAT ATTACACTTA AATGAGTACC AGAACTTAT CTTCAACCTT TTCTCATTAG
     TTAAAGTTA TAATGTGAAT TTACTCATGG TCTTGAAATA GAAGTTGGAA AAGAGTAATC

121  GCCTACAACA AAGGACATCT CGGATAGAAT TTCCCTTTTC TTTTTGCTAC TATAAGCTCT
     CGGATGTTGT TTCCTGTAGA GCCTATCTTA AAGGGAAAAG AAAAACGATG ATATTCGAGA

181  AAAATCCTC AGAACATCAG ATTTAGAAAT GTTCTTATTA GTGGTAGTGA GCATTTGCTA
     TTTTTAGGAG TCTTGTAGTC TAAATCTTTA CAAGAATAAT CACCATCACT CGTAAACGAT

241  TTTCCTACCA CTAGCTTACA AATATAATAA GCAAGTAGAC CCCACAGGCC AAATTCCTAT
     AAAGGATGGT GATCGAATGT TTATATTATT CGTTCATCTG GGGTGTCCGG TTTAAGGATA

301  TTGTTCTACA GTCGAAAGGG AATTTTTTAA AATTTAATTT CCCACTAAAG AGAAAATAT
     AACAAGATGT CAGCTTTCCC TTAAAAAATT TTAAATTAAA GGGTGATTTC TCTTTTTATA

361  ATTAACAAAT CAAATGACAG TAATTTTTAA ATTTGCTATG TGTAAATTGT TTTCCCTCAT
     TAATGTTTA GTTTACTGTC ATTAAAAATT TAAACGATAC ACATTTAACA AAAGGGAGTA

421  TATTTATAAC AATTCATACT ACAATTTAAT TTAGTAAACA TTTTTGTAGA AATATTTAA
     ATAAATATTG TTAAGTATGA TGTTAAATTA AATCATTTGT AAAAACATCT TTTATAAATT
```

*FIGURE 51B*

```
481  AACAAAGATA CTGAAAGTTA ATATNAAACC CAGTGCATGC TTCTTGTAGG CCACAGCCAT
     TTGTTTCTAT GACTTTCAAT TATANTTTGG GTCACGTACG AAGAACATCC GGTGTCGGTA

541  AACCTGTAAG CACAGAAAAA TTTGTTCTGT TACTCTAAAC ATCTACACTG GCCAAATTCC
     TTGGACATTC GTGTCTTTTT AAACAAGACA ATGAGATTTG TAGATGTGAC CGGTTTAAGG

601  AATGCTCGAA TTTAACCCCG GGATATAACC TAGTAAATGT GTCCTCTCTG TAAGGTGGGC
     TTACGAGCTT AAATTGGGGC CCTATATTGG ATCATTTACA CAGGAGAGAC ATTCCACCCG

661  ATGTCACAGA ATACAAGAAA ATAATGGTAT TCATAAACTT TTAAGAAAAT GATTCTACAC
     TACAGTGTCT TATGTTCTTT TATTACCATA AGTATTTGAA AATTCTTTTA CTAAGATGTG

721  ATGTAAAACC CACTATAACT TTTTACATTG GGGGAGAGAA AAAAGAGAT AATTTTTACC
     TACATTTTGG GTGATATTGA AAAATGTAAC CCCCTCTCTT TTTTTCTCTA TTAAAAATGG

```
           10         20         30         40         50         60
            |          |          |          |          |          |
  1 GATGCTATTT GGGCAATTTC TTATTGACAG TTTGAAATG TTAGGCTTTT ATCTCCATTT
    CTACGATAAA CCCGTTAAAG AATAACTGTC AAACTTTAC AATCCGAAAA TAGAGGTAAA

61 TTTAGTACTT AAATTTCCA ACATGGGTCT TGCTTGTTAT TTTATCAGTA TAAAATAGAA
    AAATCATGAA TTTAAAGGT TGTACCCACA ACGAACAATA AAATAGTCAT ATTTATCTT

121 GAGTGGTTCT GTTCTCGAAT TTAGTATATA CATGAGTATC TAGTGTATGT CAGCCATGAA
    CTCACCAAGA CAAGAGCTTA AATCATATAT GTACTCATAG ATCACATACA GTCGGTACTT

181 AATGAACCCT TCAGATGTTT AACTTCAGGG AACCTAATTG AGTCATTGCT CCAGACAATG
    TTACTTGGGA AGTCTACAAA TTGAAGTCCC TTGGATTAAC TCAGTAACGA GGTCTGTAAC

241 TTGCTTTGAA CCCACTATAT TNNNNNNNCT CGGGCAATGA CTCAGTGTGG CAAGGATACT
    AACGAAACTT GGGTGATATA ANNNNNNNGA GCCCGTTACT GAGTCACACC GTTCCTATGA

301 ACTGCAGGCC TGTTTCTGGA AGGCACTGGA CTCCTCTGAT GCAACTTTG GCCAGGGACT
    TGACGTCCGG ACAAGACCT TCCGTGACCT GAGGAGACTA CGTTTGAAAC CGGTCCCTGA

361 CCTTGATAGC TCTTAAATAG ATGCTGCACC AACACTCTCT TTCTTTTCTC TCTTTTTCTT
    GGAACTATCG AGAATTTATC TACGACGTGG TTGTGAGAGA AAGAAAAGAG AGAAAAGAA
```

FIGURE 52B

```
421  TATTCAATAT TAGACTACAA GCAGTCTAAG GACTTCTCAG GGTTTCTAGC TCTCTCTCAT
     ATAAGTTATA ATCTGATGTT CGTCAGATTC CTGAAGAGTC CCAAAGATCG AGAGAGAGTA

481  TTCACACATG CTTCCTAGT AATCTCTACT CAATATATCTT ACTGCTACGC TGGGGCCAGA
     AAGTGTGTAC GAAAGGATCA TTAGAGATGA GTATATAGAA TGACGATGCG ACCCCGGTCT

541  TAACNNNNNN CTTCCATTTT GTTTTATCTT TCCCCTTCTG CTTTCATTAT CTTTCATTAT
     ATTGNNNNNN GAAGGTAAAA CAAAAATAGA AGGGGAAGAC GAAAGTAATA

601  TGAAACTTTC TGCTTTCATT ATTGAAACTT TCCCAGATTT GTTCTGCTTA ACCTGGCATT
     ACTTTGAAAG ACGAAAGTAA TAACTTTGAA AGGGTCTAAA CAAGACGAAT TGGACCGTAA

661  GGAACTGTTT CCTCTCTCCCT GTGCTGCTTT CTCCCATTGC CATGTCCTTT TTTTTTTTT
     CCTTGACAAA GGAGAAGGGA CACGACGAAA GAGGGTAACG GTACAGGAAA AAAAAAAAA

721  TTTTTTTTT TGAGACAGTG TCACTCTGTT GCCCAGGCTG GAGTGCAATG GTGCAATCTT
     AAAAAAAAA ACTCTGTCAC AGTGAGACAA CGGGTCCGAC CTCACGTTAC CACGTTAGAA
```

FIGURE 52C

```
781   GGCCACTGCA ACCCCCGCCT CCCGGGTTCA AGTGATTCTC CTGCCTCAGC CTCCTGAGTA
      CCGGTGACGT TGGGGGCGGA GGGCCCAAGT TCACTAAGAG GACGGAGTCG GAGGACTCAT

841   GCTGGGATTA CAGGTGCCCA CCACTATGCC CGGCTGATTT TTGTATTTTT AGTAGAGATN
      CGACCCTAAT GTCCACGGGT GGTGATACGG GCCGACTAAA AACATAAAAA TCATCTCTAN

901   NNNNNNNTTT CACCATNGCT GATCAGGCTG GTCTCGAACT CCTGACCCCA GTGANTCCGC
      NNNNNNNAAA GTGGTANCGA CTAGTCCGAC CAGAGCTTGA GGACTGGGGT CACTNAGGCG

961   CCTCCCTTGGC CTCCCAAAGT GCTGAGATTA CAGGCATGAG TCACTGCGNC CAGCCACCAT
      GGAGGAACCG GAGGGTTTCA CGACTCTAAT GTCCGTACTC AGTGACGCNG GTCGGTGGTA

1021  TATTCTCTAG AGGTGAGAGA ACACTGGCTC TTCTAACAAG TTGAAATTTG ATAGAGACC
      ATAAGAGATC TCCACTCTCT TGTGACCGAG AAGATTGTTC AACTTTAAAC TATCTCTGG
```

FIGURE 53A

```
              10         20         30         40         50         60
              |          |          |          |          |          |
  1  CACAAAAAA GATTATTAGC CACAAAAAAA CCTTGAAGTA AGGCATTAAA ATGTAATGG
     GTGTTTTTT CTAATAATCG GTGTTTTTT GGAACTTCAT TCCGTAATTT TACAATTACC

61  ATTCACTTTA TTGAGCATCT GCTCATAATA CTTAATGAG TGCAAAGTGC TTTGAATATA
     TAAGTGAAAT AACTCGTAGA CGAGTATTAT GAAATTACTC ACGTTTCACG AAACTTATAT

121  ATACGTCATT TAAACCTTAC CATAATTCTG AGGAATTGCT ACCTCCACTT CACAGATGGG
     TATGCAGTAA ATTTGGAATG GTATTAAGAC TCCTTAACGA TGGAGGTGAA GTGTCTACCC

181  GCACAGGAGG CTTAGATAAC ATGCCCAAAG TCATGCTTCT AGTAAATGGA TATAATTAAG
     CGTGTCCTCC GAATCTATTG TACGGGTTTC AGTACGAAGA TCATTTACCT ATATTAATTC

241  ATTCAATTA TTGATAAGAA TTTGATCTGC CTTACCAGTA TCTAGTAGTA AACTCTCTGA
     TAAGTTAAT AACTATTCTT AAACTAGACG GAATGGTCAT AGATCATCAT TTGAGAGACT

301  CGCTTTCCAG AGCATGTGCT GTTGATAGAG CAACTATCTC CTTGATGTCT AACTCTCTGA AATTTTCCAT
     GCGAAAGGTC TCGTACACGA CAACTATCTC GAACTACAGA TTGAGAGACT TTAAAGGTA

361  TCTTATTTGT CTCACTGGTA TATAGTTATT TTTTACTACT TTCATACACC TACTAAGAAG
     AGAATAAACA GAGTGACCAT ATATCAATAA AAAATGATGA AAGTATGTGG ATGATTCTTC
```

FIGURE 53B

```
421 ACAGGAGGAT CAAGGATAGG ATTTCATTTA GAATGCCTAA AGCTTCACGT ATTTAATTC
    TGTCCTCCTA GTTTCTATCC TAAAGTAAAT CTTACGGATT TCGAAGTGCA TAAAATTAAG

481 AGAATAAGAT TCAGGCAGAC CACCAGTATA TGCCATGGTC CCTGGTTATC TTTCAGCAGG
    TCTTATTCTA AGTCCGTCTG GTGGTCATAT ACGGTACCAG GGACCAATAG AAAGTCGTCC

541 TGACCGAGAA AGAAAACATG GTAATGTTTA TGAAATGGTG GGTTCTTGTA GTTCACTTC
    ACTGGCTCTT TCTTTTGTAC CATTACAAAT ACTTACCAC CCAAGAACAT CAAAGTGAAG

601 AACATATCTG CCTTTACTGT ATTAAGATGA TGGATTAACT TATTCTTGAT ATGGGCATGT
    TTGTATAGAC GGAAATGACA TAATTCTACT ACCTAATTGA ATAAGAACTA TACCCGTACA

661 AAACAATAT ACTTTTACTA AACAGCTACA GAGAGACAAA TGTGTTCCA GACAAACTTA
    TTTGTTATA TGAAAATGAT TTGTCGATGT CTCTCTGTTT ACACAAGGT CTGTTTGAAT

721 AGAGACTGAG TGTTCAAACT GAATAATCTC GACCTTAATT GTAACTATAT TTTATGAAAT
    TCTCTGACTC ACAAGTTTGA CTTATTAGAG CTGGAATTAA CATTGATATA AAATACTTTA
```

*FIGURE 53C*

```
 781 CCAGCTGTAA GGCAAAAACA GACTTCTTTG GGCCTACCAC GGGCATTTTG TTCCTGTTAN
     GGTCGACATT CCGTTTTTGT CTGAAGAAAC CCGGATGGTG CCCGTAAAAC AAGGACAATN

841 NNNTACTCCA AACCTTAAAC CCACGTCCAC TTAAATAAATG GCCTGGAAAT AATGTCATT
     NNNATGAGGT TTGGAATTTG GGTGCAGGTG AATTTATTAC CGGACCTTTA TTTACAGTAA

901 ATCGATATT ATACTGAGAT GTTAGTTAT GAAATCAAAA GTGGAGAATT TCAATCTGTC
     TAGACTATAA TATGACTCTA CAATCAATA CTTTAGTTTT CACCTCTTAA AGTTAGACAG

961 CTGTAAGCTT TCTCTGCGGT CACGACCCTC ATGCACTCAG GCTGTGCGGT GCAGCATGCT
     GACATTCGAA AGAGACGCCA GTGCTGGGAG TACGTGAGTC CGACACGCCA CGTCGTACGA

1021 CTGTCATGTC TGTTTTCTTC TGCCTGTACA CGGGTGGTTG TTCCTGTCTA CCTGTTTGAG
     GACAGTACAG ACAAAGAAG ACGGACATGT GCCCACCAAC AAGGACAGAT GGACAAACTC

1081 GAAATATGAA TACGTNNNNN NCTAGAATCT ACTGCACATG CAATAAGGAA ACAATCAGTA
     CTTTATACTT ATGCANNNNN NGATCTTAGA TGACGTGTAC GTTATTCCTT TGTTAGTCAT

1141 AGAATCACTT TCTCGTGGAA AATTCATTAG AATTAACATC TCGTTTTAAA ATGCTCTATC
     TCTTAGTGAA AGAGCACCTT TTAAGTAATC TTAATTGTAG AGCAAAATTT TACGAGATAG
```

FIGURE 53D

```
1201  AAGTGTAAA TAATTCCTCT CTCTTTTCCC TTTTTCACTA AGGAGTTTGT ATATTAAACA
      TTTCACATTT ATTAAGGAGA GAGAAAAGGG AAAAAGTGAT TCCTCAAACA TATAATTTGT

1261  GAATTTCAG TAATGTATTA TAAATTTATT TAANNTATTT ACAATAAAT GCCACGTATA
      CTTAAGTTC ATTACATAAT ATTTAAATAA ATTNNATAAA TGTTATTTTA CGGTGCATAT

1321  AGCATCAAGC AACATGANNN NNNCATTGGT AGAAGCACA ATACATAGTC AAAACAGCAG
      TCGTAGTTCG TTGTACTNNN NNNGTAACCA TCTTTCGTGT TATGTATCAG TTTTGTCGTC

1381  AGTATTAAAT AAACAGAAAA TTTGCAAAG GCAAGTAAAG AATATACATA TACTTAATTA
      TCATAATTTA TTTGTCTTTT AAACGTTTTC CGTTCATTTC TTATATGTAT ATGAATTAAT

1441  TACATAAAAT ATTGATACAG GAGGTAGAAA GAAATTTAGT AAGCAGATAA TGGGGGCAAC
      ATGTATTTTA TAACTATGTC CTCCATCTTT CTTTAAATCA TTCGTCTATT ACCCCCGTTG

1501  AGAGTCCTCA GCAGAGCTTC CCTTCTAACA AAAAGCAGCC CAATAAATTA TTTTTTTTTT
      TCTCAGGAGT CGTCTCGAAG GGAAGATTGT TTTTCGTCGG GTTATTTAAT AAAAAAAAAA

1561  CTAACAAAAA GCAGCCTGAA AAATCGAGCT GCAAACATAG ATTAGCAATC GGCTGAAAGT
```

*FIGURE 53E*

```
     GATTGTTTTT CGTCGGACTT TTTAGCTCGA CGTTTGTATC TAATCGTTAG CCGACTTTCA
1621 GCGGGAGAAT GCTGGCAGCT GTGCCAATAG TAAAGGGCTA CCTGGAGCCG GGCGGTGGC
     CGCCCTCTTA CGACCGTCGA CACGGTTATC ATTTCCCGAT GGACCTCGGC CCGGCACCG
1681 TCACGCTGTA ATCCCAGCAC TTTGGGAGGG CGAGGCAACG CGGATCACCT GAGGTCGGA
     AGTGCGACAT TAGGGTCGTG AAACCCTCCC GCTCCGTTGC GCCTAGTGGA CTCCAGCCCT
1741 CTTTGAGATC AGCCCGACCA ACATGGAGAA ACCCCGTCTC TACTAAAAAA AAAAAAAA
     CAAACTCTAG TCGGGCTGGT TGTACCTCTT TGGGGCAGAG ATGATTTTTT TTTTTTTT
1801 AAAGGCAAAA AATGAGCCGG GCATGGTGGC ACATGCCTTG CACATCCCAG CTGAGGCAGG
     TTTCCGTTTT TTACTCGGCC CGTACCACCG TGTACGGAAC GTGTAGGGTC GACTCCGTCC
1861 AGAATTCACT TGAACCTGGG AGGTAGAGAT TGCGGGTGAAG CGAGATCACG TCATTGCACT
     TCTTAAGTGA ACTTGGACCC TCCATCTCTA ACGCCACTTC GCTCTAGTGC AGTAACGTGA
1921 CCAGCCTGGG CAAAAGAGC AAACTTAGT CTCAAAAAAA AAAANCAAA GAAAAAA
     GGTCGGACCC GTTTTTCTCG TTTGAATCA GAGTTTTTT TTTNNGTTT CTTTTT
```

Genomic Organization of PSM Gene

FIGURE 55A

```
         10          20          30          40
 *        *    *      *     *     *     *      *     *
CTC AAA AGG GGC CGG ATT TCC TTC TCC TGG AGG CAG ATG TTG CCT CTC 50         60          70          80          90
  *    *     *     *     *     *     *     *     *      *
TCT CTC GCT CGG ATT GGT TCA GTG CAC TCT AGA AAC ACT GCT GTG GTG 100         110         120         130         140
   *     *     *     *     *     *     *     *     *
GAG AAA CTG GAC CCC AGG GTG GTT TAT AAA ATC CTC CAA TGA AGC TAC 150         160         170         180         190
 *     *     *     *     *     *     *     *     *     *
TAA CAT TAC TCC AAA GCA TAA TAT GAA AGC ATT TTT GGA TGA ATT GAA

Met Lys Ala Phe Leu Asp Glu Leu Lys>

200         210         220         230         240
  *       *     *     *     *     *     *     *     *     *
AGC TGA GAA CAT CAA GAA GTT CTT ATA TAA TTT TAC ACA GAT ACC ACA

Ala Glu Asn Ile Lys Lys Phe Leu Tyr Asn Phe Thr Gln Ile Pro His>
```

FIGURE 55B

```
            250         260         270         280
      *       *   *       *   *       *   *       *   *
      TTT AGC AGG AAC AGA ACA AAA CTT TCA GCT TGC AAA GCA AAT TCA ATC

Leu Ala Gly Thr Glu Gln Asn Phe Gln Leu Ala Lys Gln Ile Gln Ser>

290         300         310         320         330
      *   *       *   *       *   *       *   *       *   *
      CCA GTG GAA AGA ATT TGG CCT GGA TTC TGT TGA GCT AGC ACA TTA TGA

Gln Trp Lys Glu Phe Gly Leu Asp Ser Val Glu Leu Ala His Tyr Asp>

340         350         360         370         380
      *       *   *       *   *       *   *       *   *       *
      TGT CCT GTT GTC CTA CCC AAA TAA GAC TCA TCC AAC TA CAT CTC AAT

Val Leu Leu Ser Tyr Pro Asn Lys Thr His Pro Asn Tyr Ile Ser Ile>

390         400         410         420         430
      *           *   *       *   *       *   *       *   *       *
      AAT TAA TGA AGA TGG AAA TGA GAT TTT CAA CAC ATC ATT ATT TGA ACC

Ile Asn Glu Asp Gly Asn Glu Ile Phe Asn Thr Ser Leu Phe Glu Pro>

440         450         460         470         480
      *       *   *       *   *       *   *       *   *       *
      ACC TCC TCC AGG ATA TGA AAA TGT TTC GGA TAT TGT ACC ACC TTT CAG

Pro Pro Pro Gly Tyr Glu Asn Val Ser Asp Ile Val Pro Pro Phe Ser>
```

FIGURE 55C

```
            490         500         510         520
             *     *     *     *     *     *     *     *     *
        TGC TTT CTC TCC TCA AGG AAT GCC AGA GGG CGA TCT AGT GTA TGT TAA

Ala Phe Ser Pro Gln Gly Met Pro Glu Gly Asp Leu Val Tyr Val Asn>

530         540         550         560         570
         *     *     *     *     *     *     *     *     *     *
        CTA TGC ACG AAC TGA AGA CTT CTT TAA ATT GGA ACG GCA CAT GAA AAT

Tyr Ala Arg Thr Glu Asp Phe Phe Lys Leu Glu Arg Asp Met Lys Ile>

580         590         600         610         620
         *     *     *     *     *     *     *     *     *
        CAA TTG CTC TGG GAA AAT TGT AAT TGC CAG ATA TGG GAA AGT TTT CAG

Asn Cys Ser Gly Lys Ile Val Ile Ala Arg Tyr Gly Lys Val Phe Arg>

630         640         650         660         670
         *     *     *     *     *     *     *     *     *     *
        AGG AAA TAA GGT TAA AAA TGC CCA GCT GGC AGG GGC AAA GGA GTC AT

Gly Asn Lys Val Lys Asn Ala Gln Leu Ala Gly Ala Lys Gly Val Ile>

680         690         700         710         720
         *     *     *     *     *     *     *     *     *     *
        TCT CTA CTC CGA CCC TGC TGA CTA CTT TGC TCC TGG GGT GAA GTC CTA

Leu Tyr Ser Asp Pro Ala Asp Tyr Phe Ala Pro Gly Val Lys Ser Tyr>
```

FIGURE 55D

```
         730         740         750         760
          *    *      *    *      *    *      *    *
TCC AGA TGG TTG GAA TCT TCC TGG AGG TGG TGT CCA GCG TGG AAA TAT

Pro Asp Gly Trp Asn Leu Pro Gly Gly Gly Val Gln Arg Gly Asn Ile>

770         780         790         800         810
   *    *      *    *      *    *      *    *      *    *
CCT AAA TCT GAA TGG TGC AGG AGA CCC TCT CAC ACC AGG TTA CCC AGC

Leu Asn Leu Asn Gly Ala Gly Asp Pro Leu Thr Pro Gly Tyr Pro Ala>

820         830         840         850         860
   *    *      *    *      *    *      *    *      *
AAA TGA ATA TGC TTA TAG GCG TGG AAT TGC AGA GGC TGT TGG TCT TCC

Asn Glu Tyr Ala Tyr Arg Arg Gly Ile Ala Glu Ala Val Gly Leu Pro>

870         880         890         900         910
   *    *      *    *      *    *      *    *      *    *
AAG TAT TCC TGT TCA TCC AAT GGA TA CTA TGA TGC ACA GAA GCT CCT

Ser Ile Pro Val His Pro Ile Gly Tyr Tyr Asp Ala Gln Lys Leu Leu>

920         930         940         950         960
   *    *      *    *      *    *      *    *      *    *
AGA AAA AAT GGG TGG CTC AGC ACC ACC AGA TAG CAG CTG GAG AGG AAG

Glu Lys Met Gly Gly Ser Ala Pro Pro Asp Ser Ser Trp Arg Gly Ser>
```

FIGURE 55E

```
         970         980         990        1000
    *      *    *      *    *     *    *     *     *
TCT CAA AGT GCC CTA CAA TGT TGG ACC TGG CTT TAC TGG AAA CTT TTC

Leu Lys Val Pro Tyr Asn Val Gly Pro Gly Phe Thr Gly Asn Phe Ser>

1010        1020        1030        1040        1050
  *    *      *    *      *    *      *    *     *      *
TAC ACA AAA AGT CAA GAT GCA CAT CCA CTC TAC CAA TGA AGT GAC AAG

Thr Gln Lys Val Lys Met His Ile His Ser Thr Asn Glu Val Thr Arg>

1060        1070        1080        1090        1100
    *     *    *      *    *      *    *      *    *     *
AAT TTA CAA TGT GAT AGG TAC TCT CAG AGG AGC AGT GGA ACC AGA CAG

Ile Tyr Asn Val Ile Gly Thr Leu Arg Gly Ala Val Glu Pro Asp Arg>

1110        1120        1130        1140        1150
    *      *    *      *    *      *    *      *    *      *
ATA TGT CAT TCT GGG AGG TCA CCG GGA CTC ATG GGT GTT TGG TGG TAT

Tyr Val Ile Leu Gly Gly His Arg Asp Ser Trp Val Phe Gly Gly Ile>

1160        1170        1180        1190        1200
    *      *    *      *    *      *    *      *    *      *
TGA CCC TCA GAG TGG AGC AGC TGT TGT TCA TGA AAT TGT GAG GAG CTT

Asp Pro Gln Ser Gly Ala Ala Val Val His Glu Ile Val Arg Ser Phe>

1210        1220        1230        1240
         *      *    *      *    *      *    *      *    *
TGG AAC ACT GAA AAA GGA AGG GTG GAG ACC TAG AAG AAC AAT TTT GTT

Gly Thr Leu Lys Lys Glu Gly Trp Arg Pro Arg Arg Thr Ile Leu Phe>
```

FIGURE 55F

```
       1250        1260        1270        1280        1290
         *           *           *           *           *
     TGC AAG CTG GGA TGC AGA AGA ATT TGG TCT TCT TGG TTC TAC TGA GTG

Ala Ser Trp Asp Ala Glu Glu Phe Gly Leu Leu Gly Ser Thr Glu Trp>

1300        1310        1320        1330        1340
         *           *           *           *           *
     GGC AGA GGA GAA TTC AAG ACT CCT TCA AGA GCG TGG CGT GGC TTA TAT

Ala Glu Glu Asn Ser Arg Leu Leu Gln Glu Arg Gly Val Ala Tyr Ile>

1350        1360        1370        1380        1390
         *           *           *           *           *
     TAA TGC TGA CTC ATC TAT AGA AGG AAA CTA CAC TCT GAG AGT GAT TG

Asn Ala Asp Ser Ser Ile Glu Gly Asn Tyr Thr Leu Arg Val Asp Cys>

1400        1410        1420        1430        1440
         *           *           *           *           *
     TAC ACC GCT GAT GTA CAG CTT GGT ACA CAA CCT AAC AAA AGA GCT GAA

Thr Pro Leu Met Tyr Ser Leu Val His Asn Leu Thr Lys Glu Leu Lys>

1450        1460        1470        1480
         *           *           *           *
     AAG CCC TGA TGA AGG CTT TGA AGG CAA ATC TCT TTA TGA AAG TTG GAC

Ser Pro Asp Glu Gly Phe Glu Gly Lys Ser Leu Tyr Glu Ser Trp Thr>
```

FIGURE 55G

```
1490        1500        1510        1520        1530
 *     *     *     *     *     *     *     *     *     *
TAA AAA AAG TCC TTC CCC AGA GTT CAG TGG CAT GCC CAG GAT AAG CAA

Lys Lys Ser Pro Ser Pro Glu Phe Ser Gly Met Pro Arg Ile Ser Lys>

1540        1550        1560        1570        1580
 *     *     *     *     *     *     *     *     *
ATT GGG ATC TGG AAA TGA TTT TGA GGT GTT CTT CCA ACG ACT TGG AAT

Leu Gly Ser Gly Asn Asp Phe Glu Val Phe Phe Gln Arg Leu Gly Ile>

1590        1600        1610        1620        1630
 *     *     *     *     *     *     *     *     *     *
TGC TTC AGG CAG AGC ACG GTA TAC TAA AAA TTG GGA AAC AAA CAA ATT

Ala Ser Gly Arg Ala Arg Tyr Thr Lys Asn Trp Glu Thr Asn Lys Phe>

1640        1650        1660        1670        1680
 *     *     *     *     *     *     *     *     *     *
CAG CGG CTA TCC ACT GTA TCA CAG TGT CTA TGA AAC ATA TGA GTT GGT

Ser Gly Tyr Pro Leu Tyr His Ser Val Tyr Glu Thr Tyr Glu Leu Val>

1690        1700        1710        1720
 *     *     *     *     *     *     *     *     *
GGA AAA GTT TTA TGA TCC AAT GTT TAA ATA TCA CCT CAC TGT GGC CCA

Glu Lys Phe Tyr Asp Pro Met Phe Lys Tyr His Leu Thr Val Ala Gln>
```

FIGURE 55H

```
          1730        1740        1750        1760        1770
           *     *     *     *     *     *     *     *     *     *
          GGT TCG AGG AGG GAT GGT GTT TGA GCT AGC CAA TTC CAT AGT GCT CCC

Val Arg Gly Gly Met Val Phe Glu Leu Ala Asn Ser Ile Val Leu Pro>

1780        1790        1800        1810        1820
           *     *     *     *     *     *     *     *     *  *
          TTT TGA TTG TCG AGA TTA TGC TGT AGT TTT AAG AAA GTA TGC TGA CAA

Phe Asp Cys Arg Asp Tyr Ala Val Val Leu Arg Lys Tyr Ala Asp Lys>

1830        1840        1850        1860        1870
          *    *     *     *     *     *     *     *     *     *
          AAT CTA CAG TAT TTC TAT GAA ACA TCC ACA GGA AAT GAA GAC ATA CAG

Ile Tyr Ser Ile Ser Met Lys His Pro Gln Glu Met Lys Thr Tyr Ser>

1880        1890        1900        1910        1920
           *    *     *    *     *     *    *     *    *     *     *
          TGT ATC ATT TGA TTC ACT TTT TTC TGC AGT AAA GAA TTT TAC AGA AAT

Val Ser Phe Asp Ser Leu Phe Ser Ala Val Lys Asn Phe Thr Glu Ile>
             1930        1940        1950        1960
            *     *     *    *     *     *     *     *     *
          TGC TTC CAA GTT CAG TGA GAG ACT CCA GGA CTT TGA CAA AAG CAA CCC

Ala Ser Lys Phe Ser Glu Arg Leu Gln Asp Phe Asp Lys Ser Asn Pro>
```

FIGURE 55I

```
        1970         1980         1990         2000         2010
          *     *     *     *     *     *     *     *     *     *
        AAT AGT ATT AAG AAT GAT GAA TGA TCA ACT CAT GTT TCT GGA AAG AGC

Ile Val Leu Arg Met Met Asn Asp Gln Leu Met Phe Leu Glu Arg Ala>

2020         2030         2040         2050         2060
          *     *     *     *     *     *     *     *     *
        ATT TAT TGA TCC ATT AGG GTT ACC AGA CAG GCC TTT TTA TAG GCA TGT

Phe Ile Asp Pro Leu Gly Leu Pro Asp Arg Pro Phe Tyr Arg His Val>

2070         2080         2090         2100         2110
          *     *     *     *     *     *     *     *     *     *
        CAT CTA TGC TCC AAG CAG CCA CAA CAA GTA TGC AGG GGA GTC ATT CCC

Ile Tyr Ala Pro Ser Ser His Asn Lys Tyr Ala Gly Glu Ser Phe Pro>

2120         2130         2140         2150         2160
          *     *     *     *     *     *     *     *     *     *
        AGG AAT TTA TGA TGC TCT GTT TGA TAT TGA AAG CAA AGT GGA CCC TTC

Gly Ile Tyr Asp Ala Leu Phe Asp Ile Glu Ser Lys Val Asp Pro Ser>

2170         2180         2190         2200
          *     *     *     *     *     *     *     *     *
        CAA GGC CTG GGG AGA AGT GAA GAG ACA GAT TTA TGT TGC AGC CTT CAC

Lys Ala Trp Gly Glu Val Lys Arg Gln Ile Tyr Val Ala Ala Phe Thr>

2210         2220         2230         2240         2250
          *     *     *     *     *     *     *     *     *     *
        AGT GCA GGC AGC TGC AGA GAC TTT GAG TGA AGT AGC CTA AGA GGA TTC

Val Gln Ala Ala Ala Glu Thr Leu Ser Glu Val Ala
```

*FIGURE 58J*

```
     2260          2270          2280          2290          2300
      *      *      *      *      *      *      *      *      *
TTT AGA GAA TCC GTA TTG AAT TTG TGT GGT ATG TCA CTC AGA AAG AAT 2310          2320          2330          2340          2350
     *      *      *      *      *      *      *      *      *      *
CGT AAT GGG TAT ATT GAT AAA TTT TAA AAT TGG TAT ATT TGA AAT AAA 2360          2370          2380
     *      *      *      *      *      *      *
GTT GAA TAT TAT ATA TAA AAA AAA AAA AAA AAA AA
```

FIGURE 64

Sequence Analysis of microsatellite instability in PSM gene

| Sample | Sequence | PSM EXPRESSION (IMMUNO STAIN) |
|---|---|---|
| Genomic | $T_9GC(TTTTG)_6(TTTG)_3T_7$ | |
| LNCaP | $T_9GC(TTTTG)_6(TTTG)_3T_7$ | positive |
| PC-3 | $T_9GC(TTTTG)_8(TTTG)_3T_6$ | negative |
| DU145 | $T_{10}GC(TTTTG)_5(TTTG)_2T_7$ | negative |
| T4 (tumor) | $T_{10}GC(TTTTG)_6(TTTG)_3T_7$ | positive |
| N4 (paired normal) | $T_9GC(TTTTG)_6(TTTG)_3T_7$ | positive |

Genomic Organization of PSM Gene

*Location of microsatellite in PSM Gene*

PROSTATE-SPECIFIC MEMBRANE ANTIGEN AND USES THEREOF

This application is a continuation-in-part of application Ser. No. 10/443,694 filed Oct. 21, 2003, now abandoned a continuation of application Ser. No. 08/705,477 filed Aug. 29, 1996 and issued May 27, 2003 as U.S. Pat. No. 6,569,432, a continuation-in-part of International application No. PCT/US96/02424 filed Feb. 23, 1996 in the name of Sloan Kettering Institute for Cancer Research, which is a continuation-in-part of U.S. application Ser. No. 08/466,381 now U.S. Pat. No. 6,953,668, and Ser. No. 08/470,735 now U.S. Pat. No. 7,105,159, both filed Jun. 6, 1995, which are continuations of application Ser. No. 08/394,152 filed Feb. 24, 1995, and issued Aug. 10, 1999 as U.S. Pat. No. 5,935,818.

This invention disclosed herein was made in part with Government support under Grants Nos. DK47650 and CA58192, CA-39203, CA-29502, CA-08748-29 from the National Institute of Health, U.S. Department of Health and Human Services. Accordingly, the U.S. Government has certain rights in this invention.

BACKGROUND OF THE INVENTION

Throughout this application various references are referred to within parentheses. Disclosures of these publications in their entireties are hereby incorporated by reference into this application to more fully describe the state of the art to which this invention pertains. Full bibliographic citation for these references may be found at the end of each set of Examples in the Experimental Details section.

Prostate cancer is among the most significant medical problems in the United States, as the disease is now the most common malignancy diagnosed in American males. In 1992 there were over 132,000 new cases of prostate cancer detected with over 36,000 deaths attributable to the disease, representing a 17.3% increase over 4 years (8). Five year survival rates for patients with prostate cancer range from 88% for those with localized disease to 29% for those with metastatic disease. The rapid increase in the number of cases appears to result in part from an increase in disease awareness as well as the widespread use of clinical markers such as the secreted proteins prostate-specific antigen (PSA) and prostatic acid phosphatase (PAP) (7).

The prostate gland is a site of significant pathology affected by conditions such as benign growth (BPH) neoplasia (prostatic cancer) and infection (prostatitis). Prostate cancer represents the second leading cause of death from cancer in man (7). However prostatic cancer is the leading site for cancer development in men. The difference between these two facts relates to prostate cancer occurring with increasing frequency as men age, especially in the ages beyond 60 at a time when death from other factors often intervenes. Also, the spectrum of biologic aggressiveness of prostatic cancer is great, so that in some men following detection the tumor remains a latent histologic tumor and does not become clinically significant, whereas in other it progresses rapidly, metastasizes and kills the man in a relatively short 2-5 year period (7 and 59).

In prostate cancer cells, two specific proteins that are made in very high concentrations are prostatic acid phosphatase (PAP) and prostate specific antigen (PSA) (21, 47, and 65). These proteins have been characterized and have been used to follow response to therapy. With the development of cancer, the normal architecture of the gland becomes altered, including loss of the normal duct structure for the removal of secretions and thus the secretions reach the serum. Indeed measurement of serum PSA is suggested as a potential screening method for prostatic cancer. Indeed, the relative amount of PSA and/or PAP in the cancer reduces as compared to normal or benign tissue. PAP was one of the earliest serum markers for detecting metastatic spread (47). PAP hydrolyses tyrosine phosphate and has a broad substrate specificity. Tyrosine phosphorylation is often increased with oncogenic transformation. It has been hypothesized that during neoplastic transformation there is less phosphatase activity available to inactivate proteins that are activated by phosphorylation on tyrosine residues. In some instances, insertion of phosphatases that have tyrosine phosphatase activity has reversed the malignant phenotype.

PSA is a protease and it is not readily appreciated how loss of its activity correlates with cancer development (21, and 65). The proteolytic activity of PSA is inhibited by zinc. Zinc concentrations are high in the normal prostate and reduced in prostatic cancer. Possibly the loss of zinc allows for increased proteolytic activity by PSA. As proteases are involved in metastasis and some proteases stimulate mitotic activity, the potentially increased activity of PSA could be hypothesized to play a role in the tumors metastases and spread (39).

Both PSA and PAP are found in prostatic secretions. Both appear to be dependent on the presence of androgens for their production and are substantially reduced following androgen deprivation.

Prostate-specific membrane antigen (PSM) which appears to be localized to the prostatic membrane has been identified. This antigen was identified as the result of generating monoclonal antibodies to a prostatic cancer cell, LNCaP (22).

Dr. Horoszewicz established a cell line designated LNCaP from the lymph node of a hormone refractory, heavily pre-treated patient (23). This line was found to have an aneuploid human male karyotype. It maintained prostatic differentiation functionality in that it produced both PSA and PAP. It possessed an androgen receptor of high affinity and specificity. Mice were immunized with LNCaP cells and hybridomas were derived from sensitized animals. A monoclonal antibody was derived and was designated 7E11-C5 (22). The antibody staining was consistent with a membrane location and isolated fractions of LNCaP cell membranes exhibited a strongly positive reaction with immunoblotting and ELISA techniques. This antibody did not inhibit or enhance the growth of LNCaP cells in vitro or in vivo. The antibody to this antigen was remarkably specific to prostatic epithelial cells, as no reactivity was observed in any other component. Immunohistochemical staining of cancerous epithelial cells was more intense than that of normal or benign epithelial cells.

Dr. Horoszewicz also reported detection of immunoreactive material using 7E11'-C5 in serum of prostatic cancer patients (22). The immunoreactivity was detectable in nearly 60% of patients with stage D-2 disease and in a slightly lower percentage of patients with earlier stage disease, but the numbers of patients in the latter group are small. Patients with benign prostatic hyperplasia (BPH) were negative. Patients with no apparent disease were negative, but 50-60% of patients in remission yet with active stable disease or with progression demonstrated positive serum reactivity. Patients with non prostatic tumors did not show immunoreactivity with 7E11-C5.

The 7E11-C5 monoclonal antibody is currently in clinical trials. The aldehyde groups of the antibody were oxidized and the linker-chelator glycol-tyrosyl-(n, E-diethylenetriaminepentacetic acid)-lysine (GYK-DTPA) was coupled to the reactive aldehydes of the heavy chain. The resulting antibody was designated CYT-356. Immunohistochemical staining patterns were similar except that the CYT-356 modified antibody stained skeletal muscle. The comparison of CYT-356 with 7E11-C5 monoclonal antibody suggested both had binding to type 2 muscle fibers. The reason for the discrepancy with the earlier study, which reported skeletal muscle to be negative, was suggested to be due to differences in tissue fixation techniques. Still, the most intense and definite reaction was observed with prostatic epithelial cells, especially cancerous cells. Reactivity with mouse skeletal muscle was detected with immunohistochemistry but not in imaging studies. The Indium[111]-labeled antibody localized to LNCaP tumors grown in nude mice with an uptake of nearly 30% of the injected dose per gram tumor at four days. In-vivo, no selective retention of the antibody was observed in antigen negative tumors such as PC-3 and DU-145, or by skeletal muscle. Very little was known about the PSM antigen. An effort at purification and characterization has been described at meetings by Dr. George Wright and colleagues (14 and 64).

Figure 1A:
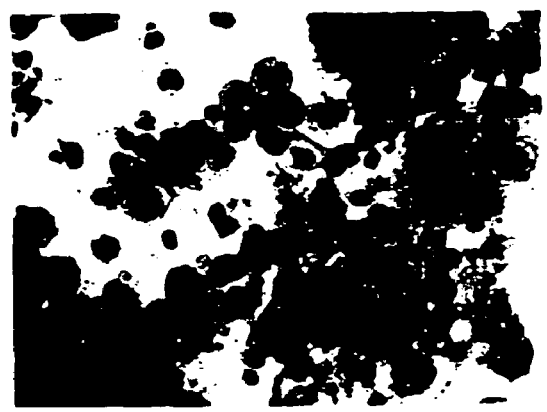
FIGS. 1A-1C: Immunohistochemical detection of PSM antigen expression in prostate cell lines. Top panel reveals uniformly high level of expression in LNCaP cells; middle panel and lower panel are DU-145 and PC-3 cells respectively, both negative.

Radiolabeled 1 kb DNA ladder (Gibco-BRL) is shown in lane 1. Undigested probe is 400 nucleotides (lane. 2), expected protected PSM band is 350 nucleotides, and tRNA control is shown (lane 3). A strong signal is seen in human prostate (lane 11), with very faint, but detectable signals seen in human brain (lane 4) and human salivary gland (lane 12). No signal was detected in lane 5 kidney, lane 6 liver, lane 7 lung, lane 8 mammary gland, lane 9 pancreas, lane 10 placenta, lane 13 skeletal muscle, lane 14 spleen, and lane 15 testes.

Figure 5:
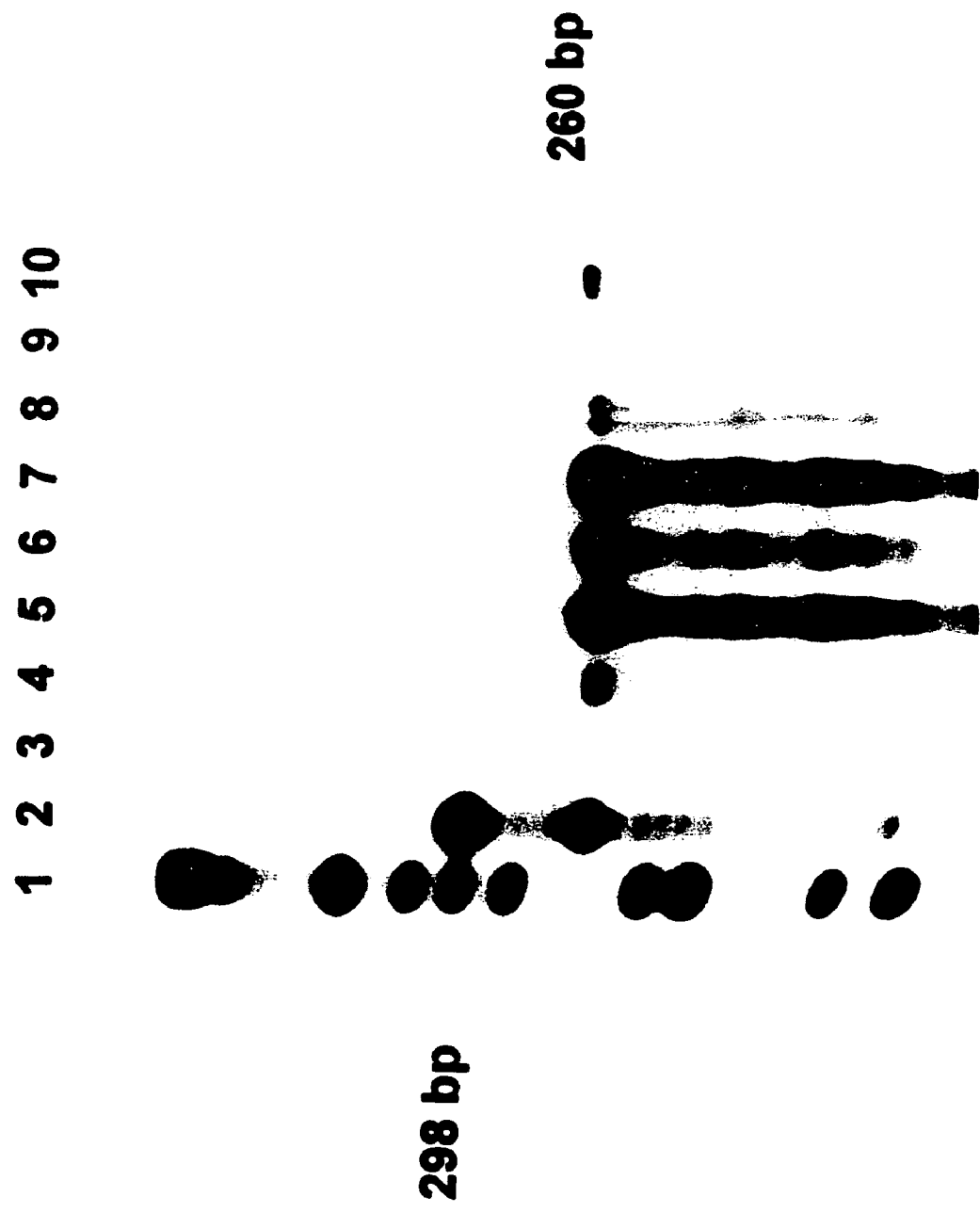

FIG. 5: Autoradiogram of ribonuclease protection gel assaying for PSM mRNA expression in LNCaP tumors grown in nude mice, and in human prostatic tissues. $^{32}$P-labeled 1 kb DNA ladder is shown in lane 1. 298 nucleotide undigested probe is shown (lane 2), and tRNA control is shown (lane 3). PSM mRNA expression is clearly detectable in LNCaP cells (lane 4), orthotopically grown LNCaP tumors in nude mice with and without matrigel (lanes 5 and 6), and subcutaneously implanted and grown LNCaP tumors in nude mice (lane 7). PSM mRNA expression is also seen in normal human prostate (lane 8), and in a moderately differentiated human prostatic adenocarcinoma (lane 10). Very faint expression is seen in a sample of human prostate tissue with benign hyperplasia (lane 9).

Figure 6:
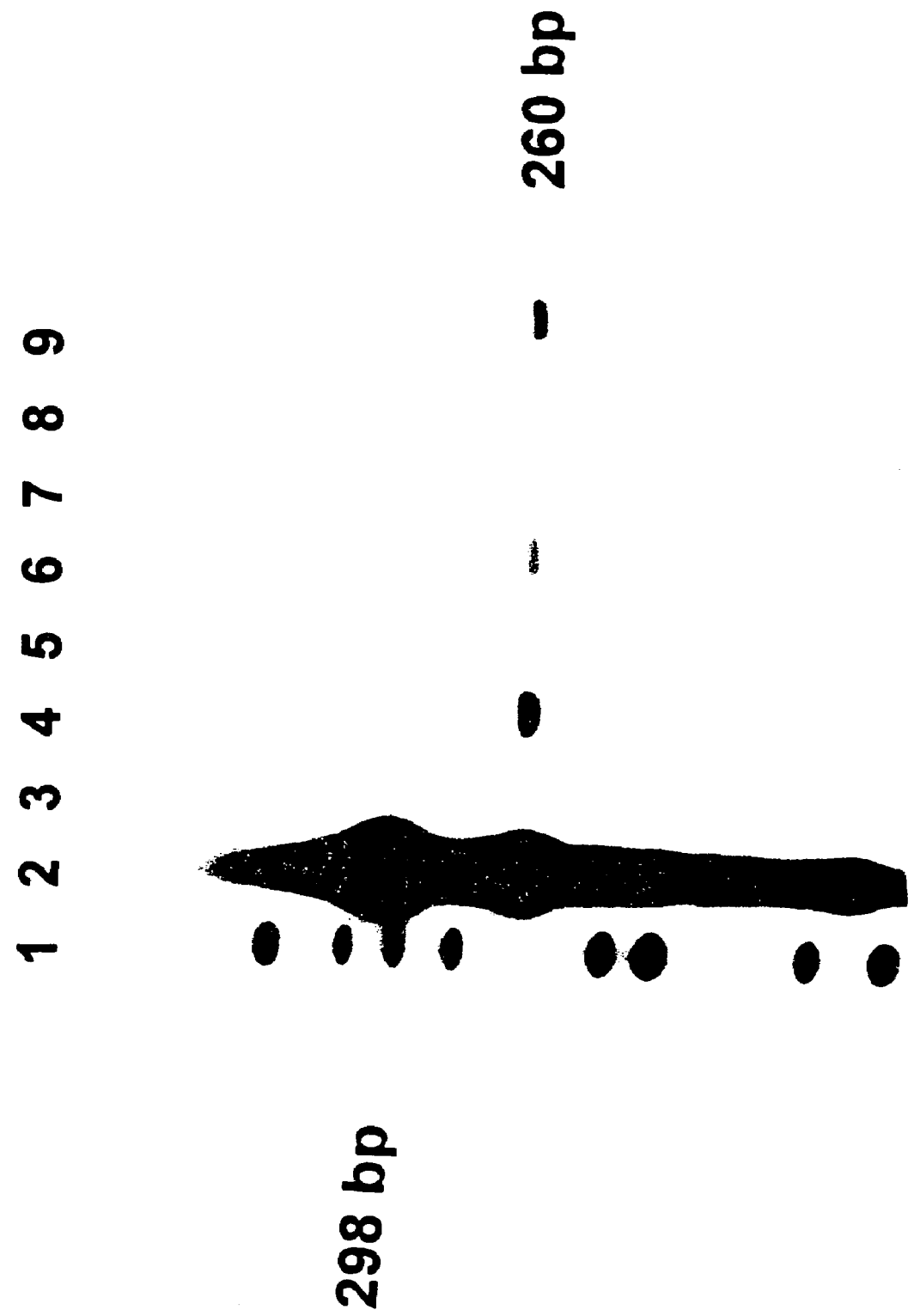

FIG. 6: Ribonuclease protection assay for PSM expression in LNCaP cells treated with physiologic doses of various steroids for 24 hours. $^{32}$P-labeled DNA ladder is shown in lane 1. 298 nucleotide undigested probe is shown (lane 2), and tRNA control is shown (lane 3). PSM mRNA expression is highest in untreated LNCaP cells in charcoal-stripped media (lane 4). Applicant see significantly diminished PSM expression in LNCaP cells treated with DHT (lane 5), Testosterone (lane 6), Estradiol (lane 7), and Progesterone (lane 8), with little response to Dexamethasone (lane 9).

Figure 8A:
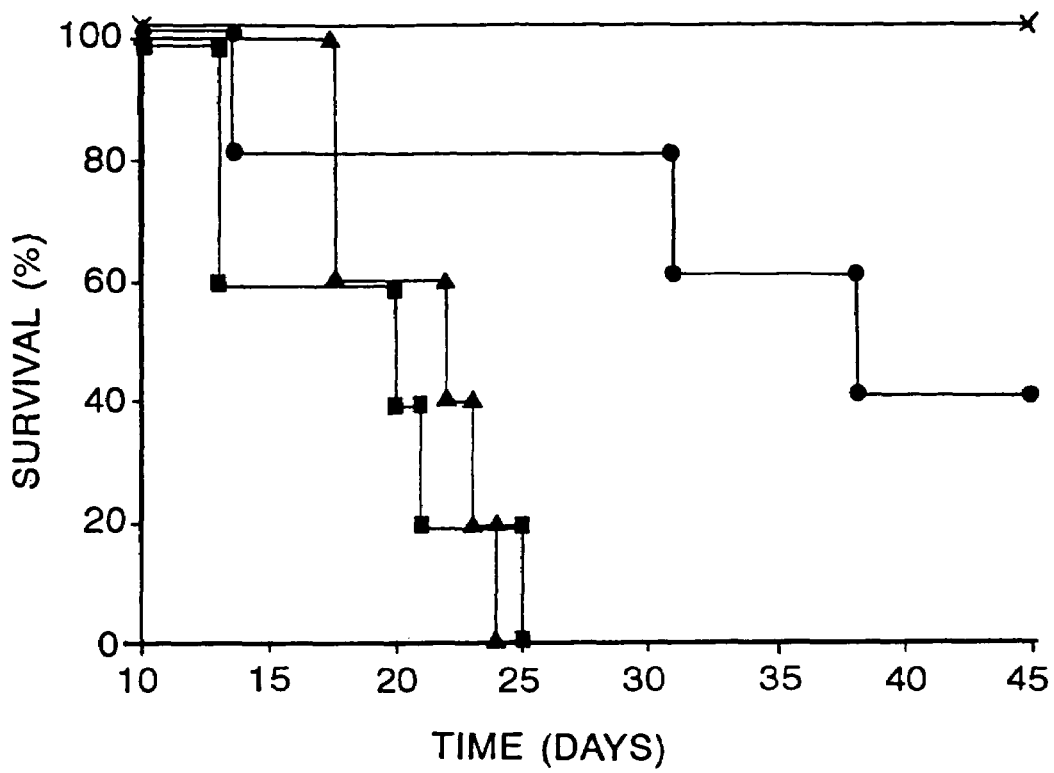
Figure 8B:
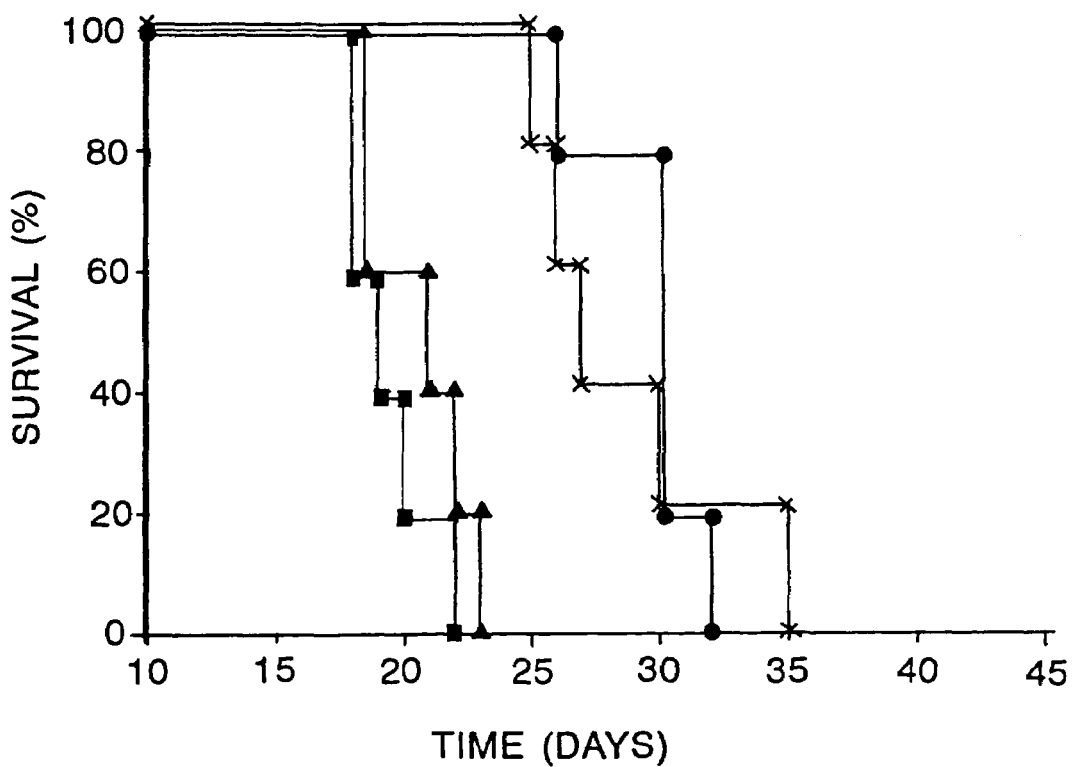

FIG. 7: Data illustrating results of PSM DNA 1' and RNA presence in transfect Dunning cell lines employing Southern and Northern blotting techniques FIGS. 8A-8B:
 FIG. A indicates the power of cytokine transfected cells to teach unmodified cells. Administration was directed to the parental flank or prostate cells. The results indicate the microenvironment considerations.
 FIG. B indicates actual potency at a particular site. The tumor was implanted in prostate cells and treated with immune cells at two different sites.

Figure 9A:
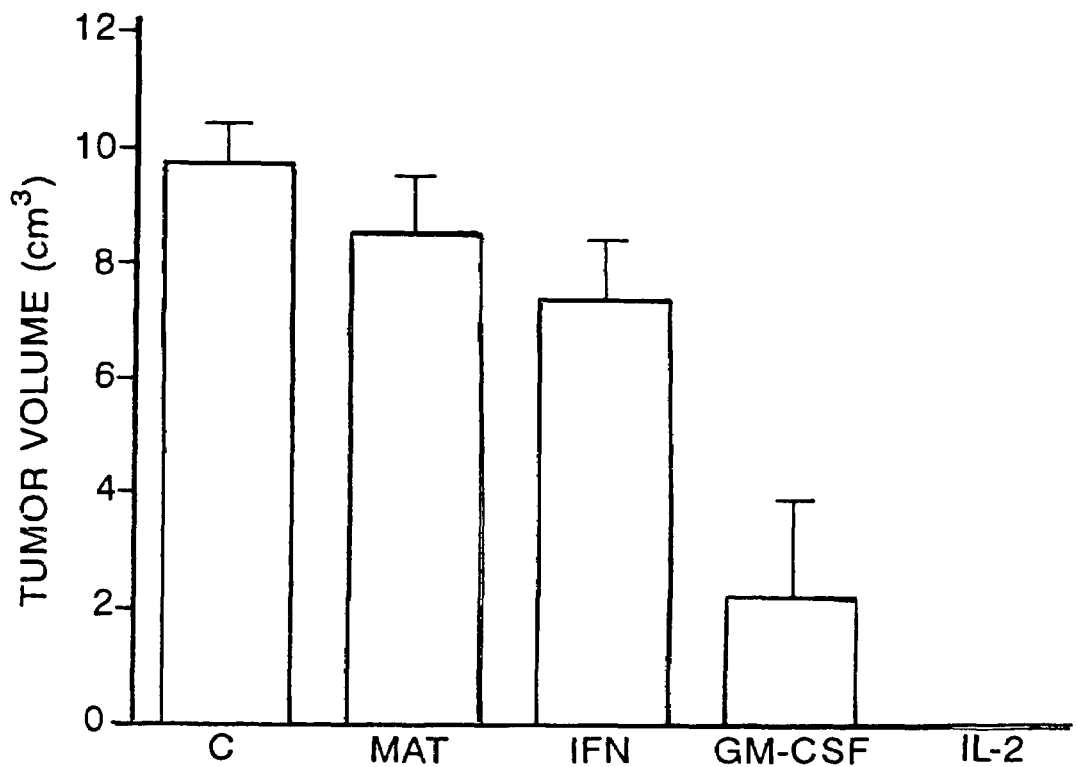
Figure 9B:
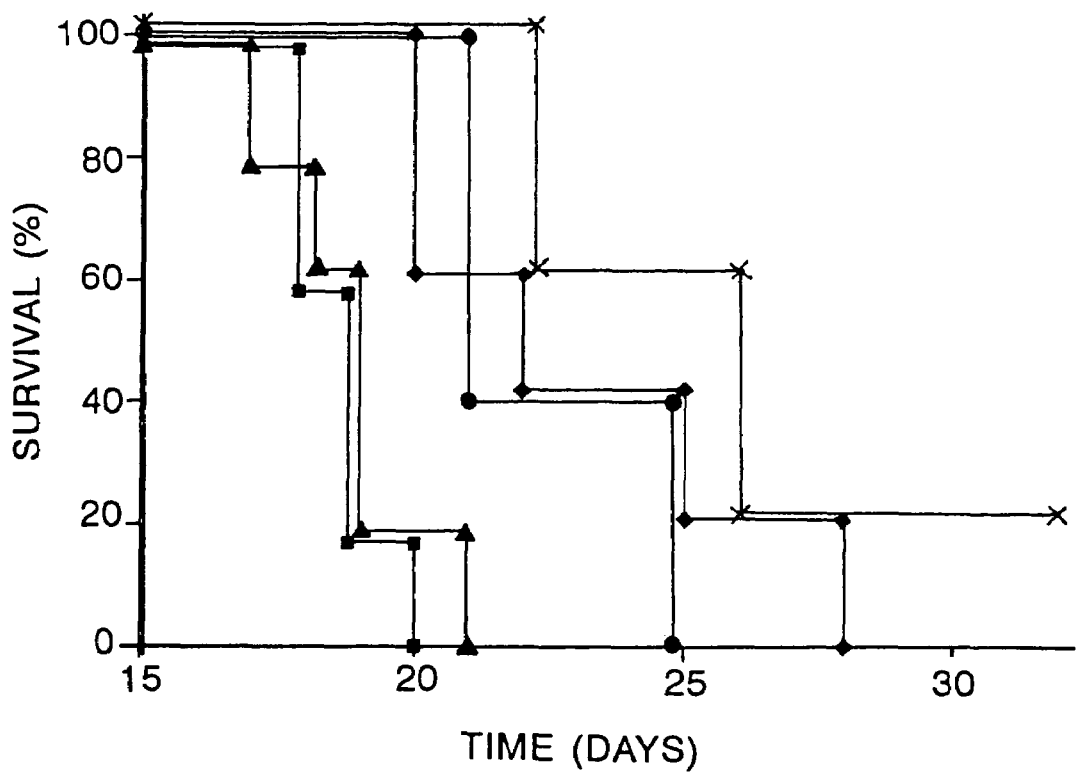

FIGS. 9A-9B: Relates potency of cytokines in 3' inhibiting growth of primary tumors. Animals administered un-modified parental tumor cells and administered as a vaccine transfected cells. Following prostatectomy of rodent tumor results in survival increase.

Figure 10:
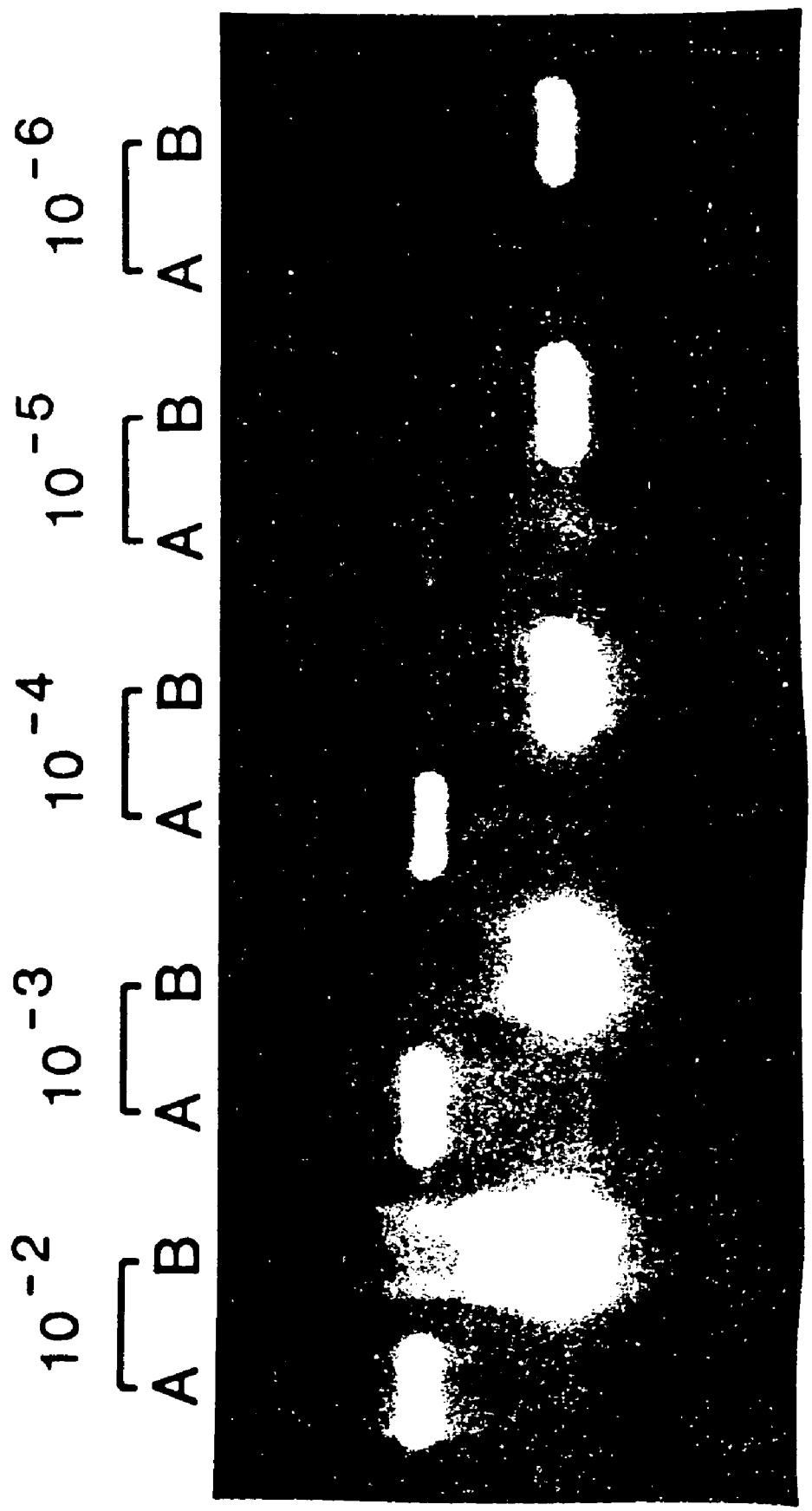

FIG. 10: PCR amplification with nested primers improved the level of detection of prostatic cells from approximately one prostatic cell per 10,000 MCF-7 cells to better than one cell per million MCF-7 cells, using PSA.

Figure 11:
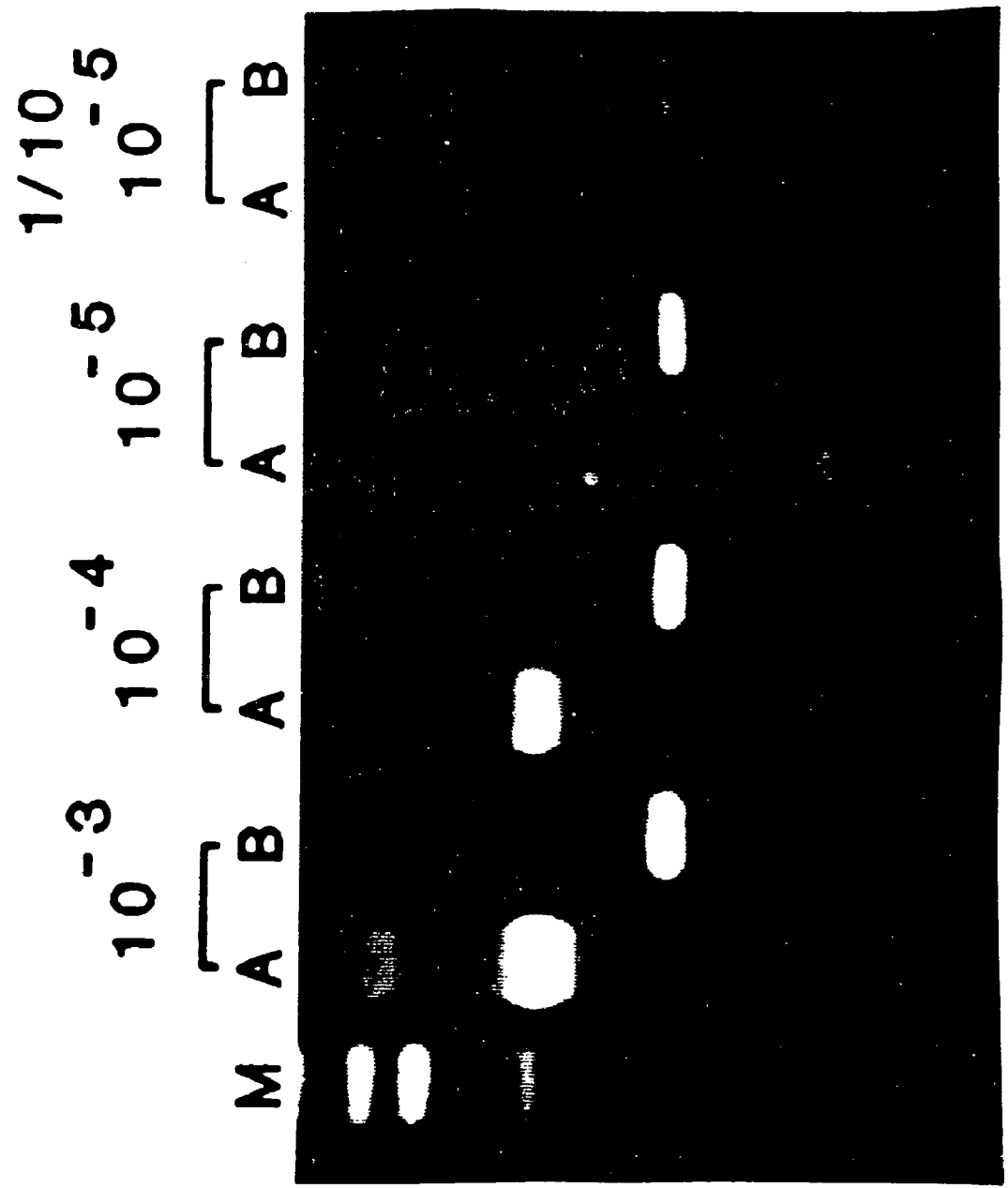

FIG. 11: PCR amplification with nested primers improved the level of detection of prostatic cells from approximately one prostatic cell per 10,000 MCF-7 cells to better than one cell per million MCF-7 cells, using PSM-derived primers.

Figure 12:
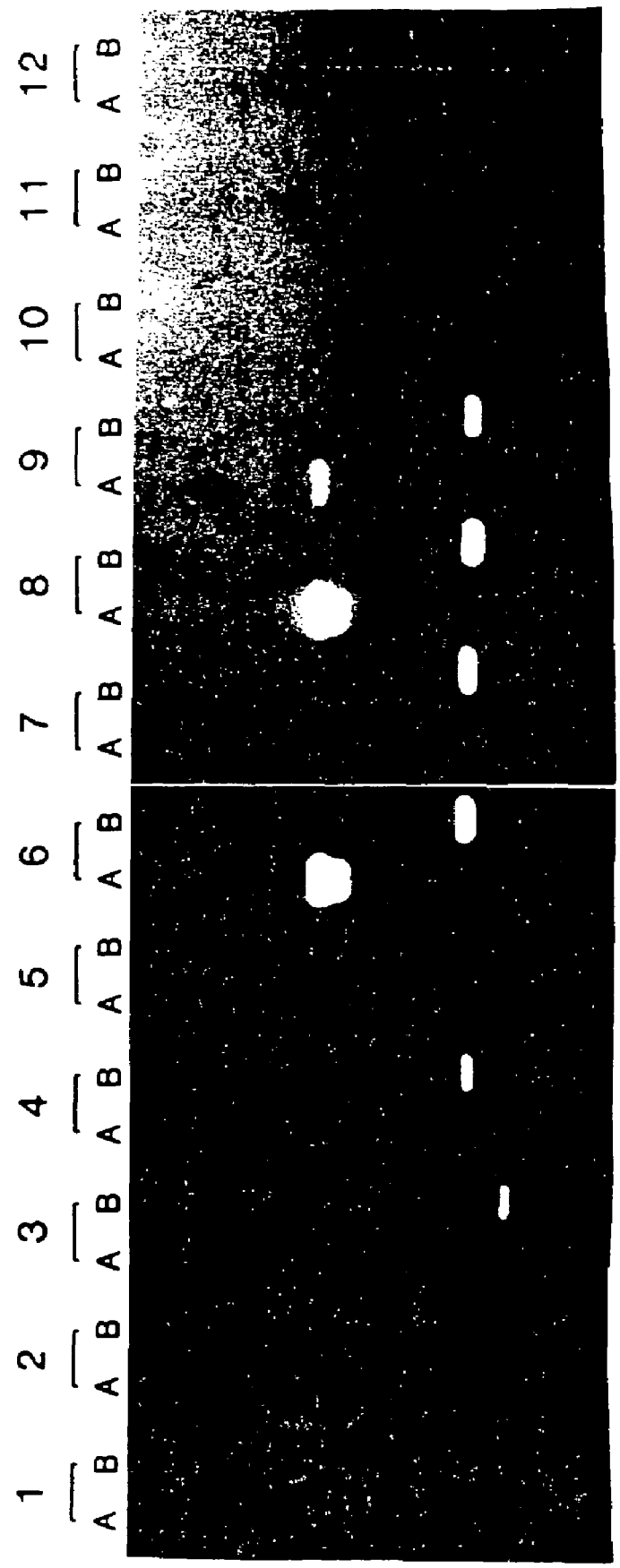

FIG. 12: A representative ethidium stained gel photograph for PSM-PCR. Samples run in lane A represent PCR products generated from the outer primers and samples in lanes labeled B are products of inner primer pairs.

Figure 13:
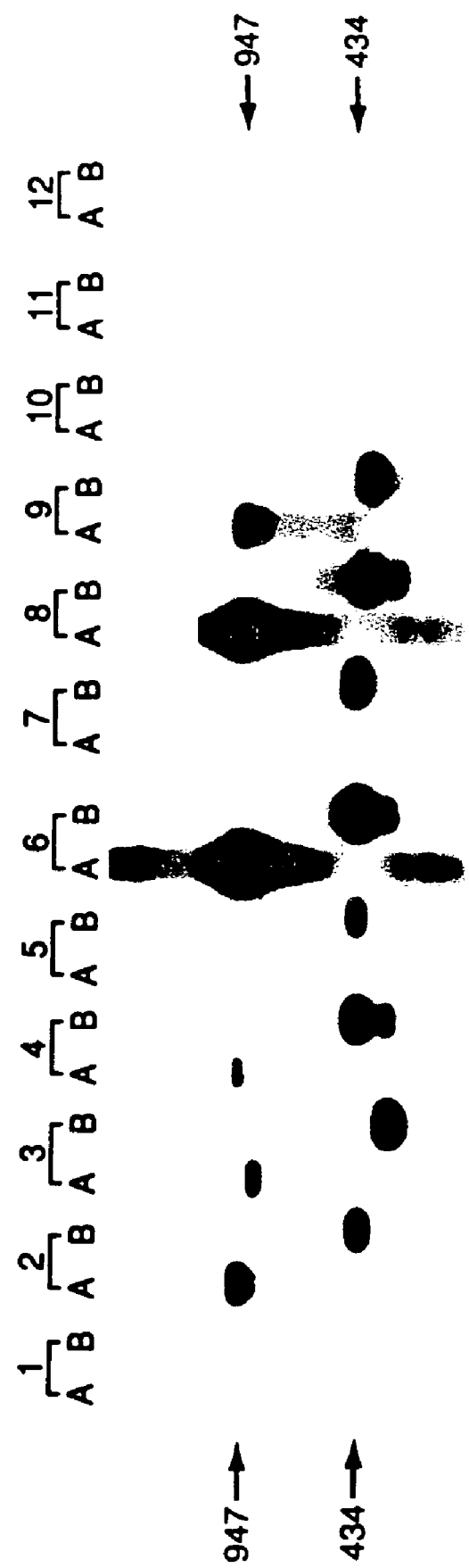

FIG. 13: PSM Southern blot autoradiograph. The sensitivity of the Southern blot analysis exceeded that of ethidium staining, as can be seen in several samples where the outer product is not visible, but is detectable by Southern blotting.

FIG. 14: Characteristics of the 16 patients analyzed with respect to their clinical stage, treatment, serum PSA and PAP values, and results of assay.

FIGS. 15A-15D: DNA sequence (SEQ ID NO: 128) containing promoter elements from nucleotide 1 to nucleotide -3017. -1 is upstream of start site of PSM.

FIGS. 16: Potential binding sites on the PSM promoter fragment: AP1 (SEQ ID NO:103), E2RS (SEQ ID NO:104), GHF (SEQ ID NO:105), JVC repeat (SEQ ID NO:106), NfkB (SEQ ID NO: 107), uteroglobi (SEQ ID NO: 108), IFN (SEQ ID NO: 109).

Figure 17:
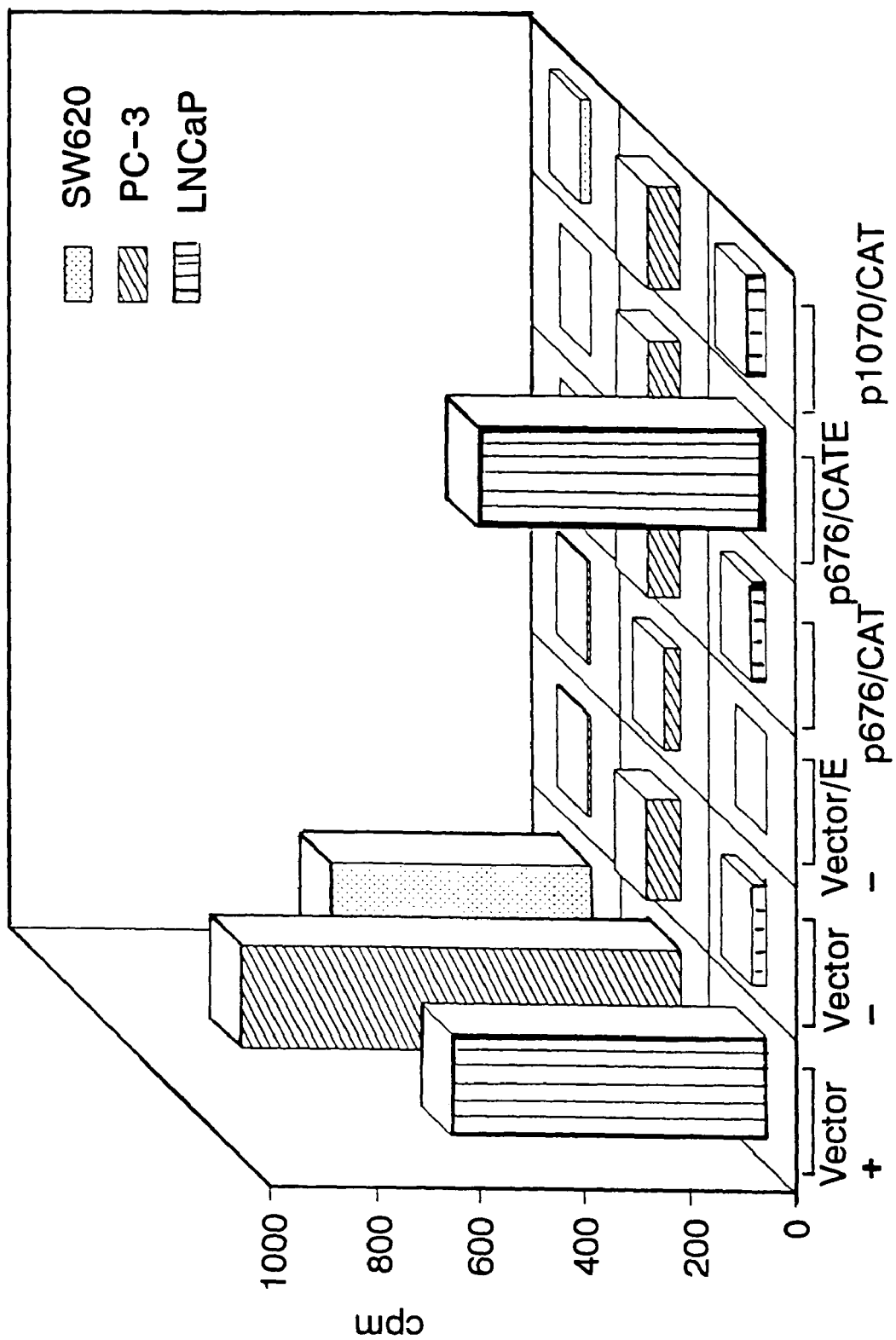

FIG. 17: Promoter activity of PSM up-stream fragment/ CAT gene chimera.

FIG. 18: Comparison between PSM and PSM' cDNA. Sequence of the 5' end of PSM cDNA (32) is shown. Underlined region (beginning at nucleotide 115 and continuing to nucleotide 380) denotes nucleotides which are absent in PSM' cDNA but present in PSM cDNA. Boxed region represents the putative transmembrane domain of PSM antigen. *Asterisk denotes the putative translation initiation site for PSM' (SEQ ID NO: 91, SEQ ID NO: 102).

Figure 19:
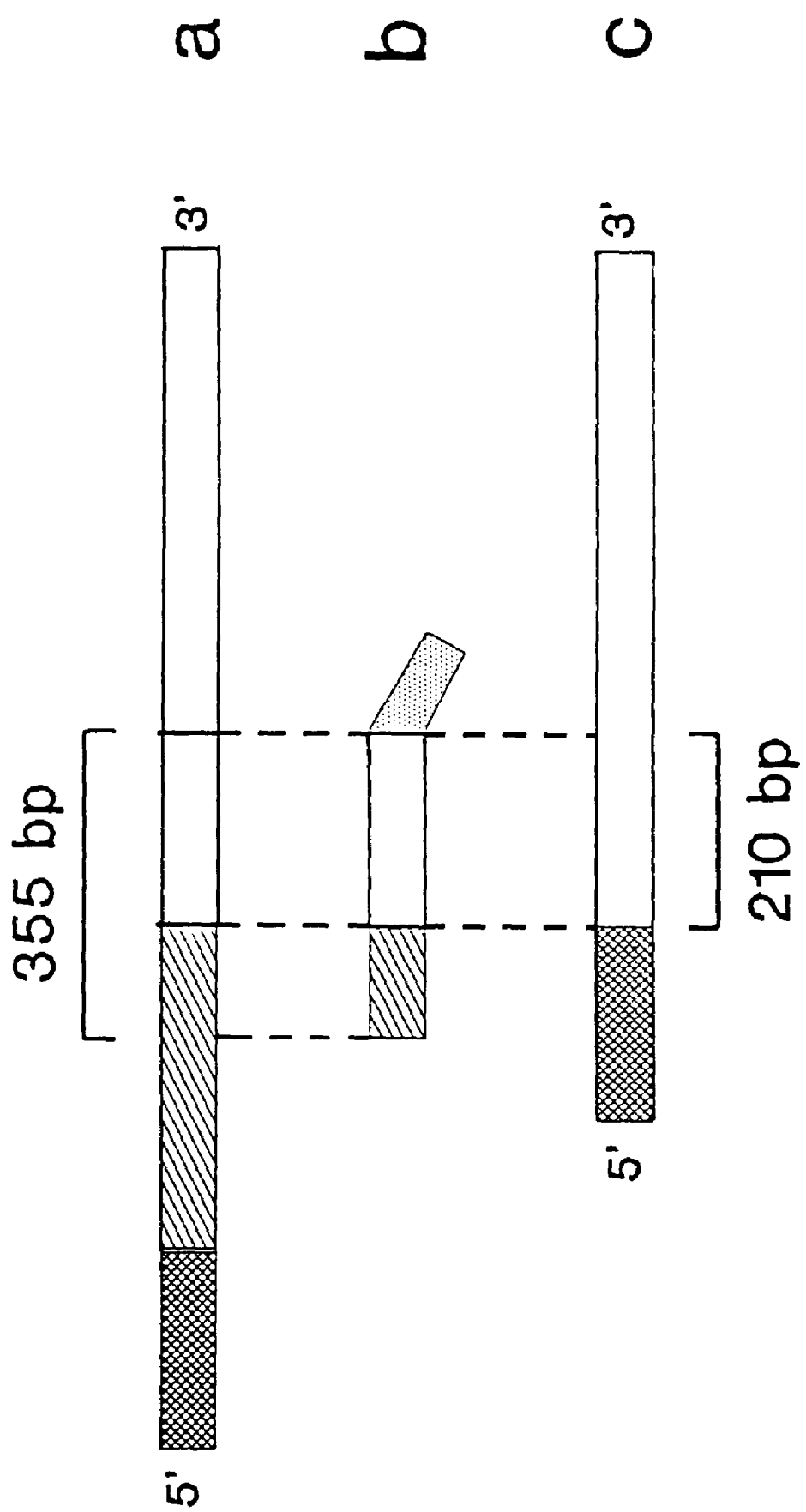

FIG. 19: Graphical representation of PSM and PSM' cDNA sequences and antisense PSM RNA probe (b). PSM cDNA sequence with complete coding region (32). (a) PSM' cDNA sequence from this study. (c) Cross hatched and open boxes denote sequences identity in PSM and PSMD. Hatched box indicates sequence absent from PSM'. Regions of cDNA sequence complementary to the antisense probe are indicated by dashed lines between the sequences.

Figure 20:
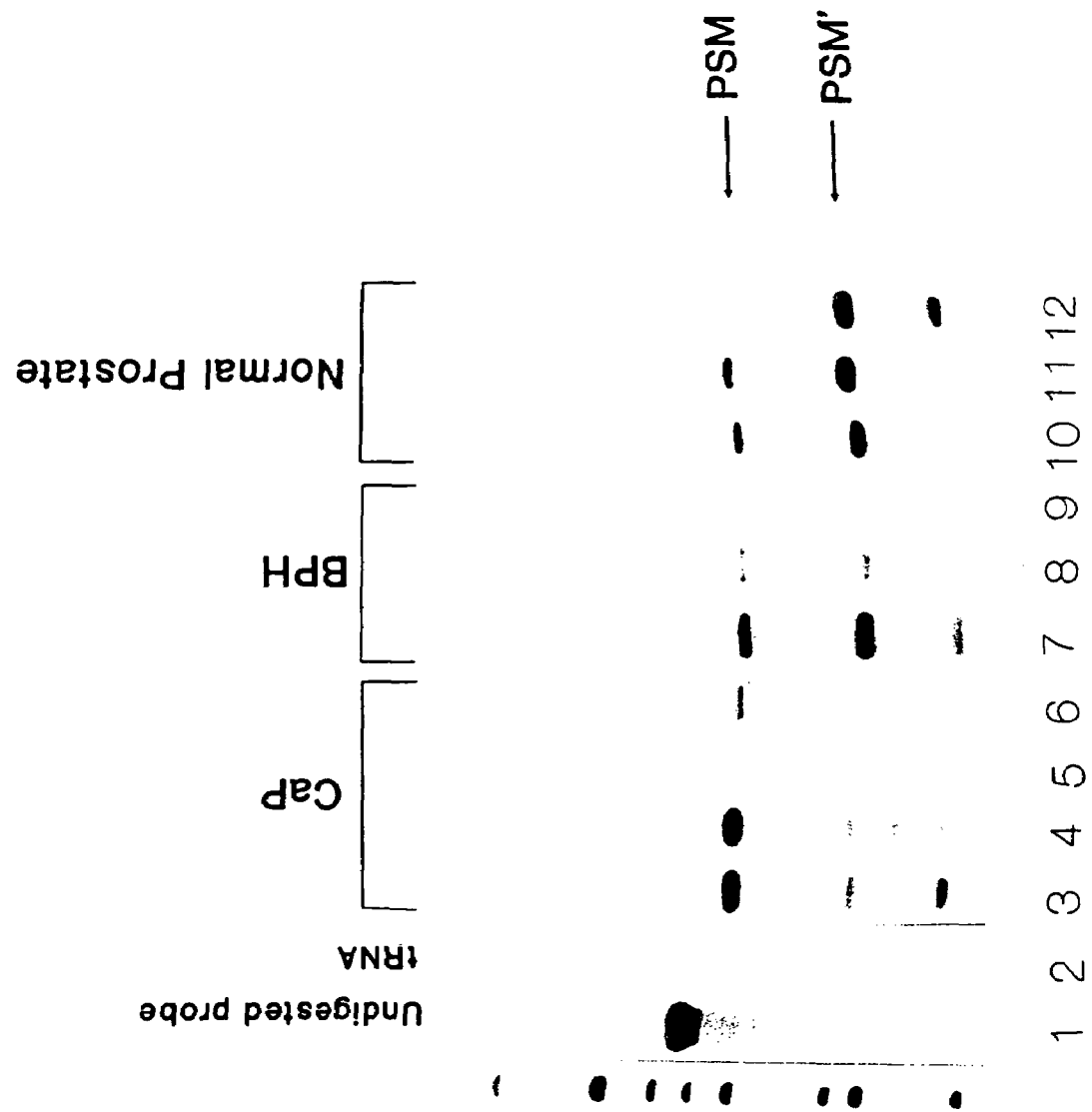

FIG. 20: RNase protection assay with PSM specific probe in primary prostatic tissues. Total cellular RNA was isolated from human prostatic samples: normal prostate, BPH, and CaP. PSM and PSM' spliced variants are indicated with arrows at right. The left lane is a DNA ladder. Samples from different patients are classified as: lanes 3-6, CaP, carcinoma of prostate; BPH, benign prostatic hypertrophy, lanes 7-9; normal, normal prostatic tissue, lanes 10-12. Autoradiograph was exposed for longer period to read lanes 5 and 9.

Figure 21:
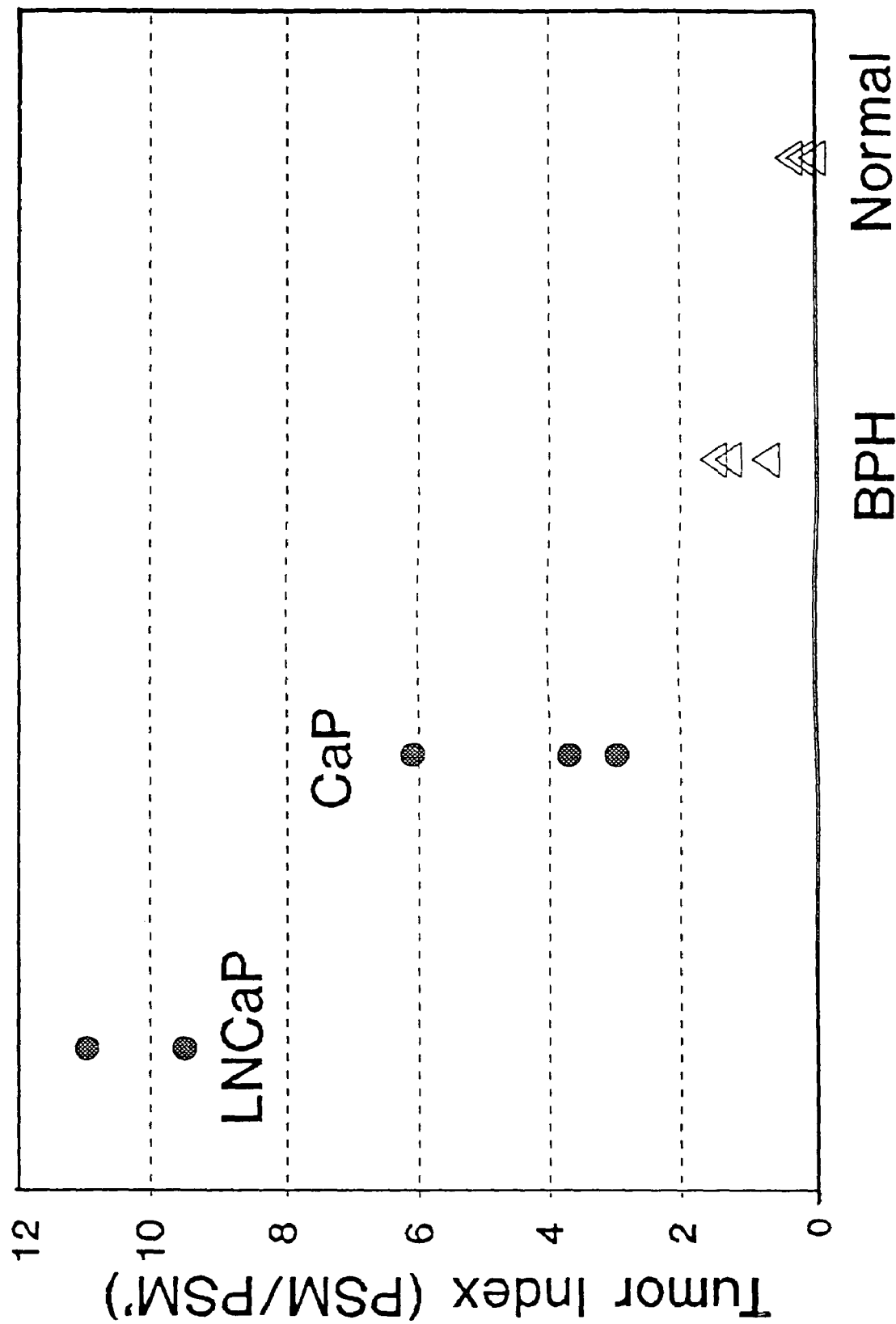

FIG. 21: Tumor Index, a quantification of the expression of PSM and PSM'. Expression of PSM and PSM' was quantified by densitometry and expressed as a ratio of PSM/PSM' on the Y-axis. Three samples each were quantitated for primary CaP, BPH and normal prostate tissues. Two samples were quantitated for LNCaP. Normal, normal prostate tissue.

Figure 22:
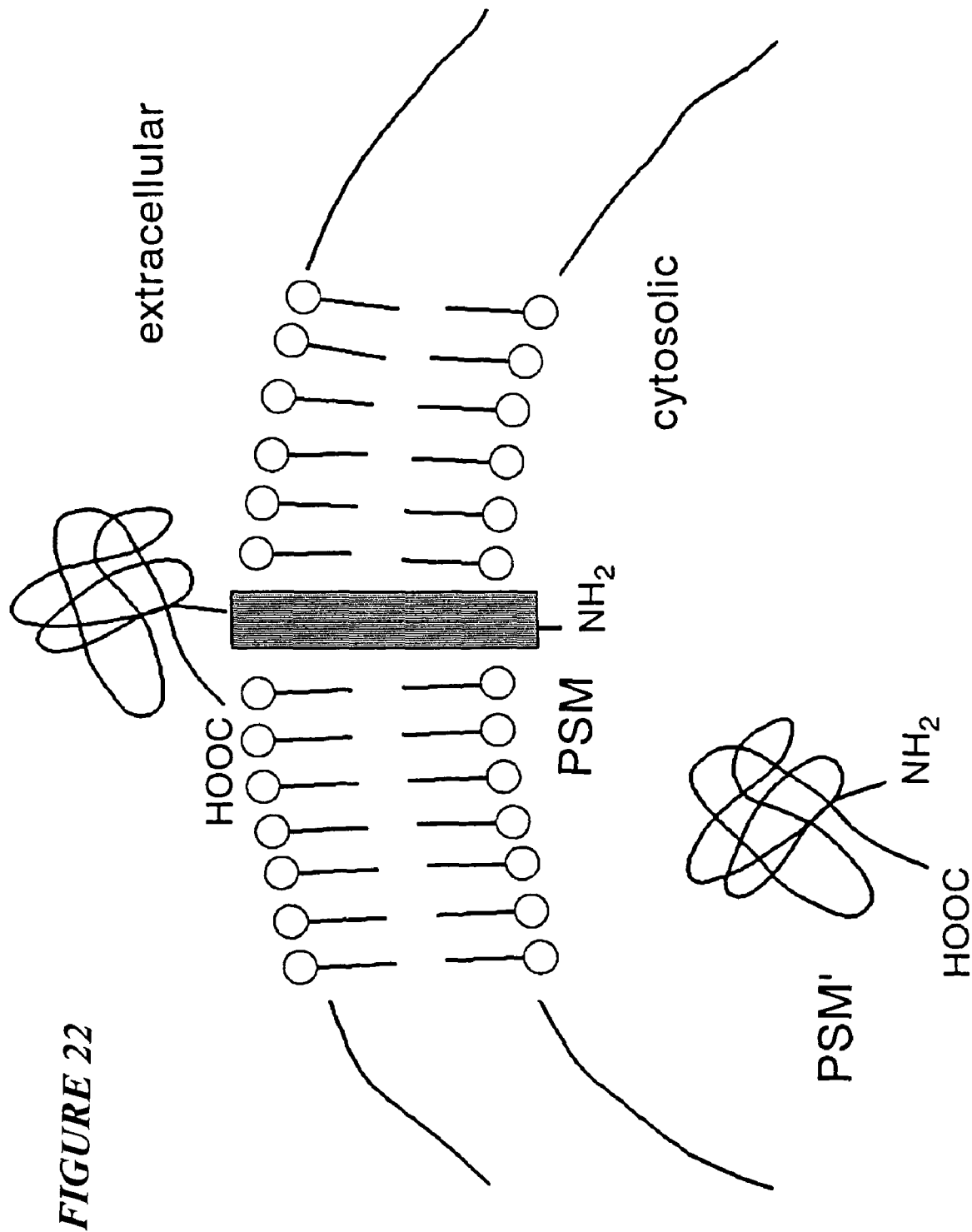

FIG. 22: Characterization of PSM membrane bound and PSM' in the cytosol.

Figure 23:
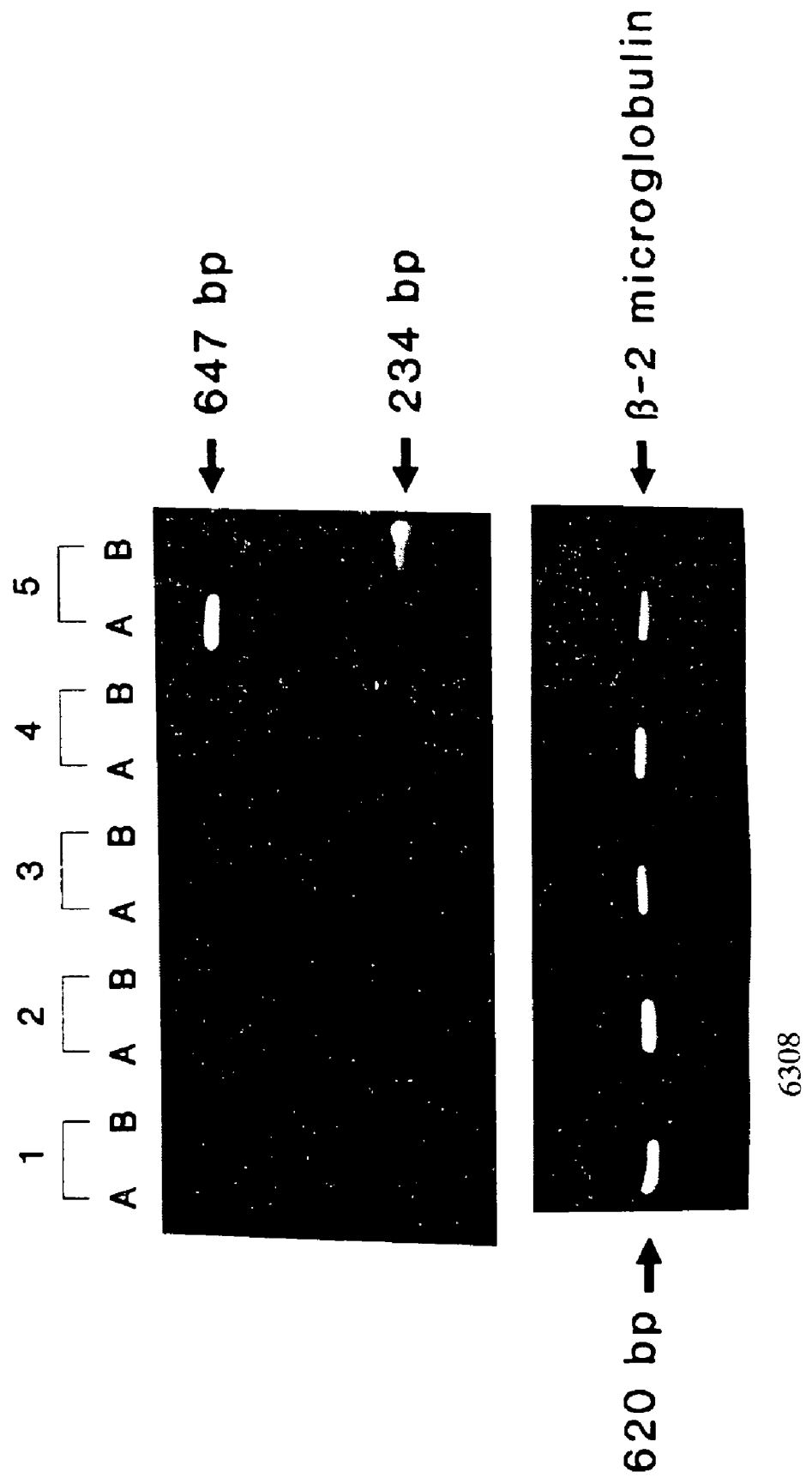

FIG. 23: Photograph of ethidium bromide stained gel depicting representative negative and positive controls used in the study. Samples 1-5 were from, respectively: male with prostatis, a healthy female volunteer, a male with BPH, a control 1:1,000,000 dilution of LNCaP cells, and a patient with renal cell carcinoma. Below each reaction is the corresponding control reaction performed with beta-2-microglobulin primers to assure RNA integrity. No PCR products were detected for any of these negative controls.

Figure 24:
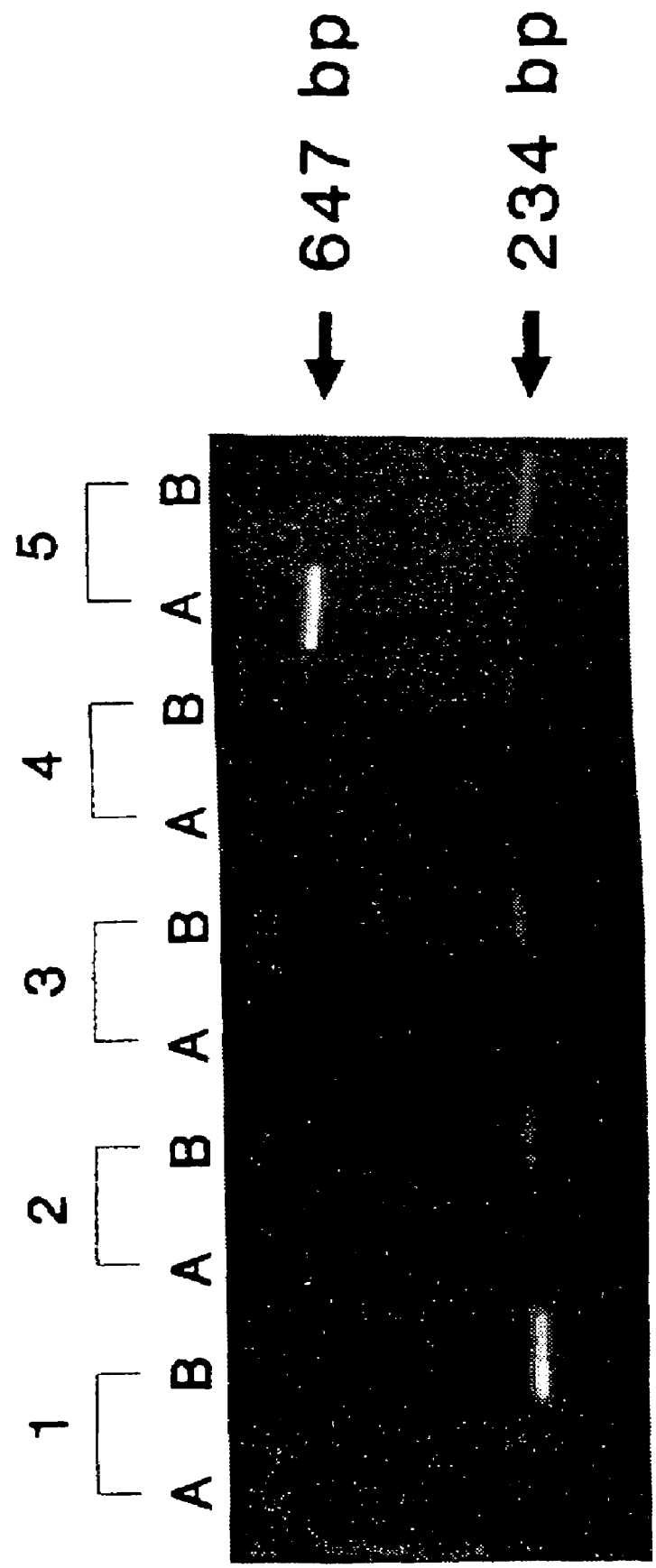

FIG. 24: Photograph of gel displaying representative positive PCR results using PSM primers in selected patients with either localized or disseminated prostate cancer. Sample 1-5 were from. respectively: a patient with clinically localized stage T1$_c$ disease, a radical prostatectomy patient with organ confined disease and a negative serum PSA, a radical prostatectomy patient with locally advanced disease and a negative serum PSA, a patient with treated stage D2 disease, and a patient with treated hormone refractory disease.

Figure 25:
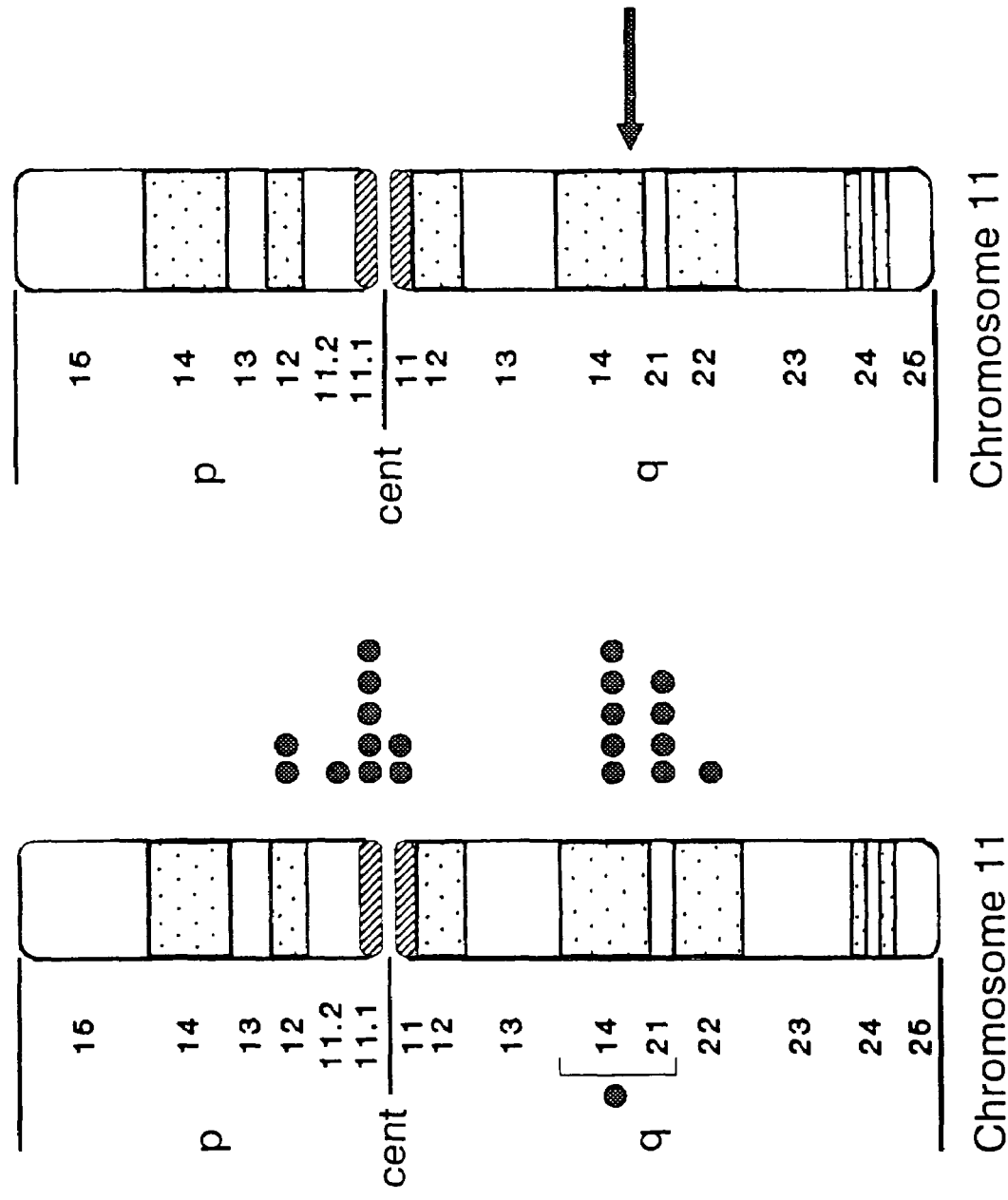

FIG. 25: Chromosomal location of PSM based on in-situ hybridization with cDNA and with genomic cosmids.

Figure 26:
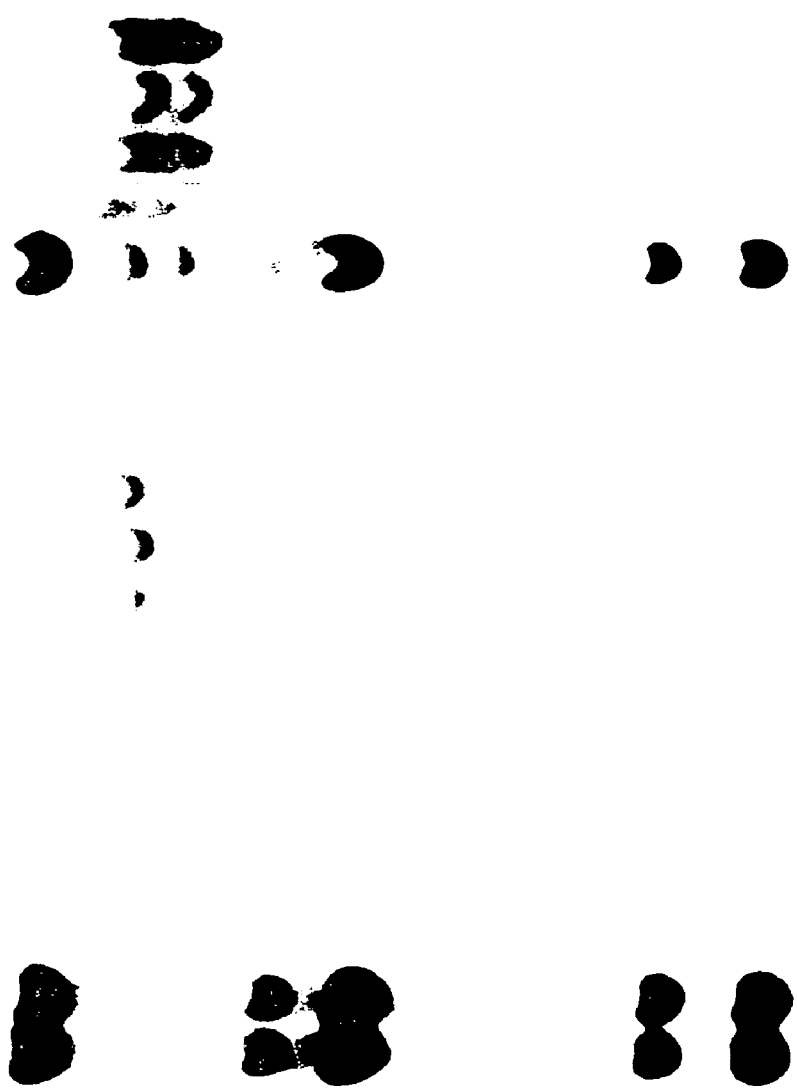

FIG. 26: Human monochromosomal somatic cell hybrid blot showing that chromosome 11 contained the PSM genetic sequence by Southern analysis. DNA panel digested with PstI restriction enzyme and probed with PSM cDNA. Lanes M and H refer to mouse and hamster DNAs. The numbers correspond to the human chromosomal DNA in that hybrid.

Figure 27:
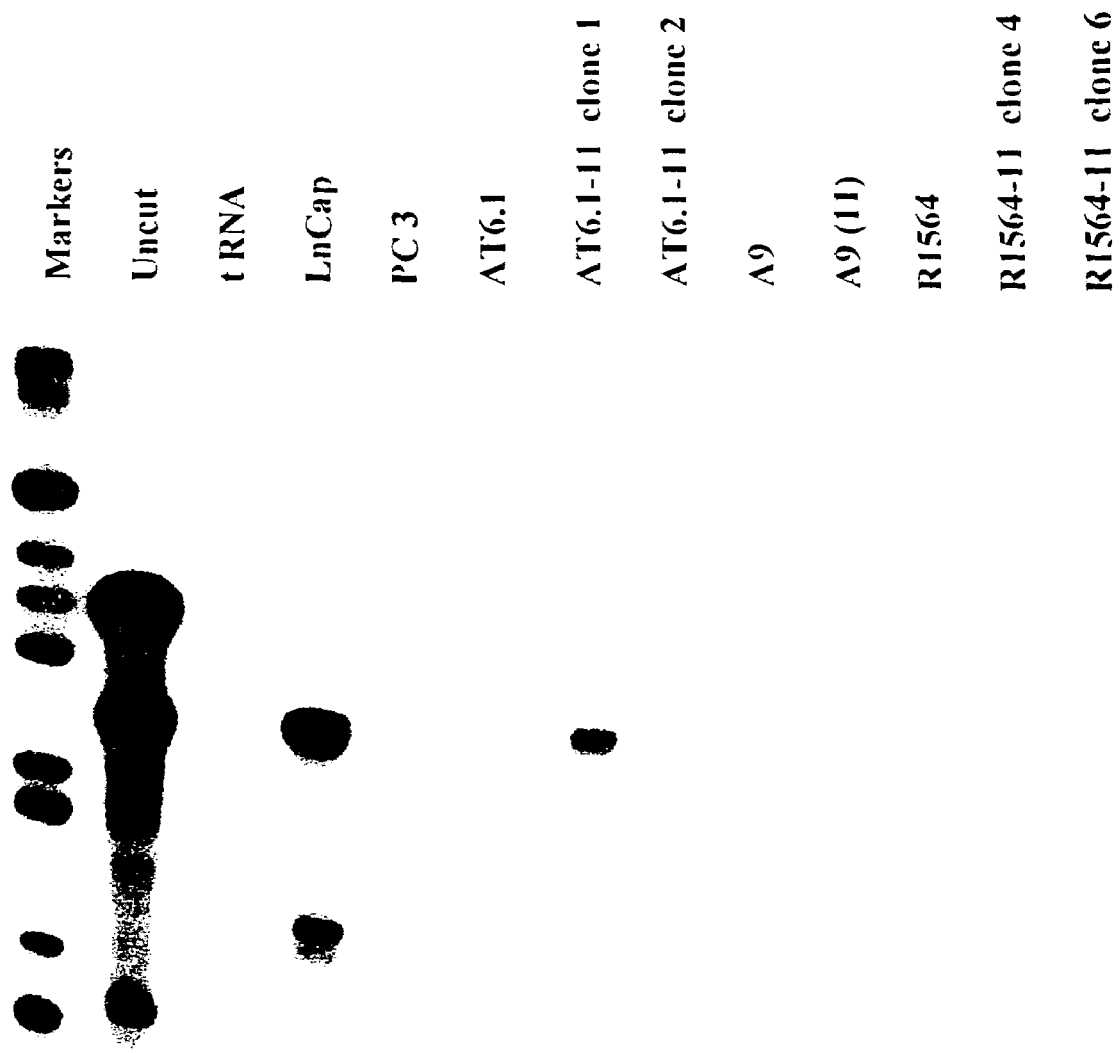

FIG. 27: Ribonuclease protection assay using PSM radiolabeled RNA probe revels an abundant PSM mRNA expression in AT6.1-11 clone 1, but not in AT6.1-11 clone 2, thereby mapping PSM to 11p11.2-13 region.

FIG. 28: Tissue specific expression of PSM RNA by Northern blotting and RNAse protection assay.

Figure 29:
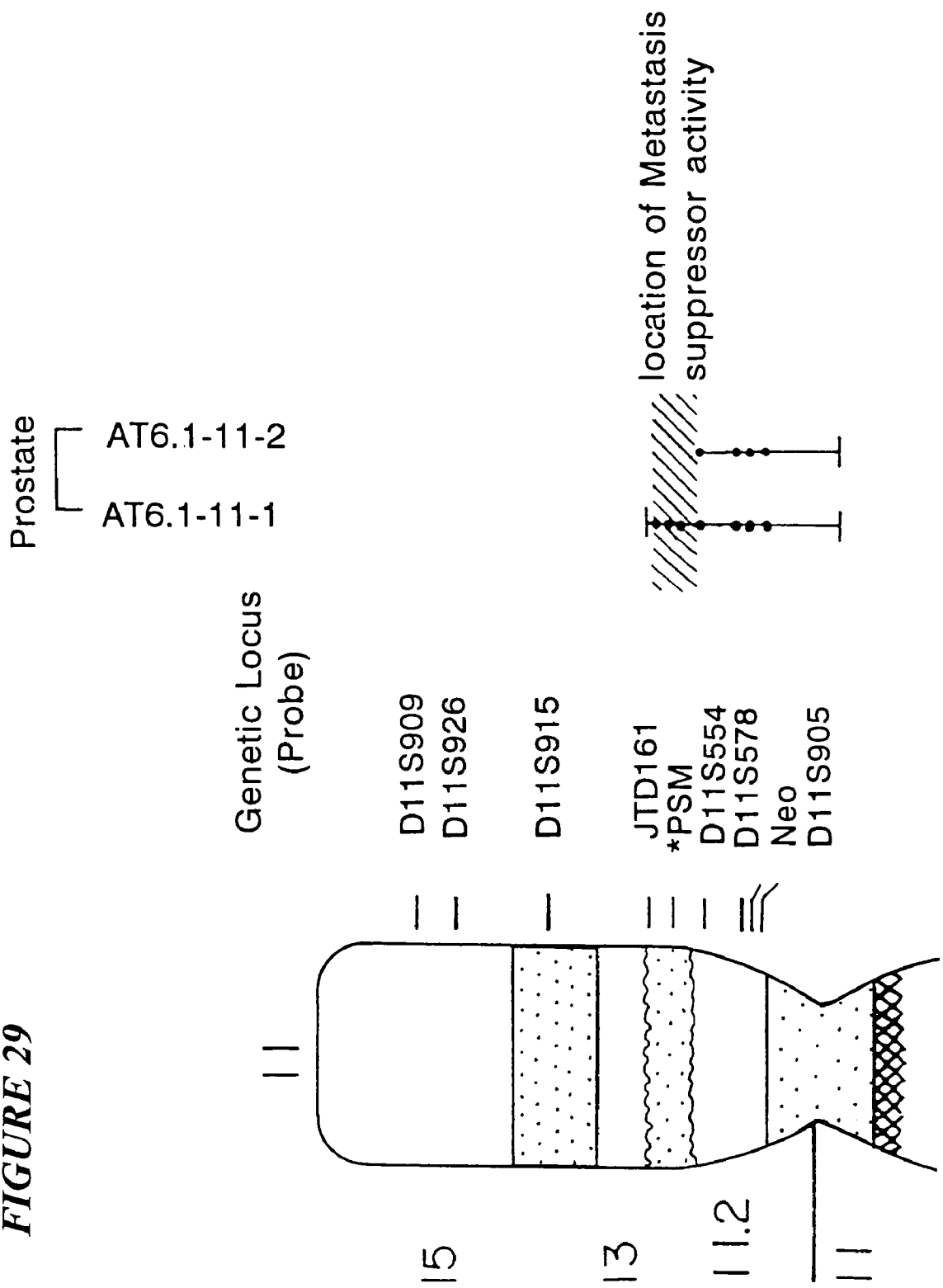

FIG. 29: Mapping of the PSM gene to the 11p11.2-p13 region of human chromosome 11 by southern blotting and in-situ hybridization.

Figures 30, 55:
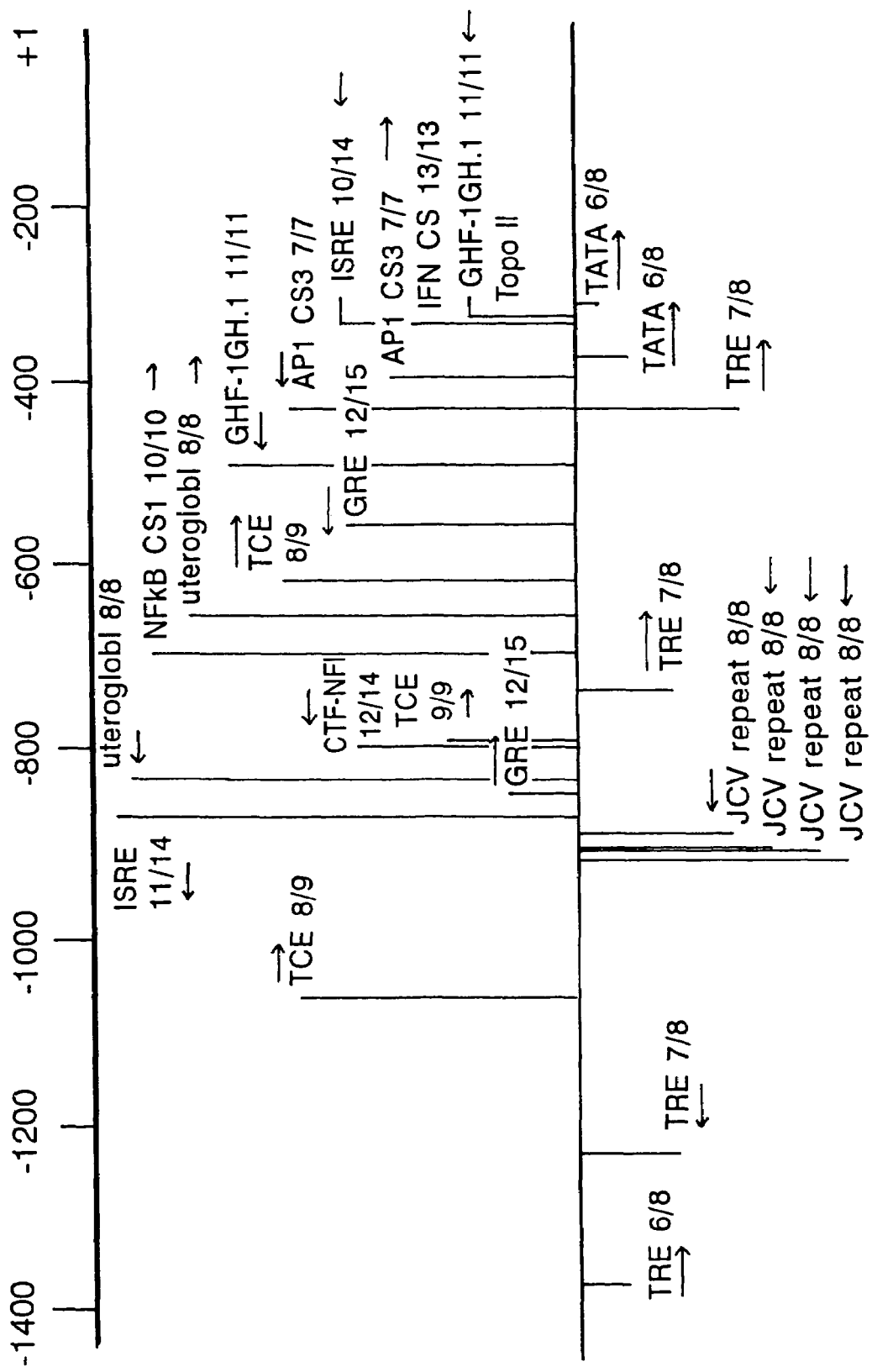

FIG. 30: Schematic of potential response elements.

Figure 31:
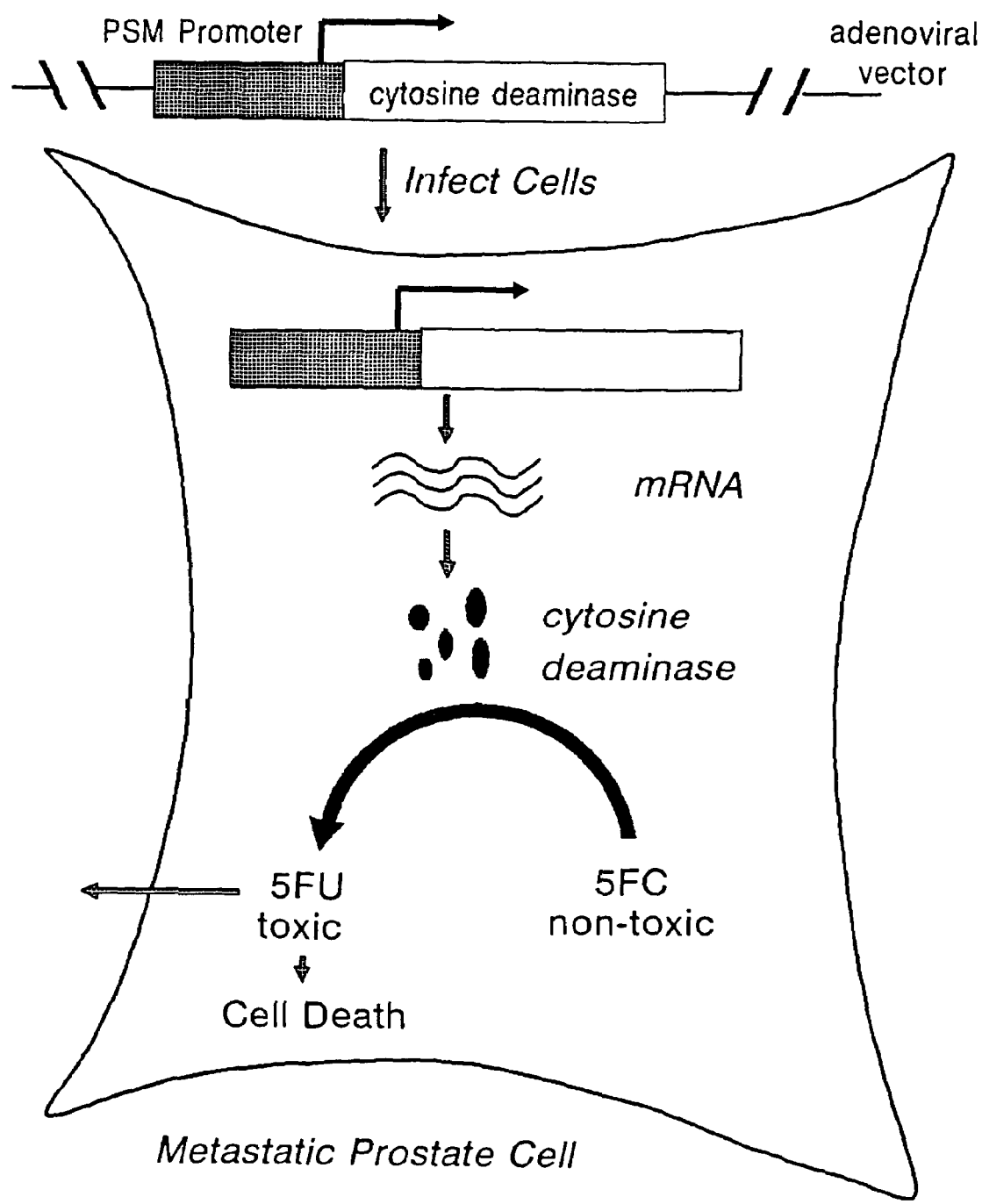

FIG. 31: Schematic depiction of metastatic prostate cell transfected with promoter for PSM which is driving expression of prodrug activating enzyme cytosine deaminase. This allows for prostate specific expression and tumor localized conversion of non-toxic 5 fluorocytosine to 5 flurouracil.

FIG. 32A-32C: Nucleic Acid of PSM genomic DNA is read 5 prime away from the transcription start site: the number on the sequences indicates the nucleotide upstream from the start site. Therefore, nucleotide #121 is actually –121 using the conventional numbering system (SEQ ID NO: 39).

FIG. 33: Representation of NAAG 1, acividin, azotomycin, and 6-diazo-5-oxo-norleucine, DON.

Figure 34:
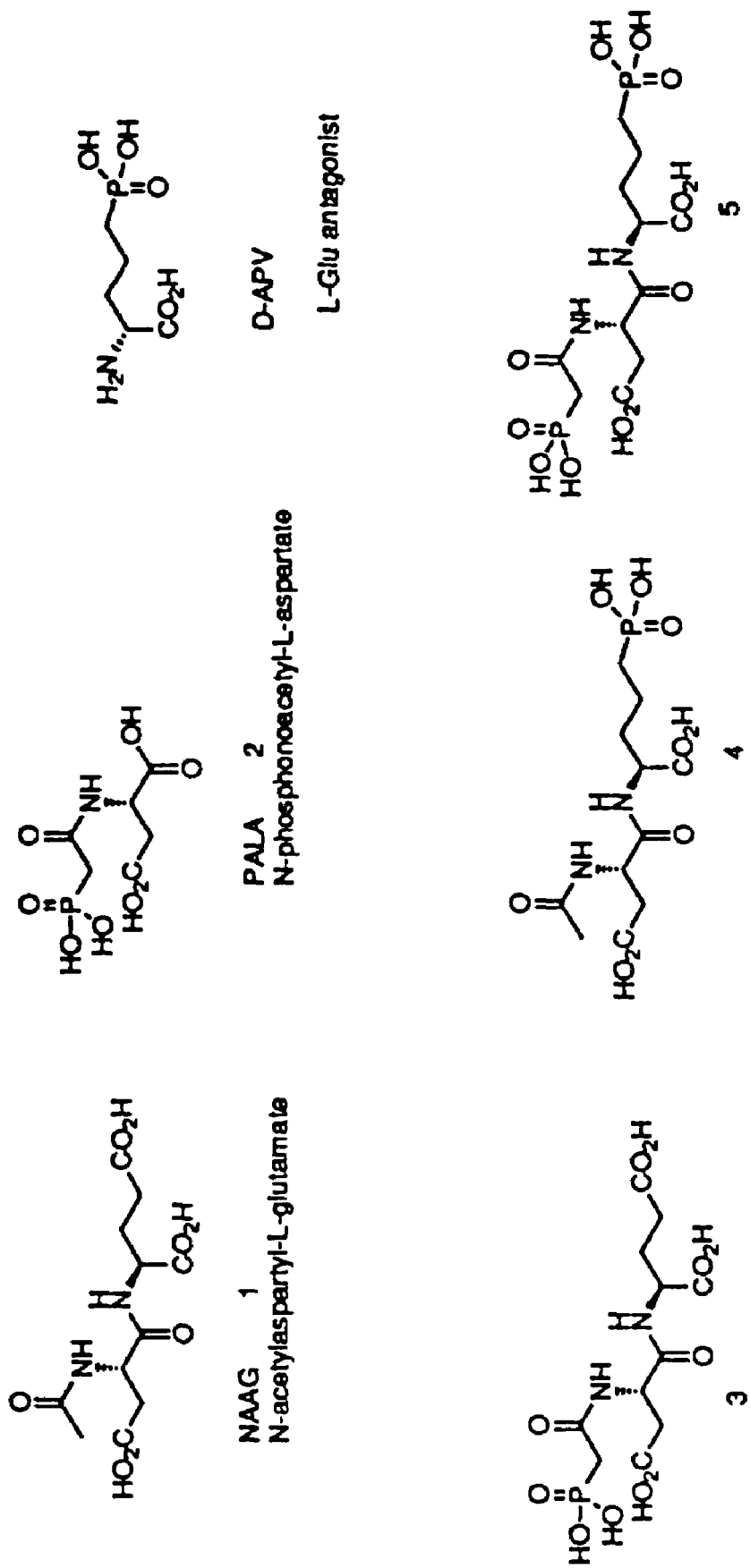

FIG. 34: Representation of N-acetylaspartylglutamate (NAAG), PALA, PALAGLU, phosphonate antagonist of glutamate receptor and phosponates of PALAGLU and NAAG.

Figure 35:
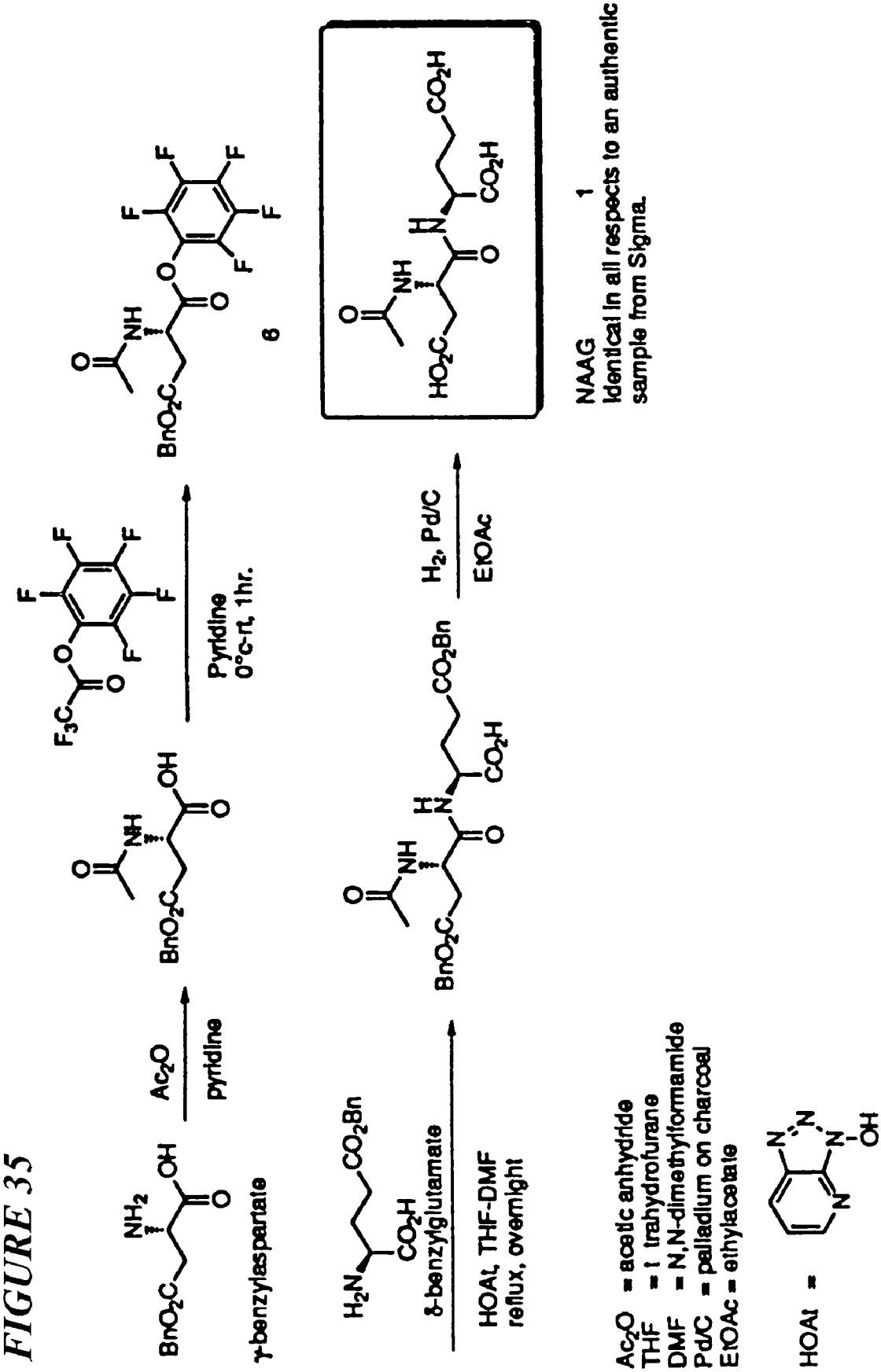

FIG. 35: Synthesis of N-acetylaspartylglutamate, NAAG 1.

Figure 36:
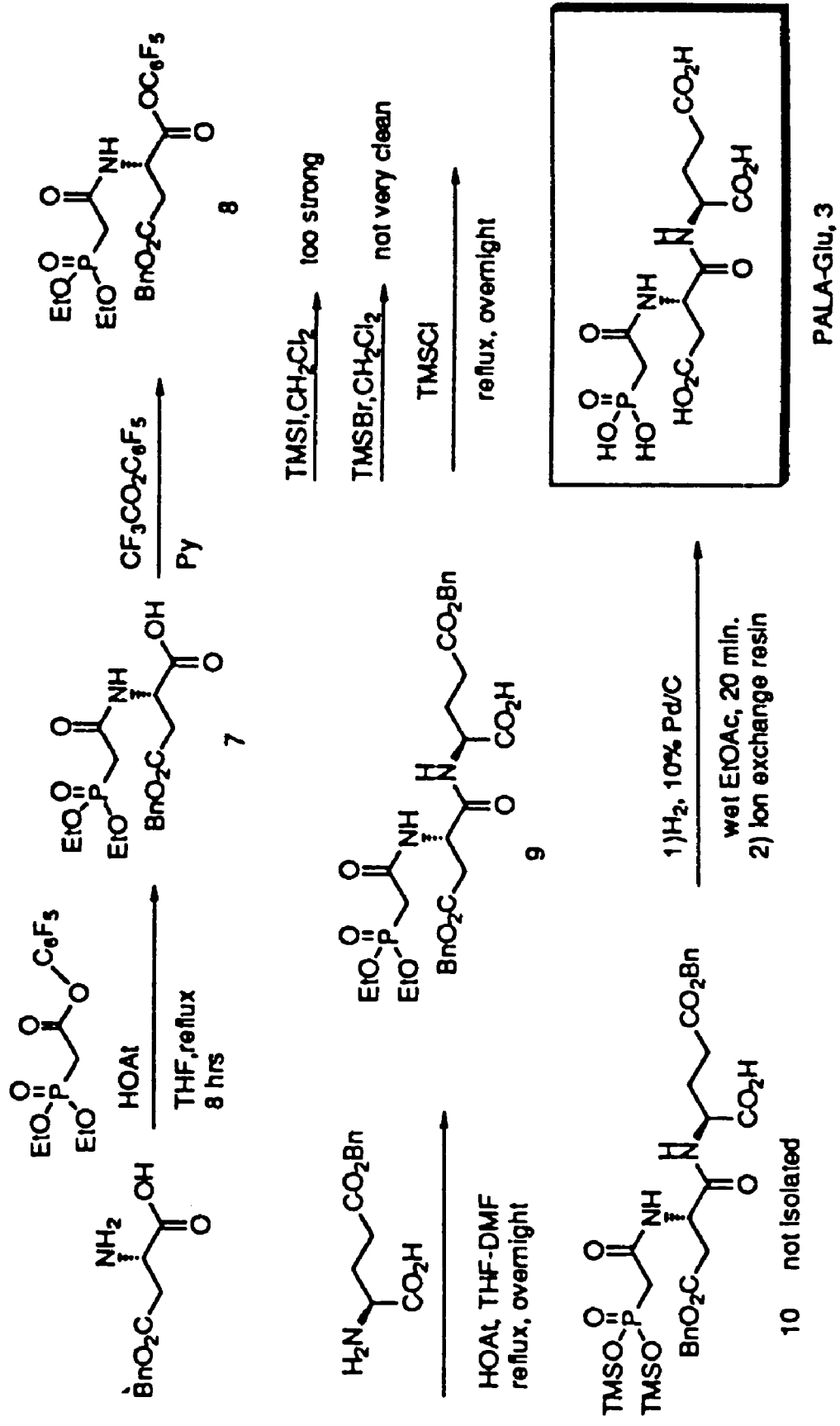

FIG. 36: Synthesis of N-phosphonoacetylaspartyl-L-glutamate.

Figure 37:
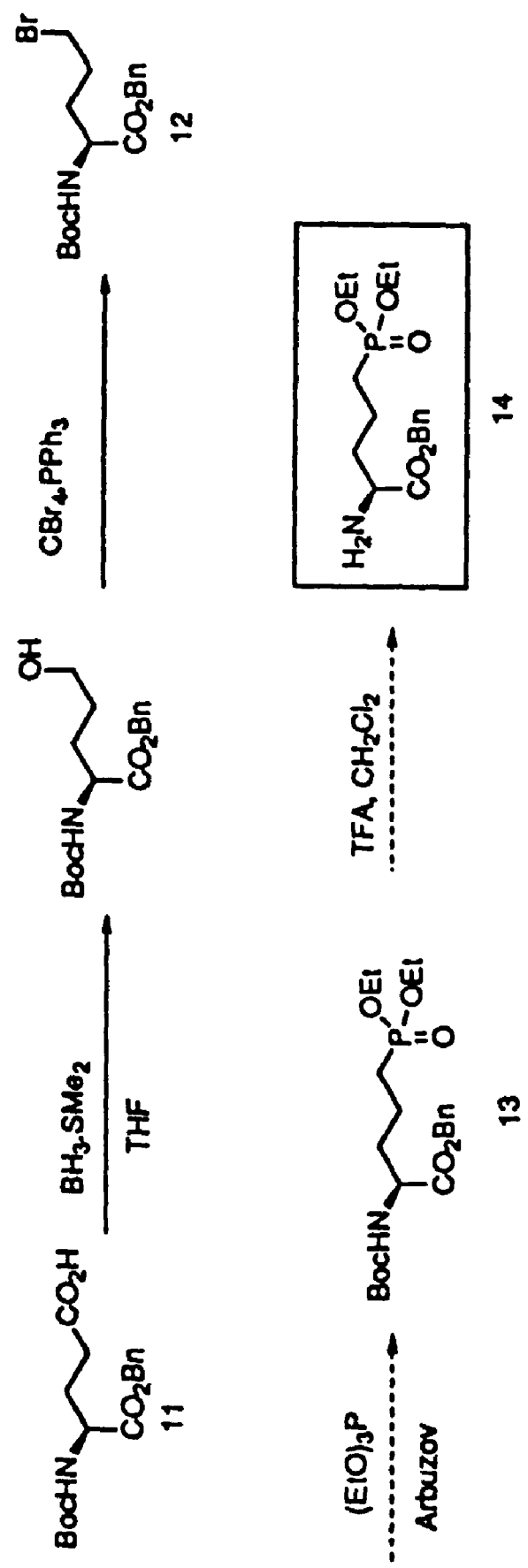

FIG. 37: Synthesis of 5-diethylphosphonon-2 amino benzylvalerate intermediate.

Figure 38:
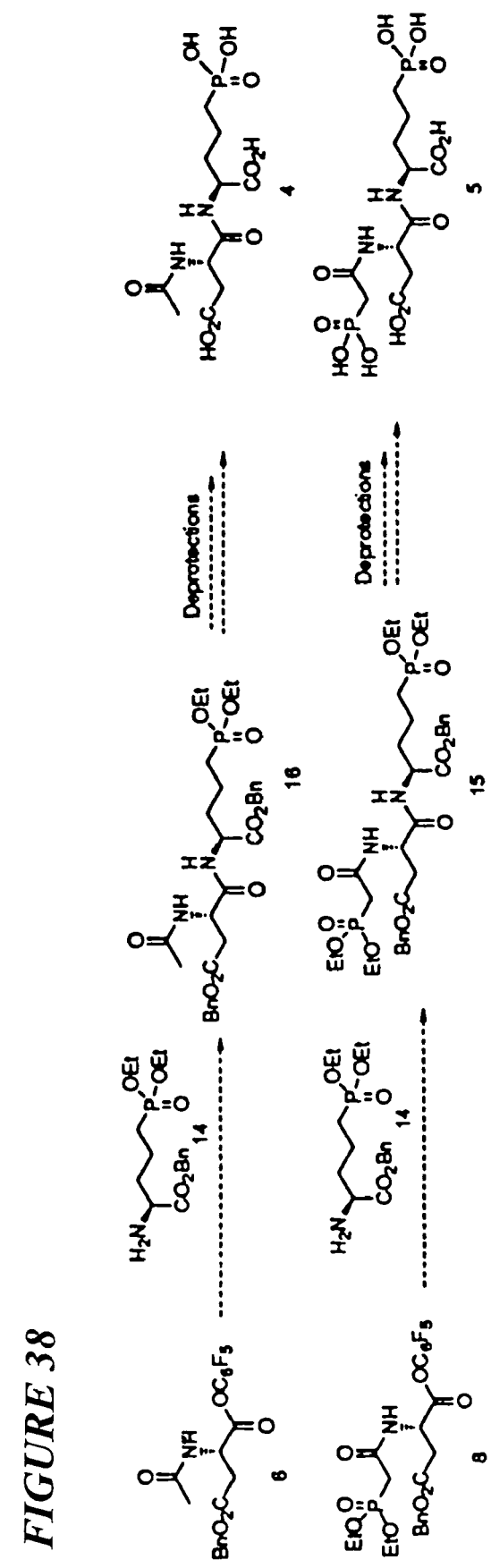

FIG. 38: Synthesis of analog 4 and 5.

Figure 39:
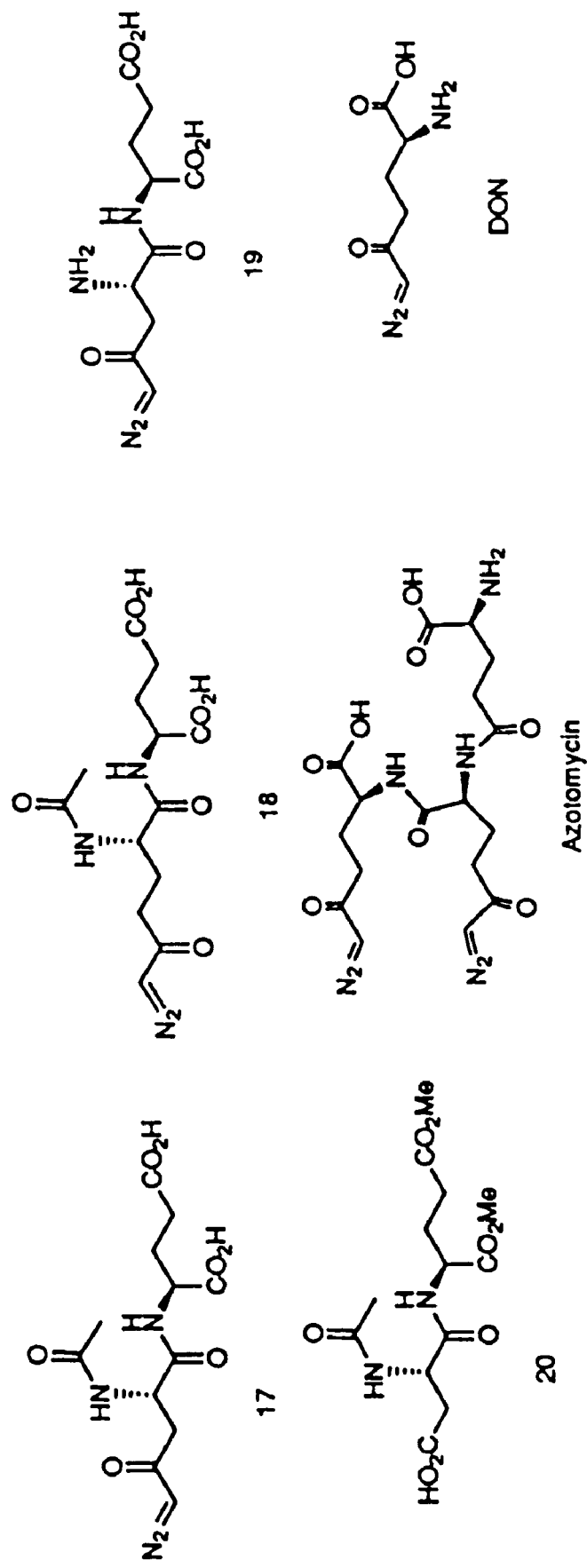

FIG. 39: Representation of DON, analogs 17-20.

FIG. 40: Substrates for targeted drug delivery, analog 21 and 22.

Figure 41:
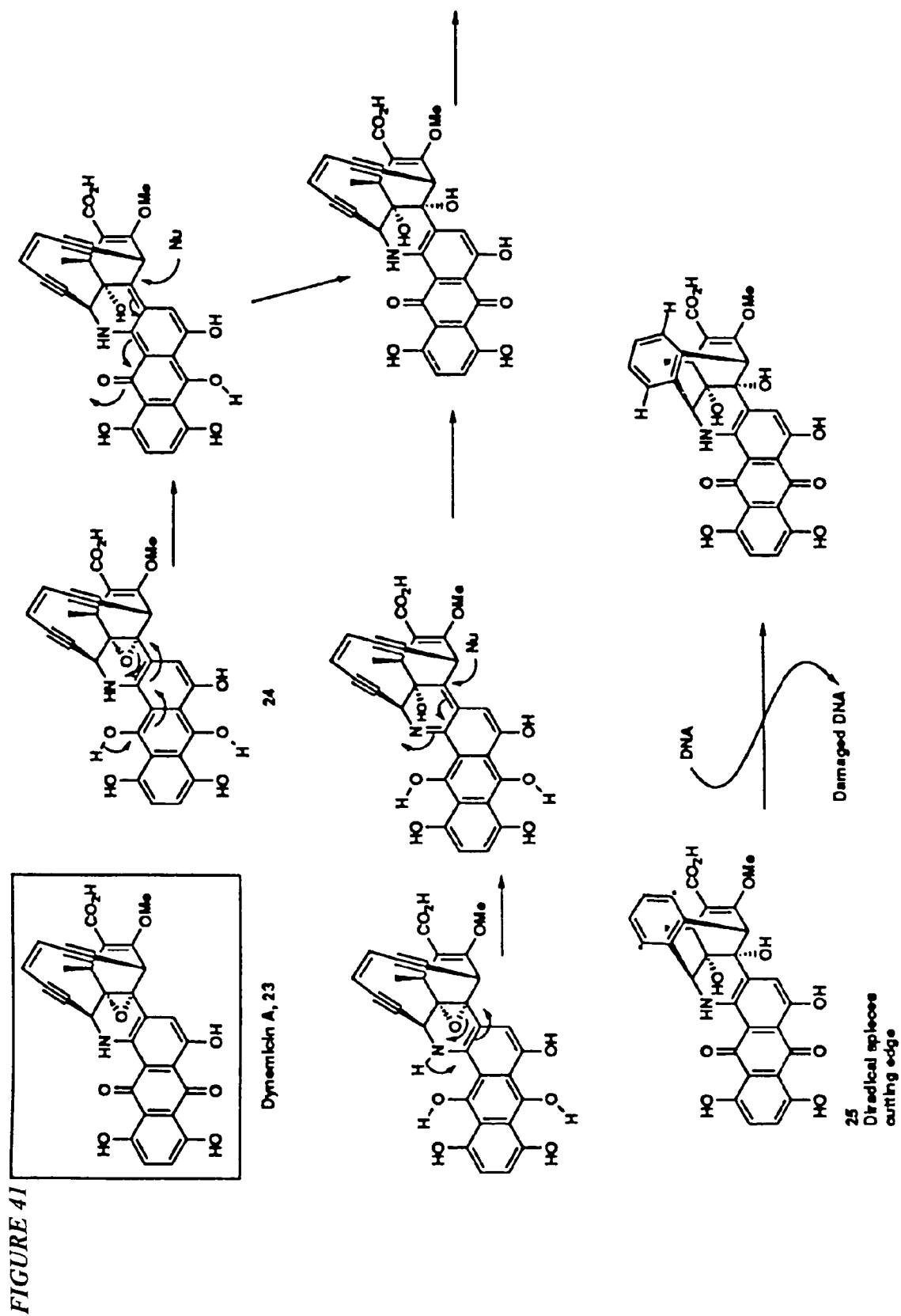

FIG. 41: Dynemycin A and its mode of action.

FIG. 42: Synthesis of analog 28.

Figure 43:
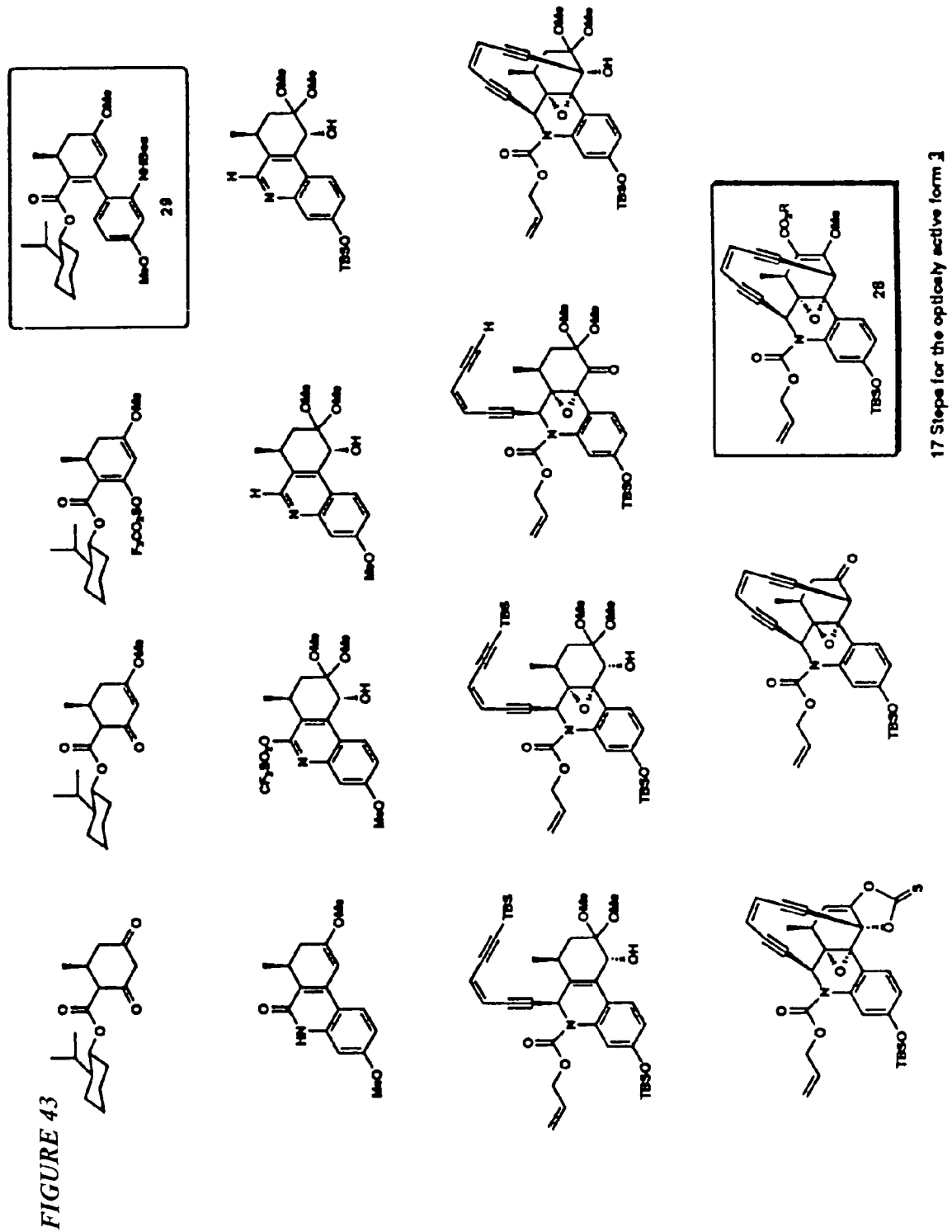

FIG. 43: Synthesis for intermediate analog 28.

Figure 44:
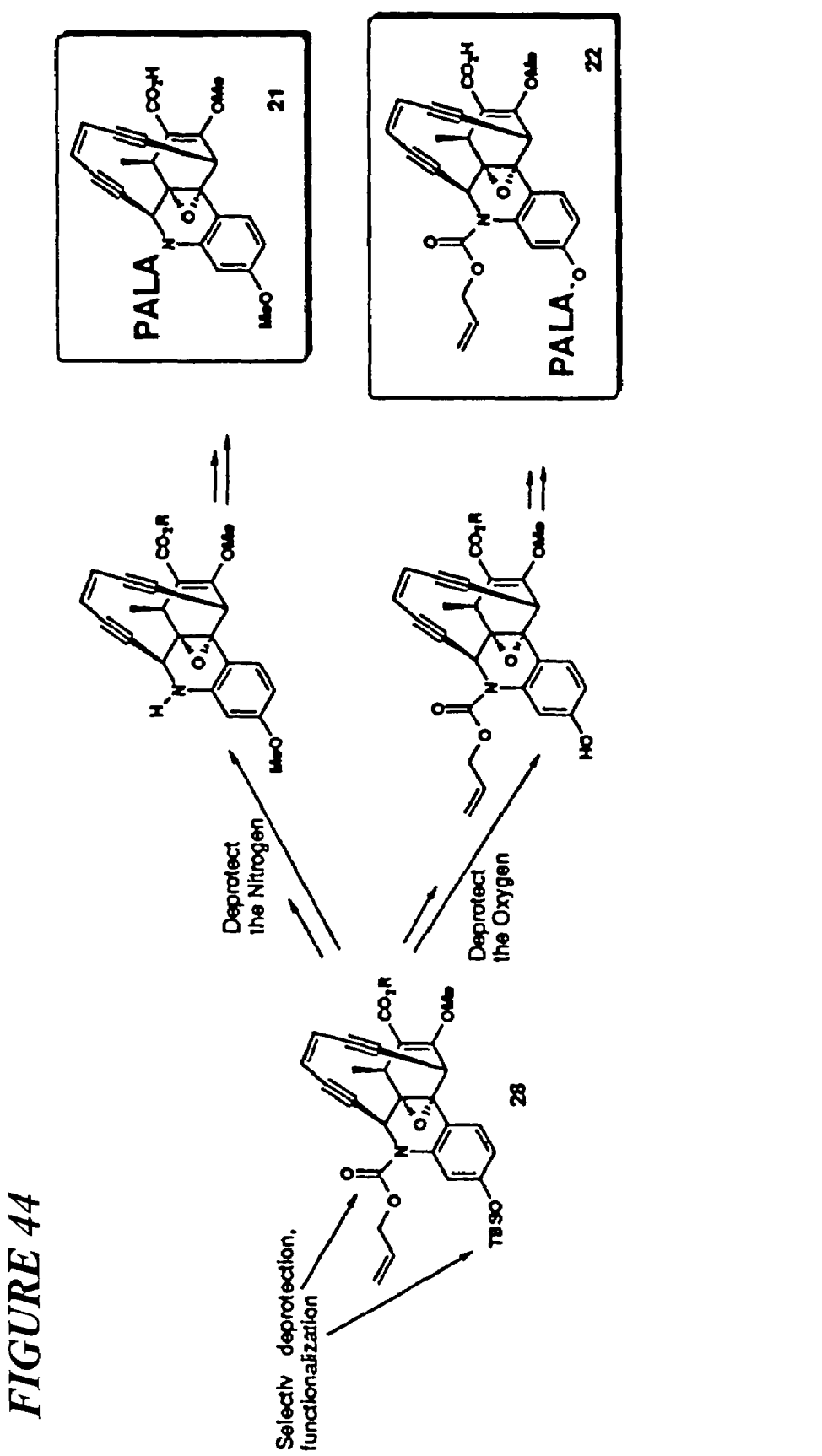

FIG. 44: Attachment points for PALA.

Figure 45:
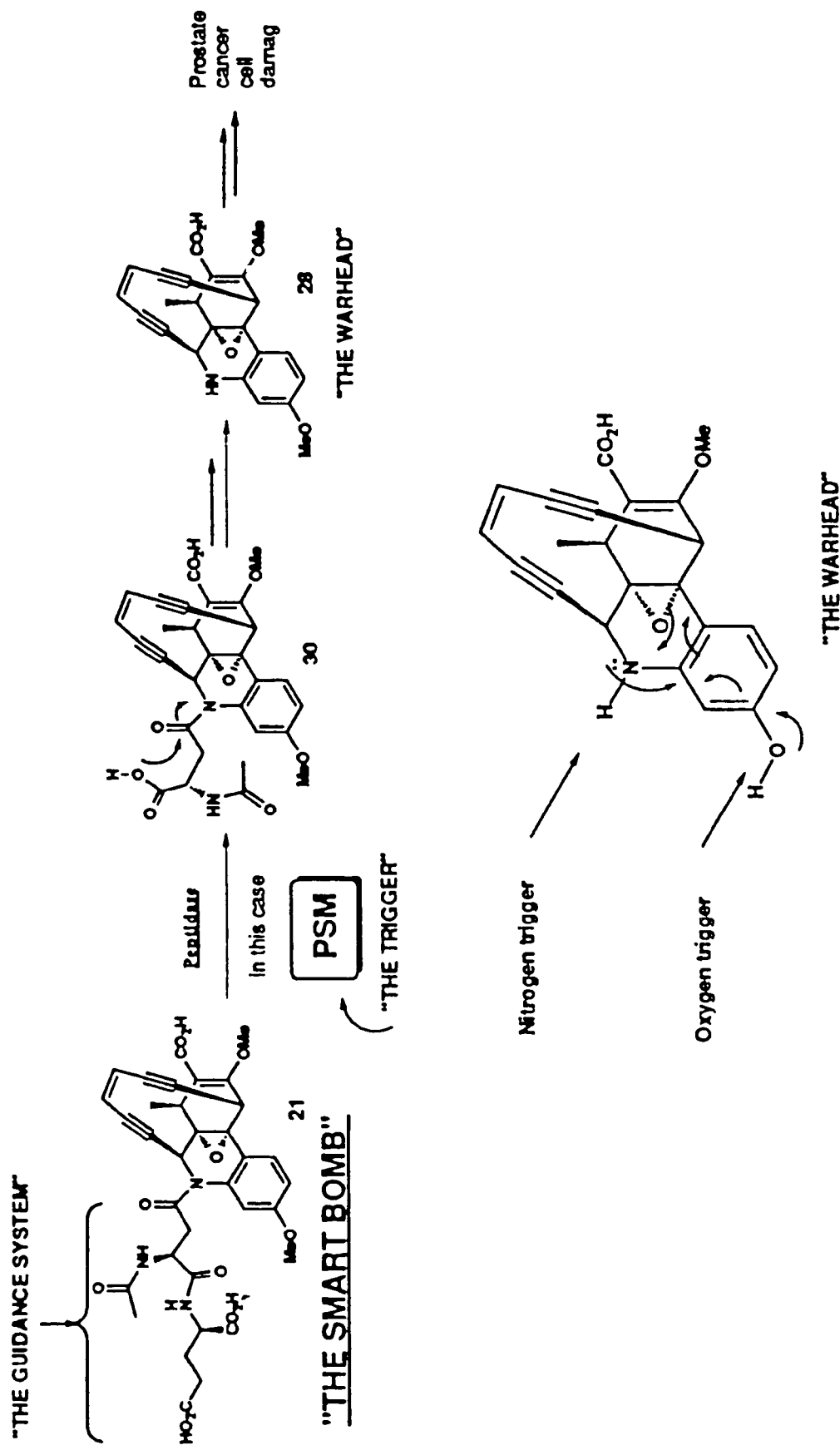

FIG. 45: Mode of action for substrate 21.

FIG. 46A-46D: Intron 1F: Forward sequence (SEQ ID NO: 92).

FIG. 47A-47E: Intron 1R: Reverse Sequence (SEQ ID NO: 93).

FIG. 48A-48C: Intron 2F: Forward Sequence (SEQ ID NO: 94).

FIG. 49A-49C: Intron 2R: Reverse Sequence (SEQ ID NO: 95).

FIG. 50A-50B: Intron 3F: Forward Sequence (SEQ ID NO: 96).

FIG. 51A-51B: Intron 3R: Reverse Sequence (SEQ ID NO: 97).

FIG. 52A-52C: Intron 4F: Forward Sequence (SEQ ID NO: 98).

FIG. 53A-53E: Intron 4RF: Reverse Sequence (SEQ ID NO: 99).

Figure 54:
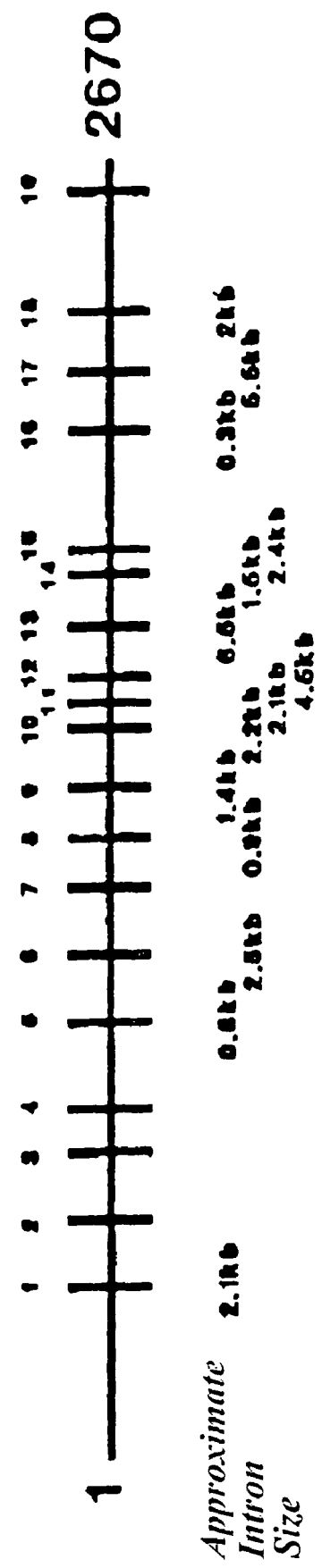

FIG. 54: PSM genomic organization of the exon and 19 intron junction sequences (SEQ ID NO: 39).

The exon/intron junctions are as follows:
1. Exon/intron 1 at bp 389-390;
2. Exon/intron 2 at bp 490-491;
3. Exon/intron 3 at bp 681-682;
4. Exon/intron 4 at bp 784-785;
5. Exon/intron 5 at bp 911-912;
6. Exon/intron 6 at bp 1096-1097;
7. Exon/intron 7 at bp 1190-1191;
8. Exon/intron 8 at bp 1289-1290;
9. Exon/intron 9 at bp 1375-1376;
10. Exon/intron 10 at bp 1496-1497;
11. Exon/intron 11 at bp 1579-1580;
12. Exon/intron 12 at bp 1643-1644;
13. Exon/intron 13 at bp 1710-1711;
14. Exon/intron 14 at bp 1803-1804;
15. Exon/intron 15 at bp 1894-1895;
16. Exon/intron 16 at bp 2158-2159;
17. Exon/intron 17 at bp 2240-2241;
18. Exon/intron 18 at bp 2334-2335;
19. Exon/intron 19 at bp 2644-2645.

FIG. 55A-55J: Alternatively spliced PSM (PSM') nucleic acid sequence (SEQ ID NO: 100) and amino acid sequence (SEQ ID NO:101).

Figure 56:
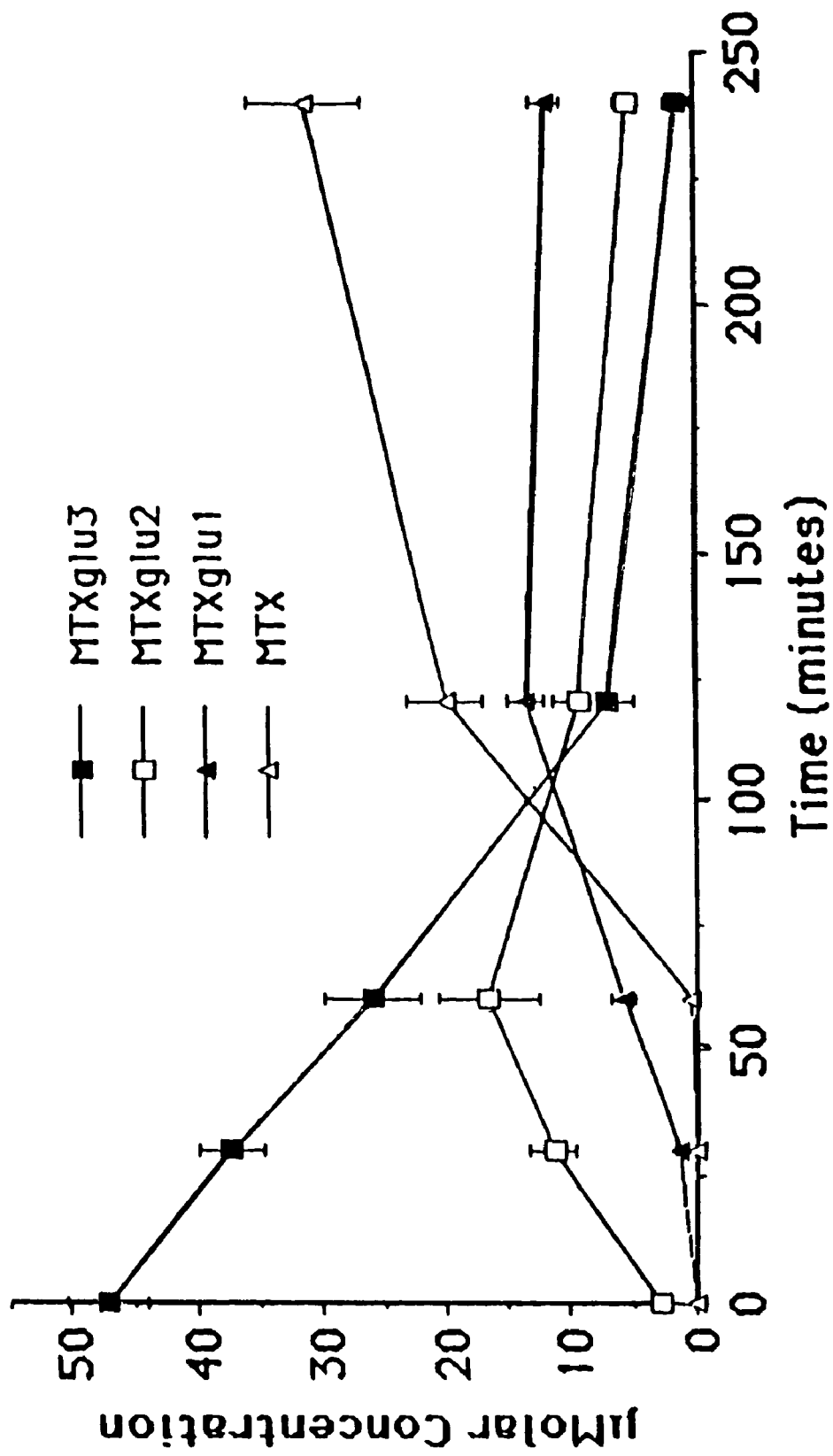

FIG. 56: PSM pteroyl (folate) hydrolase activity in LNCaP membrane preparation. Time course of MTXglu$_3$ hydrolysis (-■-) and concurrent formation of MTXglu$_2$ (- -), MTXglu$_1$ (-▲-), and MTX (- -), respectively. Membrane fractions were prepared as described in Methods. Reaction volume was 100 μL containing 50 mM acetate/Triton buffer pH 4.5, 50 μM MTXglu$_3$, 10 μg/mL protein. Values are x±S.D. from three separate LNCaP membrane preparations.

Figure 57:
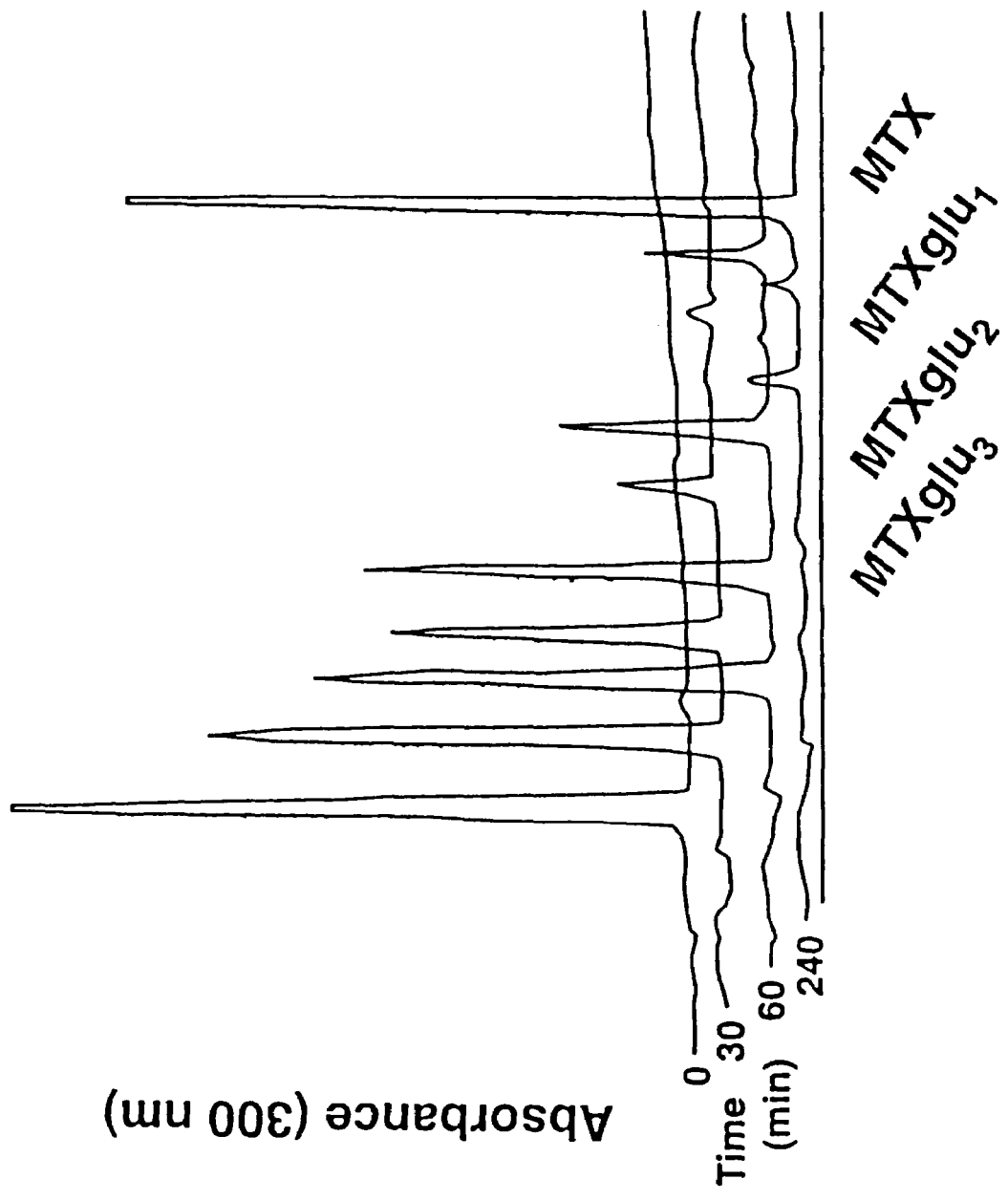

FIG. 57: PSM pteroyl (folate) hydrolase activity of immunoprecipitated PSM antigen.

Diagram shows typical capillary electrophoretic separation patterns of MTXglu$_{(n)}$ derivatives at 0, 30, 60 and 240 minute reaction times. Elution intervals for MTXglu$_3$, MTXglu$_2$, MTXglu$_1$, and MTX are 4.25, 3.95, 3.55, and 3.06 min, respectively. Total volume of reaction mixture was 100 uL containing 50 uM MTXglu$_3$.

Figure 58:
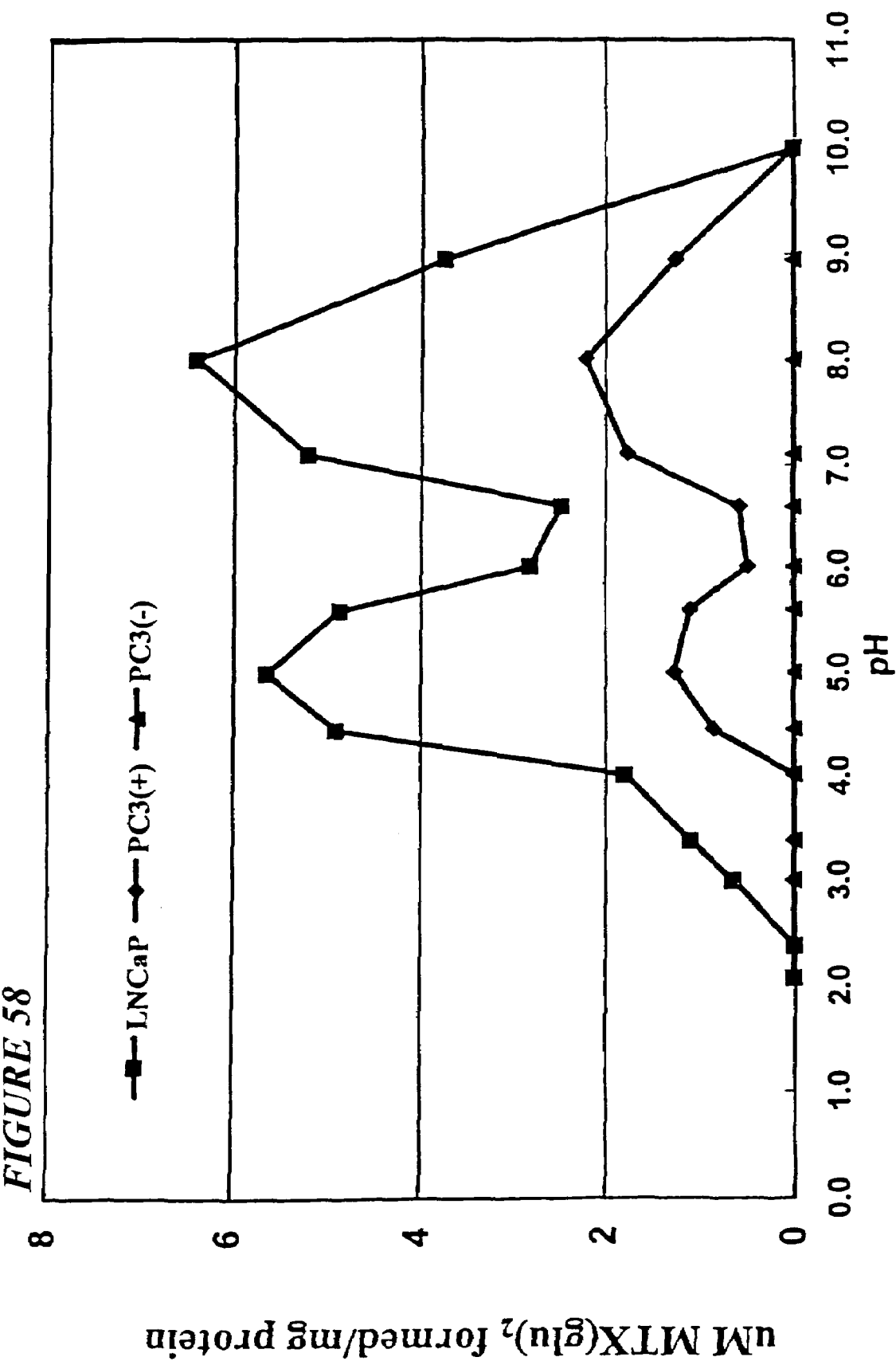

FIG. 58: Effects of pH on gamma-glutamyl hydrolase (PSM hydrolase) activity in. LNCaP, PC-3 PSM-transfected (PC-3(+)) and PSM non-transfected (PC-3(−)) cells. Enzymic activity is reported as μM MTXglu$_2$ formed/mg protein. Each value represents the mean of 3 reactions containing 50-60 μg/mL protein. The following buffers were used in 50 mM concentrations spanning a pH range of 2 to 10: glycine-HCl, pH 2.2 to 3.6; acetate, pH 3.6 to 5.6; 2-(N-morpholino) ethanesulfonic acid (MES), pH 5.6 to 6.8; Tris (hydroxymethyl) aminomethane (TRIS), pH 7 to 8.5; and glycine-NaOH, pH 8.6 to 10.0.

Figure 59:
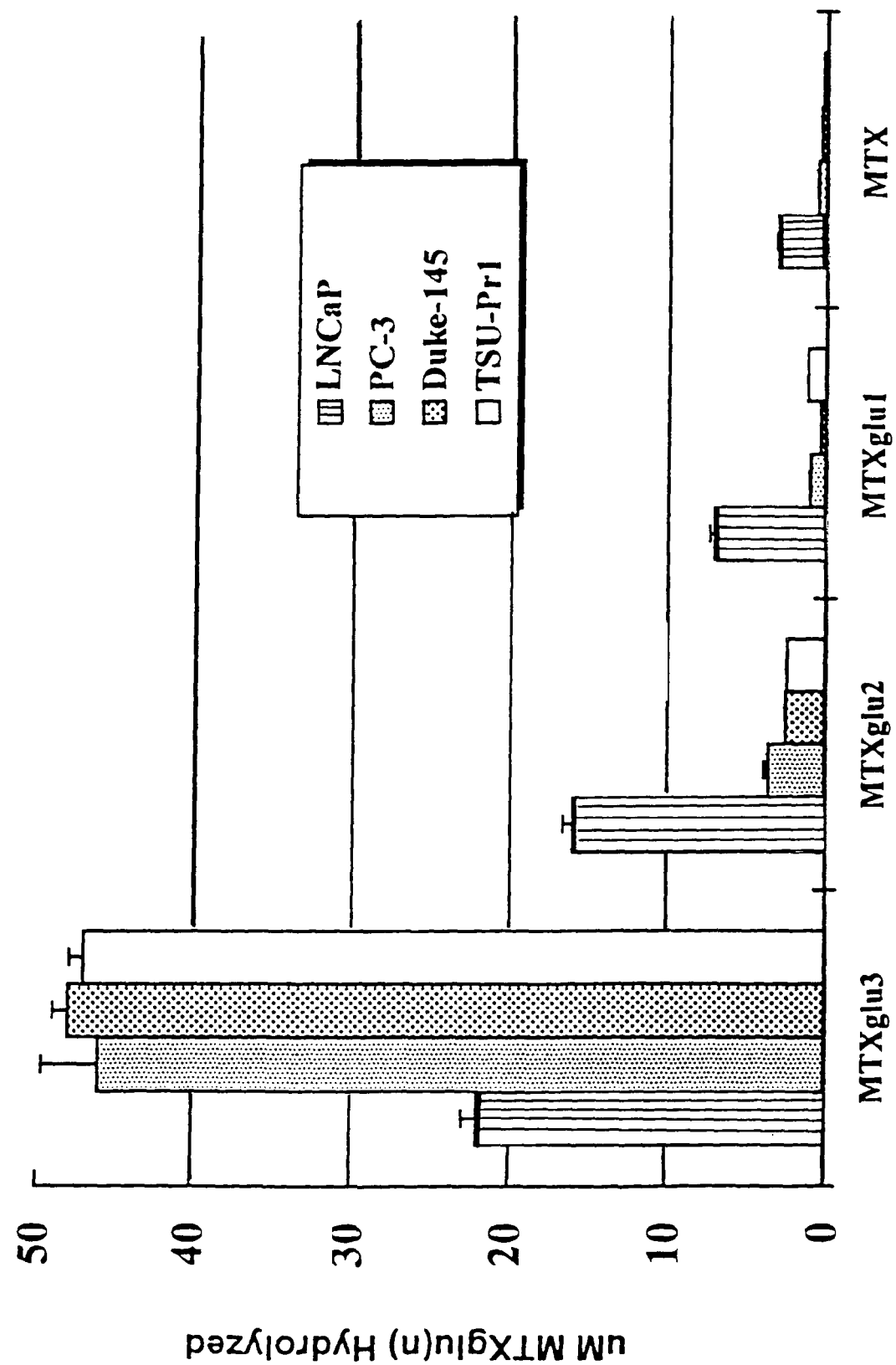

FIG. 59: Comparison of pteroyl hydrolase activity in membranes isolated from LNCaP, PC-3, TSU-Pr1, and Duke-145 adenocarcinoma cell lines. Membranes were isolated as described in Methods. Each value represents the mean of triplicate reactions normalized to 1 mg/mL protein.

Figure 60A:
Figure 60B:
Figure 60C:
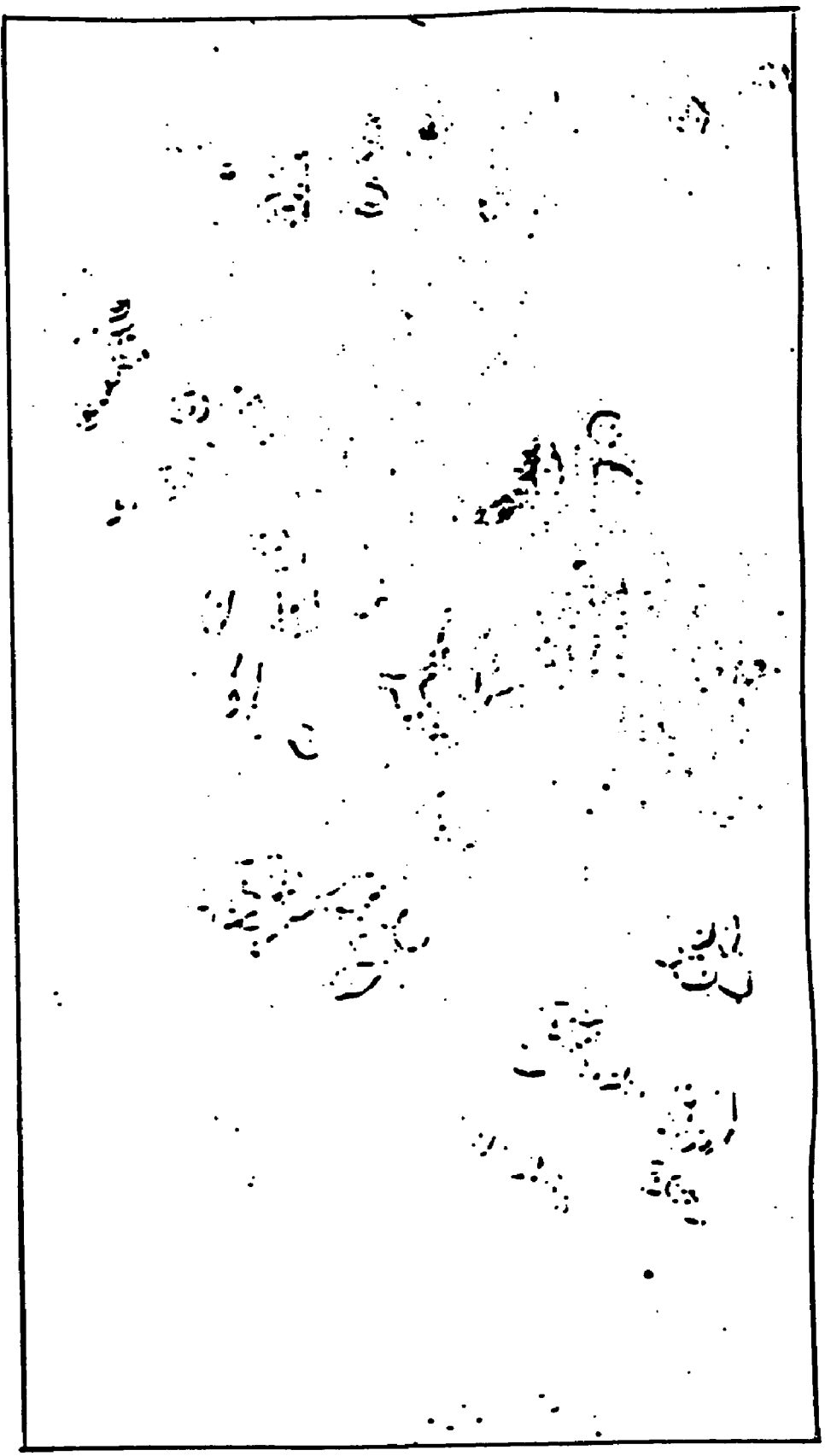

FIG. 60A-60C: Immunohistochemical analysis of LNCaP and PC-3 PSM-transfected and PSM-non-transfected cells. A 2.65 kb PSM cDNA containing a hygromycin selection vector was cloned into non PSM-antigen expressing PC-3 cells and maintained in regular media supplemented with hygromycin B. As a control, PC-3 cells were also transfected with the pREP7 vector alone (PC-3 PSM non-transfected cells). Cells were permeabilized in acetone/methanol (1:1 v/v) mixture, blocked with 5% bovine serum albumin/Tris buffered saline (TBS) and the 7E11-C5 monoclonal PSM antibody was added to cells. A secondary anti-mouse IgG$_1$ antibody conjugated with alkaline phosphatase was added and PSM-positive cell staining performed with bromochloroindolylphenol phosphate. Panel A demonstrates intense immunoreactivity associated with LNCaP cells using the monoclonal PSM antibody; In panel B, comparable staining occurs in PC-3 cells transfected with PSM expression vector. Panel C illustrates PC-3 cells expressing pREP7 hygromycin vector alone.

Figure 61:
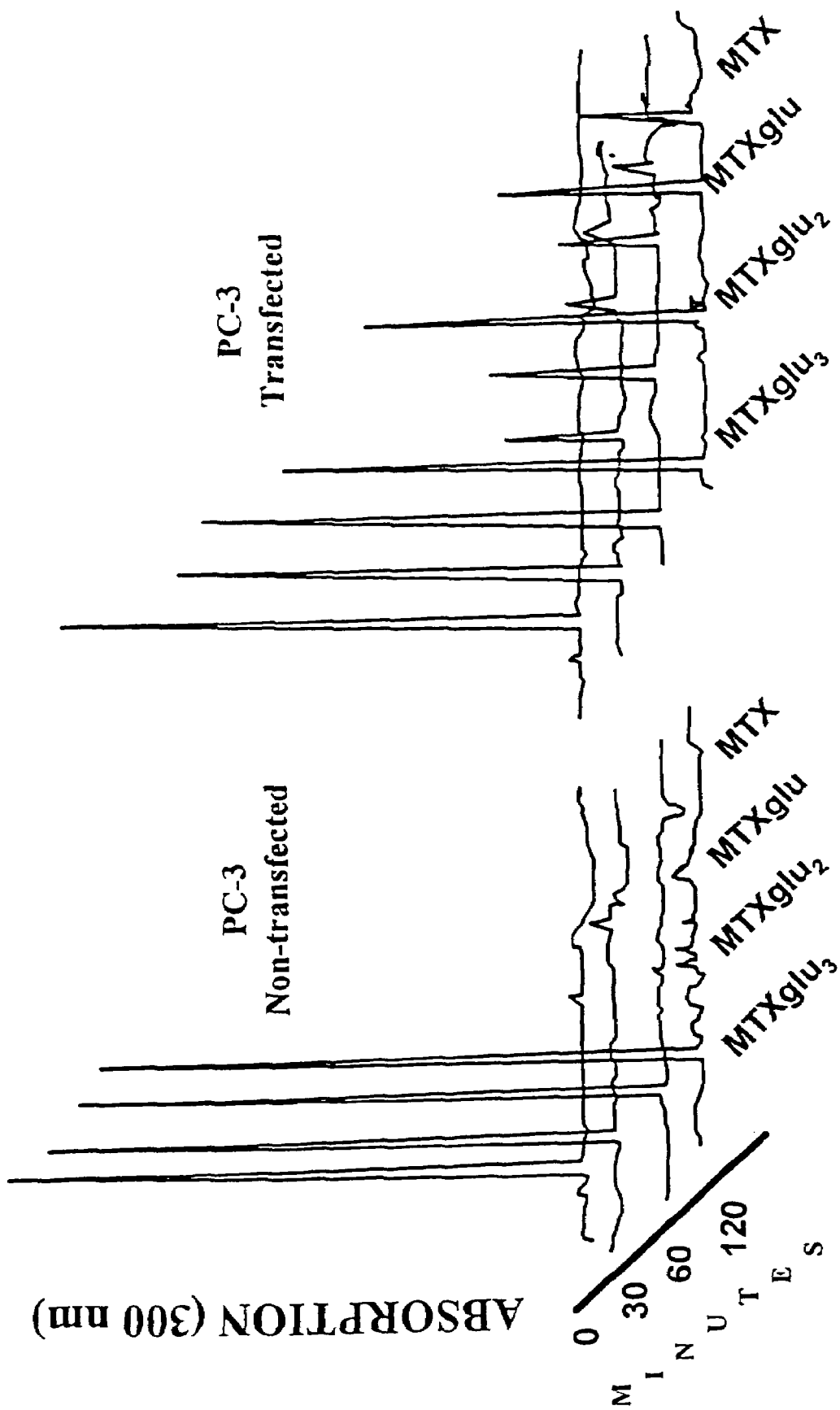

FIG. 61: Comparison of pteroyl (folate) hydrolase activity in membranes isolated from PSM expressing PC-3 cells and PC-3 cells expressing pREP7 hygromycin vector alone. Membranes were isolated as described in Methods. Each value represents the mean of triplicate reactions normalized to 1 mg/mL protein.

Figure 62:
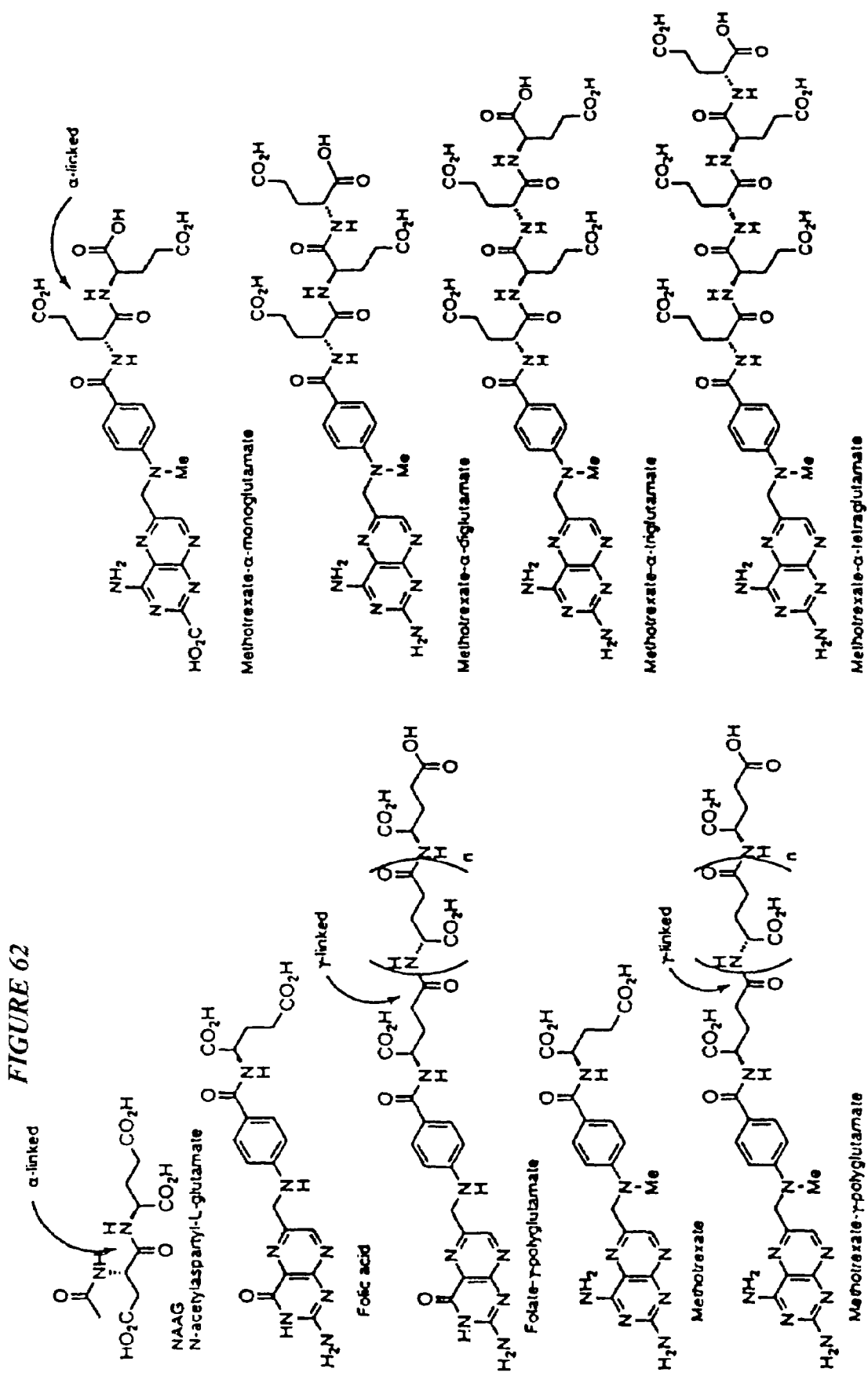

FIG. 62: Representation of N'-acetylaspartylglutamate. (NAAG), folic acid, folate-gamma-polyglutamate, methotrexate, methotrexate-gamma-polyglutamate, methotrexate-alpha-monoglutamate, methotrexate-gamma-diglutamate, methotrexate-gamma-triglutamate, methotrexate-gamma-tetraglutamate.

Figure 63A:
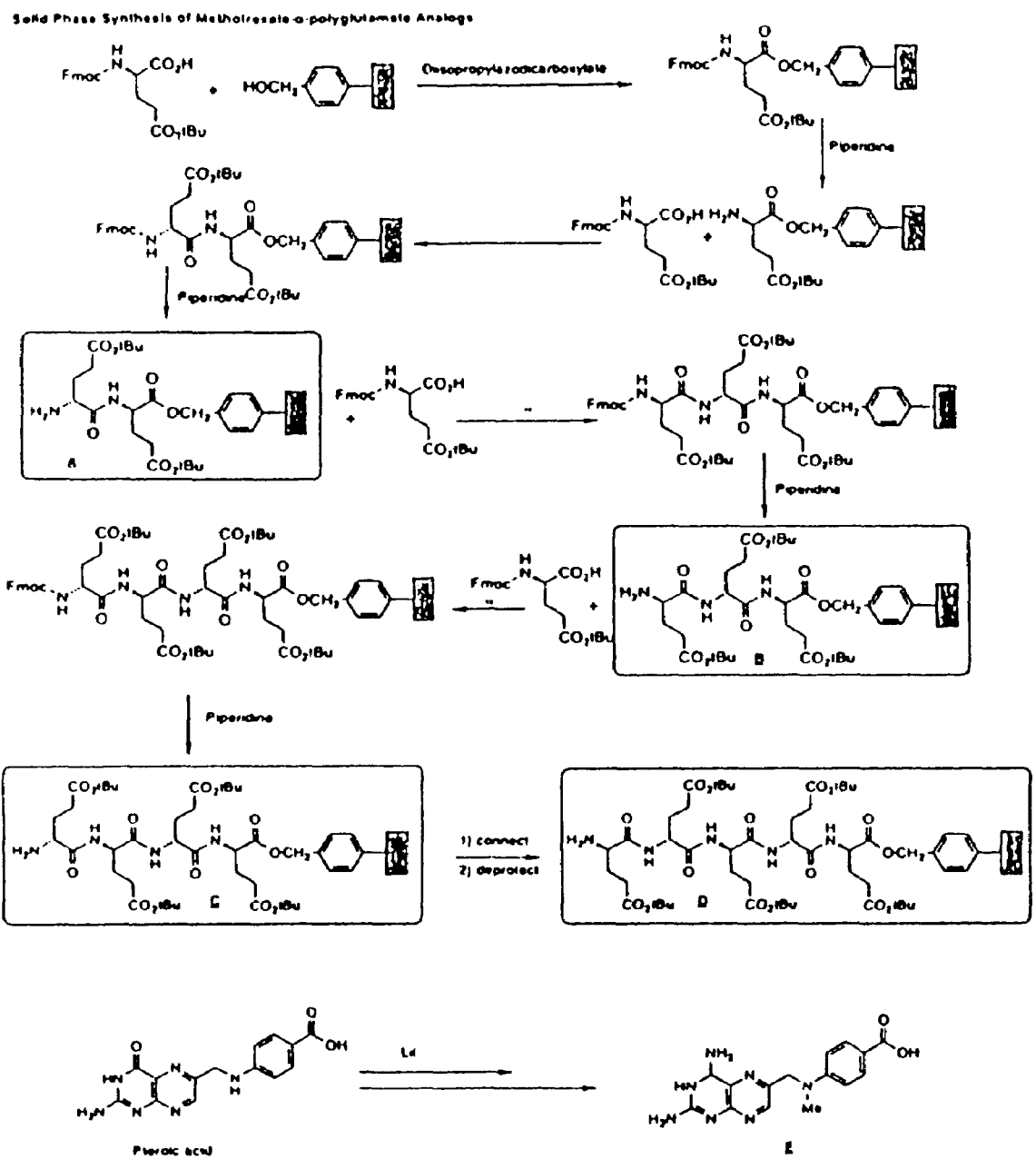
Figure 63B:
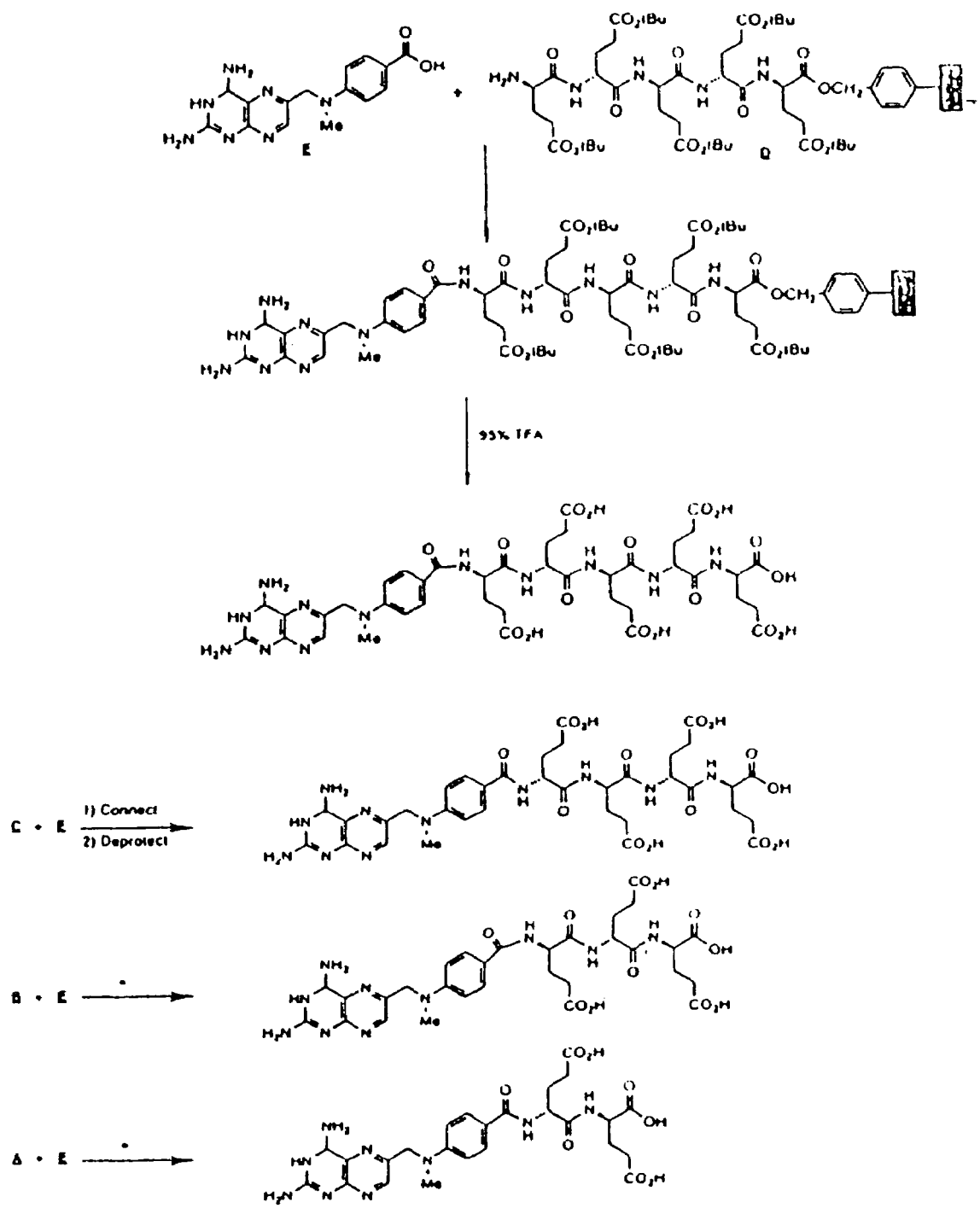

FIG. 63A-63B: Solid phase synthesis of methotrexate alpha-polyglutamatae analogs.

FIG. 64: Sequence analysis of microsatellite instability in PSM gene. Genomic (SEQ ID NO:110), LNCaP (SEQ ID NO:110), PC-3 (SEQ ID NO:111), DU145 (SEQ ID NO:112), T4(tumor) (SEQ ID NO:113), N4(paired normal) (SEQ ID NO: 114).

Figure 65:
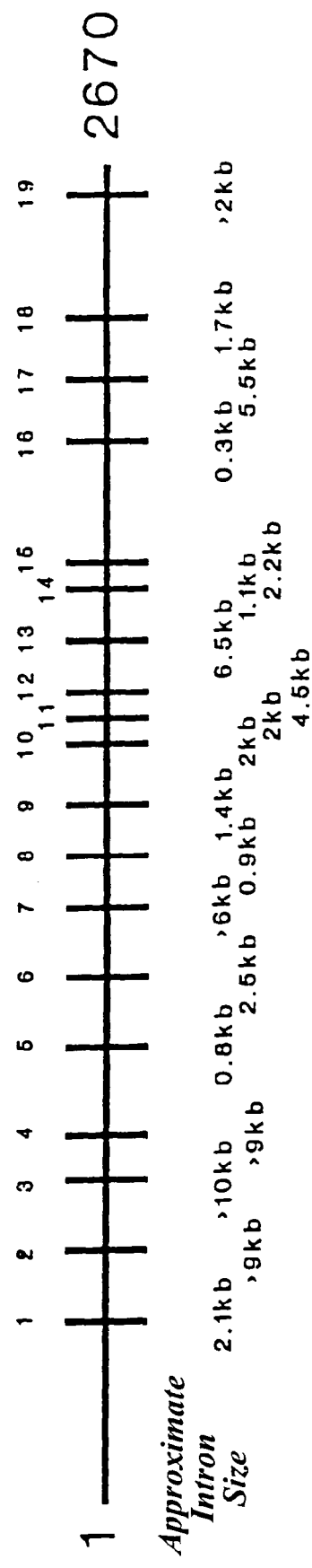

FIG. 65: PSM genomic organization.

Figure 66:
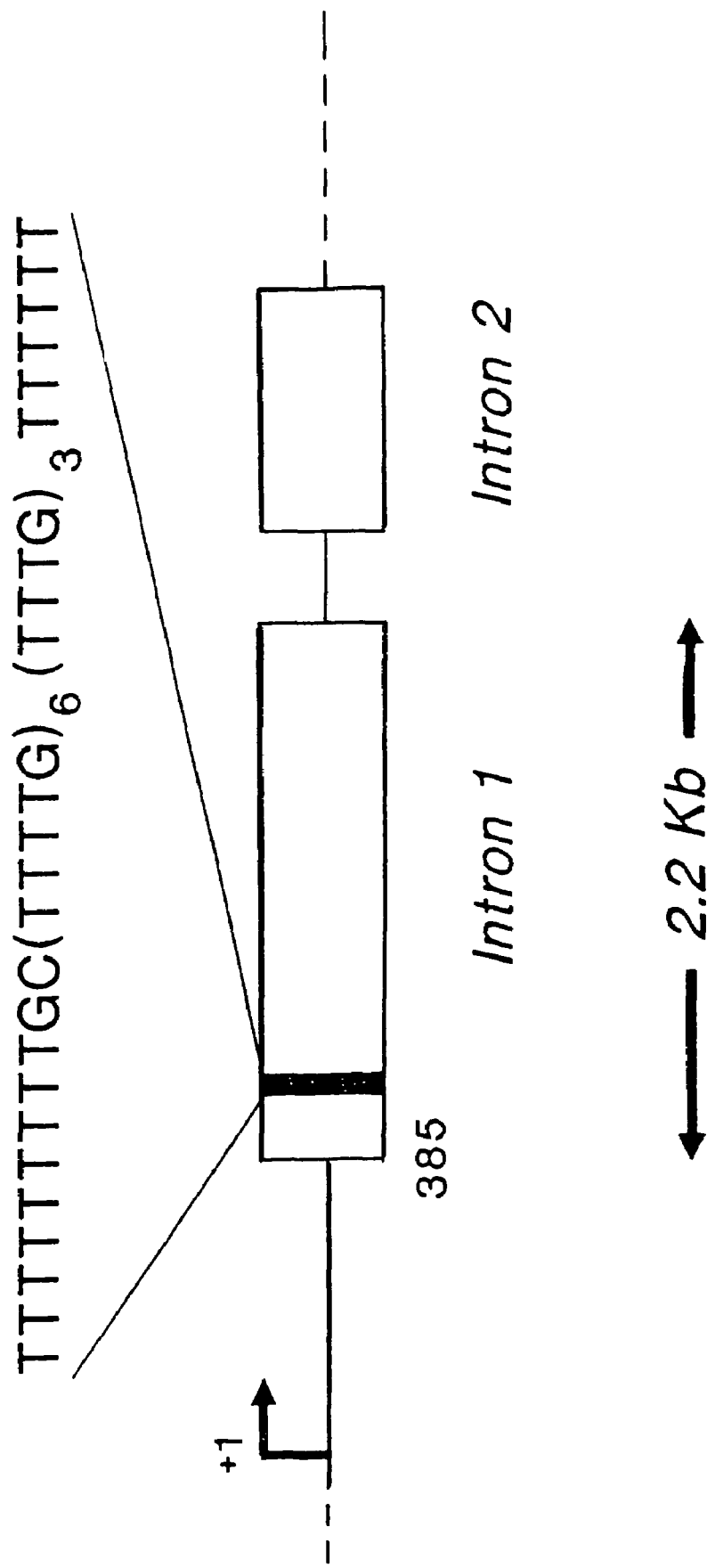

FIG. 66: Location of microsatellite in PSM gene (SEQ ID NO:115).

SUMMARY OF THE INVENTION

This invention provides an isolated nucleic acid molecule encoding an alternatively spliced human prostate-specific membrane antigen. This invention provides an isolated nucleic acid comprising a promoter sequence normally associated with the transcription of a gene encoding a human prostate-specific membrane antigen. This invention provides an isolated polypeptide having the biological activity of an alternatively spliced prostate-specific membrane antigen.

This invention provides a method of detecting a nucleic acid encoding an alternatively spliced human prostate-specific membrane antigen and a method of detecting a prostate tumor cell in a subject.

Lastly, this invention provides a pharmaceutical composition comprising a compound in a therapeutically effective amount and a pharmaceutically acceptable carrier and a method of making prostate cells susceptible to a cytotoxic agent.

DETAILED DESCRIPTION OF THE INVENTION

This invention provides an isolated nucleic acid encoding an alternatively spliced human prostate-specific membrane (PSM') antigen. As defined herein "nucleic acid encoding an alternatively spliced prostate-specific membrane (PSM') antigen" means nucleic acid encoding a prostate-specific membrane antigen which contains a deletion in the DNA sequence encoding prostate specific membrane antigen between nucleotide 115 and 380. In one embodiment the isolated nucleic acid encodes the alternatively spliced human prostate-specific membrane antigen as set forth in FIG. 55.

This invention further provides an isolated mammalian genomic DNA molecule which encodes an alternatively spliced prostate-specific membrane antigen. This invention further provides an isolated mammalian DNA molecule of an isolated mammalian nucleic acid molecule encoding an alternatively spliced prostate-specific membrane antigen. This invention also provides an isolated mammalian cDNA molecule encoding a mammalian alternatively spliced prostate-specific membrane antigen. This invention provides an isolated mammalian RNA molecule encoding a mammalian alternatively spliced prostate-specific membrane antigen.

This invention also encompasses DNAs and cDNAs which encode amino acid sequences which differ from those of PSM' antigen, but which should not produce phenotypic changes. Alternatively, this invention also encompasses DNAs and cDNAs which hybridize to the DNA and cDNA of the subject invention. Hybridization methods are well known to those of skill in the art.

This invention also provides a nucleic acid molecule of at least 15 nucleotides capable of specifically hybridizing with a sequence of a nucleic acid molecule encoding the prostate-specific membrane antigen. This molecule may either be a DNA or RNA molecule.

This invention provides a nucleic acid sequence of at least 15 nucleotides capable of specifically hybridizing to a sequence within a DNA sequence encoding prostate specific membrane antigen located between nucleotide 115 and nucleotide 380.

The nucleic acid molecule capable of specifically hybridizing with a sequence of a nucleic acid molecule encoding the prostate-specific membrane antigen can be used as a probe. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes PSM antigen into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the PSM antigen molecule downstream of a bacteriophage promoter such as T3, T7 or SP6. Large amounts of RNA probe may be produced by incubating the labeled nucleotides with the linearized PSM antigen fragment where it contains an upstream promoter in the presence of the appropriate RNA polymerase.

For example, high stringent hybridization conditions are selected at about 5° C. lower than the thermal melting point (Tm) for the specific sequence at a defined ionic strength and pH. The Tm is the temperature (under defined ionic strength and pH) at which 50 of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, ie. salt or formamide concentration, and the extent of base mismatching, the combination of parameters is more important than the absolute measure of any one. For Example high stringency may be attained for example by overnight hybridization at about 68° C. in a 6×SSC solution, washing at room temperature with 6×SSC solution, followed by washing at about 68° C. in a 6×SSC in a 0.6×SSX solution.

Hybridization with moderate stringency may be attained for example by: 1) filter pre-hybridizing and hybridizing with a solution of 3× sodium chloride, sodium citrate (SSC), 50% formamide, 0.1M Tris buffer at Ph 7.5, 5× Denhardt's solution; 2.) pre-hybridization at 37° C. for 4 hours; 3) hybridization at 37° C. with amount of labelled probe equal to 3,000,000 cpm total for 16 hours; 4) wash in 2×SSC and 0.1% SDS solution; 5) wash 4×for 1 minute each at room temperature at 4×at 60° C. for 30 minutes each; and 6) dry and expose to film.

The DNA molecules described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

Moreover, the isolated mammalian nucleic acid molecules encoding a mammalian prostate-specific membrane antigen and the alternatively spliced PSM' are useful for the development of probes to study the tumorigenesis of prostate cancer.

The nucleic acid molecules synthesized above may be used to detect expression of a PSM' antigen by detecting the presence of mRNA coding for the PSM antigen. Total mRNA from the cell may be isolated by many procedures well known to a person of ordinary skill in the art. The hybridizing conditions of the labelled nucleic acid molecules may be determined by routine experimentation well known in the art. The presence of mRNA hybridized to the probe may be determined by gel electrophoresis or other methods known in the art. By measuring the amount of the hybrid made, the expression of the PSM and PSM' antigen by the cell can be determined. The labeling may be radioactive. For an example, one or more radioactive nucleotides can be incorporated in the nucleic acid when it is made.

In one embodiment of this invention, nucleic acids are extracted by precipitation from lysed cells and the mRNA is isolated from the extract using an oligo-dT column which binds the poly-A tails of the mRNA molecules. The mRNA is then exposed to radioactively labelled probe on a nitrocellulose membrane, and the probe hybridizes to and thereby labels complementary mRNA sequences. Binding may be detected by luminescence autoradiography or scintillation counting. However, other methods for performing these steps are well known to those skilled in the art, and the discussion above is merely an example.

The probes are also useful for in-situ hybridization or in order to locate tissues which express this gene, or for other hybridization assays for the presence of this gene or its mRNA in various biological tissues. The in-situ hybridization using a labelled nucleic acid molecule is well known in the art. Essentially, tissue sections are incubated with the labelled nucleic acid molecule to allow the hybridization to occur. The molecule will carry a marker for the detection because it is "labelled", the amount of the hybrid will be determined based on the detection of the amount of the marker and so will the expression of PSM antigen.

This invention further provides isolated PSM' antigen nucleic acid molecule operatively linked to a promoter of RNA transcription. The isolated PSM' antigen sequence can be linked to vector systems. Various vectors including plasmid vectors, cosmid vectors, bacteriophage vectors and other viruses are well known to ordinary skilled practitioners. This invention further provides a vector which comprises the isolated nucleic acid molecule encoding for the PSM' antigen.

As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

Plasmid, p55A-PSM, was deposited on Aug. 14, 1992 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, p55A-PSM, was accorded ATCC Accession Number 75294.

This invention further provides a host vector system for the production of a polypeptide having the biological activity of the alternatively splced prostate-specific membrane antigen. These vectors may be transformed into a suitable host cell to form a host cell vector system for the production of a polypeptide having the biological activity of PSM' antigen.

Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

Expression vectors are useful to produce cells that express the PSM antigen.

This invention further provides an isolated DNA or cDNA molecule described hereinabove wherein the host cell is selected from the group consisting of bacterial cells (such as *E. coli*), yeast cells, fungal cells, insect cells and animal cells. Suitable animal cells include, but are not limited to Vero cells, HeLa cells, Cos cells, CV1 cells and various primary mammalian cells.

This invention provides an isolated polypeptide having the biological activity of an alternatively spliced prostate-specific membrane antigen.

This invention further provides a method of producing a polypeptide having the biological activity of the prostate-specific membrane antigen which comprising growing host cells of a vector system containing the PSM' antigen sequence under suitable conditions permitting production of the polypeptide and recovering the polypeptide so produced.

This invention provides a mammalian cell comprising a DNA molecule encoding a mammalian PSM' antigen, such as a mammalian cell comprising a plasmid adapted for expression in a mammalian cell, which comprises a DNA molecule encoding a mammalian PSM' antigen and the regulatory elements necessary for expression of the DNA in the mammalian cell so located relative to the DNA encoding the mammalian PSM' antigen as to permit expression thereof.

Numerous mammalian cells may be used as hosts, including, but not limited to, the mouse fibroblast cell NIH3T3, CHO cells, HeLa cells, Ltk⁻ cells, Cos cells, etc. Expression plasmids such as that described supra may be used to transfect mammalian cells by methods well known in the art such as calcium phosphate precipitation, electroporation or DNA encoding the mammalian PSM antigen may be otherwise introduced into mammalian cells, e.g., by microinjection, to obtain mammalian cells which comprise DNA, e.g., cDNA or a plasmid, encoding a mammalian PSM antigen.

This invention further provides ligands bound to the mammalian PSM' antigen.

This invention also provides a therapeutic agent comprising a ligand identified by the above-described method and a cytotoxic agent conjugated thereto. The cytotoxic agent may either be a radioisotope or a toxin. Examples of radioisotopes or toxins are well known to one of ordinary skill in the art.

This invention also provides a method of imaging prostate cancer in human patients which comprises administering to the patients at least one ligand identified by the above-described method, capable of binding to the cell surface of the prostate cancer cell and labelled with an imaging agent under conditions permitting formation of a complex between the ligand and the cell surface PSM' antigen. This invention further provides a composition comprising an effective imaging agent of the PSM' antigen ligand and a pharmaceutically acceptable carrier. Pharmaceutically acceptable carriers are well known to one of ordinary skill in the art. For an example, such a pharmaceutically acceptable carrier can be physiological saline.

Also provided by this invention is a purified mammalian PSM' antigen. As used herein, the term "purified alternatively spliced prostate-specific membrane antigen" shall mean isolated naturally-occurring prostate-specific membrane antigen or protein (purified from nature or manufactured such that the primary, secondary and tertiary conformation, and posttranslational modifications are identical to naturally-occurring material) as well as non-naturally occurring polypeptides having a primary structural conformation (i.e. continuous sequence of amino acid residues). Such polypeptides include derivatives and analogs.

This invention provides an isolated nucleic acid comprising a promoter sequence normally associated with the transcription of a gene encoding a human prostate-specific membrane antigen. In one embodiment regulatory elements are set forth in FIG. 15. In another embodiment the promoter is between nucleotide −1 to −641 of FIG. 15A.

This invention provides a method to identify such natural ligand or other ligand which can bind to the PSM' antigen. A method to identify the ligand comprises a) coupling the purified mammalian PSM' antigen to a solid matrix, b) incubating the coupled purified mammalian PSM' protein with the potential ligands under the conditions permitting binding of ligands and the purified PSM' antigen; c) washing the ligand and coupled purified mammalian PSM' antigen complex formed in b) to eliminate the nonspecific binding and impurities and finally d) eluting the ligand from the bound purified mammalian PSM' antigen. The techniques of coupling proteins to a solid matrix are well known in the art. Potential ligands may either be deduced from the structure of mammalian PSM' by other empirical experiments known by ordinary skilled practitioners. The conditions for binding may also easily be determined and protocols for carrying such experimentation are known to those skilled in the art. The ligand-PSM' antigen complex will be washed. Finally, the bound ligand is eluted and characterized. Standard ligands characterization techniques are well known in the art.

The above method may also be used to purify ligands from any biological source. For purification of natural ligands in the cell, cell lysates, serum or other biological samples will be used to incubate with the mammalian PSM' antigen bound on a matrix. Specific natural ligand will then be identified and purified as above described.

With the protein sequence information, antigenic areas may be identified and antibodies directed against these areas may be generated and targeted to the prostate cancer for imaging the cancer or therapies.

This invention provides an antibody directed against the amino acid sequence of a mammalian PSM' antigen.

This invention provides a method to select specific regions on the PSM' antigen to generate antibodies. The protein sequence may be determined from the PSM, DNA sequence. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to mammalian PSM antigen. For an example, hydrophilic sequences of the human PSM antigen shown in hydrophilicity plot may be easily selected. The selected peptides may be prepared using commercially available machines. As an alternative, DNA, such as a cDNA or a fragment thereof, may be cloned and expressed and the resulting polypeptide recovered and used as an immunogen.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of mammalian PSM antigen in living animals, in humans, or in biological tissues or fluids isolated from animals or humans.

In one embodiment, peptides Asp-Glu-Leu-Lys-Ala-Glu (SEQ ID NO:35), Asn-Glu-Asp-Gly-Asn-Glu (SEQ ID NO:36) and Lys-Ser-Pro-Asp-Glu-Gly (SEQ ID NO:37) of human PSM antigen are selected.

This invention further provides polyclonal and monoclonal antibody(ies) against peptides Asp-Glu-Leu-Lys-Ala-Glu (SEQ ID NO:35), Asn-Glu-Asp-Gly-Asn-Glu (SEQ ID NO:36) and Lys-Ser-Pro-Asp-Glu-Gly (SEQ ID NO:37) of human PSM antigen are selected.

This invention provides a method of imaging prostate cancer in human patients which comprises administering to the patient the monoclonal antibody directed against the peptide of the mammalian PSM' antigen capable of binding to the cell surface of the prostate cancer cell and labeled with an imaging agent under conditions permitting formation of a complex between the monoclonal antibody and the cell surface prostate-specific membrane antigen. The imaging agent is a radioisotope such as Indium$^{111}$.

This invention further provides a prostate cancer specific imaging agent comprising the antibody directed against PSM' antigen and a radioisotope conjugated thereto.

This invention also provides a composition comprising an effective imaging amount of the antibody directed against the PSM' antigen and a pharmaceutically acceptable carrier. The methods to determine effective imaging amounts are well known to a skilled practitioner. One method is by titration using different amounts of the antibody.

In addition to the standard pharmacophores that can be added to know structures, with the PSM transfectants one can identify potential ligands from combinatorial libraries that might not have been otherwise predicted such combinatorial libraries can be synthetic, peptide, or RNA based.

This invention further provides an immunoassay for measuring the amount of the prostate-specific membrane antigen in a biological sample comprising steps of a) contacting the biological sample with at least one antibody directed against the PSM' antigen to form a complex with said antibody and the prostate-specific membrane antigen, and b) measuring the amount of the prostate-specific membrane antigen in said biological sample by measuring the amount of said complex. One example of the biological sample is a serum sample.

This invention provides a method to purify mammalian prostate-specific membrane antigen comprising steps of a) coupling the antibody directed against the PSM' antigen to a solid matrix; b) incubating the coupled antibody of a) with lysate containing prostate-specific membrane antigen under the condition which the antibody and prostate membrane specific can bind; c) washing the solid matrix to eliminate impurities and d) eluting the prostate-specific membrane antigen from the coupled antibody.

This invention also provides a transgenic nonhuman mammal which comprises the isolated nucleic acid molecule encoding a mammalian PSM' antigen. This invention further provides a transgenic nonhuman mammal whose genome comprises antisense DNA complementary to DNA encoding a mammalian prostate-specific membrane antigen so placed as to be transcribed into antisense mRNA complementary to mRNA encoding the prostate-specific membrane antigen and which hybridizes to mRNA encoding the prostate specific antigen thereby reducing its translation.

Animal model systems which elucidate the physiological and behavioral roles of mammalian PSM' antigen are produced by creating transgenic animals in which the expression of the PSM' antigen is either increased or decreased, or the amino acid sequence of the expressed PSM antigen is altered, by a variety of techniques. Examples of these techniques include, but are not limited to: 1) Insertion of normal or mutant versions of DNA encoding a mammalian PSM' antigen, by microinjection, electroporation, retroviral transfection or other means well known to those skilled in the art, into appropriate fertilized embryos in order to produce a transgenic animal or 2) Homologous recombination of mutant or normal, human or animal versions of these genes with the native gene locus in transgenic animals to alter the regulation of expression or the structure of these PSM' antigen sequences. The technique of homologous recombination is well known in the art. It replaces the native gene with the inserted gene and so is useful for producing an animal that cannot express native PSM antigen but does express, for example, an inserted mutant PSM antigen, which has replaced the native PSM antigen in the animal's genome by recombination, resulting in under expression of the transporter. Microinjection adds genes to the genome, but does not remove them, and so is useful for producing an animal which expresses its own and added PSM antigens, resulting in over expression of the PSM antigens.

One means available for producing a transgenic animal, with a mouse as an example, is as follows: Female mice are mated, and the resulting fertilized eggs are dissected out of their oviducts. The eggs are stored in an appropriate medium such as Me medium (16). DNA or cDNA encoding a mammalian PSM antigen is purified from a vector by methods well known in the art. Inducible promoters may be fused with the coding region of the DNA to provide an experimental means to regulate expression of the trans-gene. Alternatively or in addition, tissue specific-regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Another use of the PSM antigen sequence is to isolate homologous gene or genes in different mammals. The gene or genes can be isolated by low stringency screening of either cDNA or genomic libraries of different mammals using probes from PSM sequence. The positive clones identified will be further analyzed by DNA sequencing techniques which are well known to an ordinary person skilled in the art. For example, the detection of members of the protein serine kinase family by homology probing.

This invention provides a method of suppressing or modulating metastatic ability of prostate tumor cells, prostate tumor growth or elimination of prostate tumor cells comprising introducing a DNA molecule encoding an alternatively spliced prostate specific membrane antigen operatively linked to a 5' regulatory element into a tumor cell of a subject, in a way that expression of the alternatively spliced prostate specific membrane antigen is under the control of the regulatory element, thereby suppressing or modulating metastatic ability of prostate tumor cells, prostate tumor growth or elimination of prostate tumor cells. The subject may be a mammal or more specifically a human.

In one embodiment, the DNA molecule is operatively linked to a 5' regulatory element forms part of a transfer vector which is inserted into a cell or organism. In addition the vector is capable or replication and expression of the alternatively spliced prostate specific membrane antigen. The DNA molecule can be integrated into a genome of a eukaryotic or prokaryotic cell or in a host cell containing and/or expressing an alternatively spliced prostate specific membrane antigen.

Further, the DNA molecule encoding alternatively spliced prostate specific membrane antigen may be introduced by a bacterial, viral, fungal, animal, or liposomal delivery vehicle. Other means are also available and known to an ordinary skilled practitioner.

Further, the DNA molecule encoding an alternatively spliced prostate specific membrane antigen operatively linked to a promoter or enhancer. A number of viral vectors have been described including those made from various promoters and other regulatory elements derived from virus sources. Promoters consist of short arrays of nucleic acid sequences that interact specifically with cellular proteins involved in transcription. The combination of different recognition sequences and the cellular concentration of the cognate transcription factors determines the efficiency with which a gene is transcribed in a particular cell type.

Examples of suitable promoters include a viral promoter. Viral promoters include: adenovirus promoter, an simian virus 40 (SV40) promoter, a cytomegalovirus (CMV) promoter, a mouse mammary tumor virus (MMTV) promoter, a Malony murine leukemia virus promoter, a murine sarcoma virus promoter, and a Rous sarcoma virus promoter.

Further, another suitable promoter is a heat shock promoter. Additionally, a suitable promoter is a bacteriophage promoter. Examples of suitable bacteriophage promoters include but not limited to, a T7 promoter, a T3 promoter, an SP6 promoter, a lambda promoter, a baculovirus promoter.

Also suitable as a promoter is an animal cell promoter such as an interferon promoter, a metallothionein promoter, an immunoglobulin promoter. A fungal promoter is also a suitable promoter. Examples of fungal promoters include but are not limited to, an ADC1 promoter, an ARG promoter, an ADH promoter, a CYC1 promoter, a CUP promoter, an ENO1 promoter, a GAL promoter, a PHO promoter, a PGK promoter, a GAPDH promoter, a mating type factor promoter. Further, plant cell promoters and insect cell promoters are also suitable for the methods described herein.

This invention provides a method of suppressing or modulating metastatic ability of prostate tumor cells, prostate tumor growth or elimination of prostate tumor cells, comprising introducing a DNA molecule encoding an alternatively spliced prostate specific membrane antigen operatively linked to a 5' regulatory element coupled with a therapeutic DNA into a tumor cell of a subject, thereby suppressing or modulating metastatic ability of prostate tumor cells, prostate tumor growth or elimination of prostate tumor cells. The subject may be a mammal or more specifically a human.

Further, the therapeutic DNA which is coupled to the DNA molecule encoding a prostate specific membrane antigen operatively linked to a 5' regulatory element into a tumor cell may code for a cytokine, viral antigen, or a pro-drug activating enzyme. Other means are also available and known to an ordinary skilled practitioner.

In addition, this invention provides a prostate tumor cell, comprising a DNA molecule isolated from mammalian nucleic acid encoding an alternatively spliced mammalian prostate-specific membrane antigen under the control a 51 regulatory element.

As used herein, DNA molecules include complementary DNA (cDNA), synthetic DNA, and genomic DNA.

This invention provides a therapeutic vaccine for preventing human prostate tumor growth or stimulation of prostate tumor cells in a subject, comprising administering an effective amount to the prostate cell, and a pharmaceutical acceptable carrier, thereby preventing the tumor growth or stimulation of tumor cells in the subject. Other means are also available and known to an ordinary skilled practitioner.

This invention provides a method of detecting hematogenous micrometastic tumor cells of a subject, comprising (A) performing nested polymerase chain reaction (PCR) on blood, bone marrow or lymph node samples of the subject using the prostate specific membrane antigen primers or alternatively spliced prostate specific antigen primers, and (B) verifying micrometastases by DNA sequencing and Southern analysis, thereby detecting hematogenous micrometastic tumor cells of the subject. The subject may be a mammal or more specifically a human.

The micrometastatic tumor cell may be a prostatic cancer and the DNA primers may be derived from prostate specific antigen. Further, the subject may be administered with simultaneously an effective amount of hormones, so as to increase expression of prostate specific membrane antigen. Further, growth factors or cytokine may be administered in separately or in conjunction with hormones. Cytokines include, but are not limited to: transforming growth factor beta, epidermal growth factor (EGF) family, fibroblast growth factors, hepatocyte growth factor, insulin-like growth factors, B-nerve growth factor, platelet-derived growth factor, vascular endothelial growth factor, interleukin 1, IL-1 receptor antagonist, interleukin 2, interleukin 3, interleukin 4, interleukin 5, interleukin-6, IL-6 soluble receptor, interleukin 7, interleukin 8, interleukin 9, interleukin 10, interleukin 11, interleukin 12, interleukin 13, angiogenin, chemokines, colony stimulating factors, granulocyte-macrophage colony stimulating factors, erythropoietin, interferon, interferon gamma, leukemia inhibitory factor, oncostatin M, pleiotrophin, secretory leukocyte protease inhibitor, stem cell factor, tumor necrosis factors, adhesion molecule, and soluble tumor necrosis factor (TNF) receptors.

This invention provides a method of abrogating the mitogenic response due to transferrin, comprising introducing a DNA molecule encoding prostate specific membrane antigen operatively linked to a 5' regulatory element into a tumor cell, the expression of which gene is directly associated with a defined pathological effect within a multicellular organism, thereby abrogating mitogen response due to transferrin. The tumor cell may be a prostate cell.

This invention provides a method of determining prostate cancer progression in a subject which comprises: a) obtaining a suitable prostate tissue sample; b) extracting RNA from the prostate tissue sample; c) performing a RNAse protection assay on the RNA thereby forming a duplex RNA-RNA hybrid; d) detecting PSM and PSM' amounts in the tissue sample; e) calculating a PSM/PSM' tumor index, thereby determining prostate cancer progression in the subject. In-situ hyribridization may be performed in conjunction with the above detection method.

This invention provides a method of detecting prostate cancer in a subject which comprises: (a) obtaining from a subject a prostate tissue sample; (b) treating the tissue sample so as to separately recover nucleic acid molecules present in the prostate tissue sample; (c) contacting the resulting nucleic acid molecules with multiple pairs of single-stranded labeled oligonucleotide primers, each such pair being capable of specifically hybridizing to the tissue sample, under hybridizing conditions; (d) amplifying any nucleic acid molecules to which a pair of primers hybridizes so as to obtain a double-stranded amplification product; (e) treating any such double-stranded amplification product so as to obtain single-stranded nucleic acid molecules therefrom; (f) contacting any resulting single-stranded nucleic acid molecules with multiple single-stranded labeled oligonucleotide probes, each such probe containing the same label and being capable of specifically hybridizing with such tissue sample, under hybridizing conditions; (g) contacting any resulting hybrids with an antibody to which a marker is attached and which is capable of specifically forming a complex with the labeled-probe, when the probe is present in such a complex, under complexing conditions; and (h) detecting the presence of any resulting complexes, the presence thereof being indicative of prostate cancer in a subject.

This invention provides a method of enhancing antibody based targeting of PSM' in prostate tissue for diagnosis or therapy of prostate cancer comprising administering to a patient b-FGF in sufficient amount to cause upregulation of PSM' expression.

This invention provides a method of enhancing antibody based targeting of PSM' in prostate tissue for diagnosis or therapy of prostate cancer comprising administering to a patient TGF in sufficient amount to cause upregulation of PSM expression or PSM'.

This invention provides a method of enhancing antibody based targeting of PSM' in prostate tissue for diagnosis or therapy of prostate cancer comprising administering to a patient EGF in sufficient amount to cause upregulation of PSM' expression.

This method provides a method of detecting in a sample the presence of a nucleic acid encoding an alternatively spliced human prostate-specific membrane antigen which comprises: a) obtaining a suitable sample; b) extracting RNA from the sample; c) contacting the RNA with reverse transcriptase under suitable conditions to obtain a cDNA; d) contacting the cDNA under hybridizing conditions with two oligonucleotide primers, i) the first primer being capable of specifically hybridizing to a sequence within a DNA sequence encoding prostate specific membrane antigen (SEQ ID NO:1) located immediately 3' of nucleotide 114 of such DNA sequence, with the proviso that the 3' end of the primer does not hybridize to any sequence located 5' of the nucleotide 114, and ii) the second primer being capable of specifically hybridizing to a sequence with in a DNA sequence encoding prostate specific membrane antigen (SEQ ID NO:1) located immediately 5' of nucleotide 381 of such DNA sequence, with the proviso that the 5' end of the primer does not hybridize to any sequence located 3' of nucleotide 381; e) amplifying any cDNA to which the primers hybridize to so as to obtain amplification product; f) determining the size of the amplification product; g) comparing the size of the amplification product to the size of the amplification product known to be obtained using the same primers with a non alternatively spliced human prostate specific membrane antigen, wherein a smaller amplification product is indicative of the presence of the alternatively spliced human prostate-specific membrane antigen sample.

In one embodiment the suitable sample may be any bodily tissue of fluid which includes but is not limited to: blood, bone marrow, and lymph nodes.

In one embodiment, the primers are at least 14-25 nucleotides in length. In another embodiment, the primers are at least 15 nucleotides in length. In another embodiment, multiple primers are used. Construction of primers which hybridize and hybridizing conditions are known to those skilled in the art. For example, based on FIG. 18 (SEQ ID NO:91), one skilled in the art may construct primers which hybridize to the prostate specific membrane antigen before nucleotide 114 and after nucleotide 381.

Further, a method of determining the amount of the amplification product or products (i.e. 2 or more bands) as well as the ratio of each product is known to those skilled in the art. For example, the amount of prostate specific membrane antigen or alternatively spliced prostate specific membrane antigen may be determined by density, binding radiolabled probes, autoradiography, UV spectrography, spectrophotometer, optical scan, and phospho-imaging.

This invention provides a method of detecting a prostate tumor cell in a subject which comprises: which comprises: a) obtaining a suitable sample; b) extracting RNA from the sample; c) contacting the RNA with reverse transcriptase under suitable conditions to obtain a cDNA; d) contacting the cDNA under hybridizing conditions with two oligonucleotide primers, i) the first primer being capable of specifically hybridizing to a sequence within a DNA sequence encoding prostate specific membrane antigen located immediately 3' of nucleotide 114 of such DNA sequence, with the proviso that the 3' end of the primer does not hybridize to any sequence located 5' of nucleotide 114, and ii) the second primer being capable of specifically hybridizing to a sequence within a DNA sequence encoding prostate specific membrane antigen located immediately 5' of nucleotide 381 of such DNA sequence, with the proviso that the 5' end of the primer does not hybridize to any sequence located 3' of nucleotide 381; d) amplifying any cDNA to which the primers hybridize to so as to obtain amplification product; e) determining the amount of the amplification product; f) comparing the amount of the amplification product to the amount of the amplification product known to be obtained using the same primers with a non alternatively spliced human prostate specific membrane antigen, wherein a greater amount of the prostate specific membrane antigen is indicative of a prostate tumor cell in the subject, so as to thereby detect prostate tumor cell in the subject.

In PCR techniques, oligonucleotide primers complementary to the two 3' borders of the DNA of the prostate specific membrane (PSM) antigen to be amplified are synthesized. Thee polymerase chain reaction is then carried out using the two primers. See *PCR Protocols: A Guide to Methods and Applications*. Hybridization of PSM antigen DNA to the above nucleic acid probes can be performed by a Southern blot under stringent hybridization conditions as described herein.

Oligonucleotides for use as probes or PCR primers are chemically synthesized according to the solid phase phosphoramidite triester method first described by Beaucage and Carruthers using an automated synthesizer, as described in Needham-VanDevanter. Purification of oligonucleotides is by either native acrylamide gel electrophoresis or by anion-exchange HPLC as described in Pearson, J. D. and Regnier, F. E. The sequence of the synthetic oligonucleotide can be verified using the chemical degradation method of Maxam, A. M. and Gilbert, W.

Accepted means for conducting hybridization assays are known and general overviews of the technology can be had from a review of: *Nucleic Acid Hybridization: A Practical Approach; Hybridization of Nucleic Acids Immobilized on Solid Supports; Analytical Biochemistry* and Innis et al., *PCR Protocols*.

If PCR is used in conjunction with nucleic acid hybridization, primers are designed to target a specific portion of the nucleic acid of DNA of the PSM antigen. From the information provided herein, those of skill in the art will be able to select appropriate specific primers.

It will be apparent to those of ordinary skill in the art that a convenient method for determining whether a probe is specific for PSM antigen or PSM' antigen utilizes a Southern blot (or Dot blot). Briefly, to identify a target specific probe DNA is isolated from the PSM or PSM' antigen. Test DNA is transferred to a solid (e.g., charged nylon) matrix. The probes are labelled following conventional methods. Following denaturation and/or prehybridization steps known in the art, the probe is hybridized to the immobilized DNAs under stringent conditions. Stringent hybridization conditions will depend on the probe used and can be estimated from the calculated $T_m$ (melting temperature) of the hybridized probe (see, e.g., Sambrook for a description of calculation of the $T_m$). For radioactively-labeled DNA or RNA probes an example of stringent hybridization conditions is hybridization in a solution containing denatured probe and 5×SSC at 65° C. for 8-24 hours followed by washes in 0.1×SSC, 0.1% SDS (sodium dodecyl sulfate) at 50-65° C. In general, the temperature and salt concentration are chosen so that the post hybridization wash occurs at a temperature that is about 5° C. below the TM of the hybrid. Thus for a particular salt concentration the temperature may be selected that is 5° C. below the $T_M$ or conversely, for a particular temperature, the salt concentration is chosen to provide a $T_M$ for the hybrid that is 5° C. warmer than the wash temperature. Following stringent hybridization and washing, a probe that hybridizes to the PSM antigen or PSM' antigen as evidenced by the presence of a signal associated with the appropriate target and the absence of a signal from the non-target nucleic acids, is identified as specific. It is further appreciated that in determining probe specificity and in utilizing the method of this invention a certain amount of background signal is typical and can easily be distinguished by one of skill from a specific signal. Two fold signal over background is acceptable.

This invention provides a therapeutic agent comprising antibodies or ligand(s) directed against PSM' antigen and a cytotoxic agent conjugated thereto or antibodies linked enzymes which activate prodrug to kill the tumor. The cytotoxic agent may either be a radioisotope or toxin.

This invention provides a compound comprising a conjugate of a cytotoxic agent and one or more amino acid residues, wherein each amino acid residue is glutamate or aspartate. In one embodiment the amino acid residues alternate.

Examples of cytotoxic chemotherapeutic agents or antineolastic agents) include, but are not limited to the following: Antimetaboloites: Denopterin, Edatrexate, Piritrexim, Pteropterin, Tomudex, Tremetrexate, Cladribine, Fludarabine, 6-Mercaptopurine, Thiamiprine, Thioguanine, Ancitabine, Azacitidine, 6-Azauridine, Carmofur, Cytarabine, Doxifluride, Emitefur, Enocitabine, Floxuridine, Fluoroucit, Gemcitabine, and Tegafur.

Alkaloids: Docetaxel, Etoposide, Irinotecan, Paclitaxel, Teniposide, Topotecan, VinblastinE, Vincristine, and Vindesine.

Alkylating agents: Alkyl Sulfonates: Busulfan, Improsulfan, Piposulfan, Aziridines, Benzodepa, Carboquone, Meuredepa, Uredepa, Ethylenimines and Methylmelamines, Altretamine, Triethylenemelamine, Triethylenophosphoramide, Triethylenethiophosphoramide, Chlorambucil, Chlornaphazine, Cyclophosphamide, Estramustine, Ifosfamide, Mechlorethamine, Mechlorethamine Oxide Hydrochloride, Melphalan, Novembiechin, Perfosfamide, Phenesterine, Prednimustine, Trofosfamide, Uracil Mustard, Carmustine, Chlorozotocin, Fotemustine, Lomustine, Nimustine, Ranimustine, Dacarbazine, Mannomustine, Mitbronitol, Mitolactol, Pipobroman, Temozolomide, Antibiotics and Analogs: Aclacinomycins, Actinomycin, Anthramycin, Azaserine, Bleomycins, Cactinomycin, Carubicin, Carzinophilin, Chromomycins, Dactinomycin, Caunorubicin, 6-Diazo-5-oxo-L-norleucine, Doxorubicin, Epirubicin, Idarubicin, Menogaril, Mitomycins, Mycophenolic Acid, Nogalamycin, Olivomycins, Peplomycin, Pirarubicin, Plicamycin, Porfiromycin, Puromycin, Streptonigrin, Streptozocin, Tubercidin, Zinostatin, Zorubicin, and L-Asparaginase.

Immunodulators: Interferon, Interferon-B, Interferon-Y, Interleukin-2, Lentinan, Propagermanium, PSK, Roquinimex, Sizofran, and Ubenimex. Platinum complexes: Carboplatin, Cisplatin, Miboplatin, and Oxaliplatin.

Others: Aceglatone, Amsacrine, Bisantrene, Defoosfamide, Demecolcine, Diaziqone, Eflornithine, Eliptinium Acetate, Etoglucid, Fenertinide, Gallium Nitrate, Hydroxyurea, Lonidamine, Miltefosine, Mitoguazone, Mitoxantrone, Mopidamol, Nitracirine, Pentostatin, Phenamet, Podophyllinic Acid 2-Ethyl-hydrazide, Procarbazine, Razoxane, Sobuzoxane, Spirogermanium, Tenuazonic Acid, Triaziquone, Urethan, Calusterone, Dromostanolone, Epitiostanol, Mepitiostane, Testolactone, Amiglutehimide, Mitotane, Trilostane, Droloxifene, Tamoxifen, Toremifene, Aminoglutethimide, Anastrozole, Fadrozole, Formestane, Letrozole, Fosfestrol, Hexestrol, Polyestradiol Phosphate, Buserlin, Goserlin, Leuprolide, Triptorelin, Chlormadinone Acetate, Medroxyprogesterone, Megerstrol Acetate, Melengestrol, Porfimer Sodium, Americium, Chromic Phosphate, Radioactive. Cobalt, I-Ehtiodized Oil, Gold, Radioactive, Colloidal, Iobenguane, Radium, Radon, Sodium Iodide, Sodium Phosphate, Radioactive, Batimastat, Folinic Acid, Amifostine, Etanidazole, Etamidozole, and Mesna.

This invention provides a compound, wherein the compound has the structure:

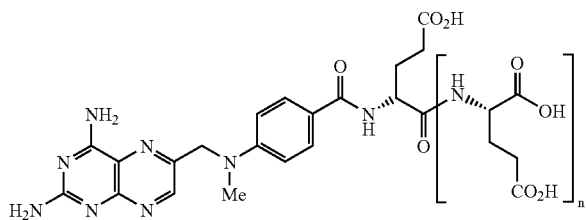

wherein n is an integer from 1-10 inclusive.

In one embodiment glutamate may be in L or D to form either 4-amino-$N^1$-methyl pteroyl-L-glutamate or 4-amino-$N^{10}$-methyl pteroyl-D-glutamate. In another embodiment aspartate may substitute the glutamate to form 4-amino-$N^{10}$-methyl pteroyl-L-aspartate. In another embodiment aspartate may substitute the glutamate to form 4-amino-$N^{10}$-methyl pteroyl-D-aspartate. In another embodiment the 4-amino-$N^{10}$-methyl pteroyl may have alternating glutamate or aspartat moieties. The glutamate or aspartate are bound to the methotrexate at the alpha carbon position of methotrexate.

This invention provides a compound, wherein the compound has the structure:

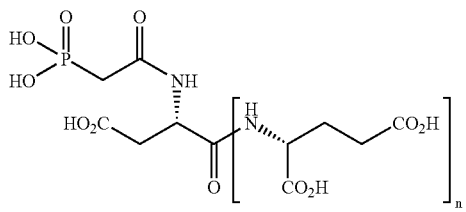

wherein n is an integer from 1-10 inclusive.

In one embodiment glutamate may be in the L or D to form either N-phosphonoacetyl-L-aspartyl (PALA)-glutamate or N-phsophonoacetyl-D-aspartyl-glutamate. In another embodiment aspartate may substitute the glutamate to form N-phsophonoacetyl-L-aspartyl-aspartate. In another embodiment the 4-amino-$N^{10}$-methyl pteroyl may have alternating glutamate or aspartate moieties.

This invention provides a compound, wherein the compound has the structure:

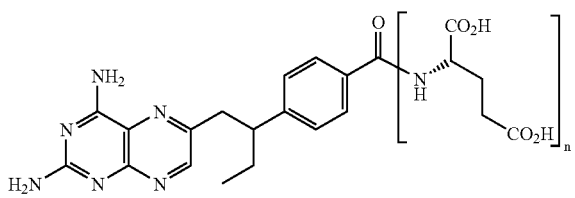

wherein n is an integer from 1-10 inclusive.

In one embodiment glutamate may be in the L or D to form either 4-amino-10-ethyl-10-deazapteroyl (EDAM)-L-glutamate or 4-amino-10-ethyl-10-deazapteroyl-D-glutamate. In another embodiment aspartate may substitute the glutamate to form 4-amino-10-ethyl-10-deazapteroyl-L-aspartate. In another embodiment the 4-amino-10-ethyl-10-deazapteroyl may have alternating glutamate or aspartat moieties.

This invention provides a pharmaceutical composition comprising any of the above compounds in a therapeutically effective amount and a pharmaceutically acceptable carrier.

This invention provides a method of making prostate cells susceptible to a cytotoxic agent, which comprises contacting the prostate cells with any of the above compounds in an amount effective to render the prostate cells susceptible to the cytotoxic chemotherapeutic agent.

This invention provides a pharmaceutical composition comprising an effective amount the alternatively spliced PSM' and a carrier or diluent. Further, this invention provides a method for administering to a subject, preferably a human, the pharmaceutical composition. Further, this invention provides a composition comprising an amount of the alternatively spliced PSM' and a carrier or diluent. Specifically, this invention may be used as a food additive.

The compositions are administered in a manner compatible with the dosage formulation, and in a therapeutically effective amount. Precise amounts of active ingredient required to be administered depend on the judgment of the practitioner and are peculiar to each subject.

In one embodiment the therapeutic effective amount is 100-10,000 mg/m$^2$ IV with rescue. In another embodiment the therapeutic effective amount is 300-1000 mg/m$^2$ IV or continuous infusion. In another embodiment the therapeutic effective amount is 100 mg/m$^2$ IV continuous infusion. In another embodiment the therapeutic effective amount is 40-75 mg/m$^2$ rapidly. In another embodiment the therapeutic effective amount is 30 mg/m$^2$ for 3 days by continuous IV.

Suitable regimes for initial administration and booster shots are also variable, but are typified by an initial administration followed by repeated doses at one or more hour intervals by a subsequent injection or other administration.

As used herein administration means a method of administering to a subject. Such methods are well known to those skilled in the art and include, but are not limited to, administration topically, parenterally, orally, intravenously, intramuscularly, subcutaneously or by aerosol. Administration of PSM may be effected 5 continuously or intermittently.

The pharmaceutical formulations or compositions of this invention may be in the dosage form of solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include other carriers, adjuvants; or nontoxic, nontherapeutic, nonimmunogenic stabilizers and the like. Effective amounts of such diluent or carrier are those amounts which are effective to obtain a pharmaceutically acceptable formulation in terms of solubility of components, or biological activity, etc This invention also provides a method of detecting a subject with cancer comprising a) contacting a cell of the neovasculature of a subject with a ligand which binds to the extraccelular domain of the PSM antigen under conditions permitting formation of a complex; and b) detecting the complex with a labelled imaging agent, thereby detecting a subject with cancer.

In one embodiment the cancer is, but is not limited to: kidney, colon, or bladder. In one embodiment the ligand is CYT-356. In another embodiment the ligand is any antibody, monoclonal or polyclonal which binds to the extracellular domain of PSM antigen. In one embodiment the cells of endothelial cells of the neo-vasculature of a subject with cancer.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

EXAMPLE 1

Expression of the Prostate Specific Membrane Antigen

A 2.65 kb complementary DNA encoding PSM was cloned. Immunohistochemical analysis of the LNCaP, DU-145, and PC-3 prostate cancer cell lines for PSM expression using the 7E11-C5.3 antibody reveals intense staining in the LNCaP cells, with no detectable expression in both the DU-145 and PC-3 cells. Coupled in-vitro transcription/translation of the 2.65 kb full-length PSM cDNA yields an 84 kDa protein corresponding to the predicted polypeptide molecular weight of PSM. Post-translational modification of this protein with pancreatic canine microsomes yields the expected 100 kDa PSM antigen. Following transfection of PC-3 cells with the full-length PSM cDNA in a eukaryotic expression vector applicant's detect expression of the PSM glycoprotein by Western analysis using the 7E11-C5.3 monoclonal antibody. Ribonuclease protection analysis demonstrates that the expression of PSM mRNA is almost entirely prostate-specific in human tissues. PSM expression appears to be highest in hormone-deprived states and is hormonally modulated by steroids, with DHT down regulating PSM expression in the human prostate cancer cell line LNCaP by 8-10 fold, testosterone down regulating PSM by 3-4 fold, and corticosteroids showing no significant effect. Normal and malignant prostatic tissues consistently show high PSM expression, whereas heterogeneous, and at times absent, from expression of PSM in benign prostatic hyperplasia. LNCaP tumors implanted and grown both orthotopically and subcutaneously in nude mice, abundantly express PSM providing an excellent in-vivo model system to study the regulation and modulation of PSM expression.

Materials and Methods:

Cells and Reagents: The LNCaP, DU-145, and PC-3 cell lines were obtained from the American Type Culture Collection. Details regarding the establishment and characteristics of these cell lines have been previously published. Unless specified otherwise, LNCaP cells were grown in RPMI 1640 media supplemented with L-glutamine, nonessential amino acids, and 5% fetal calf serum (Gibco-BRL, Gaithersburg, Md.) in a $CO_2$ incubator at 37 C. DU-145 and PC-3 cells were grown in minimal essential medium supplemented with 10% fetal calf serum. All cell media were obtained from the MSKCC Media Preparation Facility. Restriction and modifying enzymes were purchased from Gibco-BRL unless otherwise specified.

Immunohistochemical Detection of PSM: Avidin-biotin method of detection was employed to analyze prostate cancer cell lines for PSM antigen expression. Cell cytospins were made on glass slides using $5 \times 10^4$ cells/100 ul per slide. Slides were washed twice with PBS and then incubated with the appropriate suppressor serum for 20 minutes. The suppressor serum was drained off and the cells were incubated with diluted 7E11'-C5.3 (5 g/ml) monoclonal antibody for 1 hour. Samples were then washed with PBS and sequentially incubated with secondary antibodies for 30 minutes and with avidin-biotin complexes for 30 minutes. Diaminobenzidine served as the chromogen and color development followed by hematoxylin counterstaining and mounting. Duplicate cell cytospins were used as controls for each experiment. As a positive control, the anti-cytokeratin monoclonal antibody CAM 5.2 was used following the same procedure described above. Human EJ bladder carcinoma cells served as a negative control.

In-Vitro Transcription/Translation of PSM Antigen: Plasmid 55A containing the full length 2.65 kb PSM cDNA in the plasmid pSPORT 1 (Gibco-BRL) was transcribed in-vitro using the Promega TNT system (Promega Corp. Madison, Wis.). T7 RNA polymerase was added to the cDNA in a reaction mixture containing rabbit reticulocyte lysate, an amino acid mixture lacking methionine, buffer, and $^{35}S$-Methionine. (Amersham) and incubated at 30 C for 90 minutes. Post-translational modification of the resulting protein was accomplished by the addition of pancreatic canine microsomes into the reaction mixture (Promega Corp. Madison, Wis.). Protein products were analyzed by electrophoresis on 10% SDS-PAGE gels which were subsequently treated with Amplify autoradiography enhancer (Amersham, Arlington Heights, Ill.) according to the manufacturers instructions and dried at 80 C in a vacuum dryer. Gels were autoradiographed overnight at −70 C using Hyperfilm MP (Amersham).

Transfection of PSM into PC-3 Cells: The full length PSM cDNA was subcloned into the pREP7 eukaryotic expression vector (Invitrogen, San Diego, Calif.). Plasmid DNA was purified from transformed DH5-alpha bacteria (Gibco-BRL) using Qiagen maxi-prep plasmid isolation columns (Qiagen Inc., Chatsworth, Calif.). Purified plasmid DNA (6-log) was diluted with 900 ul of Optimem media (Gibco-BRL) and mixed with 30 ul of Lipofectin reagent (Gibco-BRL) which had been previously diluted with 900l of Optimem media. This mixture was added to T-75 flasks of 40-50% confluent PC-3 cells in Optimem media. After 24-36 hours, cells were trypsinized and split into 100 mm dishes containing RPMI 1640 media supplemented with 10% fetal calf serum and 1 mg/ml of Hygromycin B (Calbiochem, La Jolla, Calif.). The dose of Hygromycin B used was previously determined by a time course/dose response cytotoxicity assay. Cells were maintained in this media for 2-3 weeks with changes of media and Hygromycin B every 4-5 days until discrete colonies appeared. Colonies were isolated using 6 mm cloning cylinders and expanded in the same media. As a control, PC-3 cells were also transfected with the pREP7 plasmid alone. RNA was isolated from the transfected cells and PSM mRNA expression was detected by both RNase Protection analysis (described later) and by Northern analysis.

Western Blot Detection of PSM Expression: Crude protein lysates were isolated from LNCaP, PC-3, and PSM-transfected PC-3 cells as previously described. LNCaP cell membranes were also isolated according to published methods. Protein concentrations were quantitated by the Bradford method using the BioRad protein reagent kit (BioRad, Richmond, Calif.). Following denaturation, 20 µg of protein was electrophoresed on a 10% SDS-PAGE gel at 25 mA for 4 hours. Gels were electroblotted onto Immobilon P membranes (Millipore, Bedford, Mass.) overnight at 4 C. Membranes were blocked in 0.15M NaCl/0.01M Tris-HCl (TS) plus 5% BSA followed by a 1 hour incubation with 7E11-C5.3 monoclonal antibody (10 µg/ml). Blots were washed 4 times with 0.15M NaCl/0.01M Tris-HCl/0.05% Triton-X 100 (TS-X) and incubated for 1 hour with rabbit anti-mouse IgG (Accurate Scientific, Westbury, N.Y.) at a concentration of 10 µg/ml.

Blots were then washed 4 times with TS-X and labeled with $^{125}I$-Protein A (Amersham, Arlington Heights, Ill.) at a concentration of 1 million cpm/ml. Blots were then washed 4 times with TS-X and dried on Whatman 3 MM paper, followed by overnight autoradiography at −70 C using Hyperfilm MP (Amersham).

Orthotopic and Subcutaneous LNCaP Tumor Growth in Nude Mice: LNCaP cells were harvested from sub-confluent cultures by a one minute exposure to a solution of 0.25% trypsin and 0.02 k-EDTA. Cells were resuspended in RPMI 1640 media with 5% fetal bovine serum, washed and diluted in either Matrigel (Collaborative Biomedical Products, Bedford, Mass.) or calcium and magnesium-free Hank's balanced salt solution (HBSS). Only single cell suspensions with greater than 90% viability by trypan blue exclusion were used for in vivo injection. Male athymic Swiss (nu/nu) nude mice 4-6 weeks of age were obtained from the Memorial Sloan-Kettering Cancer Center Animal Facility. For subcutaneous tumor cell injection one million LNCaP cells resuspended in 0.2 mls. of Matrigel were injected into the hindlimb of each mouse using a disposable syringe fitted with a 28 gauge needle. For orthotopic injection, mice were first anesthetized with an intraperitoneal injection of Pentobarbital and placed in the supine position. The abdomen was cleansed with Betadine and the prostate was exposed through a midline incision. 2.5 million LNCaP tumor cells in 0.1 ml. were injected directly into either posterior lobe using a 1 ml disposable syringe and a 28 gauge needle. LNCaP cells with and without Matrigel were injected. Abdominal closure was achieved in one layer using Autoclip wound clips (Clay Adams, Parsippany, N.J.). Tumors were harvested in 6-8 weeks, confirmed histologically by faculty of the Memorial Sloan-Kettering Cancer Center Pathology Department, and frozen in liquid nitrogen for subsequent RNA isolation.

RNA Isolation: Total cellular RNA was isolated from cells and tissues by standard techniques (3 and 17) as well as by using RNAzol B (Cinna/Biotecx, Houston, Tex.). RNA concentrations and quality were assessed by UV spectroscopy on a Beckman DU 640 spectrophotometer and by gel analysis. Human tissue total RNA samples were purchased from Clontech Laboratories, Inc., Palo Alto, Calif.

Ribonuclease Protection Assays: A portion of the PSM cDNA was subcloned into the plasmid vector pSPORT 1 (Gibco-BRL) and the orientation of the cDNA insert relative to the flanking T7 and SP6 RNA polymerase promoters was verified by restriction analysis. Linearization of this plasmid upstream of the PSM insert followed by transcription with SP6 RNA polymerase yields a 400 nucleotide antisense RNA probe, of which 350 nucleotides should be protected from RNase digestion by PSM RNA. This probe was used in FIG. 20. Plasmid IN-20, containing a 1 kb partial PSM cDNA in the plasmid pCR II (Invitrogen) was also used for riboprobe synthesis. IN-20 linearized with Xmn I (Gibco-BRL) yields a 298 nucleotide anti-sense RNA probe when transcribed using SP6 RNA polymerase, of which 260 nucleotides should be protected from RNase digestion by PSM mRNA. This probe was used in FIGS. 21 and 22. Probes were synthesized using SP6 RNA polymerase (Gibco-BRL), rNTPs (Gibco-BRL), RNAsin (Promega), and $^{32}$P-rCTP (NEN, Wilmington, Del.) according to published protocols (44). Probes were purified over NENSORB 20 purification columns (NEN) and approximately 1 million cpm of purified, radiolabeled PSM probe was mixed with 10 μ of each RNA and hybridized overnight at 45 C using buffers and reagents from the RPA II kit (Ambion, Austin, Tex.). Samples were processed as per manufacturer's instructions and analyzed on 5% polyacrilamide/7M urea denaturing gels using Seq ACRYL reagents (ISS, Natick, Mass.). Gels were pre-heated to 55 C and run for approximately 1-2 hours at 25 watts. Gels were then fixed for 30 minutes in 10% methanol/10% acetic acid, dried onto Whatman 3 MM paper at 80 C in a BioRad vacuum dryer and autoradiographed overnight with Hyperfilm MP (Amersham). Quantitation of PSM expression was determined by using a scanning laser densitometer (LKB, Piscataway, N.J.).

Steroid Modulation Experiment: LNCaP cells (2 million) were plated onto T-75 flasks in RPMI 1640 media supplemented with 5% fetal calf serum and grown 24 hours until approximately 30-40% confluent. Flasks were then washed several times with phophate-buffered saline and RPMI medium supplemented with 5% charcoal-extracted serum was added. Cells were then grown for another 24 hours, at which time dihydrotesterone, testosterone, estradiol, progesterone, and dexamethasone (Steraloids Inc., Wilton, N.H.) were added at a final concentration of 2 nM. Cells were grown for another 24 hours and RNA was then harvested as previously described and PSM expression analyzed by ribonuclease protection analysis.

Experimental Results

Immunohistochemical Detection of PSM: Using the 7E11-C5.3 anti-PSM monoclonal antibody, PSM expression is clearly detectable in the LNCaP prostate cancer cell line, but not in the PC-3 and DU-145 cell lines (FIGS. 17A-17C). All normal and malignant prostatic tissues analyzed stained positively for PSM expression.

In-Vitro Transcription/Translation of PSM Antigen: As shown in FIG. 18, coupled in-vitro transcription/translation of the 2.65 kb full-length PSM cDNA yields an 84 kDa protein species in agreement with the expected protein product from the 750 amino acid PSM open reading frame. Following post-translational modification using pancreatic canine microsomes were obtained a 100 kDa glycosylated protein species consistent with the mature, native PSM antigen.

Detection of PSM Antigen in LNCaP Cell Membranes and Transfected PC-3 Cells:. PC-3 cells transfected with the full length PSM cDNA in the pREP7 expression vector were assayed for expression of SM mRNA by Northern analysis. A clone with high PSM mRNA expression was selected for PSM antigen analysis by Western blotting using the 7E11-C5.3 antibody. In FIG. 19, the 100 kDa PSM antigen is well expressed in LNCaP cell lysate and membrane fractions, as well as in PSM-transfected PC-3 cells but not in native PC-3 cells. This detectable expression in the transfected PC-3 cells proves that the previously cloned 2.65 kb PSM cDNA encodes the antigen recognized by the 7E11-C5.3 anti-prostate monoclonal antibody.

PSM mRNA Expression: Expression of PSM mRNA in normal human tissues was analyzed using ribonuclease protection assays. Tissue expression of PSM appears predominantly within the prostate, with very low levels of expression detectable in human brain and salivary gland (FIG. 20). No detectable PSM mRNA expression was evident in non-prostatic human tissues when analyzed by Northern analysis. On occasion it is noted that detectable PSM expression in normal human small intestine tissue, however this mRNA expression is variable depending upon the specific riboprobe used. All samples of normal human prostate and human prostatic adenocarcinoma assayed have revealed clearly detectable PSM expression, whereas generally decreased or absent expression of PSM in tissues exhibiting benign hyperplasia (FIG. 21). In human LNCaP tumors grown both orthotopically and subcutaneously in nude mice abundant PSM expression with or without the use of matrigel, which is required for the growth of subcutaneously implanted LNCaP cells was detected (FIG. 21). PSM mRNA expression is distinctly modulated by the presence of steroids in physiologic doses (FIG. 22). DHT downregulated expression by 8-10 fold after 24 hours and testosterone diminished PSM expression by 3-4 fold. Estradiol and progesterone also downregulated PSM expression in LNCaP cells, perhaps as a result of binding to the mutated androgen receptor known to exist in the LNCaP cell. Overall, PSM expression is highest in the untreated LNCaP cells grown in steroid-depleted media, a situation that simulates the hormone-deprived (castrate) state in-vivo. This experiment was repeated at steroid dosages ranging from 2-200 nM and at time points from 6 hours to 7 days with similar results; maximal downregulation of PSM mRNA was seen with DHT at 24 hours at doses of 2-20 nM.

Experimental Discussion

Previous research has provided two valuable prostatic biomarkers, PAP and PSA, both of which have had a significant impact on the diagnosis, treatment, and management of prostate malignancies. The present work describing the preliminary characterization of the prostate-specific membrane antigen (PSM) reveals it to be a gene with many interesting features. PSM is almost entirely prostate-specific as are PAP and PSA, and as such may enable further delineation of the unique functions and behavior of the prostate. The predicted sequence of the PSM protein (30) and its presence in the LNCaP cell membrane as determined by Western blotting and immunohistochemistry, indicate that it is an integral membrane protein. Thus, PSM provides an attractive cell surface epitope for antibody-directed diagnostic imaging and cytotoxic targeting modalities. The ability to synthesize the PSM antigen in-vitro and to produce tumor xenografts maintaining high levels of PSM expression provides us with a convenient and attractive model system to further study and characterize the regulation and modulation of PSM expression. Also, the high level of PSM expression in the LNCaP cells provides an excellent in-vitro model system. Since PSM expression is hormonally-responsive to steroids and may be highly expressed in hormone-refractory disease. The detection of PSM mRNA expression in minute quantities in brain, salivary gland, and small intestine warrants further investigation, although these tissues were negative for expression of PSM antigen by immunohistochemistry using the 7E11-C5.3 antibody. In all of these tissues, particularly small intestine, mRNA expression using a probe corresponding to a region of the PSM cDNA near the 3' end, whereas expression when using a 5' end PSM probe was not detected. These results may indicate that the PSM mRNA transcript undergoes alternative splicing in different tissues.

Applicants approach is based on prostate tissue specific promotor: enzyme or cytokine chimeras. Promotor specific activation of prodrugs such as non toxic gancyclovir which is converted to a toxic metabolite by herpes simplex thymidine kinase or the prodrug 4-(bis(2chloroethyl)amino)benzoyl-1-glutamic acid to the benzoic acid mustard alkylating agent by the pseudomonas carboxy peptidase G2 was examined. As these drugs are activated by the enzyme (chimera) specifically in the tumor the active drug is released only locally in the tumor environment, destroying the surrounding tumor cells. Promotor specific activation of cytokines such as IL-12, IL-2 or GM-CSF for activation and specific antitumor vaccination is examined. Lastly the tissue specific promotor activation of cellular death genes may also prove to be useful in this area.

Gene Therapy Chimeras: The establishment of "chimeric DNA" for gene therapy requires the joining of different segments of DNA together to make a new DNA that has characteristics of both precursor DNA species involved in the linkage. In this proposal the two pieces being linked involve different functional aspects of DNA, the promotor region which allows for the reading of the DNA for the formation of mRNA will provide specificity and the DNA sequence coding for the mRNA will provide for therapeutic functional DNA.

DNA-Specified Enzyme or Cytokine mRNA: When effective, antitumor drugs can cause the regression of very large amounts of tumor. The main requirements for antitumor drug activity is the requirement to achieve both a long enough time (t) and high enough concentration (c) (cxt) of exposure of the tumor to the toxic drug to assure sufficient cell damage for cell death to occur. The drug also must be "active" and the toxicity for the tumor greater than for the hosts normal cells. The availability of the drug to the tumor depends on tumor blood flow and the drugs diffusion ability. Blood flow to the tumor does not provide for selectivity as blood flow to many normal tissues is often as great or greater than that to the tumor. The majority of chemotherapeutic cytotoxic drugs are often as toxic to normal tissue as to tumor tissue. Dividing cells are often more sensitive than non-dividing normal cells, but in many slow growing solid tumors such as prostatic cancer-this does not provide for antitumor specificity.

Previously a means to increase tumor specificity of antitumor drugs was to utilize tumor associated enzymes to activate nontoxic prodrugs to cytotoxic agents. A problem with this approach was that most of the enzymes found in tumors were not totally specific in their activity and similar substrate active enzymes or the same enzyme at only slightly lower amounts was found in other tissue and thus normal tissues were still at risk for damage.

To provide absolute specificity and unique activity, viral, bacterial and fungal enzymes which have unique specificity for selected prodrugs were found which were not present in human or other animal cells. Attempts to utilize enzymes such as herpes simplex thymidine kinase, bacterial cytosine deaminase and carboxypeptidase G-2 were linked to antibody targeting systems with modest success. Unfortunately, antibody targeted enzymes limit the number of enzymes available per cell. Also, most antibodies do not have a high tumor target to normal tissue ratio thus normal tissues are still exposed reducing the specificity of these unique enzymes. Antibodies are large molecules that have poor diffusion properties and the addition of the enzymes molecular weight further reduces the antibodies diffusion.

Gene therapy could produce the best desired result if it could achieve the specific expression of a protein in the tumor and not normal tissue in order that a high local concentration of the enzyme be available for the production in the tumor environment of active drug.

Cytokines:

Results demonstrated that tumors such as the bladder and prostate were not immunogenic, that is the administration of irradiated tumor cells to the animal prior to subsequent administration of non-irradiated tumor cells did not result in a reduction of either the number of tumor cells to produce a tumor nor did it reduce the growth rate of the tumor. But if the tumor was transfected with a retrovirus and secreted large concentrations of cytokines such as Il-2 then this could act as an antitumor vaccine and could also reduce the growth potential of an already established and growing tumor. IL-2 was the best, GM-CSF also had activity whereas a number of other cytokines were much less active. In clinical studies just using IL-2 for immunostimulation, very large concentrations had to be given which proved to be toxic. The key to the success of the cytokine gene modified tumor cell is that the cytokine is produced at the tumor site locally and is not toxic and that it stimulates immune recognition of the tumor and allows specific and non toxic recognition and destruction of the tumor. The exact mechanisms of how IL-2 production by the tumor cell activates immune recognition is not fully understood, but one explanation is that it bypasses the need for cytokine production by helper T cells and directly stimulates tumor antigen activated cytotoxic CD8 cells. Activation of antigen presenting cells may also occur.

Tissue Promotor-Specific Chimera DNA Activation

Non-Prostatic Tumor Systems:

It has been observed in non-prostatic tumors that the use of promotor specific activation can selectively lead to tissue specific gene expression of the transfected gene. In melanoma the use of the tyrosinase promotor which codes for the enzyme responsible for melanin expression produced over a 50 fold greater expression of the promotor driven reporter gene expression in melanoma cells and not non melanoma cells. Similar specific activation was seen in the melanoma cells transfected when they were growing in mice. In that experiment no non-melanoma or melanocyte cell expressed the tyrosinase drive reporter gene product. The research group at Welcome Laboratories have cloned and sequenced the promoter region of the gene coding for carcinoembryonic antigen (CEA). CEA is expressed on colon and colon carcinoma cells but specifically on metastatic. A gene chimera was generated which cytosine deaminase. Cytosine deaminase which converts 5 flurorocytosine into 5 fluorouracil and observed a large increase in the ability to selectively kill CEA promotor driven colon tumor cells but not normal liver cells. In vivo they observed that bystander tumor cells which were not transfected with the cytosine deaminase gene were also killed, and that there was no toxicity to the host animal as the large tumors were regressing following treatment. Herpes simplex virus, (HSV), thymidine kinase similarly activates the prodrug gancyclovir to be toxic towards dividing cancer cells and HSV thymidine kinase has been shown to be specifically activatable by tissue specific promoters.

Prostatic Tumor Systems: The therapeutic key to effective cancer therapy is to achieve specificity and spare the patient toxicity. Gene therapy may provide a key part to specificity in that non-essential tissues such as the prostate and prostatic tumors produce tissue specific proteins, such as acid phosphatase (PAP), prostate specific antigen (PSA), and a gene which was cloned, prostate-specific membrane antigen (PSM). Tissues such as the prostate contain selected tissue specific transcription factors which are responsible for binding to the promoter region of the DNA of these tissue specific mRNA. The promoter for PSA has been cloned. Usually patients who are being treated for metastatic prostatic cancer have been put on androgen deprivation therapy which dramatically reduces the expression of mRNA for PSA. PSM on the other hand increases in expression with hormone deprivation which-means it would be even more intensely expressed on patients being treated with hormone therapy.

EXAMPLE 3

Cloning and Characterization of the Prostate Specific Membrane Antigen (PSM) Promoter.

The expression and regulation of the PSM gene is complex. By immunostaining, PSM antigen was found to be expressed brilliantly in metastasized tumor, and in organ confined tumor, less so in normal prostatic tissue and more heterogenous in BPH. PSM is strongly expressed in both anaplastic and hormone refractory tumors. PSM mRNA has been shown to be down regulated by androgen. Expression of PSM RNA is also modulated by a host of cytokines and growth factors. Knowledge of the regulation of PSM expression should aid in such diagnostic and therapeutic strategies as imunoscintigraphic imaging of prostate cancer and prostate-specific promoter-driven gene therapy.

Sequencing of a 3 kb genomic DNA clone revealed that two stretches of about 300 B.P. (−260 to −600; and −1325 to −1625) have substantial homology (79-87%) to known genes. The promoter lacks a GC rich region, nor does it have a consensus TATA box. However, it contains a TA-rich region from position −35 to −65.

Several consensus recognition sites for general transcription factors such as AP1, AP2, NFkB, GRE and E2-RE were identified. Chimeric constructs containing fragments of the upstream region of the PSM gene fused to a promoterless chloramphenicol acetyl transferase gene were transfected into, and transiently expressed in LNCaP, PC-3, and SW620 (a colonic cell line). With an additional SV40 enhancer, sequence from −565 to +76 exhibited promoter activity in LNCaP but not in PC-3 nor in SW620.

Materials and Methods

Cell Lines. LNCaP and PC-3 prostatic carcinoma cell lines (American Type Culture Collection) were cultured in RPMI and MEM respectively, supplemented with 5% fetal calf serum at 37° C. and 5% $CO_2$. SW620, a colonic cell line.

Polymerase Chain Reaction. The reaction was performed in a 50 volume with a final concentration of the following reagents: 16.6 mM $NH_4SO_4$, 67 mM Tris-HCl pH 8.8, acetylated BSA 0.2 mg/ml, 2 mM $MgCl_2$, 250 µM dNTPs, 10 mM: β-mercaptoethanol, and 1 U of the 111 Taq polymerase (Boehringer Mannhiem, Calif.). A total of 25 cycles were completed with the following profile: cycle 1, 94° C. 4 min.; cycle 2 through 25, 94° C. 1 min, 60° C. 1 min, 72° C. 1 min. The final reaction was extended for 10 min at 72° C. Aliquots of the reaction were electrophoresed on 1 k agarose gels in 1× Tris-acetate-EDTA buffer.

Cloning of PSM promoter. A bacteriophage P1 library of human fibroblast genomic DNA (Genomic Systems, Inc., St. Louis, Mo.), was screened using a PCR method of Pierce et al. Primers located at the 5' end of PSM cDNA were used: 5'-CTCAAAAGGGGCCGGATTTCC-3' (SEQ ID NO:116) and 5' CTCTCAATCTACTAATGCCTC-3' (SEQ ID NO:117). A positive clone, p683, was digested with XhoI restriction enzyme. Southern analysis of the restricted fragments using a DNA probe from the extreme 5' to the Ava-1 site of the PSM cDNA confirmed that a 3Kb fragment contains the 5' regulatory sequence of the PSM gene. The 3 kb XhoI fragment was subcloned into pKSBluescript vectors and sequenced using the dideoxy method.

Functional Assay of PSM Promoter. Chloramphenicol Acetyl Transferase, (CAT) gene plasmids were constructed from the Sma1-HindIII fragments or subfragements (using either restriction enzyme subfragments or PCR) by insertion into promoterless pCAT basic or pCAT-enhancer vectors (Promega). pCAT-constructs were cotransfected with pSVβ-gal plasmid (5 µg of each plasmid) into cell lines in duplicates, using a calcium phosphate method (Gibco-BRL, Gaithersburg, Md.). The transfected cells were harvested 72 hours later and assayed (15 µg of lysate) for CAT activity using the LSC method and for βgal activity (Promega). CAT activities were standardized by comparision to that of the βgal activities.

Results

Sequence of the 5' end of the PSM gene.

The DNA sequence of the 3 kb XhoI fragment of p683 which includes 3017 bp of DNA from the RNA start site was determined. (FIG. 15) The sequence from the XhoI fragment displayed a remarkable arrays of elements and motifs which are characteristic of eukaryotic promoters and regulatory regions found in other genes (FIG. 16).

Functional Analysis of upstream PSM genomic elements for promoter activity.

Various pCAT-PSM promoter constructs were tested for promoter activities in two prostatic cell lines: LNCaP, PC-3 and a colonic SW620 (FIG. 17). Induction of CAT activity was neither observed in p1070-CAT which contained a 1070 bp PSM 5' promoter fragment, nor in p676-CAT which contained a 641 bp PSM 5' promoter fragment. However, with an additional SV-40 enhancer, sequence from −641 to −1 (p676-CATE) exhibited promoter activity in LNCaP but not in PC-3 nor in SW6.20.

Therefore, a LNCaP specific promoter fragment from −641 to −1 has been isolated which can be used in PSM promoter-driven gene therapy.

EXAMPLE 4

Alternatively Spliced Variants of Prostate Specific Membrane Antigen RNA: Ratio of Expression as a Potential Measurement of Progression Materials and Methods Cell Lines. LNCaP and PC-3 prostatic carcinoma cell lines were cultured in RPMI and MEM respectively, supplemented with 5% fetal calf serum at 37° C. and 5% $CO_2$.

Primary tissues. Primary prostatic tissues were obtained from MSKCC's in-house tumor procurement; service. Gross specimen were pathologically staged by MSKCC's pathology service.

RNA Isolation. Total RNA was isolated by a modified guanidinium thiocynate/phenol/chloroform method using a RNAzol B kit (Tel-Test, Friendswood, Tex.). RNA was stored in diethyl pyrocarbonate-treated water at −80° C. RNA was quantified using spectrophometric absorption at 260 nm.

cDNA synthesis. Two different batches of normal prostate mRNAs obtained from trauma-dead males (Clontech, Palo Alto, Calif.) were denatured at 70° C. for 10 min., then reverse transcribed into cDNA using random hexamers and Superscript II reverse transcriptase (GIBCO-BRL, Gaithersburg, Md.) at 50° C. for 30 min. followed by a 94° C. incubation for 5 min.

Polymerase Chain Reaction. Oligonucleotide primers (5'-CTCAAAAGGGGCCGGATTTCC-3' (SEQ ID NO:116) and 5' CTCTCAATCTACTAATGCCTC-3'(SEQ ID NO:117)), specific for the 5' and 3' ends of PSM cDNA were designed to span the cDNA sequence. The reaction was performed in a 50 µl volume with a final concentration of the following reagents: 16.6 mM $NH_4SO_4$, 67 mM Tris-HCl pH 8.8, acetylated BSA 0.2 mg/ml, 2mM MgCl2, 250 µM dNTPs, 10 mM β-mercaptoethanol, and 1 U of rTth polymerase (Perkin Elmer, Norwalk, Conn.). A total of 25 cycles were completed with the following profile: cycle 1, 94° C. 4 min.; cycle 2 through 25, 94° C. 1 mm 60° C. 1 min, 72° C. 1 min. The final reaction was extended for 10 min at 72° C. Aliquots of the reaction were electrophoresed on 1% agarose gels in lx Tris-acetated-EDTA buffer.

Cloning of PCR products. PCR products were cloned by the TA cloning method into pCRII vector using a kit from Invitrogen (San Diego, Calif.). Ligation mixture were transformed into competent *Escherichia coli* Inv5α.

Sequencing. Sequencing was done by the dideoxy method using a sequenase kit from US Biochemical (Cleveland, Ohio). Sequencing products were electrophoresed on a 5% polyacrylamide/7M urea gel at 52° C.

RNase Protection Assays. Full length PSM cDNA clone was digested with NgoM 1 and Nhe1. A 350 b.p. fragment was isolated and subcloned into pSPORT1 vector (GIBCO-BRL, Gaithersburg, Md.). The resultant plasmid, pSP350, was linearized, and the insert was transcribed by SP6 RNA polymerase to yield antisense probe of 395 nucleotide long, of which 355 nucleotides and/or 210 nucleotides should be protected from RNAse digestion by PSM RNA respectively. Total celluar RNA (20 µg) from different tissues were hybridized to the aforementioned antisense RNA probe. Assays were performed as described. tRNA was used as negative control. RPAs for LNCaP and PC-3 were repeated.

Results

RT-PCR of mRNA from normal prostatic tissue. Two independent RT-PCR of mRNA from normal prostates were performed as described in Materials and Methods. Subsequent cloning and sequencing of the PCR products revealed the presence of an alternatively spliced variant, PSM'. PSM' has a shorter cDNA (2387 nucleotides) than PSM (2653 nucleotides). The results of the sequence analysis are shown in FIG. 18. The cDNAs are identical except for a 266 nucleotide region near the 5' end of PSM cDNA (nucleotide 114 to 380) that is absent in PSM' cDNA. Two independent repetitions of RT-PCR of different mRNA samples yielded identical results.

RNase Protection Assays. An RNA probe complementary to PSM RNA and spanning the 3' splice junction of PSM' RNA was used to measure relative expression of PSM and PSM' mRNAs (FIG. 19). With this probe, both PSM and PSM' RNAs in LNCaP cells was detected and the predominant form was PSM. Neither PSM nor PSM' RNA was detected in PC-3 cells, in agreement with previous Northern and Western blot data. FIG. 20 showed the presence of both splice variants in human primary prostatic tissues. In primary prostatic tumor, PSM is the dominant form. In contrast, normal prostate expressed more PSM' than PSM. BPH samples showed about equal expression of both variants.

Tumor Index. The relative expression of PSM and PSM' (FIG. 36) was quantified by densitometry and expressed as a tumor index (FIG. 21). LNCaP has an index ranging from 9-11; CaP from 3-6; BPH from 0.75 to 1.6; normal prostate has values from 0.075 to 0.45.

Discussion

Sequencing data of PCR products derived from human normal prostatic mRNA with 5' and 3' end PSM oligonucleotide primers revealed a second splice variant, PSM', in addition to the previously described PSM cDNA.

PSM is a 750 a.a. protein with a calculated molecular weight of 84,330. PSM was hypothesized to be a type II integral membrane protein. A classic type II membrane protein is the transferrin receptor and indeed PSM has a region that has modest homology with the transferrin receptor. Analysis of the PSM amino acid sequence by either the methods of Rao and Argos or Eisenburg et. al. strongly predicted one transmembrane helix in the region from a.a.#20 to #43. Both programs found other regions that could be membrane associated but were not considered likely candidates for being transmembrane regions.

PSM' antigen, on the other hand, is a 693 a.a. protein as deduced from its mRNA sequence with a molecular weight of 78,000. PSM' antigen lacks the first 57 amino acids present in the PSM antigen (FIG. 18) (SEQ ID NO: 102) It is likely the at PSM' antigen is cytosolic.

The function of PSM and PSM' are probably different. The cellular location of PSM antigen suggests that it may interact with either extra- or intra-cellular ligand(s) or both; while that of PSM' implies that PSM' can only react with cytosolic ligand(s). Furthermore, PSM antigen has 3 potential phosphorylation sites on its cytosolic domain. These sites are absent in PSM' antigen. On the other hand, PSM' antigen has 25 potential phosphorylation sites, 10 N-myristoylation sites and 9 N-glycosylation sites. For PSM antigen, all of these potential sites would be on the extracellular surface. The modifications of these sites for these homologous proteins would be different depending on their cellular locations. Consequently, the function(s) of each form would depend on how they are modified.

The relative differences in expression of PSM and PSM' by RNase protection assays was analyzed. Results of expression of PSM and PSM' in primary prostatic tissues strongly suggested a relationship between the relative expression of these variants and the status of the cell: either-normal or cancerous. While it is noted here that the sample size of the study is small (FIGS. 20 and 21), the consistency of the trend is evident. The samples used were gross specimens from patients. The results may have been even more dramatic if specimens that were pure in content of CaP, BPH or normal had been used. Nevertheless, in these specimens, it is clear that there is a relative increase of PSM over PSM' mRNA in the change from normal to CaP. The Tumor Index (FIG. 21) could be useful in measuring the pathologic state of a given sample. It is also possible that the change in expression of PSM over PSM' may be a reason for tumor progression. A more differentiated tumor state may be restored by PSM' either by transfection or by the use of differentiation agents.

EXAMPLE 5

Enhanced Detection of Prostatic Hematogenous Micro-Metastases with PSM Primers as Compared to PSA Primers Using a Sensitive Nested Reverse Transcriptase-PCR Assay 77 randomly selected samples were analyzed from patients with prostate cancer and reveals that PSM and PSA primers detected circulating prostate cells in 48 (62.3%) and 7 (9.1%) patients, respectively. In treated stage D disease patients, PSM primers detected cells in 16 of 24 (66.7%), while PSA primers detected cells in 6 of 24 patients (25%). In hormone-refractory prostate cancer (stage D3), 6 of 7 patients were positive with both PSA and PSM primers. All six of these patients died within 2-6 months of their assay, despite aggressive cytotoxic chemotherapy, in contrast to the single patient that tested negatively in this group and is alive 15 months after his assay, suggesting that PSA-PCR positivity may serve as a predictor of early mortality. In post-radical prostatectomy patients with negative serum PSA values, PSM primers detected metastases in 21 of 31 patients (67.7%), while PSA primers detected cells in only 1 of 33 (3.0%), indicating that micrometastatic spread may be a relatively early event in prostate cancer. The analysis of 40 individuals without known prostate cancer provides evidence that this assay is highly specific and suggests that PSM expression may predict the development of cancer in patients without clinically apparent prostate cancer. Using PSM primers, micrometastases were detected in 4 of 40 controls, two of whom had known BPH by prostate biopsy and were later found to have previously undetected prostate cancer following repeat prostate biopsy performed for a rising serum PSA value. These results show the clinical significance of detection of hematogenous micrometastatic prostate cells using PSM primers and potential applications of this molecular assay.

EXAMPLE 6

Modulation of Prostate Specific Membrane Antigen (PSM) Expression in Vitro by Cytokines and Growth Factors The effectiveness of CYT-356 imaging is enhanced by manipulating expression of PSM. PSM mRNA expression is downregulated by steroids. This is consistent with the clinical observations that PSM is strongly expressed in both anaplastic and hormone refractory lesions. In contrast, PSA expression is decreased following hormone withdrawal. In hormone refractory disease, it is believed that tumor cells may produce both growth factors and receptors, thus establishing an autocrine loop that permits the cells to overcome normal growth constraints. Many prostate tumor epithelial cells express both TGFα and its receptor, epidermal growth factor receptor. Results indicate that the effects of TGFα and other selected growth factors and cytokines on the expression of PSM in-vitro, in the human prostatic carcinoma cell line LNCaP.

$2 \times 10^6$ LNCaP cells growing in androgen-depleted media were treated for 24 to 72 hours with EGF, TGFα, TNFβ or TNFα in concentrations ranging from 0.1 ng/ml to 100 ng/ml. Total RNA was extracted from the cells and PSM mRNA expression was quantitated by Northern blot analysis and laser densitometry. Both b-FGF and TGFα yielded a dose-dependent 10-fold upregulation of PSM expression, and EGF a 5-fold upregulation, compared to untreated LNCaP. In contrast, other groups have shown a marked downregulation in PSA expression induced by these growth factors in this same in-vitro model. TNFα, which is cytotoxic to LNCaP cells, and TNFβ downregulated PSM expression 8-fold in androgen depleted LNCaP cells.

TGFα is mitogenic for aggressive prostate cancer cells. There are multiple forms of PSM and only the membrane form is found in association with tumor progression. The ability to manipulate PSM expression by treatment with cytokines and growth factors may enhance the efficacy of Cytogen 356 imaging, and therapeutic targeting of prostatic metastases.

EXAMPLE 7

Neoadjuvant Androgen-Deprivation Therapy (ADT) Prior to Radical Prostatectomy Results in a Significantly Decreased Incidence of Residual Micrometastatic Disease as Detected by Nested RT-PCT with Primers Radical prostatectomy for clinically localized prostate cancer is considered by many the "gold standard" treatment. Advances over the past decade have served to decrease morbidity dramatically. Improvements intended to assist clinicians in better staging patients preoperatively have been developed, however the incidence of extra-prostatic spread still exceeds 50%, as reported in numerous studies. A phase III prospective randomized clinical study designed to compare the effects of ADT for 3 months in patients undergoing radical prostatectomy with similarly matched controls receiving surgery alone was conducted. The previously completed phase II study revealed a 10% margin positive rate in the ADT group (N=69) as compared to a −33% positive rate (N=72) in the surgery alone group.

Patients who have completed the phase III study were analyzed to determine if there are any differences between the two groups with respect to residual micrometastatic disease. A positive PCR result in a post-prostatectomy patient identifies viable metastatic cells in the circulation.

Nested RT-PCR was performed with PSM primers on 12 patients from the ADT group and on 10 patients from the control group. Micrometastatic cells were detected in 9/10 patients (90%) in the control group, as compared to only 2/12 (16.7%) in the ADT group. In the ADT group, 1 of 7 patients with organ-confined disease tested positively, as compared to 3 of 3 patients in the control group. In patients with extra-prostatic disease, 1 of 5 were positive in the ADT group, as compared to 6 of 7 in the control group. These results indicate that a significantly higher number of patients may be rendered tumor-free, and potentially "cured" by the use of neoadjuvant ADT.

EXAMPLE 8

Sensitive Nested RT-PCR Detection of Circulation Prostatic Tumor Cells—Comparison of PSM and PSA-Based Assays Despite the improved and expanded arsenal of modalities available to clinician today, including sensitive serum PSA assays, CT scan, transrectal ultrasonography, endorectal co.I MRI, etc., many patients are still found to have metastatic disease at the time of pelvic lymph node dissection and radical prostatectomy. A highly sensitive reverse transcription PCR assay capable of detecting occult hematogenous micrometastatic prostatic cells that would otherwise go undetected by presently available staging modalities was developed. This assay is a modification of similar PCR assays performed in patients with prostate cancer and other malignancies. The assay employs PCR primers derived from the cDNA sequences of prostate-specific antigen[6] and the prostate-specific membrane antigen recently cloned and sequenced.

Materials and Methods

Cells and Reagents. LNCaP and MCF-7 cells were obtained from the American Type Culture Collection (Rockville, Md.). Details regarding the establishment and characteristics of these cell. Cells grown in RPMI 1640 medium and supplemented with L-glutamine, nonessential amino acids, and 5% fetal calf serum (Gibco-BRL, Gaithersburg, Md.) In a 5% $CO_2$ incubator at 37° C. All cell media was obtained from the MSKCC Media Preparation Facility. Routine chemical reagents were of the highest grade possible and were obtained from Sigma Chemical Company (St. Louis, Mo.).

Patient Blood Specimens. All blood specimens used in this study were from patients seen in the outpatient offices of urologists on staff at MSKCC. Two anti-coagulated tubes per patient were obtained at the time of their regularly scheduled blood draws. Specimens were obtained with informed consent of each patient, as per a protocol approved by the MSKCC Institutional Review Board. Samples were promptly brought to the laboratory for immediate processing. Seventy-seven specimens from patients with prostate cancer were randomly selected and delivered to the laboratory "blinded" along with samples from negative controls for processing. These included 24 patients with stage D disease (3 with $D_0$, 3 with $D^1$, 11 with $D^2$, and 7 with $D^3$), 31 patients who had previously undergone radical prostatectomy and had undetectable postoperative serum PSA levels (18 with pT2 lesions, 11 with pT3, and 2 pT4), 2 patients with locally recurrent disease following radical prostatectomy, 4 patients who had received either external beam radiation therapy or interstitial 1125 implants, 10 patients with untreated clinical stage T1-T2 disease, and 6 patients with clinical stage T3 disease on anti-androgen therapy. The forty blood specimens used as negative controls were from 10 health males, 9 males with biopsy-proven BPH and elevated serum PSA levels, 7 healthy females, 4 male patients with renal cell carcinoma, 2 patients with prostatic intraepithelial neoplasia (PIN), 2 patients with transitional cell carcinoma of the bladder and a pathologically normal prostate, 1 patient with acute prostatitis, 1 patient with acute promyelocytic leukemia, 1 patient with testicular cancer, 1 female patient with renal cell carcinoma, 1 patient with lung cancer, and 1 patient with a cyst of the testicle.

Blood Sample Processing/RNA Extraction. 4 ml of whole anticoagulated venous blood was mixed with 3 ml of ice cold PBS and then carefully layered atop 8 ml of Ficoll (Pharmacia, Uppsala, Sweden) in a 14-ml polystyrene tube. Tubes were centrifuged at 0.200× g for 30 min. at 4° C. The buffy coat layer (approx. 1 ml.) was carefully removed and rediluted to 50 ml with ice cold PBS in a 50 ml polypropylene tube. This tube was then centrifuged at 2000× g for 30 min. at 4° C. The supernatant was carefully decanted and the pellet was allowed to drip dry. One ml of RNazol B was then added to the pellet and total RNA was isolated as per manufacturers directions (Cinna/Biotecx, Houston, Tex.) RNA concentrations and purity were determined by UV spectroscopy on a Beckman DU 640 spectrophotometer and by gel analysis.

D termination of PCR Sensitivity. RNA was isolated from LNCaP cells and from mixtures of LNCaP and MCF-7 cells at fixed ratios (i.e. 1:100, 1:1,000, etc.) using RNAzol B. Nested PCR was then performed as described below with both PSA and PSM primers in order to determine the limit of detection for the assay.

LNCaP:MCF-7 (1:100,000) cDNA was diluted with distilled water to obtain concentrations of 1:1,000,000. The human breast cancer cell line MCF-7 was chosen because they had previously been tested by us and shown not to express either PSM nor PSA by both immunohistochemistry and conventional and nested PCR.

Polymerase Chain Reaction. The PSA outer primer sequences are nucleotides 494-513 (sense) in exon 4 and nucleotides 960-979 (antisense) in exon 5 of the PSA cDNA. These primers yield a 486 bp PCR product from PSA cDNA that can be distinguished for a product synthesized from the possible contaminating genomic DNA.

```
                                       (SEQ ID NO:118)
PSA-494     5'-TAC CCA CTG CAT CAG GAA CA-3'

(SEQ ID NO:119)
PSA-960     5'-CCT TGA AGC ACA CCA TTA CA-3'
```

The PSA upstream primer begins a nucleotide 559 and the downstream primer at nucleotide 894 to yeild a 355 bp PCR product.

```
                                       (SEQ ID NO:120)
PSA-559     5'-ACA CAG GCC AGG TAT TTC AG-3'

(SEQ ID NO:121)
PSA-894     5'-GTC CAG CGT CCA GCA CAC AG-3'
```

All primers were synthesized by the MSKCC Microchemistry Core Facility. 5 µg of total RNA was reverse-transcribed into cDNA using random hexamer primers (Gibco-BRL) and Superscript II reverse transcriptase (Gibco-BRL) according to the manufactures recommendations. 1 µl of the CDNA served as the starting template for the outer primer PCR reaction. 20 µl PCR mix included: 0.5U Tag polymerase (Promega) Promega reaction buffer, 1.5 mM $MgCl_{2, 200}$ µM dNTPs and 1.0 µM of each primer. This mix was then transferred to a Perkin Elmer 9600 DNA thermal cycle and incubated for 25 cycles. The PCR profile was as follows: 94° C.×15 sec., 60° C.×15 sec., and 72° C. for 45 sec. After 25 cycles, samples were placed on ice, and 1 µl of this reaction mix served as the template for another 25 cycles using the inner primers. The first set of tubes were returned to the thermal cycler for 25 additional cycles. The PSM outer upstream primer sequences are nucleotides 1368-1390 and the downstream primers are nucleotides 1995-2015, yielding a 67 bp PCR product.

```
                                            (SEQ ID NO:122)
PSM-1368    5'-CAG ATA TGT CAT TCT GGG AGG TC-3'

(SEQ ID NO:123)
PSM-2015    5'-AAC ACC ATC CCT CCT CGA ACC-3'
```

The PSM inner upstream primer span nucleotides 1689-1713 and the downstream primer span nucleotides 1899-1923, yielding a 234 bp PCR product.

```
                                            (SEQ ID NO:124)
PSM-1689    5'-CCT AAC AAA AGA GCT GAA AAG CCC-3'

(SEQ ID NO:125)
PSM-1923    5'-ACT GTG ATA CAG TGG ATA GCC GCT-3'
```

2 µl of cDNA was used as the starting DNA template in the PCR assay. The 50 µl PCR mix included: 1 U Taq polymerase (Boehringer Mannheim), 250 µM dNTPs, 10 µM β-mercaptoethanol, 2mM MgCl2, and 5 µl of a 10 × buffer mix containing 166 mM $NH_4SO_4$, 67 mM Tris-HCl pH 8.8, and 2mg/ml of acetylated BSA. PCR was carried out in a Perkin Elmer 480 DNA thermal cycler with the following parameters: 94° C.×4 minutes for 1 cycle, 94° C.×30 sec., 58° C.×1 minute, and 72° C.×1 minute for 25 cycles followed by 72° C.×10 minutes. Sample were then iced and 2.5 µl of this reaction mix was used as the template for another 25 cycles with a new reaction mix containing the inner PSM primers. cDNA quality was verified by performing control reactions using primers derived from the β-2-microglobulin gene sequence[10] a ubiquitous housekeeping gene. These primers span exons 2-4 and generate a 620 bp PCR product. The sequences for these primers are:

```
                                            (SEQ ID NO:126)
β2 (exon 2)   5'-AGC AGA GAA TGG AAA GTC AAA-3'

(SEQ ID NO:127)
β2 (exon 4)   5'-TGT TGA TGT TGG ATA AGA GAA-3'
```

Cloning and Sequencing of PCR Products. PCR products were cloned into the pCR II plasmid vector using the TA cloning system (Invitrogen). These plasmids were transformed into competent E. coli cells using standard methods[11] and plasmid DNA was isolated using Magic Minipreps (Promega) and screened by restriction analysis. Double-stranded TA clones were then sequenced by the dideoxy method using $^{35}$S-cCTP (NEN) and Sequenase (U.S. Biochemical). Sequencing products were then analyzed on 6% polyacrilamide/7M urea gels, which were fixed, dried, and autoradiographed as described.

Southern Analysis. PCR products were transferred from ethidium-stained agarose gels to Nytran nylon membranes (Schletcher and Schuell) by pressure blotting with a Posi-blotter (Stratagene) according to the manufacturer's instructions. DNA was cross-linked to the membrane using a UV Stratalinker (Stratagene). Blots were pre-hybridized at 65° C. for 2 hours and subsequently hybridized with denatured $^{32}$P-labeled, random-primed cDNA probes (either PSA or PSM).[6,7] Blots were washed twice in 1×SSC/0.5% SDS at 42° C. and twice in 0.1×SSC/0.1% SDS at 50 C for 20 minutes each. Membranes were air-dried and autoradiographed for 1-3 hours at room temperature with Hyperfilm MP (Amersham).

Results

Figure 1B:
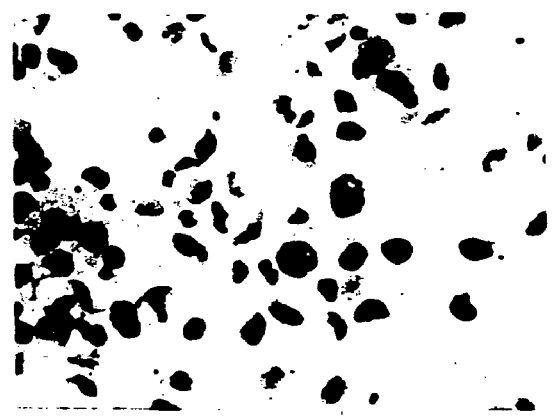
Figure 1C:
Figure 2:
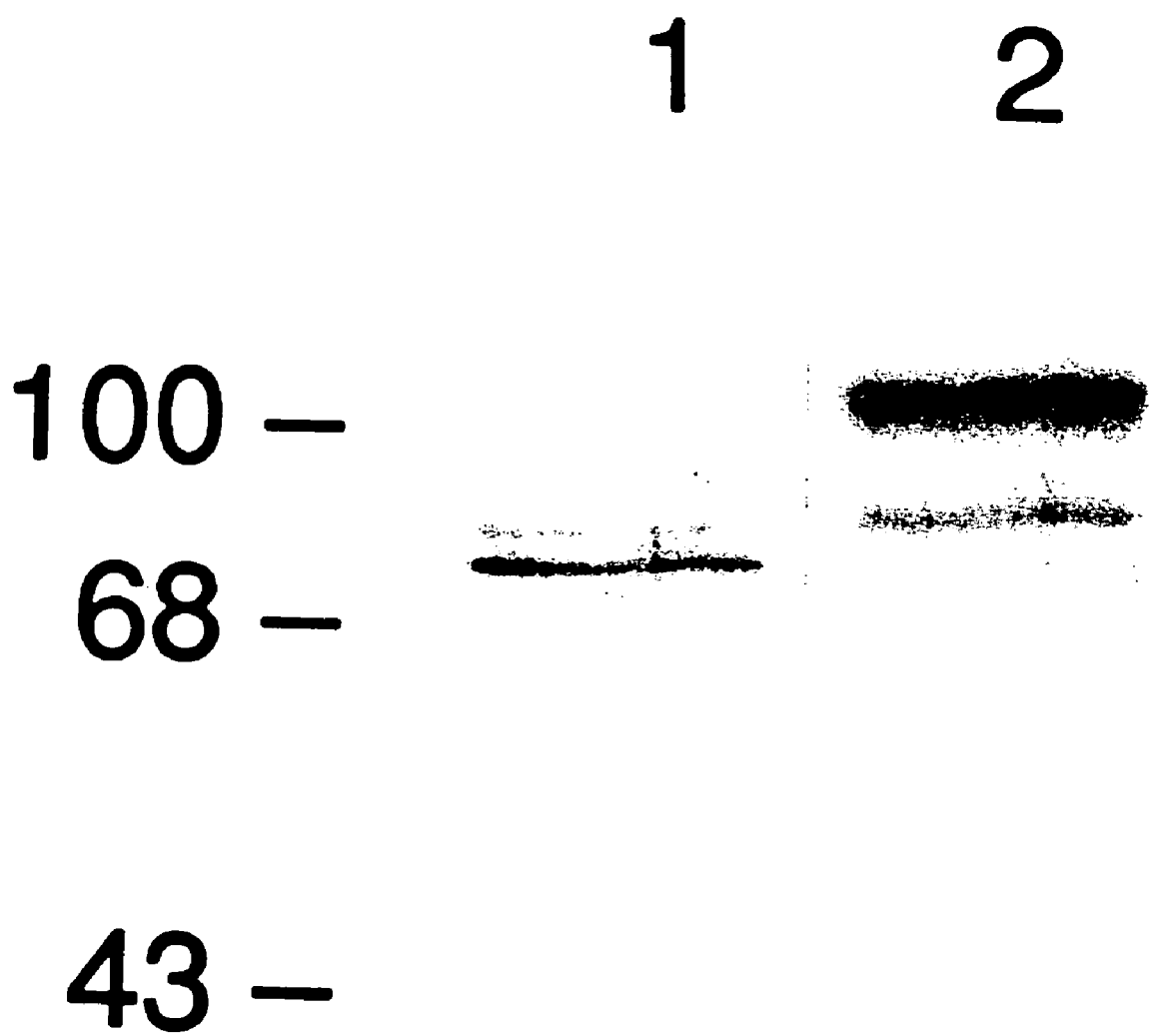
FIG. 2: Autoradiogram of protein gel revealing products of PSM coupled in-vitro transcription/translation. Non-glycosylated PSM polypeptide is seen at 84 kDa (lane 1) and PSM glycoprotein synthesized following the addition of microsomes is seen at 100 kDa (lane 2)
Figure 3:
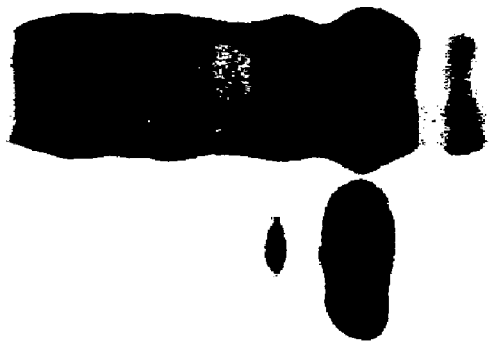
FIG. 3: Western Blot analysis detecting PSM expression in transfected non-PSM expressing PC-3 cells. 100 kDa PSM glycoprotein species is clearly seen in LNCaP membranes (lane 1), LNCaP crude lysate (lane 2), and PSM-transfected PC-3 cells (lane 4), but is undetectable in native PC-3 cells (lane 3).
Figure 4:
FIG. 4: Autoradiogram of ribonuclease protection gel assaying for PSM mRNA expression in normal human tissues.

PSA and PSM Nested PCR Assays: The application of nested PCR increased the level of detection from an average of 1:10,000 using outer primers alone, to better than 1:1,000,000. Dilution curves demonstrating this added sensitivity are shown for PSA and PSM-PCR in FIGS. 1 and 2 respectively. FIG. 1 shows that the 486 bp product of the PSA outer primer set is clearly detectable with ethidium staining to 1:10,000 dilutions, whereas the PSA inner primer 355 bp product is clearly detectable in all dilutions shown. In FIG. 2 the PSM outer primer 647 bp product is also clearly detectable in dilutions to only 1:10,000 with conventional PCR, in contrast to the PSM inner nested PCR 234 bp product which is detected in dilutions as low as 1:1,000,000. Southern blotting was performed on all controls and most of the patient samples in order to confirm specificity. Southern blots of the respective dilution curves confirmed the primer specificities but did not reveal any significantly increased sensitivity.

PCR in Negative Controls: Nested PSA and PSM PCR was performed on 40 samples from patients and volunteers as described in the methods and materials section. FIG. 48 reveals results from 4 representative negative control specimens, in addition to a positive control. Each specimen in the study was also assayed with the 1-2-microglobulin control, as shown in the figure, in order to verify RNA integrity. Negative results were obtained on 39 of these samples using the PSA primers, however PSM nested PCR yielded 4 positive results. Two of these "false positives" represented patients with elevated serum PSA values and an enlarged prostate who underwent a transrectal prostate biopsy revealing stromal and fibromuscular hyperplasia. In both of these patients the serum PSA level continued to rise and a repeat prostate biopsy performed at a later date revealed prostate cancer. One patient who presented to the clinic with a testicular cyst was noted to have a positive PSM nested PCR result which has been unable to explain. Unfortunately, this patient never returned for follow up, and thus have not been able to obtain another blood sample to repeat this assay. Positive result were obtained with both PSA and PSM primers in a 61 year old male patient with renal cell carcinoma. This patient has a normal serum PSA level and a normal digital rectal examination. Overall, if the two patients were excluded in whom a positive PCR, but no other clinical test, accurately predicted the presence of prostate cancer, 36/38 (94.7%) of the negative controls were negative with PSM primers, and 39/40 (97.5%) were negative using PSA primers.

Patient Samples: In a "blinded" fashion, in which the laboratory staff were unaware of the nature of each specimen, 117 samples from 77 patients mixed randomly with 40 negative controls were assayed. The patient samples represented a diverse and heterogeneous group as described earlier. Several representative patient samples are displayed in FIG. 49, corresponding to positive results from patients with both localized and disseminated disease. Patients 4 and 5, both with stage D prostate cancer exhibit positive results with both the outer and inner primer pairs, indicating a large circulating tumor cell burden, as compared to the other samples. Although the PSM and PSA primers yielded similar sensitivities in LNCaP dilution curves as previously shown, PSM primers detected micrometastases in 62.3% of the patient samples, whereas PSA primers only detected 9.1%. In patients with documented metastatic prostate cancer (stages $D_0$-$D_3$) receiving anti-androgen treatment, PSM primers detected micrometastases in 16/24 (66.7%), whereas PSA primers detected circulating cells in only 6/24 (25%). In the study 6/7 patients with hormone-refractory prostate cancer (stage $D_3$) were positive. In the study, PSA primers revealed micrometastatic cells in only 1/15 (6.7%) patients with either pT3 or pT4 (locally-advanced) prostate cancer following radical prostatectomy. PSM primers detected circulating cells in 9/15 (60%) of these patients. Interestingly, circulating cells 13/18 (72.2%) patients with pT2 (organ-confined) prostate cancer following radical prostatectomy using PSM primers was detected. None of these patient samples were positive by PSA-PCR.

Improved and more sensitive method for the detection of minimal, occult micrometastic disease have been reported for a number of malignancies by use of immunohistochemical methods, as well as the polymerase chain reaction. The application of PCR to detect occult hematogenous micrometastases in prostate cancer was first described by Moreno, et al. using conventional PCR with PSA-derived primers.

When human prostate tumors and prostate cancer cells in-vitro were studied by immunohistochemistry and mRNA analysis, PSM appeared to be highly expressed in anaplastic cells, hormone-refractory cells, and bony metastases, in contrast to PSA. If cells capable of hematogenous micrometastasis represent the more aggressive and poorly-differentiated cells, they may express a higher level of PSM per cell as compared to PSA, enhancing their detectibility by RT-PCR.

Nested RT-PCR assays are both sensitive and specific. Results have been reliably reproduced on repeated occasions. Long term testing of both cDNA and RNA stability is presently underway. Both assays are capable of detecting one prostatic cell in at least one million non-prostatic cells of similar size. This confirms the validity of the comparison of PSM vs. PSA primers. Similar levels of PSM expression in both human prostatic cancer cells in-vivo and LNCaP cells in-vitro resulted. The specificity of the PSM-PCR assay was supported by the finding that two "negative control" patients with positive PSM-PCR results were both subsequently found to have prostate cancer. This suggests an exciting potential application for this technique for use in cancer screening. In contrast to recently published data, significant ability for PSA primers to accurately detect micrometastatic cells in patients with pathologically with pathologically organ-confined prostate cancer, despite the sensitivity of the assay failed to result. Rather a surprisingly high percentage of patients with localized prostate cancer that harbor occult circulating prostate cells following "curative" radical prostatectomy results which suggests that micrometastasis is an early event in prostate cancer.

The application of this powerful new modality to potentially stage and/or follow the response to therapy in patients with prostate cancer certainly merits further investigation. In comparison to molecular detection of occult tumor cells, present clinical modalities for the detection of prostate cancer spread appear inadequate.

Transition of prostate cancer from androgen dependent to androgen independent state is a clinically important step which may be caused or accompanied by genetic changes. Expression of prostate specific membrane antigen (PSM) is most intense in LNCap cells, an androgen dependent prostate carcinoma cell line: and is not detectable in PC-3 nor in DU-145 cells, which are androgen independent prostate carcinoma cell lines. A microsatellite repeat of (TTTTG), (TTTG), has been found in the first intron of the PSM gene. Our hypothesis is that this Microsatellite repeat could be a cis-acting element in the regulation of PSM expression. A polymeric chain reaction amplifying this repeat was used to look for any gene alteration in several cell lines: LNCap, PC-3, PC-3M, DU-145 as well as in 20 paired normal and early prostatic cancers (p12-4, NO). In addition, immunohistochemistry (IHC) was used to analyze PSM expression in patient samples. By IHC, no detectable expression in DU-145, PC-3, and PC-3M was found, but all tumor expressed PSM. Further sequencing data of the microsatellite repeat confirmed no change in LNCap, and in contrast, an amplification in PC-3 and a gross deletion in DU-145. Alteration of a T segment adjacent to the microsatellite repeat was found in one tumor sample. These results suggest that there is rarely alteration in the intronic microsatellite sequence of the PSM gene in early prostate cancer. The abnormal pattern in the absence of expression suggest genetic instability in the more aggressive tumor lines such as the PC-3, PC-3M and DU-145 cells.

EXAMPLE 9

Chromosomal Localization of Cosmid Clones 194 and 683 by Fluorescence in-situ Hybridization PSM was initially mapped as being located on chromosome 11p11.2-p13 (FIGS. 25-27). Further information from the cDNA in-situ hybridizations experiments demonstrated as much hybridization on the q as p arms. Much larger fragments of genomic DNA was obtained as cosmids and two of these of about 60 kilobases each one going 3' and the other 5' both demonstrated binding to chromosome 11 p and q under low stringency. However under higher stringency conditions only the binding at 11q14-q21 remained. This result suggests that there is another gene on lip that is very similar to PSM because it is so strongly binding to nearly 120 kilobases of genomic DNA (FIG. 28).

Purified DNA from cosmid clones 194 and 683 was labelled with biotin dUTP by nick translation. Labelled probes were combined with sheared human DNA and independently hybridized to normal metaphase chromosomes derived from PHA stimulated peripheral blood lymphocytes in a solution containing 30% formamide, 10% dectran sulfate, and 2×SSC. Specific hybridization signals were detected by incubating the hybridized slides in fluoresein conjugated avidin. Following signal detection the slides were counterstained with propidium iodide and analyzed. These first experiments resulted in the specific labelling of a group C chromosome on both the long and short arms. This chromosome was believed to be chromosome 11 on the basis of its size and morphology. A second set of experiments were performed in which a chromosome 11 centromere specific probe was cohybridized with the cosmid clones. These experiments were carried out in 60% formamide in an attempt to eliminate the cross reactive signal which was observed when low stringency hybridizations were done. These experiments resulted in the specific labelling of the centromere and the long arm of chromosome 11. Measurements of 10 specifically labelled chromosomes 11 demonstrated that the cosmid clones are located at a position which is. 44% of the distance from the centromere to the telomere of chromosome arm 11q, an area that corresponds to band 14q. A total of 160 metaphase cells were examined with 153 cells exhibiting specific labelling.

Cloning of the 5' upstream and 3' downstream regions of the PSM genomic DNA. A bacteriophage P1 library of human fibroblast genomic DNA (Genomic Systems, St. Louis, Mich.) was screened using the PCR method of Pierce et. al. Primer pairs located at either the 5' or 3' termini of PSM cDNA were used. Positive cosmid clones were digested with restriction enzymes and confirmed by Southern analysis using probes which were constructed from either the 5' or 3' ends of PSM cDNA. Positive clone p683 contains the 5' region of PSM cDNA and about 60 kb upstream region. Clone −194 contains the 3' terminal of the PSM cDNA and about 60 kb downstream.

EXAMPLE 10

Peptidase Enzymatic Activity

PSM is a type two membrane protein. Most type two membrane proteins are binding proteins, transport proteins or peptidases. Prostate Specific Membrane Antigen has activity as a carboxypeptidase and acts on both gamma linked or alpha linked amino acids which have acidic amino acids such as glutamate in the carboxy terminus.

Prostate specific membrane antigen is found in high concentration in the seminal plasma. When examining LNCaP cells, PSM antigen has enzymatic activity with N-acetylaspartylglutamate as a substrate and enzymatic action results in the release of, N-acetylaspartate and glutamic acid. In vitro translated PSM message also had this peptidase activity. Because PSM action will release glutamate, and because it is well known that the seminal fluid is highly enriched in its content of glutamic acid, the action of PSM antigen of endogenous protein/peptide substrates may be responsible for generating the glutamic acid present.

It is also uncertain as to the role that seminal plasma glutamic acid plays in fertility functions. It may be that interruption of PSM antigen enzymatic activity may block the generation of glutamate and could impact on seminal plasma glutamic acid levels and its attendant fertility functions. Thus agents which inhibit PSM antigen may prove to be useful in attenuating male fertility.

Thus one skilled in this art would be able to design inhibitors to enhance the activity of the non degraded normal substrate if its increased level will have a biologic desired activity. Also biologic activity can be measured to see how it correlates with the level of message. Tissue may be examined for activity directly rather than indirectly using in-situ analysis or immunohistochemical probes. Because there is another gene highly similar on the other arm of chromosome 11 when isolated the expressed cloned genes can be used to determine what the substrate differences are and one may use those substrates for identification of PDM related activity, for example, in circulating cells when looking for metastases.

PSM specific substrates can be designed that could activate pro-drugs at the site of prostate tumor cells to kill those cells.

EXAMPLE 11

Ionotropicglutamate Receptors in Prostate Tissue

Prostate Specific Membrane antigen acts on N-acetylaspartylglutamic acid to release glutamate and because a homologous protein has been found in the rat brain which acts on N-acetlyaspartylglutamate to free glutamate and N-acetylaspartate and because these amino acids are considered to function as neurotransmitters, the enzyme is considered to be potentially important in modulating neurotransmitter excitatory amino acid signalling as a neurocarboxypeptidase. This could be important in the prostate as well, because of the neuroendocrine nature of a subpopulation of cells in the prostate which are considered to be important synthesizeing neuropeptide signaling molecules. PSM antigen from the LNCaP cell was isolated and LNCaP cells can be induced to exhibit a "neuron like" phenotype.

Excitatory neurotransmission in the central nervous system (CNS) is mediated predominantly by glutamate receptors. Two types of glutamate receptors have been identified in the human CNS: metabotropic receptors, which serve G-protein coupled second messenger signaling systems, and ionotropic receptors, which serve as ligand gated ion channels. Ionotropic glutamate channels can increase the inward flow of ions such as calcium ions. This can result in the subsequent stimulation of nitric oxide, and nitric oxide modulation of a number of signaling pathways. Nitric oxide has been found to be a major signaling mechanism involved in cell growth and death, response to inflammation, smooth muscle cell contraction, etc. The presence of ionotropic glutamate receptors in human prostate tissue was investigated.

Methods: Detection of glutamate receptor expression was performed using anti-gluR2/3 and antigluR4 polyclonal antibodies and antibiotin immunohistochemical techniques in paraffin-embedded human prostate tissues. PSM antigen is a neurocarboxypeptidase that acts to release glutamate. In the CNS glutamate acts as a neurotransmitter by acting on glutaminergic ion channels and increases the flow of ions like calcium ions. One way the glutamate signal is transduced into cell activity is the activation of nitric oxide synthase. and nitric oxide synthase has recently been found to be present in human prostatic tissue. NO is a major signalling mechanism and is involved in control of cell growth and death, in response to inflammation, in smooth muscle cell contraction. etc. In the prostate much of the stroma is smooth muscle. It was discovered that the prostate is rich in glutaminergic receptors and we have begun to define this relationship. Stromal abnormalities are the key feature of BPH. Stromal epithelial interactions are of importance in both BPH and Cap. The other glutaminergic receptors through G proteins to change the metabolism of the cell.

Results: Anti-gluR2/3 immunoreactivity was unique to prostatic stroma and was absent in the prostatic epithelial compartment. Strong anti-gluR4 immunoreactivity was observed in the basal cells of the prostate. This implied a differential location and function of glutamate receptors as defined by these antibodies.

Discussion: PSM antigen is a neurocarboxypeptidase that acts to release glutamate from NAAG 1, also as a potential nerotransmitter. In the CNS glutamate acts as a neurotransmitter by acting on glutaminergic ion channels and increases the flow of ions such as calcium ions. One way the glutamate signal is transduced into cell activity is the activation of nitric oxide synthase, and nitric oxide synthase has recently been found to be present in human prostatic tissue. NO is a major signaling mechanism and is involved in control of cell growth and death, in response to inflammation, in smooth muscle cell contraction, etc. In the prostate much of the stroma is smooth muscle. The prostate is rich in glutaminergic receptors. Stromal abnormalities are the key feature of BPH. Stromal epithelial interactions are of importance in both BPH and CaP. The other glutaminergic receptors through G proteins to change the metabolism of the cell. Glutamate can be produced in the cerebral cortex through the carboxypeptidase activity of the prostatespecific membrane antigen (PSMA). In this location, PSMA cleaves glutamate from acetyl-aspartylglutamate. Taken together, these observations suggest a function for PSMA in the human prostate; glutamate may be an autocrine and/or paracrine signalling molecule, possibly mediating epithelial-stromal interactions. Ionotropic glutamate receptors display a unigue compartmental distribution in the human prostate.

The differential distribution of ionotropic glutamate receptor subtypes between the stromal and epithelial compartments of in the prostate has not been described. Prostate-specific membrane antigen(PSMA) has an analogous prostatic distribution, with expression restricted to the epithelial compartment. Basal cells are considered the precursor cell for the prostatic acinar and neuroendocrine cells of the prostate. Glutamate receptors may provide signaling functions in their interactions with the prostate stroma and acinar cells, and PSM may be involved in that interaction. Thus inhibition or enhancement of PSM activity could serve to modulate activity of the basal cells and prove to be a valuable aid for controlling basal cell function in the prostate.

The finding of glutamate like receptors in the stroma is of interest because a large part of the prostate volume is due to stromal cells. Current observation have suggested that these stromal cells have a smooth muscle cell phenotype and thus the presence of glutamate receptors may play a role in their biologic function and regulation of differentiation. A most common disease in men is the abnormal benign growth of the prostate termed benign prostatic hyperplasia, BPH.

In areas of BPH a decrease in the level of expression of PSM antigen was observed. If PSM antigen activity is providing an aspect of the signalling for normal stromal function then the abnormal growth seen in BPH may be a response to that decreased activity and agents to restore its function could play a role in the treatment or prevention of BPH.

PSM carboxypeptidase may serve to process neuropeptide transmitters in the prostate. Neuropeptide transmitters are associated with the neuroendocrine cells of the prostate and neuroendocrine cells are thought to play a role in prostatic tumor progression. Interestingly, PSM antigen's expression is upregulated in cancer. Peptides known to act as prostatic growth factors such as TGF-a and bFGF, up regulate the expression of the antigen. TNF on the other hand downregulate PSM. TGF and FGF act through the mitogen activated signaling pathway, while TNF acts through the stress activated protein kinase pathway. Thus modulation of PSM expression is useful for enhancing therapy.

Because of PSM's carboxypeptidaselike activity and due to the fact that one of its substrates is the dipeptide N-acetyl-aspartyl glutamic acid, NAAG, which is one of the best substrates found to date to act as a neurotransmitter in the central nervous system, altering PSM antigen function may also have beneficial actions outside the prostate. In the rat CNS a protein homology to PSM antigen was discovered and provides a rational to consider prostate specific membrane antigen as a neurocarboxypeptidase. Abnormalities or alterations in its function may occur in neurotoxic disorders such as epilepsy, or ALS, alzheimers, and multiple sclerosis.

EXAMPLE 12

Identification of a Membrane-Bound Pteroylpolygammaglutamyl Carboxypeptidase (Folate Hydrolase) That is Expressed in Human Prostatic Carcinoma As described PSM functions as a carboxypeptidase to hydrolyze both alpha and gamma peptide linkages with amino acids such as glutamate in the terminal carboxy position. The proximal small intestine (duodenum-strong expression PSM) but not the distal small intestine (ileum-absent PSM) was also very rich in expression of message for prostate specific membrane antigen in RNase protection assays. PSM antigen by immunohistochemistry was observed in the brush border membranes of the duodenum. This location was consistent with a hydrolase known as folate conjugase (folate hydrolase as a carboxypeptidase, not an endopeptidase) that had been described in the older literature, with the protein having been partially purified from the human small intestine. No cloning or sequencing of this gene had been done. There is a form of folate hydrolase that is found in all cells in the lysosomes and it was recently sequenced. There is no sequence relationship between the lysosomal endopeptidase. Membrane fraction of the LNCaP cells was very rich in folate hydrolase activity. The PSM specific monoclonal could be used to immunoprecipitate the folate hydrolase activity. This result always has the possibility that the folate hydrolase activity is not the same as PSM antigen but is a coprecipitating contaminant. Therefore PSM antigen was transfected into PC-3 cells. PC-3 cells do not express PSM nor do they have membrane folate hydrolase activity. In cells transfected with PSM antigen however expression of folate hydrolase activity was observed in the membranes. Thus PSM is a novel folate hydrolase, folate carboxypeptidase, and is active in sequentially removing the terminal gamma-linked glutamates. In the proximal small intestine it is understandable why this enzyme would be in such a place, as the majority of folate available from food is polygammglutamated and this enzyme is responsible for its hydrolysis.

Materials: Methotrexate triglutamate (4-$NH_2$-10-$CH_3$-Pte-$Glu_4$ ($MTXglu_3$)), pteroylpentaglutamate ($PteGlu_3$), and para-aminobenzoylpentaglutamate, ($pABAGlu_5$) were purchased from Dr. B. Schircks Laboratories (Jona, Switzerland) and samples were >98% pure when evaluated by HPLC. N-acetyl-α-aspartylglutamate (NAAG) (40 Ci/mmol) was purchased from New England Nuclear (Boston, Mass.). Protein A Sepharose 4 Fast Flow was purchased from Pharmacia (Piscataway, N.J.). The 7E11-C5 monoclonal antibody to prostate specific membrane antigen was obtained from Cytogen Corporation, Princeton, N.J. All other reagents (p-hydroxymercuribenzoate, homocysteine, dithiothreitol (DTT), reduced glutathione) were of the highest purity commercially available from Sigma Chemical Co. (St. Louis, Mo.).

Culture and growth of human prostate adenocarcinoma cells (LNCaP, PC-3, TSU-Pr1, and Duke-145): LNCaP cells were maintained in defined culture medium, RPMI-1640 medium supplemented with non-essential amino acids, 5 mM glutamine, and 5% heat-inactivated fetal calf serum. Duke-145, PC-3, and TSU-Pr1 cells were grown in minimal essential medium (MEM), Ham's F-12K, and MEM, respectively, containing 5% fetal calf serum. No antibiotic was included in the media. Cells ($1\times10^6$) were plated in T-75 tissue culture flasks containing 15 mL of medium and incubated at 37° C. in a humidified atmosphere of 5% $CO_2$. Cell numbers were determined using a Model Z F Coulter Counter (Coulter Electronic, Inc.). Prostate cells were harvested from plates by gentle scraping at 4° C. into phosphate buffered saline (136.9 mM NaCl, 2.68 mM KCl, 8.10 mM $Na_2HPO_4$, 1.47 mM $KH_2PO_4$, pH 7.34, PBS) and centrifuged at 500× g to obtain a cell pellet. Sedimented cells were routinely rinsed twice with 15 mL volumes of PBS.

Transfection of PSM into PC-3 Prostate Cell Line: The full length 2.65 kb PSM cDNA was subcloned into a pREP7 eukaryotic expression vector (Invitrogen, San Diego, Calif.) as previously described. Plasmid DNA was purified from transfected DH5-α (Gibco-BRL) using a Qiagen maxi prep plasmid isolation kit (Qiagen Inc., Chatsworth, Calif.). Purified plasmid DNA (5 μg) was diluted with 300 μL of serum free RPMI media and mixed with 45 μL of lipofectamine (Gibco-BRL) which was previously diluted with 300 μL of serum free RPMI media to allow an DNA-liposome complex to form. The mixture was kept at room temperature for 30 minutes, then added to a 60 mm petri dish containing 60-70% confluent PC-3 cells in 2.4 mL serum free RPMI. The DNA-liposome complex containing serum free media was mixed gently to ensure uniform distribution and was then incubated for 6 h at 37° C. in a $CO_2$ incubator. Following incubation, the media containing liposome-DNA complex was aspirated and replaced with 6 mL of regular growth media (10% fetal bovine serum, 1% penicillin-streptomycin, 1% glutamine).

After 48 hours, cells were trypsinized and split 1:3 into 60 mm dishes containing regular media supplemented with 200 μg/mL of hygromycin B (Calbiochem, LaJolla, Calif.). Cells were maintained for 2 weeks with changes of media containing hygromycin B every third day until discrete colonies appeared. Colonies were isolated using a 6 mm cloning cylinder and were expanded in the same media. As a control, PC-3 cells were also transfected with the pREP7 vector alone.

Immunohistochemistry: The 7E11-CS monoclonal antibody to prostate specific antigen was used. This antibody recognizes a portion of carbohydrate-containing peptide epitope on the amino terminal end of PSM that is located on the inner portion of the cytosolic membrane. After permeabilization of LNCaP and PC-3 transfected and non-transfected cells with a mixture of acetone and methanol (1:1 v/v) and blocking with 5% bovine serum albumin in 50 mM Tris buffered saline (TBS) pH 7.45, samples were incubated with 7E11-CS antibody (20 μg/mL) for 1 h at room temperature. Negative controls were generated by substituting the same concentration of mouse IgG2ak for the PSM antibody. Using a secondary $IgG_1$ anti-mouse antibody conjugated with alkaline phosphatase, samples were re-incubated for 1 h, rinsed in TBS, and stained with bromochloroindolylphenol phosphate in 2-amino-2-methyl-1-propanol buffer. Cells expressing PSM demonstrate an intense blue staining.

Cell Membrane Preparation: Cell lysates were prepared by sonicating approximately $6 \times 10^6$ cells in 50 mM Tris pH 7.4 buffer (2×10 s pulses at 20 mwatts) in an ice-bath. Membrane fractions were obtained by centrifuging lysates at 100,000× g for 30 mins. The supernatant fractions were saved and pelleted membranes were re-suspended by gentle trituration and re-sedimented at 100,000× g for 30 mins through 10 mL of cold 50 mM Tris pH 7.4 buffer. Washed membrane fractions were dissolved in 50 mM Tris pH 7.4 buffer containing 0.1% Triton X-100 (Tris/Triton). Enzymatic activity and immunoprecipitation preparations were performed using this membrane preparation.

Immunoprecipitation of PSM from Membrane: Membrane pellets (~1 mg protein) solubilized in Tris/Triton buffer were incubated at 4° C. for 1 h in the presence of 7E11-C5 anti-prostate monoclonal antibody (6 ug protein). Protein A Sepharose gel equilibrated in Tris/Triton buffer was added to the immunocomplex.

This preparation was subsequently incubated for an additional hour at 4° C. Sepharose beads were centrifuged at 500× g for 5 mins and rinsed twice with Tris/Triton buffer at pH 7.4. Isolated beads were resuspended in 0.1 M glycine buffer pH 3.0, vortexed, and the supernatant fraction was assayed for hydrolase activity using $MTXglu_3$.

Pteroyl Gamma-Glutamyl Hydrolase Assay: Hydrolase activity was determined using capillary electrophoresis. The standard assay mixture contained 50 uM $MTXGlu_3$, 50 mM acetate buffer (pH 4.5) and enzyme to a final volume of 100 uL. A sample preparation without enzyme was incubated concurrently with enzymatic assays and reactions were conducted for times varying between 0 and 240 min at 37° C. Activities were also determined in standard reaction mixture at varied pHs for 60 min. Reactions were terminated in a boiling water bath for 5 min and samples were stored frozen (−20° C.) until analysis. Following centrifugation (7,000× g) to remove precipitated debris, capillary separation of MTX glutamated analogues was performed with a Spectra Phoresis 1000 instrument (Thermo Separation, San Jose, Calif.) with a 75 μm id×50 cm silica capillary (Polymicro Technology, Phoenix, Ariz.). Separation of pteroyl(glutamate)$_n$ derivatives is achieved with an electrolyte of 20 mM sodium borate with 15 mM sodium dodecylsulfate (pH 9.5) with +20 Kev at 25° C. Samples were applied hydrodynamically for 1-2 s and absorbance monitored at 300 nm. Data were recorded with an IBM computer using CE-1000 software (Thermo Separation).

Protein determination: Protein concentrations of isolated membrane or supernatant fractions were determined by incubating diluted aliquots with BCA reagent (Pierce Chemical Co., Rockford, Ill.) at 37° C. for 30 min. The spectrophotometric quantitation of protein was conducted by determining the absorbance at 562 nm against bovine serum albumin standard.

Statistical Analysis: Data were analyzed by using the Statgraphics version 4.0 program (Statistical graphics Corporation, Rockville, Md.) and where summarized are expressed as mean±S.D. Student's unpaired t test was used to determine significance of differences.

Results:

Membrane fractions isolated from human prostate adenocarcinoma cells (LNCaP) were incubated using primarily $MTXglu_3$ as substrate. The time course of hydrolysis of the gamma-linked triglutamate derivative and the subsequent appearance of $MTXglu_2$, $MTXglu_1$, and MTX after 30, 60, 120, and 240 min of incubation are illustrated in FIG. 82. The semipurified PSM antigen exhibits pteroyl poly gamma-glutamyl exopeptidase activity that progressively liberates all of the possible glutamates from $MTXGlu_3$ with accumulation of MTX.

The PSM antigen was immunoprecipitated in the presence of 7E11-C5 anti-prostate monoclonal antibody and the PSM antigen-antibody complex was adsorbed onto a Protein A Sepharose Gel column. Following twice washing of the sepharose beads with 2 mL volumes of buffer and re-solubilization of the antigen-antibody complex by adjusting the elution pH to 3.0, the supernatant fraction was assayed for hydrolase activity. FIG. 55 shows the capillary electrophoretic separation of successively cleaved glutamyl moieties from $MTXglu_3$ after 0, 30, 60 and 240 min incubations. Results similar to these in FIG. 82 were obtained using pteglu$_5$ with formation of folate (pteglu$_1$)

The optimum pH activity profiles of the immunoprecipitated PSM hydrolase from LNCaP cells and of the membrane fractions from PC-3 PSM-transfected and non-transfected (vector alone) cells are shown in FIG. 57. The reaction was monitored as a function of pH from 2 to 10 after an 1 h incubation with $MTXglu_3$. The extent of reaction was expressed as the concentration of $MTXglu_2$ formed per mg protein. Although all reaction products were detectable as illustrated in FIG. 56, $MTXglu_2$ was the predominant hydrolyzed species at incubation times ranging from 10 to 60 min. The pH profile of membrane fractions isolated from both LNCaP and PC-3 PSM-transfected cells are identical and exhibit two maxima of PSM hydrolase activity at pH 5 and 8 with no measurable activity above pH 10.

To determine whether non-PSM expressing human adenocarcinoma cell lines (PC-3, TSU-Pr1, and Duke-145) exhibit folate hydrolase activity, isolated membrane preparations from these cell lines were analyzed (FIG. 83). The less differentiated, hormone refractory prostate cell lines (PC-3, TSU-Pr1, and Duke-145) exhibit no appreciable activity after 2 h incubations. These results are in agreement with previous findings that demonstrate neither a presence of a mRNA for PSM nor antigen immunoreactivity with 7E11-C5 in these cells.

In further studies in which the cDNA for PSM was transfected-into non-PSM antigen expressing PC-3 cells, a close correlation between PSM antigen immunoreactivity and hydrolase activity was observed with MTXglu$_3$ in membranes of LNCaP and PC-3 PSM-transfected cells (FIGS. 58 and 59). Immunohistochemical analyses of LNCaP (FIG. 58) and PSM antigen expressing PC-3 (FIG. 85B) cells revealed distinct positive staining with 7 μl-C5 anti-prostate monoclonal antibody. FIG. 85C illustrates no immunoreactivity in PC-3 cells expressing the pREP7 hygromycin vector alone. In preparations of negative controls, all three cell lines were reacted with IgG2aK rather than with 7E11-C5 antibody. No background staining resulted with the secondary antibody conjugated with alkaline phosphatase.

To compare PSM hydrolase activity with that of other gamma-glutamyl hydrolases that either reside within the lysosome or are secreted as observed in several neoplastic cells, its reactivity in the presence of thiol-containing reducing agents, namely, reduced glutathione, homocysteine, and dithiothreitol (DTT), and the thiol reagent, p-hydroxymercuribenzoate (PHMB), at concentrations ranging from 0.05-0.5 mM was observed. Of the reduced sulfhydryl derivatives, it was discovered that only DTT ($\geqq$0.2 mM) was slightly inhibitory (86±3% of control). Unlike gamma-linked peptide hydrolase retained within the lysosome, PSM hydrolase activity was maintained in the presence of 0.5 mM PHMB.

The reactivity of PSM hydrolase against an α-glutamate dipeptide, N-acetyl-α-aspartylglutamate (NAAG), has been investigated and that the PSM enzyme from either LNCaP or PSM transfected PC-3 cell membranes hydrolyses NAAG producing N-acetylaspartate and glutamate was observed. Furthermore, MTXglu$_3$, pteglu$_5$, and pABAglu$_5$ were potent inhibitors of the PSM-mediated NAAG hydrolysis.

Discussion:

Membrane-bound PSM antigen has pteroyl poly gamma-glutamyl carboxypeptidase (folate hydrolase) activity. Prostate specific membrane antigen was immuno precipitated from the prostate cancer cell line LNCaP and demonstrated it to be rich in folate hydolase activity, with gammaglutamated folate or polyglutamated methotrexate being much more potent inhibitors of the neuropeptidase activity than was guispualate, which was the most potent inhibitor reported up to this time and consistent with the notion that polyglutamated folates may be the preferred substrate. Gamma-glutamyl hydrolase activity is also present in lysosomes of cells and these enzymes may be responsible for regulating the length of exogenous and endogenous folyl polyglutamate chain lengths. A characteristic difference between these two hydrolases is that the PSM enzyme exhibits substantial activity at pH values 7.5 to 8.0 in addition to having an acidic pH 4.5 to 5 optimum. Moderate levels of hydrolase activity are present within LNCaP cytosolic compartment and may represent the short intracellular fragment of this class II enzyme. This reflects an interesting situation in these cells where the majority of RNA codes for the membrane-bound enzyme that is localized extracellularly. The ratio of the mRNAs in these samples that code for the class II membrane and the cytosolic proteins is ten to one. In normal prostate tissue, the mRNA coding for the membrane protein is only one-tenth that of the cytosolic form.

It is clear from this study that the prostate specific membrane antigen functions as a folate hydrolase and is unique in that it has activity on both the gamma-linked as well as the alpha linked peptide bonds. This is interesting for a number of reasons. First in the normal prostate it was demonstrated that the majority of the mRNA encodes a protein, PSM', that is likely to be cytosolic and would imply that it may be that in the prostate that folates could exists in the lesser glutamated species. If so then it means that the folate in the prostate can readily leak out and that the prostate may be subjected to "microenviromental folate deficiencies" This may be related to the high worldwide incidence of "microscopic prostate cancer" as folate deficiencies are associated with carcinogenesis in a number of tissues.

Benign enlargement of the prostate and prostate cancer occur in older men. It also occurs that the uptake of folate decreases with aging. If folate uptake decreases with aging this may be due to decreased PSM folate hydrolase activity in the proximal intestine. To correct such a deficiency it might be possible to use PSM folate hydrolase in foods to release the folate before consumption or take it with foods as is done with lactase in lactose intolerant individuals. If the prostate in men is susceptible to folate depletion then nutritional supplementation may help reduce the development of the microscopic lesion, indeed in some cancers such as cancer of the colon, folate supplementation was found to reduce cancer formation.

Why would the prostate cells prefer to have the lesser glutamated forms of folate? It may be that methionine synthase which is an enzyme key to folate uptake and folate utilization for one carbon methyl transfer metabolism may utilize the nonglutamated folate preferentially. In addition to folate deficiency, choline and methionine deficiency is also associated with tumor development. If shown to modulate one carbon-transfers, it might be useful to inhibit this enzyme as a means to inhibit cancer development and thus serve as a chemopreventative agent. Again modulation of PSM folate hydrolase may play a role in tumor prevention and modulation of tumor growth.

A feature that cell biologists use in transfecting DNA into cells often requires selection of the transfected gene and often multiple transfections are performed. These are done with drugs that are toxic to cells such as Hygromycin and use genes that code for Hygromycin resistance which are bacterial. It may be that PSM could be used as a selectable marker by growing the transfected cells in folate free media and including polyglutamated folate which would be able to rescue cells from folate deficiency if they expressed PSM.

PSM folate hydrolase activity can possibly be used as a prodrug converting enzyme. Prodrugs may be generated which would activate at the site of the tumor such as N-phosphonoacetyl-1-aspartate-glutamate. PALglu is an inhibitor of the enzyme activity with NAAG as a substrate. In the normal prostate PSM is intracellular. In the transformed cell the majority of the protein and its attendance enzymatic activity is extracellular in location. It may be that as the enzymes associated with cell growth require the polyglutamated forms the cancer finds a way to remove PSM folate hydrolase from the interior by alternative splicing to an extracellular enzyme. PSM is a membrane protein and is found to predominate in cancer, but PSM' is likely a cytosolic protein which predominates in the normal condition.

This implies that development of a prodrug that requires metabolism before it can be taken up by the tumor cell could be activated by the PSM folate hydrolase which is predominate in the, cancer.

For the cytotoxic drug methotrexate to be a tumor toxin it has to get into the cell and be polygammaglutamated to be active, because polyglutamated forms serve as the enzyme substrates and because polyglutamated forms or toxins are also retained by the cell. Folate hydrolase is a competing reaction and deglutamates methotrexate which then can diffuse back out of the cell. Cells that overexpose folate hydrolase activity are resistant to methotrexate. Prostate cancer has always been absolutely refractory to methotrexate therapy and this may explain why, since the prostate and prostate cancer has a lot of folate hydolase activity.

Methotrexate triglutamate was one of the agents used to identify the enzymatic activity of PSM antigen. Methotrexate triglutamate would not be able to use the transport protein to be taken into tumor cells, because there are specific structural requirements for folate, or methotrexate transport. If one removes the gamma-linked glutamates then methotrexate can be taken into cells and can exerts its antifolate, antitumor growth action.

Therfore methotrexategammatriglutamate was used to examine the action of this compound on the in vitro growth of PC-3 cells transfected with a plasmid with a selectable marker versus a plasmid with a selectable marker that expresses PSM antigen as well. the PC-3 cells that were transfected with PSM were inhibited. 85% in growth by day four by 10 uM methotrexate triglutamate, while the PC-3 plasmid only transfectants did not exhibit any significant inhibition of growth.

PSM's folate hydrolase activity hydrolyses down to the last glutamate which is in alpha linked position but does not remove it. Because it does not remove the last glutamate, PSM antigen's folate hydrolase activity better serves the prodrug activation requirements of such a prodrug. Also because it is a human enzyme it is less likely than the carboxypeptidase G2 will cause an immune response because PSM antigen is normally present in the body.

In addition PSM could also be used as part of a prodrug strategy that utilized gene transfer and a tissue or tumor specific promoter, say such that it would be linked to CEA promoter and PSM expressed in colon tumors and the patients subsequently given the prodrug such as methotrexate triglutamate. The same is also true for the protein itself, either the whole protein or the components of the active site or a modified version that would have increased prodrug activating activity could be linked to a delivery vehicle such as an antibody or other specific targeting ligand, delivered to the tumor for localization and subsequent activation.

Methotrexate as a prodrug may be enhanced in specificity by using alpha linked glutamates rather than gamma linked glutamates because the ubiquitous lysosomal hydrolase enzyme is specific for the gamma linked bond. A pro-drug with all alpha linked glutamates would not be a substrate, but would be a substrate for the PSM folate hydrolase.

In addition to methotrexate a number of potential enzyme substrates can be employed as cytotoxic prodrugs. The synthesis of potential prodrugs, PALAglu, and a number of other potential agents are described.

Alpha-linked methotrexate material is synthesized by the following Merifield solid phase scheme (see FIG. 88). The scheme is based on a modification of the standard Merifield solid peptide synthesis that was applied to the synthesis of methotrexate y polyglutamates. In brief the N-Fmoc-4-terbutylglutamate is first connected to the resin under standard coupling conditions using diisoprpylazodicarboxylate as a coupling reagent. The Fmoc protecting group is then removed with piperidine, and this cycle would be reiterated for as many times as glutamates would be needed to obtain the desired analog. For example say the pentaglutamate on solid support is the intermediate required for the preparation of methotrexate-alpha-tetraglutamate. It is deprotected at the terminal nitrogen by treatment with piperidine, then coupled with pteroic acid analogue under the same conditions used above. The terbutyl and the resin are all removed in one step with 95% trifluoroacetic acid (TFA) to provide the desired material. This process is applied to every analog. The gamma linked material is provided in a similar manner for use comparative studies with the alpha-linked material (see FIG. 89).

Because of the carboxypeptidase activity a number of combination of alpha and gamma linked acidic amino acid can be optimized for their utilization of the enzyme and for in vivo activity. In addition to the folate like antagonists, a number of amino acid analogs were found in the past to have antitumor activity but lacked in vivo specificity. These agents are targetable by attaching a glutamate to the carboxy terminus of the amino acid as described and shown in the figures.

Penta-gammaglutamyl-folate is a very potent inhibitor of activity (inhibition of the activity of the enzyme is with 0.5 um Ki.) As penta-gammaglutamyl-folate may also be a substrate and as folates have to be depolygammaglutamated in order to be transported into the cell, this suggests that this enzyme may also play a role in folate metabolism. Folate is necessary for the support of cell function and growth and thus this enzyme may serve to modulate folate access to the prostate and prostate tumor. The other area where PSM is expressed is in the small intestine. It turns out that a key enzyme of the small intestine that is involved in folate uptake acts as a gammacarboxypeptidase in seguentially proteolytically removing the terminal gammaglutaminyl group from folate. In the bone there is a high level of unusual gammaglutamate modified proteins in which the gamma glutamyl group is further carboxylated to produce gammacarboxyglutamate, or GLA. One such protein is osteonectin.

Using capillary electrophoresisis pteroyl poly-gammaglutamate carboxypeptidase (hydrolase) activity was investigated in membrane preparations from androgen sensitive human prostatic carcinoma cells (LNCaP). The enzyme immunologically cross-reacts with a derivative of an anti-prostate monoclonal antibody (7E11-C5) that recognizes prostate specific membrane (PSM) antigen. The PSM enzyme hydrolyzes gamma-glutamyl linkages and is an exopeptidase as it liberates progressively glutamates from methotrexate triglutamate (MTXGlu$_3$) and folate pentaglutamate (Pte Glu$_3$) with accumulation of MTX and Pte Glu respectively. The semi-purified membrane-bound enzyme has a broad activity from pH 2 to 10 and is maximally active at pH4.0 Enzymatic activity was weakly inhibited by dithfothreitol ($\geq$0.2 mM) but not by reduced glutathione, homocysteine, or p-hydroxymercuribenzoate (0.05 mM). By contrast to LNCaP cell membranes, membranes isolated from androgen insensitive human prostate (TSU-Prl, Duke-145, PC-3) and estrogen-sensitive mammary adenocarcinoma (MCF-7) cells do not exhibit comparable hydrolase activity nor do they react with 7E11-C5. Thus, a folate hydrolase was identified in LNCap cells that exhibits exopeptidase activity and is strongly expressed by these cells.

PALA-Glutamate 3 was tested for efficacy of the prodrug strategy by preparing N-acetylaspartylglutamate, NAAG 1(FIG. 33). NAAG was synthesized from commercially available gamma-benzylaspartate which was acetylated with acetic anhydride in pyridine to afford N-acetylgamma-benzyl aspartate in nearly quantitative yield. The latter was activated as its pentafluorophenyl ester by treatment with pentafluorophenyltrifluoroacetate in pyridine at 0 deg. C. for an hour. This activated ester constitutes the central piece in the preparation of compounds 1 and 4 (FIG. 34). When 6 is reacted with epsilon-benzyl-L-glutamate in the presence of HOAT(1-hydroxy azabenzotriazole) in THF-DMF (tetrahydrofuran, N,N- dimethylformamide) at ref lux for an overnight period and after removal of the benzyl protecting groups by hydrogenolysis (H2, 30 psi, 10% Pd/C in ethylacetate) gave a product which was identical in all respects to commercially available NAAG (Sigma).

PALA-Glutamate 3 and analog 5, was synthesized in a similar manner with the addition to the introduction of a protected phosphonoacetate moiety instead of a simple acetate. It is compatible with the function of diethylphosphonoacetic acid which allows the removal of the ethyl groups under relatively mild conditions.

Commercially available diethylphosphonoacetic acid was treated with perfluorophenyl acetate in pyridine at 0 deg.C to room temperature for an hour to afford the corresponding pentafluorophenyl ester in nearly quantitative yield after short path column chromatography. This was then reacted with gamma-benzylaspartate and HOAT in tetrahydrofuran for half an hour at reflux temperature to give protected PALA 7 (N-phosphonoacetylaspartate) in 90% yield after flash column chromatography. The free acid was then activated as its pentafluorophenyl ester 8, then it was reacted with delta-benzyl-L-glutamate and HOAT in a mixture of THF-DMF (9:1, v/v) for 12 hours at reflux to give fully protected PALA-Glutamate 9 in 66% yield after column chromatography. Sequential removal of the ethyl groups followed by the debenzylation was accomplished for a one step deprotection of both the benzyl and ethyl groups. Hence protected PALA-Glutamate was heated up to reflux in neat trimethylsilylchloride for an overnight period. The resulting bistrimethylsilylphosphonate ester 10 was submitted without purification to hydrogenolysis ($H_2$ 30 psi, 10% Pd/C, ethylacetate). The desired material 3 was isolated after purification by reverse phase column chromatography and ion exchange resin.

Analogs 4 and 5 were synthesized by preparation of phosphonoglutamate 14 from the alpha-carboxyl-protected glutamate.

Commercially available alpha-benzyl-N-Boc-L-glutamate 11 was treated at refluxing THF with neat boranedimethylsulfide complex to afford the corresponding alcohol in 90% yield. This was transformed into bromide 12 by the usual procedure ($Pph_3$, $CBr_4$).

The Michaelis-Arbuzov reaction using triethylphosphite to give the corresponding diethylphosphonate 13 which would be deprotected at the nitrogen with trifluoroacetic acid to give free amine 14. The latter would be condensed separately with either pentafluorophenylesters 6 or 8 to give 16 and 15 respectively, under conditions similar to those described for 3. 15 and 16 would be deprotected in the same manner as for 3 to yield desired analogs 4 and 5.

An inhibitor of the metabolism of purines and pyrimidine like DON (6-diazo-5-oxo-norleucine) or its aspartate-like 17, and glutamate-like 18 analogs would be added to the series of substrates.

Analog 20 is transformed into compound 17 by treatment with oxalyl chloride followed by diazomethane and deprotection under known conditions to afford the desired analogs. In addition, azotomycin is active only after in vivo conversion to DON which will be released after action of PSM on analogs 17, 18, and 19.

In addition, most if not all chemotherapies rely on one hypothesis; fast growing cells possess a far higher appetite for nutrients than normal cells. Hence, they uptake most of the chemotherapeutic drugs in their proximity. This is why chemotherapy is associated with serious secondary effects (weakening of the immune system, loss of hair, . . . ) that sometimes put the patient's life in danger. A selective and effective drug that cures where it should without damaging what it shouldn't damage is embodied in representative structures 21 and 22.

Representative compounds, 21 and 22, were designed based on some of the specific effects and properties of PSM, and the unique features of some newly discovered cytotoxic molecules with now known mode of action. The latter, referred to commonly as enediynes, like dynemycin A 23 and or its active analogs. The recent isolation of new natural products like Dynemycin A 23, has generated a tremendous and rapidly growing interest in the medical and chemical sciences. They have displayed cytotoxicities to many cancer cell lines at the sub-nanomolar level. One problem is they are very toxic, unstable, and non-selective. Although they have been demonstrated, in vitro, to exert their activity through DNA damage by a radical mechanism as described below, their high level of toxicity might imply that they should be able to equally damage anything in their path, from proteins to enzymes.

These molecules possess unusual structural features that provide them with exceptional reactivities. Dynemycin A 23 is relatively stable until the anthraquinone moiety is bioreduced into hydrcanthraquinone 24. This triggers a chain of events by which a diradical species 25 is generated as a result of a Bergman cycloaromatization[F]. Diradical species 25 is the ultimate damaging edge of dynemycin A. It subtracts 2(two) protons from any neighboring molecule or molecules (ie. DNA) producing radicals therein. These radicals in turn combine with molecular oxygen to give hydroperoxide intermediates that, in the case of DNA, lead to single and double strand incision, and consequent cell death. Another interesting feature was provided by the extensive work of many organic chemists who not only achieved the total synthesis of (+)-dynemycin A 23 and other enediynes. but also designed and efficiently prepared simpler yet as active analogs like 26.

Enediyne 26 is also triggerable and acts by virtue of the same mechanism as for 23. This aspect is very relevant to the present proposed study in that 27 (a very close analog of 26) is connected to NAAG such that the NAAG-27 molecule, 21, would be inert anywhere in the body (blood, organs, normal prostate cells) except in the vicinity of prostate cancer, and metastatic cells. In this connection NAAG plays a multiple role:

Solubilization and transport: analogs of 26-type are hydrophobic and insoluble in aqueous media, but with a water soluble dipeptide that is indigenous to the body, substrate 21 should follow the ways by which NAAG is transported and stored in the body.

Recognition, guidance, and selectivity: Homologs of PSM are located in the small intestines and in the brain.

In the latter, a compound like 27 when attached to a multiply charged dipeptide like NAAG, has no chance of crossing the blood brain barrier. In the former case, PSM homolog concentration in the small intestines is in the brush border and is low compared to that of PSM in the prostate cancer cells and is thus not likely to be exposed to prodrugs in the serum. In addition, one could enhance the selectivity of delivery of the prodrug by local injection in the prostate. Another image of this strategy could be formulated as follows. If prostate cancer were a war in which one needed a "smart bomb" to minimize the damage within the peaceful surroundings of the war zone, then 21 would be that "smart bomb". NAAG would be its guidance system, PSM would be the trigger, and 27would be the warhead.

26 and its analogs are established active molecules that portray the activity of clynemycin A. Their synthesis is described in the literature. The total synthesis of optically active 27 has been described[6]. The synthetic scheme that for the preparation of 28 is almost the same as that of 27. However, they differ only at the position of the methoxy group which is meta to the nitrogen in the case of 28. This requires an intermediate of type 29 prepared by modification of the Myers' method. Compound 28 is perhaps the closest optically active analog to 26, and the activity of the latter is known and very high. Since NAAG is optically pure, its combination with racemic material sometimes complicates purification of intermediates. In addition, to be able to modify the components of this system one at a time, optically pure intermediates of the type 21 and 22 are prepared. 27 was prepared in 17 steps starting from commercially available material. Another interesting feature of 27 is demonstrated in a very close analog 26, it possesses two(2) triggers as shown by the arrows.

The oxygen and the nitrogen can both engender the Bergman cycloaromatization and hence the desired damage. The simple protection deprotection manipulation of either functionality should permit the selective positioning of NAAG at the nitrogen or at the oxygen centers. PSM should recognize the NAAG portion of 21 or 22, then it would remove the glutamic acid moiety. This leaves 27 attached to N-acetylaspartate.

Intramolecular assisted hydrolysis of systems like N-acetylaspartyle is well documented in the literature. The aminoacid portion should facilitate the hydrolysis of such a linkage. In the event this would not work when NAAG is placed on the nitrogen, an alternative would be to attach NAAG to the oxygen giving rise to phenolic ester 22 which is per se labile and removable under milder conditions. PSM specific pro-drugs can be designed that could activate pro-drugs at the site of prostatic tumor cells to kill those cells. PSM specific substrates may also be used in the treatment of benign prostatic hyperplasia.

EXAMPLE 13

Genomic Organization OF PSM EXON/INTRON Junction Sequences

RNA is synthesized and then processed by having variable numbers of variable sized fragments cut out and remain in the nucleus (introns) and the remaining fragments (exons) joined together and transported out of the nucleus (mRNA) for use in translation into protein in the cytoplasm. This mRNA is what make the unique protein products of the cell, proteins of specialized cells are often made in a great abundance as are their respective coding mRNA's. These tissue specific mRNA's can be reverse transcribed (RT) into DNA by reverse transcriptase and amplified for detection by polymerase chain reaction (PCR) technology and thus the technique is called RT-PCR. If DNA is a contaminant of the mRNA fraction it would contain the message even though it was not being transcribed.

Knowledge of the intron exon junctions allows for the selection of primer pairs that cross an intron junction and thus allow the determination of DNA contamination of the RNA preparation, if present. If the intron junction were large it would be unlikely to be amplified with primers, while if the intron junction were small it would still produce a fragment that would be much larger than the predicted fragment size which is based on the cDNA sequence. Thus knowledge of the intron/exon junctions provides a control to determine if the RT-PCR product is contaminated with DNA. Another form of DNA that could also be amplified undesirably if present as a contaminant are pseudo genes, which are intronless forms of the mRNA that reside as DNA but are not expressed as RNA. Thus, optimized primers for detection of PSM mRNA in samples would preferably contain sequences hybridizing across the intron/exon junction which are as follows:

```
EXON 1                        Intron 1
1F. strand
CGGCTTCCTCTTCGG
(SEQ ID NO:40)

cggcttcctcttcgg               taggggggcgcctcgcggag . . . tattt ttca
                              (SEQ ID NO:41)

1R. strand                            . . . ataaaaagtCACCAAA (SEQ ID NO:42)

Exon 2                        Intron 2
2F. strand
ACATCAAGAAGTTCT
(SEQ ID NO:43)

acatcaagaagttct               caagtaagtccatactcgaag . . .
                              (SEQ ID NO:44)

2R. strand                    . . . caagtggtcATATATTAAAATG
                              (SEQ ID NO:45)

Exon 3                        Intron 3
3F. strand
GAAGATGGAAATGAG
(SEQ ID NO:46)

gaagatggaaatgag               gtaaaatataaataaataaataa . . .
                              (SEQ ID NO:47)

3R. strand                           . . . TAAAAGTTGTGTAGT
                              (SEQ ID NO:48)

Exon 4                        Intron 4
4F. strand
AAGGAATGCCAGAGG
(SEQ ID NO:49)

aaggaatgccagagg               taaaaacacagtgcaacaaa . . .
                              (SEQ ID NO:50)
```

```
                            -continued 4R. strand                  . . . agagttgCCGCTAGATCACA
                            (SEQ ID NO:51)

Exon 5                      Intron 5
5F. strand
CAGAGGAAATAAGGT
(SEQ ID NO:52)

cagaggaaataaggt             aggtaaaaattatctctttttt . . .
                            (SEQ ID NO:53)

5R. strand                  . . .gtgttttctATTTTTACGGGT
                            (SEQ ID NO:54)

Exon 6                      Intron 6
6F. strand
GTTACCCAGCAAATG
(SEQ ID NO:55)

gttacccagcaatg              gtgaatgatcaatccttgaat . . .
                            (SEQ ID NO:56)

6R. strand                  . . . aaaaaaagtTTATACGAATA
                            (SEQ ID NO:57)

Exon 7                      Intron 7
7F. strand
ACAGAAGCTCCTAGA
(SEQ ID NO:58)

acagaagctcctaga             gtaagtttgtaagaaaccargg . . .
                            (SEQ ID NO:59)

7R. strand                  . . . aaacacaggttatcTTTTTACCCA
                            (SEQ ID NO:60)

Exon 8                      Intron 8
8F. strand
AAACTTTTCTACACA
(SEQ ID NO:61)

aaacttttctacaca             gttaagagactatataaatttta . . .
                            (SEQ ID NO:62)

8R. strand                      . . . . aaacgtaatcaTTTTCAGTTCTAC
                            (SEQ ID NO:63)

Exon 9                      Intron 9
9F. strand
AGCAGTGGAACCAG
(SEQ ID NO:64)

agcagtggaaccag              gtaaaggaatcgtttgctagca . . .
                            (SEQ ID NO:65)

9R. strand                  . . . aaagaTGTCTATACAGTAA
                            (SEQ ID NO:66)

Exon 10                     Intron 10
10F. Strand
CTGAAAAAGGAAGG
(SEQ ID NO:67)

ctgaaaaaggaagg              taatacaaacaaatagcaagaa . . .
                            (SEQ ID NO:68)

Exon 11                     Intron 11
11F. Strand
TGAGTGGGCAGAGG
(SEQ ID NO:69)

agaggttagttggtaatttgctataatata . . .
                            (SEQ ID NO:70)

Exon 12                     Intron 12
12F. strand
ATCTATAGAAGG
```

-continued (SEQ ID NO:71)

gtagtttcct       gaaaaataagaaaagaatagat . . .
(SEQ ID NO:72)

Exon 13       Intron 13
13F. strand
CTAACAAAAGAG
(SEQ ID NO:73)

agggcttttcagct   acacaaattaaaagaaaaaaag . . .
(SEQ ID NO:74)

Exon 14       Intron 14
14F. strand
GTGGCATGCCCAGG
(SEQ ID NO:75)

gtggcatgcccagg   taaataaatgaatgaagtttcca . . .
(SEQ ID NO:76)

Exon 15       Intron 15
15F. strand
CTAAAAATTGGC
(SEQ ID NO:77)

aatttgtttgtttcc  tacagaaaaaacaacaaaaca . . .
(SEQ ID NO:78)

Exon 16       Intron 16
16F. strand
CAGTGTATCATTTG
(SEQ ID NO:79)

cagtgtatcatttg   gtatgttacccttccttttcaaatt . . .
(SEQ ID NO:80)

16R. strand     . . . aaagtcTAAGTGAAAA
(SEQ ID NO:81)

Exon 17       Intron 17
17F. strand
TTTGACAAAAGCAA
(SEQ ID NO:82)

tttgacaaaagcaa   gtatgttctacatatatgtgcatat . . .
(SEQ ID NO:83)

17R. strand     . . . aaagagtcGGGTTATCAT
(SEQ ID NO:84)

Exon 18       Intron 18
18F. strand
GGCCTTTTTATAGG
(SEQ ID NO:85)

ggccttttatagg    taaganaagaaaatatgactcct . . .
(SEQ ID NO:86)

18R. strand     . . . aatagttgGTACAGTAGATA
(SEQ ID NO:87)

Exon 19       Intron 19
19F. strand
GAATATTATATATA
(SEQ ID NO:88)

gaatattatatata   gttatgtgagtgtttatatatgtgtgt . . .
(SEQ ID NO:89)

Notes:
F: Forward strand
R: Reverse strand

REFERENCES

1. Abdel-Nabi, H., Wright, G. L., Gulfo, J. V., Petrylak, D. P., Neal, C. E., Texter, J. E., Begun, F. P., Tyson, I., Heal, A., Mitchell, E., Purnell, G., and Harwood, S. J. Monoclonal antibodies and radioimmunoconjugates in the diagnosis and treatment of prostate cancer. Semin. Urol., 10: 45-54, 1992.
2. Antonie, P. Springer, C. J., Bagshawe, F., Searle, F., Melton, R. G., Rogers, G. T., Burke, P. J., Sherwood, R. F.

Disposition of the prodrug 4-bis(2chloroethyl) amino) benzoyl-1-glutamic acid and its active parent drug in mice. Br. J. Cancer 62:909-914, 1990.
3. Aviv, H., and Leder, P. Purification of biologically active globin messenger RNA by chromatography on oligo-thymidylic acid cellulose. Proc. Natl. Acad. Sci. USA, 69: 1408-1412, 1972.
4. Axelrod, H. R., Gilman, S. C., D'Aleo, C. J., Petrylak, D., Reuter, V., Gulfo, J. V., Saad, A., Cordon-Cardo, C., and Scher, H. I. Preclinical results and human immunohistochemical studies with $^{90}$Y-CYT-356; a new prostatic cancer therapeutic agent. AUA Proceedings, Abstract 596, 1992.
5. Boring, C. C., Squires, T. S., Tong, T., and Montgomery, S. Cancer Statistics, 1994. CA., 44: 7-26, 1994.
6. Chiarodo, A. National Cancer Institute roundtable on prostate cancer; future research directions. Cancer Res., 51: 2498-2505, 1991.
7. Chiaroda, A. (1991) National roundtable of prostate cancer: research directions. Cancer Res. 51: 2498-2505.
8. Coffey, D. S. Prostate Cancer—An overview of an increasing dilemma. Cancer Supplement, 71,3: 880-886, 1993.
9. Connor, J. Bannerji, R., Saito, S., Heston, W. D. W., Fair, W. R., Gilboa, E. Regression of bladder tumors in mice treated with interleukin 2 gene-modified tumor cells. J. Exp. Med. 177:1127-1134, 1993. (appendix)
10. Deguchi, T., Doi, T., Ehara, H., Ito, S., Takahashi, Y., Nishino, Y., Fujihiro, S., Kawamura, T., Komeda, H., Horie, M., Kaji, H., Shimokawa, K., Tanaka, T., and Kawada, Y. Detection of micrometastic prostate cancer cells in lymph nodes by reverse-transcriptase polymerase chain reaction. Cancer Res. 53:5350-4, 1993.
11.
12. Eisenburg, D., Schwarz, E., Komaromy, M. and Wall, R. Analysis of membrane and surface protein sequences with the hydrophbic moment plot, J. Mol. Biol. 179:125-142, 1984.
13. Feinberg, A. P., and Vogelstein, B. A technique for radiolabeling DNA restriction endonuclease fragments to high specific activity. Anal. Biochem., 132:6-13, 1983.
14. Feng, Q., et al., (1991) Purification and biochemical characterization of the 7 μl-C5 prostate carcinoma associated antigen. Proc. Amer. Assoc. Cancer Res. 32:239.
15. Fey, M. F., Kulozik, A. E., and Hansen-Hagge, T. E.: The polymerase chain reactipn: A new tool for the detection of minimal residual disease in hematological malignacies. Eur. J. Cancer, 27: 89-94, 1991.
16. Gussow, D., Rein, R., Ginjaar, I., Hochstenbach, F., Seemann, G., Kottman, A., Ploegh, H. L. The human β-2-Microglobulin gene. Primary structure and definition of the transcriptional unit. J. of Immunol. 139:3132-3138, 1987.
17. Glisin, V., Crkvenjakov, R.; and Byus, C. Ribonucleic acid isolated by cesium chloride centrifugation. Biochemistry, 13: 2633-2637, 1974.
18. Ghossein, R., Scher, H., Gerald, W., Hoffman, A., Kelley, W., Curely, T., Libertz, C., and Rosai, J. Detection of cirulating tumor cells in peripheral blood of patients with advanced prostatic carcinoma. Proc. Amer. Soc. of Clin. Oncol., 13:237, 1994.
19. Hanahan, D.: Studies on transformation of *Escherichia coli* with plasmids. J. Mol. Biol., 166:557-580, 1983.
20. Harlow, E., and Lane, D. Antibodies: A Laboratory Manual. New York: Cold Spring Harbor Laboratory, p. 449, 1988.
21. Henttu, P., et al., (1989) cDNA coding for the entire human prostate specific antigen show high homologies to the human tissue kallikrein genes. Bioch. Biophys. Res. Comm. 160:903-908.
22. Horoszewicz, J. S., Kawinski, E., and Murphy, G. P. Monoclonal antibodies to a new antigenic marker in epithelial cells and serum of prostatic cancer patients. Isaeli, R. S., Powell, C. T., Fair, W. R., and Heston, W. D. W.: Molecular cloning of a complementary, DNA encoding a prostate-specific membran antigen. Cancer Res., 53: 227-230, 1993.
23. Horoszewicz, J. S., Leong, S. S., Kawinski, E., Karr, J. P., Rosenthal, H., Chu, T. M., Mirand, E. A., and Murphy, G. P.: LNCaP model of human prostactic carcinoma. Cancer Res., 43: 1809-1818, 1983. Anticancer Res., 7: 927-936, 1987.
24. Horoszewicz, J. S., Leong, S. S., Kawinski, E., Karr, J. P., Rosenthal, H., Chu, T. M., Mirand, E. A., and Murphy, G. P. LNCaP model of human prostatic carcinoma. Cancer Res., 43: 1809-1818, 1983.
25. Horoszewicz, J. S., Kawinski, E., and Murphy, G. P. Monoclonal antibodies to a new antigenic marker in epithelial cells and serum of prostatic cancer patients. Anticancer Res., 7:927-936,1987.
26. Horoszewicz, J. S., Leong, S. S., Kawinski, E., Karr, J. P., Rosenthal, H., Chu, T. M., Mirand, E. A. and Murphy, G. P. LNCaP model of human prostatic Carcinoma. Cancer Res., 43:1809-1818,1983. 8.
27. Horoszewicz, J. S., et al. (1987) Monoclonal antibodies to a new antigenic marker in epithelial prostatic cells and serum of prostatic cancer patients. Anticancer Res. 7:927-936.
28. Horoszewicz, J. S., et al. (1983) LNCaP model of human prostatic carcinoma. Cancer Res., 43:1809-1818.
29. Hsut, S. M., Raine, L., and Fanger, H. Review of present methods of immunohistochemical detection. Am. J. Clin. Path. 75: 734-738, 1981.
30. Israeli, R. S., Powell, C. T., Fair, W. R., and Heston, W. D. W. Molecular cloning of a complementary DNA encoding a prostate-specific membrane antigen. Cancer Res., 53: 227-230, 1993.
31. Israeli, R. S., Miller Jr., W. H., Su, S. L., Powell, C. T., Fair, W. R., Samadi, D. S., Huryk, R. F., DelBlasio, A., Edwards, E. T, and Heston, W. D. W. Sensitive Nested Reverse Transcription Polymerase Chain Reaction Detection of Circulating Prostatic Tumor Cells: Comparision of Prostate-specific Membrane Antigen and Prostate-specific Antigen-based Assays. Cancer Res., 54: 6325-6329,1994.
32. Israeli, R. S., Powell, C. T., Fair, W. R. and Heston, W. D. W. Molecular cloning of a complementary DNA encoding a prostate-specific membrane antigen. Cancer Res.,53: 227-230,1993.
33. Israeli, R. S., Powell, C. T., Corr, J. G., Fair, W. R. and Heston, W. D. W. Expression of the prostate-specific membrane antigen. Cancer Res., 54:1807-1811,1994.
34. Israeli, R. S., Miller, W. H., Jr., Su, S. L., Samadi, D. S., Powell, C. T., Heston, W. D. W., Wise, G. J., and Fair, W. R. Sensitive detection of prostatic hematogenous micrometastases using prostate-specific antigen (PSA) and prostate-specific membran antigen (PSM) derived primers in the polymerase chain reaction. J. Urol. 151:373A, 1994.
35. Israeli, R. S., Powel, C. T., Corr, J. G., Fair, W. R., and Heston, W. D. W.: Expression of the prostate-specific membrane antigen. Cancer Res., 54:1807-1811, 1994.
36. Israeli, R. S., Miller, W. H., Jr., Su, S. L, Samadi, D. S., Powell, C. T. Heston, W. D. W., Wise, G. J., and Fair, W. S. Sensitive detection of prostatic hematogenous micrometastases using PsA and PSM-derived primers in the polymerase chain reaction. In press—J. Urology.
37. Kaign, M. E., Narayan, K. S., Ohnuki, Y., and Lechner, J. F. Establishment and characterization of a human prostatic carcinoma cell line (PC-3). Invest. Urol., 17: 16-23, 1979.
38. Katz, A. E., Olsson, C. A., Raffo, A. J., Cama, C., Perlman, H., Seaman, E., O'Toole, K. M., McMahon, D., Benson, M., and Buttyan, R., Molecular staging of prostate cancer with the use of an enhanced reverse transcriptase-PCR assay. Urology 43:765-775, 1994.
39. Liotta, L. A. (1986) Tumor invasion and metastases: role of the extracellular matrix. Cancer Res. 46:1-7.
40. Liotta, L. A., Kleinerman, J., and Saidel, G. M.: Quantitative relationships of intravascular tumor cells, tumors vessels, and pulmonary metastases following tumore implantation. Cancer Res., 34:997-1003, 1974.
41. Lopes, D., et al. (1990) Immunohistochemical and pharmacokinetic characterization of the site-specific immunoconjugate CYT-356, derived from anti-prostate monoclonal antibody 7 µl-C5. Cancer Res., 50:6423-6429.
42. Lopes, A. D., Davis, W. L., Rosenstraus, M. J., Uveges, A. J., and Gilman, S. C. Immunohistochemical and pharmacokinetic characterization of the site-specific immunoconjugate CYT-356 derived from antiprostate monoclonal antibody 7 µl-C5. Cancer Res., 50: 6423-6429, 1990.
43. Lundwall, A., and Lilja, H: Molecular cloning of a human prostate specific antigen cDNA. FEBS Letters, 214: 317, 1987. 7.
44. Melton, D. A., Krieg, P. A., Rebagliati, M. R., Maniatis, T. A., Zinn, K., and Careen, M. R. Efficient in-vitro synthesis of biologically active RNA and RNA hybridization probes from plasmids containing a bacteriophage SP6 promoter. Nucl. Acids. Res. 12: 7035-7056, 1984.
45. Miller, W. H., Jr., Levine, K., DeBlasio, A., Frankel, S. R., Dmitrovsky, E., and Warrell, R. P., Jr. Detection of mininal residual disease in Acute Promyelocytic Leukemia by a reverse transciption polymerase chain reaction assay for th PML/RAR-α fusion mRNA. Blood, 82: 1689-1694, 1993. Moreno, J. G., Croce, C. M., Fischer, R., Monne, M., Vihko, P., Mulholland, S. G., and Gomella, L. G., Detection of hematogenous micrometastasis in patients with prostate cancer. Cancer Res., 52:6110-6112, 1992.
46. Murphy, G. P. Report on the American Urologic Association/American Cancer Society Scientific Seminar on the Detection and treatment of Early-Stage Prostate Cancer. CA Cancer J. Clin. 44:91-95,1994.
47. Nguyen, L., et al., (1990) Prostatic acid phosphatase in the serum of cancer patients with prostatic cancer is a specific phosphotyrosine acid phosphatase. Clin. Chem. 35:1450-1455.
48. Oberneder, R., Riesenberg, R., Kriegmair, M., Bitzer, U., Klammert, R., Schneede, P., Hofstetter, A., Riethmuller, G., and Pantel, K. Immunocytochemcical detection and phenytypic characterization of micrometastatic tumour cells in bone marrow of patients with prostate cancer. Urol. Res. 22:3-8, 1994.
49. Rao, M. J. K. and Argos, P. A conformational preference parameter to predict helices in integral membrane proteins. Biochim. Biophys. Acta, 869:197-214,1986.
50. Roemer, K., Friedmann, T. Concepts and strategies for human gene therapy. FEBS. 223:212-225.
51. Sanger, F., Nicklen, S., and Coulson, A. R.: DNA seqencing with chain-terminating inhibitors. Proc. Natl. Acad. Sci. USA, 74:5463-5467, 1977.
52. Soule, H. D., Vazquez, J., Long, A., Albert, S., and Brennan, M.: A human cell line from a pleural effusion derived from a breast carcinoma. J. Natl. Can. Inst., 51: 1409-1416, 1973.
53. Stone, K. R., Mickey, D. D., Wunderli, H., Mickey, G. H., and Paulson, D. F. Isolation of a human prostate carcinoma cell line (DU-145). Int. J. Cancer, 21: 274-281, 1978.
54. Troyer, J. K. and Wright Jr., G. L.
Biochemical characterization and mapping of 7E-11 C-5.3. Epitope of the prostate specific membrane antigen (PSMA). American Association for Cancer Research Special Conference: Basic and Clinical Aspect of Prostate Cancer. Abstract C-38, 1994.
55. Troyer, J. K., Qi, F., Beckett, M. L., Morningstar, M. M., and Wright, G. L. molecular characterization of the 7 µl-CS prostate tumor-associated antigen. AUA Proceedings. Abstract 482, 1993.
56. Vessella, R., Stray, J., Arman, E., Ellis, W., and Lange, P. Reverse transcription polymerase chain reaction (RT-PCR) detects metastatic prostate cancer cells in lymph nodes, blood and potentially bone marrow using PSA-mRNA as template, J. Urol. 151:412A, 1994.
57. Vile R., Hart, I. R. In vitro and in vivo targeting of gene expression to melanoma cells. Cancer Res. 53:962-967, 1993.
58. Vile, R. G., Hart, I. R. Use of tissue specific expression of the herpes simplex virus thymidine kinase gene to inhibit growth of established murine melanomas following direct intratumoral injection of DNA. Cancer Res. 53:3860-3864, 1993.
59. Warner, J. A., Heston, W. D. W. Future developments of nonhormonal systemic therapy for prostatic carcinoma. Urologic Clinics of North America 18:25-33, 1991.
60. Warner, J. A., et al., (1991) Future developments of non-hormonal systemic therapy for prostatic carcinoma. Urologic Clin. North Amer. 18:25-33.
61. Wright, Jr., et al., (1990) Characterization of a new carcinoma associated marker:7E11-C5. Antibod. Immunoconj. Radiopharm.3:(abst#193).
62. Wu, A., Ben-Ezra, J., and Colombero, A.: Detection of micrometastasis in breast cancer by the polymerase chain reaction. Lab. Ivest., 62: 109A, 1990.
63. Wood, D. P., Jr., Banks, E. R., Humphries, S., McRoberts, J. W., and Rangenkar, V. M. Identification of micrometastases in paitents with prostate cancer. J. Urol. 151:303A, 1994.
64. Wright, G. L., Jr., Haley, C., Beckett, M. L., and Schellhammer, P. F. Expression of the prostate biomaker 7E11-C5 in primary and metastic prostate carcinoma. Proc. Amer. Ass. for Can. Res. 35:233, 1994.
65. Yong, CY-F., et al., (1991) Hormonal regulation of prostate-specific antigen messenger RNA in human prostatic adenocarcinoma cell line LNCaP. Cancer Res. 51:3748-3752.

SEQUENCE LISTING

<160> NUMBER OF SEQ ID NOS: 128

<210> SEQ ID NO 1
<211> LENGTH: 2653
<212> TYPE: DNA
<213> ORGANISM: Homo sapiens

<400> SEQUENCE: 1

| | | | | | |
|---|---|---|---|---|---|
| ctcaaaaggg | gccggatttc | cttctcctgg | aggcagatgt | tgcctctctc | tctcgctcgg | 60 |
| attggttcag | tgcactctag | aaacactgct | gtggtggaga | aactggaccc | caggtctgga | 120 |
| gcgaattcca | gcctgcaggg | ctgataagcg | aggcattagt | gagattgaga | gagactttac | 180 |
| cccgccgtgg | tggttggagg | gcgcgcagta | gagcagcagc | acaggcgcgg | gtcccgggag | 240 |
| gccggctctg | ctcgcgccga | gatgtggaat | ctccttcacg | aaaccgactc | ggctgtggcc | 300 |
| accgcgcgcc | gcccgcgctg | gctgtgcgct | ggggcgctgg | tgctggcggg | tggcttcttt | 360 |
| ctcctcggct | tcctcttcgg | gtggtttata | aaatcctcca | atgaagctac | taacattact | 420 |
| ccaaagcata | atatgaaagc | attttttggat | gaattgaaag | ctgagaacat | caagaagttc | 480 |
| ttatataatt | ttacacagat | accacattta | gcaggaacag | aacaaaactt | tcagcttgca | 540 |
| aagcaaattc | aatcccagtg | gaaagaattt | ggcctggatt | ctgttgagct | agcacattat | 600 |
| gatgtcctgt | tgtcctaccc | aaataagact | catcccaact | acatctcaat | aattaatgaa | 660 |
| gatgaaaatg | agatttttcaa | cacatcatta | tttgaaccac | ctcctccagg | atatgaaaat | 720 |
| gtttcggata | ttgtaccacc | tttcagtgct | ttctctcctc | aaggaatgcc | agagggcgat | 780 |
| ctagtgtatg | ttaactatgc | acgaactgaa | gacttcttta | aattggaacg | ggacatgaaa | 840 |
| atcaattgct | ctgggaaaat | tgtaattgcc | agatatggga | aagttttcag | aggaaataag | 900 |
| gttaaaaatg | cccagctggc | aggggccaaa | ggagtcattc | tctactccga | ccctgctgac | 960 |
| tactttgctc | ctgggggtgaa | gtcctatcca | gatggttgga | atcttcctgg | aggtggtgtc | 1020 |
| cagcgtggaa | atatcctaaa | tctgaatggt | gcaggagacc | ctctcacacc | aggttaccca | 1080 |
| gcaaatgaat | atgcttatag | gcgtggaatt | gcagaggctg | ttggtcttcc | aagtattcct | 1140 |
| gttcatccaa | ttggatacta | tgatgcacag | aagctcctag | aaaaaatggg | tggctcagca | 1200 |
| ccaccagata | gcagctggag | aggaagtctc | aaagtgccct | acaatgttgg | acctggcttt | 1260 |
| actggaaact | tttctacaca | aaaagtcaag | atgcacatcc | actctaccaa | tgaagtgaca | 1320 |
| agaatttaca | atgtgatagg | tactctcaga | ggagcagtgg | aaccagacag | atatgtcatt | 1380 |
| ctgggaggtc | accgggactc | atgggtgttt | ggtggtattg | accctcagag | tggagcagct | 1440 |
| gttgttcatg | aaattgtgag | gagctttgga | acactgaaaa | aggaagggtg | gagacctaga | 1500 |
| agaacaattt | tgtttgcaag | ctgggatgca | gaagaatttg | gtcttcttgg | ttctactgag | 1560 |
| tgggcagagg | agaattcaag | actccttcaa | gagcgtggcg | tggcttatat | taatgctgac | 1620 |
| tcatctatag | aaggaaacta | cactctgaga | gttgattgta | caccgctgat | gtacagcttg | 1680 |
| gtacacaacc | taacaaaaga | gctgaaaagc | cctgatgaag | ctttgaagg | caaatctctt | 1740 |
| tatgaaagtt | ggactaaaaa | aagtccttcc | ccagagttca | gtggcatgcc | caggataagc | 1800 |
| aaattgggat | ctgaaatga | ttttgaggtg | ttcttccaac | gacttggaat | tgcttcaggc | 1860 |
| agagcacggt | atactaaaaa | ttgggaaaca | aacaaattca | gcggctatcc | actgtatcac | 1920 |
| agtgtctatg | aaacatatga | gttggtggaa | aagtttatg | atccaatgtt | taaatatcac | 1980 |
| ctcactgtgg | cccaggttcg | aggagggatg | gtgtttgagc | tagccaattc | catagtgctc | 2040 |

```
ccttttgatt gtcgagatta tgctgtagtt ttaagaaagt atgctgacaa aatctacagt    2100
atttctatga acatccaca ggaaatgaag acatacagtg tatcatttga ttcactttt      2160 tctgcagtaa agaattttac agaaattgct tccaagttca gtgagagact ccaggacttt    2220
gacaaaagca acccaatagt attaagaatg atgaatgatc aactcatgtt tctggaaaga    2280
gcatttattg atccattagg gttaccagac aggccttttt ataggcatgt catctatgct    2340
ccaagcagcc acaacaagta tgcagggagt cattcccag gaatttatga tgctctgttt     2400
gatattgaaa gcaaagtgga cccttccaag gcctggggag aagtgaagag acagatttat    2460
gttgcagcct tcacagtgca ggcagctgca gagactttga gtgaagtagc ctaagaggat    2520
tctttagaga atccgtattg aatttgtgtg gtatgtcact cagaaagaat cgtaatgggt    2580
atattgataa attttaaaat tggtatattt gaaataaagt tgaatattat atataaaaaa    2640
aaaaaaaaaa aaa                                                       2653
```

<210> SEQ ID NO 2
<211> LENGTH: 750
<212> TYPE: PRT
<213> ORGANISM: Homo sapiens

<400> SEQUENCE: 2

```
Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255
```

```
Asn Ile Leu Asn Leu Asn Gly Ala Gly Asp Pro Leu Thr Pro Gly Tyr
            260                 265                 270
Pro Ala Asn Glu Tyr Ala Tyr Arg Gly Ile Ala Glu Ala Val Gly
        275                 280                 285
Leu Pro Ser Ile Pro Val His Pro Ile Gly Tyr Tyr Asp Ala Gln Lys
            290                 295                 300
Leu Leu Glu Lys Met Gly Gly Ser Ala Pro Asp Ser Ser Trp Arg
305                 310                 315                 320
Gly Ser Leu Lys Val Pro Tyr Asn Val Gly Pro Gly Phe Thr Gly Asn
                325                 330                 335
Phe Ser Thr Gln Lys Val Lys Met His Ile His Ser Thr Asn Glu Val
            340                 345                 350
Thr Arg Ile Tyr Asn Val Ile Gly Thr Leu Arg Gly Ala Val Glu Pro
            355                 360                 365
Asp Arg Tyr Val Ile Leu Gly Gly His Arg Asp Ser Trp Val Phe Gly
            370                 375                 380
Gly Ile Asp Pro Gln Ser Gly Ala Ala Val Val His Glu Ile Val Arg
385                 390                 395                 400
Ser Phe Gly Thr Leu Lys Lys Glu Gly Trp Arg Pro Arg Arg Thr Ile
                405                 410                 415
Leu Phe Ala Ser Trp Asp Ala Glu Glu Phe Gly Leu Leu Gly Ser Thr
            420                 425                 430
Glu Trp Ala Glu Glu Asn Ser Arg Leu Leu Gln Glu Arg Gly Val Ala
            435                 440                 445
Tyr Ile Asn Ala Asp Ser Ser Ile Glu Gly Asn Tyr Thr Leu Arg Val
            450                 455                 460
Asp Cys Thr Pro Leu Met Tyr Ser Leu Val His Asn Leu Thr Lys Glu
465                 470                 475                 480
Leu Lys Ser Pro Asp Glu Gly Phe Glu Gly Lys Ser Leu Tyr Glu Ser
                485                 490                 495
Trp Thr Lys Lys Ser Pro Ser Pro Glu Phe Ser Gly Met Pro Arg Ile
                500                 505                 510
Ser Lys Leu Gly Ser Gly Asn Asp Phe Glu Val Phe Phe Gln Arg Leu
            515                 520                 525
Gly Ile Ala Ser Gly Arg Ala Arg Tyr Thr Lys Asn Trp Glu Thr Asn
            530                 535                 540
Lys Phe Ser Gly Tyr Pro Leu Tyr His Ser Val Tyr Glu Thr Tyr Glu
545                 550                 555                 560
Leu Val Glu Lys Phe Tyr Asp Pro Met Phe Lys Tyr His Leu Thr Val
                565                 570                 575
Ala Gln Val Arg Gly Gly Met Val Phe Glu Leu Ala Asn Ser Ile Val
            580                 585                 590
Leu Pro Phe Asp Cys Arg Asp Tyr Ala Val Val Leu Arg Lys Tyr Ala
            595                 600                 605
Asp Lys Ile Tyr Ser Ile Ser Met Lys His Pro Gln Glu Met Lys Thr
            610                 615                 620
Tyr Ser Val Ser Phe Asp Ser Leu Phe Ser Ala Val Lys Asn Phe Thr
625                 630                 635                 640
Glu Ile Ala Ser Lys Phe Ser Glu Arg Leu Gln Asp Phe Asp Lys Ser
                645                 650                 655
Asn Pro Ile Val Leu Arg Met Met Asn Asp Gln Leu Met Phe Leu Glu
            660                 665                 670
Arg Ala Phe Ile Asp Pro Leu Gly Leu Pro Asp Arg Pro Phe Tyr Arg
```

-continued

```
                    675                 680                 685
His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
                740                 745                 750

<210> SEQ ID NO 3
<211> LENGTH: 8
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: x=any amino acid
<220> FEATURE:
<221> NAME/KEY: MISC_FEATURE
<222> LOCATION: (6)..(6)
<223> OTHER INFORMATION: Xaa=any amino acid

<400> SEQUENCE: 3

Ser Leu Tyr Glu Ser Xaa Thr Lys
1               5

<210> SEQ ID NO 4
<211> LENGTH: 15
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa=any amino acid
<220> FEATURE:
<221> NAME/KEY: MISC_FEATURE
<222> LOCATION: (6)..(6)
<223> OTHER INFORMATION: Xaa=any amino acid
<220> FEATURE:
<221> NAME/KEY: MISC_FEATURE
<222> LOCATION: (12)..(12)
<223> OTHER INFORMATION: Xaa=any amino acid

<400> SEQUENCE: 4

Xaa Tyr Pro Asp Gly Xaa Asn Leu Pro Gly Gly Xaa Val Gln Arg
1               5                   10                  15

<210> SEQ ID NO 5
<211> LENGTH: 7
<212> TYPE: PRT
<213> ORGANISM: Homo sapiens

<400> SEQUENCE: 5

Phe Tyr Asp Pro Met Phe Lys
1               5

<210> SEQ ID NO 6
<211> LENGTH: 9
<212> TYPE: PRT
<213> ORGANISM: Homo sapiens

<400> SEQUENCE: 6

Ile Tyr Asn Val Ile Gly Thr Leu Lys
1               5
```

```
<210> SEQ ID NO 7
<211> LENGTH: 22
<212> TYPE: PRT
<213> ORGANISM: Homo sapiens
<220> FEATURE:
<221> NAME/KEY: MISC_FEATURE
<222> LOCATION: (4)..(5)
<223> OTHER INFORMATION: Xaa=any amino acid

<400> SEQUENCE: 7

Phe Leu Tyr Xaa Xaa Thr Gln Ile Pro His Leu Ala Gly Thr Glu Gln
1               5                   10                  15

Asn Phe Gln Leu Ala Lys
            20

<210> SEQ ID NO 8
<211> LENGTH: 17
<212> TYPE: PRT
<213> ORGANISM: Homo sapiens

<400> SEQUENCE: 8

Gly Val Ile Leu Tyr Ser Asp Pro Ala Asp Tyr Phe Ala Pro Asp Val
1               5                   10                  15

Lys

<210> SEQ ID NO 9
<211> LENGTH: 17
<212> TYPE: PRT
<213> ORGANISM: Homo sapiens

<400> SEQUENCE: 9

Pro Val Ile Leu Tyr Ser Asp Pro Ala Asp Tyr Phe Ala Pro Gly Val
1               5                   10                  15

Lys

<210> SEQ ID NO 10
<211> LENGTH: 15
<212> TYPE: PRT
<213> ORGANISM: Homo sapiens

<400> SEQUENCE: 10

Ala Phe Ile Asp Pro Leu Gly Leu Pro Asp Arg Pro Phe Tyr Arg
1               5                   10                  15

<210> SEQ ID NO 11
<211> LENGTH: 19
<212> TYPE: PRT
<213> ORGANISM: Homo sapiens

<400> SEQUENCE: 11

Tyr Ala Gly Glu Ser Phe Pro Gly Ile Tyr Asp Ala Leu Phe Asp Ile
1               5                   10                  15

Glu Ser Lys

<210> SEQ ID NO 12
<211> LENGTH: 22
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa=any amino acid
<220> FEATURE:
<221> NAME/KEY: MISC_FEATURE
<222> LOCATION: (14)..(16)
```

```
<223> OTHER INFORMATION: Xaa=any amino acid

<400> SEQUENCE: 12

Thr Ile Leu Phe Ala Ser Xaa Asp Ala Glu Glu Phe Gly Xaa Xaa Xaa
1               5                   10                  15

Ser Thr Glu Glu Ala Glu
            20

<210> SEQ ID NO 13
<211> LENGTH: 17
<212> TYPE: DNA
<213> ORGANISM: Homo sapiens
<220> FEATURE:
<221> NAME/KEY: misc_feature
<222> LOCATION: (12)..(12)
<223> OTHER INFORMATION: n=any nucleotide

<400> SEQUENCE: 13
ttytaygayc cnatgtt                                                       17

<210> SEQ ID NO 14
<211> LENGTH: 17
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n=any nucleotide

<400> SEQUENCE: 14
aacatnggrt crtaraa                                                       17

<210> SEQ ID NO 15
<211> LENGTH: 17
<212> TYPE: DNA
<213> ORGANISM: Homo sapiens
<220> FEATURE:
<221> NAME/KEY: misc_feature
<222> LOCATION: (12)..(12)
<223> OTHER INFORMATION: n=any nucleotide

<400> SEQUENCE: 15
athtayaayg tnathgg                                                       17

<210> SEQ ID NO 16
<211> LENGTH: 17
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n=any nucleotide

<400> SEQUENCE: 16
ccdatnacrt trtadat                                                       17

<210> SEQ ID NO 17
<211> LENGTH: 17
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n=any nucleotide
<220> FEATURE:
<221> NAME/KEY: misc_feature
<222> LOCATION: (6)..(6)
<223> OTHER INFORMATION: n=any nucleotide
```

```
<400> SEQUENCE: 17
ccngcngayt ayttygc                                                    17

<210> SEQ ID NO 18
<211> LENGTH: 17
<212> TYPE: DNA
<213> ORGANISM: Homo sapiens
<220> FEATURE:
<221> NAME/KEY: misc_feature
<222> LOCATION: (12)..(12)
<223> OTHER INFORMATION: n=any nucleotide
<220> FEATURE:
<221> NAME/KEY: misc_feature
<222> LOCATION: (15)..(15)
<223> OTHER INFORMATION: n=any nucleotide

<400> SEQUENCE: 18
gcraartart cngcngg                                                    17

<210> SEQ ID NO 19
<211> LENGTH: 20
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n=any nucleotide

<400> SEQUENCE: 19
acngarcara ayttycarct                                                 20

<210> SEQ ID NO 20
<211> LENGTH: 20
<212> TYPE: DNA
<213> ORGANISM: Homo sapiens
<220> FEATURE:
<221> NAME/KEY: misc_feature
<222> LOCATION: (18)..(18)
<223> OTHER INFORMATION: n=any nucleotide

<400> SEQUENCE: 20
agytgraart tytgytcngt                                                 20

<210> SEQ ID NO 21
<211> LENGTH: 17
<212> TYPE: DNA
<213> ORGANISM: Homo sapiens

<400> SEQUENCE: 21
garcaraayt tycarct                                                    17

<210> SEQ ID NO 22
<211> LENGTH: 17
<212> TYPE: DNA
<213> ORGANISM: Homo sapiens

<400> SEQUENCE: 22
agytgraart tytgytc                                                    17

<210> SEQ ID NO 23
<211> LENGTH: 20
<212> TYPE: DNA
<213> ORGANISM: Homo sapiens
<220> FEATURE:
<221> NAME/KEY: misc_feature
<222> LOCATION: (9)..(9)
```

```
<223> OTHER INFORMATION: n=any nucleotide

<400> SEQUENCE: 23
tgggaygcng argarttygg                                              20

<210> SEQ ID NO 24
<211> LENGTH: 20
<212> TYPE: DNA
<213> ORGANISM: Homo sapiens
<220> FEATURE:
<221> NAME/KEY: misc_feature
<222> LOCATION: (12)..(12)
<223> OTHER INFORMATION: n=any nucleotide

<400> SEQUENCE: 24
ccraaytcyt cngcrtccca                                              20

<210> SEQ ID NO 25
<211> LENGTH: 17
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n=any nucleotide

<400> SEQUENCE: 25
tgggaygcng argartt                                                 17

<210> SEQ ID NO 26
<211> LENGTH: 17
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n=any nucleotide

<400> SEQUENCE: 26
aaytcytcng crtccca                                                 17

<210> SEQ ID NO 27
<211> LENGTH: 780
<212> TYPE: DNA
<213> ORGANISM: Homo sapiens
<220> FEATURE:
<221> NAME/KEY: misc_feature
<222> LOCATION: (82)..(84)
<223> OTHER INFORMATION: n=any nucleotide
<220> FEATURE:
<221> NAME/KEY: misc_feature
<222> LOCATION: (193)..(193)
<223> OTHER INFORMATION: n=any nucleotide
<220> FEATURE:
<221> NAME/KEY: misc_feature
<222> LOCATION: (196)..(197)
<223> OTHER INFORMATION: n=any nucleotide
<220> FEATURE:
<221> NAME/KEY: misc_feature
<222> LOCATION: (217)..(219)
<223> OTHER INFORMATION: n=any nucleotide
<220> FEATURE:
<221> NAME/KEY: misc_feature
<222> LOCATION: (232)..(233)
<223> OTHER INFORMATION: n=any nucleotide
<220> FEATURE:
<221> NAME/KEY: misc_feature
<222> LOCATION: (237)..(238)
<223> OTHER INFORMATION: n=any nucleotide
<220> FEATURE:
<221> NAME/KEY: misc_feature
```

```
<222> LOCATION: (253)..(256)
<223> OTHER INFORMATION: n=any nucleotide
<220> FEATURE:
<221> NAME/KEY: misc_feature
<222> LOCATION: (263)..(263)
<223> OTHER INFORMATION: n=any nucleotide
<220> FEATURE:
<221> NAME/KEY: misc_feature
<222> LOCATION: (600)..(601)
<223> OTHER INFORMATION: n=any nucleotide
<220> FEATURE:
<221> NAME/KEY: misc_feature
<222> LOCATION: (721)..(724)
<223> OTHER INFORMATION: n=any nucleotide

<400> SEQUENCE: 27
tacacttatc ccattcggac atgcccacct tggaactgga gacccttaca ccccaggctt      60
cccttcgttc aaccacaccc annngtttcc accagttgaa tcttcaggac taccccacat     120
tgctgttcag accatctcta gcagtgcagc agccaggctg ttcagcaaaa tggatggaga     180
cacatgctct ganagnngtt ggaaaggtgc gatccannnt tcctgtaagg tnngacnnaa     240
caaagcagga gannnngcca gantaatggt gaaactagat gtgaacaatt ccatgaaaga     300
caggaagatt ctgaacatct tcggtgctat ccagggattt gaagaacctg atcggtatgt     360
tgtgattgga gcccagagag actcctgggg cccaggagtg gctaaagctg gcactggaac     420
tgctatattg ttggaacttg cccgtgtgat ctcagacata gtgaaaaacg agggctacaa     480
accgaggcga agcatcatct ttgctagctg gagtgcagga gactacggag ctgtgggtgc     540
tactgaatgg ctggagggt actctgccat gctgcatgcc aaagctttca cttacatcan      600
ngcttggatg ctccagtcct gggagcaagc catgtcaaga tttctgccag ccccttgctg     660
tatatgctgc tggggagtat tatgaagggg gtgaagaatc cagcagcagt ctcagagagc     720
nnnnctctat aacagacttg cccagactgg gtaaaagca gttgttcctc ttggcctgga     780

<210> SEQ ID NO 28
<211> LENGTH: 660
<212> TYPE: DNA
<213> ORGANISM: Homo sapiens
<220> FEATURE:
<221> NAME/KEY: misc_feature
<222> LOCATION: (224)..(224)
<223> OTHER INFORMATION: n=any nucleotide
<220> FEATURE:
<221> NAME/KEY: misc_feature
<222> LOCATION: (255)..(255)
<223> OTHER INFORMATION: n=any nucleotide
<220> FEATURE:
<221> NAME/KEY: misc_feature
<222> LOCATION: (412)..(414)
<223> OTHER INFORMATION: n=any nucleotide
<220> FEATURE:
<221> NAME/KEY: misc_feature
<222> LOCATION: (433)..(433)
<223> OTHER INFORMATION: n=any nucleotide
<220> FEATURE:
<221> NAME/KEY: misc_feature
<222> LOCATION: (520)..(521)
<223> OTHER INFORMATION: n=any nucleotide
<220> FEATURE:
<221> NAME/KEY: misc_feature
<222> LOCATION: (536)..(543)
<223> OTHER INFORMATION: n=any nucleotide

<400> SEQUENCE: 28
tgcagaaaag ctattcaaaa acatggaagg aaactgtcct cctagttgga atatagattc      60
ctcatgtaag ctggaactttt cacagaatca aaatgtgaag ctcactgtga acaatgtact    120
```

-continued

```
gaaagaaaca agaatactta acatctttgg cgttattaaa ggctatgagg aaccagaccg      180
ctacattgta gtaggagccc agagagacgc ttggggcect ggtngttgcg aagtccagtg      240
tgggaacagg tcttnctgtt gaaacttgcc caagtattct cagatatgat ttcaaaagat      300
ggatttagac ccagcaggag tattatcttt gccagctgga ctgcaggaga ctatggagct      360
gttggtccga ctgagtggct ggaggggtac ctttcatctt tgcatctaaa gnnngctttc      420
acttacatta atnctggata aagtcgtcct gggtactagc aacttcaagg tttctgccag      480
ccccctatta tatacactta tggggaagat aatgcaggan ncgtaaagca tccgannnnn      540
nnnttgatgg aaaatatcta tatcgaaaca gtaattggat tagcaaaatt gaggaacttt      600
ccttggacaa tgctgcattc ccttttcttg catattcagg aatcccagca gtttctttct      660
```

<210> SEQ ID NO 29
<211> LENGTH: 540
<212> TYPE: DNA
<213> ORGANISM: Homo sapiens
<220> FEATURE:
<221> NAME/KEY: misc_feature
<222> LOCATION: (214)..(214)
<223> OTHER INFORMATION: n=any nucleotide
<220> FEATURE:
<221> NAME/KEY: misc_feature
<222> LOCATION: (377)..(377)
<223> OTHER INFORMATION: n=any nucleotide

<400> SEQUENCE: 29

```
tatggaagga gactgtccct ctgactggaa aacagactct acatgtagga tggtaacctc       60
agaaagcaag aatgtgaagc tcactgtgag caatgtgctg aaagagataa aaattcttaa      120
catctttgga gttattaaag gctttgtaga accagatcac tatgttgtag ttggggccca      180
gagagatgca tggggccctg gagctgcaaa atcncggtgt aggcacagct ctcctattga      240
aacttgccca gatgttctca gatatggtct taaaagatgg gtttcagccc agcagaagca      300
ttatctttgc cagttggagt gctggagact ttggatcggt tggtgccact gaatggctag      360
agggatacct ttcgtcncct gcatttaaag gctttcactt atattaatct ggataaagcg      420
gttcttggta ccagcaactt caaggtttct gccagcccac tgttgtatac gcttattgag      480
aaaacaatgc aaaatgtgaa gcatccggtt actgggcaat ttctatatca ggacagcaac      540
```

<210> SEQ ID NO 30
<211> LENGTH: 27
<212> TYPE: DNA
<213> ORGANISM: Homo sapiens

<400> SEQUENCE: 30

```
acggagcaaa actttcagct tgcaaag                                           27
```

<210> SEQ ID NO 31
<211> LENGTH: 9
<212> TYPE: PRT
<213> ORGANISM: Homo sapiens

<400> SEQUENCE: 31

Thr Glu Gln Asn Phe Gln Leu Ala Lys
1               5

<210> SEQ ID NO 32
<211> LENGTH: 36
<212> TYPE: DNA
<213> ORGANISM: Homo sapiens

<400> SEQUENCE: 32
ctcttcggca tcccagcttg caaacaaaat tgttct                                36

<210> SEQ ID NO 33
<211> LENGTH: 36
<212> TYPE: DNA
<213> ORGANISM: Homo sapiens

<400> SEQUENCE: 33
agaacaattt tgtttgcaag ctgggatgcc aaggag                                36

<210> SEQ ID NO 34
<211> LENGTH: 12
<212> TYPE: PRT
<213> ORGANISM: Homo sapiens

<400> SEQUENCE: 34

Arg Thr Ile Leu Phe Ala Ser Trp Asp Ala Glu Glu
1               5                   10

<210> SEQ ID NO 35
<211> LENGTH: 6
<212> TYPE: PRT
<213> ORGANISM: Homo sapiens

<400> SEQUENCE: 35

Asp Glu Leu Lys Ala Glu
1               5

<210> SEQ ID NO 36
<211> LENGTH: 6
<212> TYPE: PRT
<213> ORGANISM: Homo sapiens

<400> SEQUENCE: 36

Asn Glu Asp Gly Asn Glu
1               5

<210> SEQ ID NO 37
<211> LENGTH: 6
<212> TYPE: PRT
<213> ORGANISM: Homo sapiens

<400> SEQUENCE: 37

Lys Ser Pro Asp Glu Gly
1               5

<210> SEQ ID NO 38
<211> LENGTH: 17
<212> TYPE: PRT
<213> ORGANISM: Homo sapiens

<400> SEQUENCE: 38

Ala Gly Ala Leu Val Leu Ala Gly Gly Phe Phe Leu Leu Gly Phe Leu
1               5                   10                  15

Phe

<210> SEQ ID NO 39
<211> LENGTH: 3017
<212> TYPE: DNA
<213> ORGANISM: Homo sapiens

<400> SEQUENCE: 39

```
aagggtgctc cttaggctga atgcttgcag acaggatgct tggttacaga tgggctgtga      60
ctcgagtgga gttttataag ggtgctcctt aggctgaatg cttgcagaca ggatgcttgg     120
ttacagatgg gctgtgagct gggtgcttgt aagaggatgc ttgggtgcta agtgagccat     180
ttgcagttga ccctattctt ggaacattca ttcccctcta ccctgtttc tgttcctgcc      240 agctaagccc attttcatt tttcttttaa ctccttagcg ctccgcaaaa cttaatcaat      300
ttctttaaac ctcagttttc ttatctgtaa aaggtaaata ataatacagg gtgcaacaga     360
aaaatctagt gtggtttaca taatcacctg ttagagattt taaattattt caggataagt     420
catgataatt aaatgaaata atgcacataa agcacatagt gtggtgtcct ccatatagaa     480
aatgctcagt atattggtta ttaactactt gttgaaggtt tatcttctcc actaaactgt     540
aagttccaca agccttacaa tatgtgacag atattcattc attgtctgaa ttcttcaaat     600
acatcctctt caccatagcg tcttattaat tgaattatta attgaataaa ttctattgtt     660 caaaatcac ttttatattt aactgaaatt tgcttactta taatcacatc taaccttcaa     720
agaaaacaca ttaaccaact gtactgggta atgttactgg gtgatcccac gttttacaaa    780
tgagaagata tattctggta agttgaatac ttagcaccca ggggtaatca gcttggacag    840
gaccaggtcc aaagactgtt aagagtcttc tgactccaaa ctcagtgctc cctccagtgc    900
cacaagcaaa ctccataaag gtatcctgtg ctgaatagag actgtagagt ggtacaaagt    960
aagacagaca ttatattaag tcttagcttt gtgacttcga atgacttacc taatctagct    1020
aaatttcagt tttaccatgt gtaaatcagg aagagtaata gaacaaacct tgaagggtcc    1080
caatggtgat taaatgaggt gatgtacata acatgcatca ctcataataa gtgctcttta    1140
aatattagtc actattatta gccatctctg attagatttg acaataggaa cattaggaaa    1200
gatatagtac attcaggatt tgttagaaa gagatgaaga aattcccttc cttcctgccc     1260
taggtcatct aggagttgtc atggttcatt gttgacaaat taattttccc aaatttttca    1320
ctttgctcag aaagtctaca tcgaagcacc caagactgta caatctagtc catcttttc     1380 cacttaactc atactgtgct ctccctttct caaagcaaac tgtttgctat tccttgaata    1440
cactctgagt tttctgcctt tgcctactca gctggcccat ggcccctaat gtttcttctc    1500
atctccactg ggtcaaatcc tacctgtacc ttatggttct gttaaaagca gtgcttccat    1560
aaagtactcc tagcaaatgc acggcctctc tcacggatta taagaacaca gtttatttta    1620
taaagcatgt agctattctc tccctcgaaa tacgattatt attattaaga atttatagca    1680
gggatataat tttgtatgat gattcttctg gttaatccaa ccaagattga ttttatatct    1740
attacgtaag acagtagcca gacatagccg ggatatgaaa ataaagtctc tgccttcaac    1800
aagttccagt attctttct ttcctcccct ccctcccct cccttccct ccccttcctt       1860 cccttccct tcccttcctt tctttcttga gggagtctca ctctgtcacc aggctccagt    1920
gcagtggcgc tatcttggct gactgcaacc tccgcctccc cggttcaagc gattctcctg    1980
cctcagcctc ctgagtagct gggactacag gagcccgcca ccacgccag ctaattttg      2040 tattttagt agagatgggg tttcaccatg ttggccagga tggtctcgat ttctcgactt    2100
cgtgatccgc ctgtctgggc ctcccaaagt gctgggatta caggcgtgag ccaccacgcc    2160
cggctttaaa aaatggtttt gtaatgtaag tggaggataa taccctacat gtttattaat    2220
aacaataata ttctttagga aaagggcgc ggtggtgatt tacactgatg acaagcattc     2280
ccgactatgg aaaaaaagcg cagcttttc tgctctgctt ttattcagta gagtattgta    2340
gagattgtat agaatttcag agttgaataa aagttcctca taattatagg agtggagaga    2400
```

```
ggagagtctc tttcttcctt tcattttat atttaagcaa gagctggaca ttttccaaga    2460 aagtttttt ttttaaggc gcctctcaaa aggggccgga tttccttctc ctggaggcag    2520
atgttgcctc tctctctcgc tcggattggt tcagtgcact ctagaaacac tgctgtggtg    2580
gagaaactgg accccaggtc tggagcgaat tccagcctgc agggctgata agcgaggcat    2640
tagtgagatt gagagagact ttaccccgcc gtggtggttg gagggcgcgc agtgagcag    2700 cagcacaggc gcgggtcccg ggaggccggc tctgctcgcg ccgagatgtg gaatctcctt    2760
cacgaaaccg actcggctgt ggccaccgcg cgccgcccgc gctggctgtg cgctggggcg    2820
ctggtgctgg cgggtggctt ctttctcctc ggcttcctct tcggtagggg ggcgcctcgc    2880
ggagcaaacc tcgagtctt ccccgtggtg ccgcggtgct gggactcgcg ggtcagctgc    2940
cgagtgggat cctgttgctg gtcttcccca ggggcggcga ttagggtcgg ggtaatgtgg    3000
ggtgagcacc cctcgag                                                  3017
```

```
<210> SEQ ID NO 40
<211> LENGTH: 15
<212> TYPE: DNA
<213> ORGANISM: Homo sapiens

<400> SEQUENCE: 40
cggcttcctc ttcgg                                                    15

<210> SEQ ID NO 41
<211> LENGTH: 44
<212> TYPE: DNA
<213> ORGANISM: Homo sapiens

<400> SEQUENCE: 41
cggcttcctc ttcggtaggg gggcgcctcg cggagtattt ttca                    44

<210> SEQ ID NO 42
<211> LENGTH: 16
<212> TYPE: DNA
<213> ORGANISM: Homo sapiens

<400> SEQUENCE: 42
ataaaaagtc accaaa                                                   16

<210> SEQ ID NO 43
<211> LENGTH: 15
<212> TYPE: DNA
<213> ORGANISM: Homo sapiens

<400> SEQUENCE: 43
acatcaagaa gttct                                                    15

<210> SEQ ID NO 44
<211> LENGTH: 36
<212> TYPE: DNA
<213> ORGANISM: Homo sapiens

<400> SEQUENCE: 44
acatcaagaa gttctcaagt aagtccatac tcgaag                             36

<210> SEQ ID NO 45
<211> LENGTH: 22
<212> TYPE: DNA
<213> ORGANISM: Homo sapiens
```

```
<400> SEQUENCE: 45
caagtggtca tatattaaaa tg                                          22

<210> SEQ ID NO 46
<211> LENGTH: 15
<212> TYPE: DNA
<213> ORGANISM: Homo sapiens

<400> SEQUENCE: 46
gaagatggaa atgag                                                  15

<210> SEQ ID NO 47
<211> LENGTH: 38
<212> TYPE: DNA
<213> ORGANISM: Homo sapiens

<400> SEQUENCE: 47
gaagatggaa atgaggtaaa atataaataa ataaataa                         38

<210> SEQ ID NO 48
<211> LENGTH: 15
<212> TYPE: DNA
<213> ORGANISM: Homo sapiens

<400> SEQUENCE: 48
taaaagttgt gtagt                                                  15

<210> SEQ ID NO 49
<211> LENGTH: 15
<212> TYPE: DNA
<213> ORGANISM: Homo sapiens

<400> SEQUENCE: 49
aaggaatgcc agagg                                                  15

<210> SEQ ID NO 50
<211> LENGTH: 35
<212> TYPE: DNA
<213> ORGANISM: Homo sapiens

<400> SEQUENCE: 50
aaggaatgcc agaggtaaaa acacagtgca acaaa                            35

<210> SEQ ID NO 51
<211> LENGTH: 20
<212> TYPE: DNA
<213> ORGANISM: Homo sapiens

<400> SEQUENCE: 51
agagttgccg ctagatcaca                                             20

<210> SEQ ID NO 52
<211> LENGTH: 15
<212> TYPE: DNA
<213> ORGANISM: Homo sapiens

<400> SEQUENCE: 52
cagaggaaat aaggt                                                  15

<210> SEQ ID NO 53
<211> LENGTH: 37
<212> TYPE: DNA
<213> ORGANISM: Homo sapiens
```

```
<400> SEQUENCE: 53
cagaggaaat aaggtaggta aaaattatct cttttt                               37

<210> SEQ ID NO 54
<211> LENGTH: 21
<212> TYPE: DNA
<213> ORGANISM: Homo sapiens

<400> SEQUENCE: 54
gtgttttcta tttttacggg t                                               21

<210> SEQ ID NO 55
<211> LENGTH: 15
<212> TYPE: DNA
<213> ORGANISM: Homo sapiens

<400> SEQUENCE: 55
gttacccagc aaatg                                                      15

<210> SEQ ID NO 56
<211> LENGTH: 35
<212> TYPE: DNA
<213> ORGANISM: Homo sapiens

<400> SEQUENCE: 56
gttacccagc aatggtgaat gatcaatcct tgaat                                35

<210> SEQ ID NO 57
<211> LENGTH: 20
<212> TYPE: DNA
<213> ORGANISM: Homo sapiens

<400> SEQUENCE: 57
aaaaaaagtt tatacgaata                                                 20

<210> SEQ ID NO 58
<211> LENGTH: 15
<212> TYPE: DNA
<213> ORGANISM: Homo sapiens

<400> SEQUENCE: 58
acagaagctc ctaga                                                      15

<210> SEQ ID NO 59
<211> LENGTH: 37
<212> TYPE: DNA
<213> ORGANISM: Homo sapiens

<400> SEQUENCE: 59
acagaagctc ctagagtaag tttgtaagaa accargg                              37

<210> SEQ ID NO 60
<211> LENGTH: 24
<212> TYPE: DNA
<213> ORGANISM: Homo sapiens

<400> SEQUENCE: 60
aaacacaggt tatctttta ccca                                             24

<210> SEQ ID NO 61
<211> LENGTH: 15
<212> TYPE: DNA
```

```
<213> ORGANISM: Homo sapiens

<400> SEQUENCE: 61
aaacttttct acaca                                                      15

<210> SEQ ID NO 62
<211> LENGTH: 38
<212> TYPE: DNA
<213> ORGANISM: Homo sapiens

<400> SEQUENCE: 62
aaacttttct acacagttaa gagactatat aaatttta                             38

<210> SEQ ID NO 63
<211> LENGTH: 24
<212> TYPE: DNA
<213> ORGANISM: Homo sapiens

<400> SEQUENCE: 63
aaacgtaatc attttcagtt ctac                                            24

<210> SEQ ID NO 64
<211> LENGTH: 14
<212> TYPE: DNA
<213> ORGANISM: Homo sapiens

<400> SEQUENCE: 64
agcagtggaa ccag                                                       14

<210> SEQ ID NO 65
<211> LENGTH: 36
<212> TYPE: DNA
<213> ORGANISM: Homo sapiens

<400> SEQUENCE: 65
agcagtggaa ccaggtaaag gaatcgtttg ctagca                               36

<210> SEQ ID NO 66
<211> LENGTH: 19
<212> TYPE: DNA
<213> ORGANISM: Homo sapiens

<400> SEQUENCE: 66
aaagatgtct atacagtaa                                                  19

<210> SEQ ID NO 67
<211> LENGTH: 14
<212> TYPE: DNA
<213> ORGANISM: Homo sapiens

<400> SEQUENCE: 67
ctgaaaaagg aagg                                                       14

<210> SEQ ID NO 68
<211> LENGTH: 36
<212> TYPE: DNA
<213> ORGANISM: Homo sapiens

<400> SEQUENCE: 68
ctgaaaaagg aaggtaatac aaacaaatag caagaa                               36

<210> SEQ ID NO 69
<211> LENGTH: 14
```

```
<212> TYPE: DNA
<213> ORGANISM: Homo sapiens

<400> SEQUENCE: 69
tgagtgggca gagg                                                      14

<210> SEQ ID NO 70
<211> LENGTH: 30
<212> TYPE: DNA
<213> ORGANISM: Homo sapiens

<400> SEQUENCE: 70
agaggttagt tggtaatttg ctataatata                                     30

<210> SEQ ID NO 71
<211> LENGTH: 12
<212> TYPE: DNA
<213> ORGANISM: Homo sapiens

<400> SEQUENCE: 71
atctatagaa gg                                                        12

<210> SEQ ID NO 72
<211> LENGTH: 32
<212> TYPE: DNA
<213> ORGANISM: Homo sapiens

<400> SEQUENCE: 72
gtagtttcct gaaaaataag aaagaatag at                                   32

<210> SEQ ID NO 73
<211> LENGTH: 12
<212> TYPE: DNA
<213> ORGANISM: Homo sapiens

<400> SEQUENCE: 73
ctaacaaaag ag                                                        12

<210> SEQ ID NO 74
<211> LENGTH: 36
<212> TYPE: DNA
<213> ORGANISM: Homo sapiens

<400> SEQUENCE: 74
agggcttttc agctacacaa attaaaagaa aaaaag                              36

<210> SEQ ID NO 75
<211> LENGTH: 14
<212> TYPE: DNA
<213> ORGANISM: Homo sapiens

<400> SEQUENCE: 75
gtggcatgcc cagg                                                      14

<210> SEQ ID NO 76
<211> LENGTH: 37
<212> TYPE: DNA
<213> ORGANISM: Homo sapiens

<400> SEQUENCE: 76
gtggcatgcc caggtaaata aatgaatgaa gtttcca                             37

<210> SEQ ID NO 77
```

```
<211> LENGTH: 12
<212> TYPE: DNA
<213> ORGANISM: Homo sapiens

<400> SEQUENCE: 77
ctaaaaattg gc                                                          12

<210> SEQ ID NO 78
<211> LENGTH: 36
<212> TYPE: DNA
<213> ORGANISM: Homo sapiens

<400> SEQUENCE: 78
aatttgtttg tttcctacag aaaaaacaac aaaaca                                36

<210> SEQ ID NO 79
<211> LENGTH: 14
<212> TYPE: DNA
<213> ORGANISM: Homo sapiens

<400> SEQUENCE: 79
cagtgtatca tttg                                                        14

<210> SEQ ID NO 80
<211> LENGTH: 40
<212> TYPE: DNA
<213> ORGANISM: Homo sapiens

<400> SEQUENCE: 80
cagtgtatca tttggtatgt taccttcct ttttcaaatt                             40

<210> SEQ ID NO 81
<211> LENGTH: 16
<212> TYPE: DNA
<213> ORGANISM: Homo sapiens

<400> SEQUENCE: 81
aaagtctaag tgaaaa                                                      16

<210> SEQ ID NO 82
<211> LENGTH: 14
<212> TYPE: DNA
<213> ORGANISM: Homo sapiens

<400> SEQUENCE: 82
tttgacaaaa gcaa                                                        14

<210> SEQ ID NO 83
<211> LENGTH: 39
<212> TYPE: DNA
<213> ORGANISM: Homo sapiens

<400> SEQUENCE: 83
tttgacaaaa gcaagtatgt tctacatata tgtgcatat                             39

<210> SEQ ID NO 84
<211> LENGTH: 18
<212> TYPE: DNA
<213> ORGANISM: Homo sapiens

<400> SEQUENCE: 84
aaagagtcgg gttatcat                                                    18
```

<210> SEQ ID NO 85
<211> LENGTH: 14
<212> TYPE: DNA
<213> ORGANISM: Homo sapiens

<400> SEQUENCE: 85
ggccttttta tagg                                                        14

<210> SEQ ID NO 86
<211> LENGTH: 37
<212> TYPE: DNA
<213> ORGANISM: Homo sapiens
<220> FEATURE:
<221> NAME/KEY: misc_feature
<222> LOCATION: (20)..(20)
<223> OTHER INFORMATION: n=any nucleotide

<400> SEQUENCE: 86
ggccttttta taggtaagan aagaaaatat gactcct                               37

<210> SEQ ID NO 87
<211> LENGTH: 20
<212> TYPE: DNA
<213> ORGANISM: Homo sapiens

<400> SEQUENCE: 87
aatagttggt acagtagata                                                  20

<210> SEQ ID NO 88
<211> LENGTH: 14
<212> TYPE: DNA
<213> ORGANISM: Homo sapiens

<400> SEQUENCE: 88
gaatattata tata                                                        14

<210> SEQ ID NO 89
<211> LENGTH: 41
<212> TYPE: DNA
<213> ORGANISM: Homo sapiens

<400> SEQUENCE: 89
gaatattata tagttatg tgagtgttta tatatgtgtg t                            41

<210> SEQ ID NO 90
<211> LENGTH: 3077
<212> TYPE: DNA
<213> ORGANISM: Homo sapiens

<400> SEQUENCE: 90
gcgccttaaa aaaaaaaac tttcttggaa aatgtccagc tcttgcttaa atataaaaat        60
gaaaggaaga aagagactct cctctctcca ctcctataat tatgaggaac ttttattcaa      120
ctctgaaatt ctatacaatc tctacaatac tctactgaat aaaagcagag cagaaaaagc     180
tgcgcttttt ttccatagtc gggaatgctt gtcatcagtg taaatcacca ccgcgccctt     240
tttcctaaag aatattattg ttattaataa acatgtaggg tattatcctc cacttacatt     300
acaaaaccat tttttaaagc cgggcgtggt ggctcacgcc tgtaatccca gcactttggg     360
aggcccagac aggcggatca cgaagtcgag aaatcgagac catcctggcc aacatggtga    420
aaccccatct ctactaaaaa tacaaaaatt agctgggcgt ggtggcgggc tcctgtagtc    480
ccagctactc aggaggctga ggcaggagaa tcgcttgaac cggggaggcc gaggttgcag    540

-continued

```
tcagccaaga tagcgccact gcactggagc ctggtgacag agtgagactc cctcaagaaa    600
gaaaggaagg gaagggaaag ggaaggaagg ggaggggaag ggaggggagg ggaggggagg    660
aaagaaaaga atactggaac ttgttgaagg cagagacttt attttcatat cccggctatg    720
tctggctact gtcttacgta atagatataa aatcaatctt ggttggatta accagaagaa    780
tgagaagata tattctggta agttgaatac ttagcaccca ggggtaatca gcttggacag    840
gaccaggtcc aaagactgtt aagagtcttc tgactccaaa ctcagtgctc cctccagtgc    900
cacaagcaaa ctccataaag gtatcctgtg ctgaatagag actgtagagt ggtacaaagt    960
aagacagaca ttatattaag tcttagcttt gtgacttcga atgacttacc taatctagct   1020
aaatttcagt tttaccatgt gtaaatcagg aagagtaata gaacaaacct tgaagggtcc   1080
caatggtgat taaatgaggt gatgtacata acatgcatca ctcataataa gtgctcttta   1140
aatattagtc actattatta gccatctctg attagatttg acaataggaa cattaggaaa   1200
gatatagtac attcaggatt ttgttagaaa gagatgaaga aattcccttc cttcctgccc   1260
taggtcatct aggagttgtc atggttcatt gttgacaaat taattttccc aaattttttca  1320
ctttgctcag aaagtctaca tcgaagcacc aagactgta  caatctagtc catctttttc   1380
cacttaactc atactgtgct ctcccttct caaagcaaac tgtttgctat tccttgaata    1440
cactctgagt tttctgcctt tgcctactca gctggcccat ggcccctaat gtttcttctc   1500
atctccactg ggtcaaatcc tacctgtacc ttatggttct gttaaaagca gtgcttccat   1560
aaagtactcc tagcaaatgc acggcctctc tcacgcatta taagaacaca gtttattta   1620
tttcatgagg atcgtttacg tgccggagag agtgcctaat attcttgtgt caaataaaat   1680
taaagcatgt agctattctc tccctcgaaa tacgattatt attattaaga atttatagca   1740
gggatataat tttgtatgat gattcttctg gttaatccaa ccaagattga ttttatatct   1800
attacgtaag acagtagcca gacatagccg ggatatgaaa ataaagtctc tgccttcaac   1860
aagttccagt attctttct ttcctcccct ccctcccct cccttcccct cccttcctt    1920
ccctttccct tcccttcctt tctttcttga gggagtctca ctctgtcacc aggctccagt   1980
gcagtgccgc tatcttggct gactgcaacc tccgcctccc cggttcaagc gattctcctg   2040
cctcagcctc ctgagtagct ggcactacag gagcccgcca ccacgcccag ctaattttg   2100
tattttagt agagatgggg tttcaccatg ttggccagga tggtctcgat ttctcgactt   2160
cgtgatccgc ctgtctggc ctcccaaagt gctgggatta caggcgtgag ccaccacgcc   2220
cgcctttaaa aaatggtttt gtaatgtaag tggaggataa taccctacat gtttattaat   2280
aacaataata ttctttagga aaaggccgc ggtggtgatt tacactgatg acaagcattc    2340
ccgactatgg aaaaaaagcg cagctttttc tgctctgctt ttattcagta gagtattgta   2400
gagattgtat agaatttcac agttgaataa aagttcctca taattatagg agtgggagaga  2460
ggagagtctc tttcttcctt tcatttttat atttaagcaa gagctggaca tttttccaaga  2520
aagttttttt tttttaaggc gcctctcaaa aggggccgga tttccttctc ctggaggcag   2580
atgttgcctc tctctctcgc tcggattggt tcagtgcact ctagaaacac tgctgtggtg   2640
gagaaactgg acccccaggtc tgcagcgaat tccagcctgc agggctgata agcgaggcat   2700
tagtgagatt gagagagact ttaccccgcc gtggtggttg gagggcgcgc agtagagcag   2760
cagcacaggc gcgggtcccg ggaggccggc tctgctcgcg ccgagatgtg gaatctcctt   2820
cacgaaaccg actcggctgt ggccaccgcg cgccgcccgc gctggctgtg cgctggggcg   2880
ctggtgctgg cgggtggctt cttctcctc ggcttcctct tcggtagggg ggcgcctcgc   2940
```

```
ggagcaaacc tcggagtctt ccccgtggtg ccgcgctgct gggactcgcg ggtcagctgc      3000
cgagtgggat cctgttgctg gtcttcccca ggggcggcga ttagggtcgg ggtaatgtgg      3060
ggtgagcacc cctcgag                                                    3077

<210> SEQ ID NO 91
<211> LENGTH: 519
<212> TYPE: DNA
<213> ORGANISM: Homo sapiens

<400> SEQUENCE: 91
ctcaaaaggg gccggatttc cttctcctgg aggcagatgt tgcctctctc tctcgctcgg       60
attggttcag tgcactctag aaacactgct gtggtggaga aactggaccc caggtctgga      120
gcgaattcca gcctgcaggg ctgataagcg aggcattagt gagattgaga gagactttac      180
cccgccgtgg tggttggagg gcgcgcagta gagcagcagc acaggcgcgg gtcccgggag      240
gccggctctg ctcgcgccga gatgtggaat ctccttcacg aaaccgactc ggctgtggcc      300
accgcgcgcc gcccgcgctg gctgtgcgct ggggcgctgg tgctggcggg tggcttcttt      360
ctcctcggct tcctcttcgg atggtttata aaatcctcca atgaagctac taacattact      420
ccaaagcata atatgaaagc attttggat gaatggaaag ctgagaacat caagaagttc      480
ttatataatt ttacacagat accacattta gcaggaaca                            519

<210> SEQ ID NO 92
<211> LENGTH: 2125
<212> TYPE: DNA
<213> ORGANISM: Homo sapiens

<400> SEQUENCE: 92 tagggggggcg cctcgcggag aaacctcgga gtcttccccg tggtgccgcg gtgctgggac       60
tcgcgggtca gctgccgagt gggatcctgt tgctggtctt ccccaggggc ggcgattagg      120
gtcggggtaa tgtggggtga gcacccctcg agttaggagg agggtagctg gaacggtgc       180 agggctgagt tctcgacaag ctgctggtag gacagtcact caggttgagg gtagaactga      240
gagaacctga aactgggcgt aggaaggttc caagtgctgg agccctgcaa gacagaggaa      300
gttttttttt tgcttttgtt ttgttttgtt ttgttttgtt ttgttttgtt tgtttgtttg      360
tttttttacc tctctgtgca ttcttcttc cttggaagta acagaggcaa gcttgggaac      420
tgtgtgaacc aggtcaccaa tctcgacagg tctttaccag cgggtctttt gctgttttc      480 ctgggtactg atttgcagac ttgatccaac tttctaagaa aagcagaacc acacaggcaa      540
gctcagactc ttttattaaa ttccagtttt gactttgcca cttcttagtg gccttgaaca      600
agttaccgag tccctctcag cgttagttac cctatttat gatgaggata atattatctg      660
caaattattg gtaatagtaa ataatatagc atgtaaatct cctagcacag tactgggatt      720
ttcgccactt tatttcttct tttaccaaga tactcctcat tggactttaa tacacaggac      780
tagtctaagg tatcaccagg tagtccactc ctgctcggaa ttcttgaccc ctttcgggga      840
tttagaagaa tagggcatgg accagatggg tttaaacaaa ttcaatatct tccactagct      900
tcaccttggg gttgttaaaa gattttgaa ccacacactg tgctcataac aatcttcatc      960
tcttaaaagg attttattct tcctggtatt gccctcactc tcatccctgt attccgtgct     1020
cagtggctga cacagaagag ttcttttattg atgtccgccc ccacccact aggattctct     1080 gctctcccct ccccctacag gcctccatcc tcttcatcct gttcattttt cagatctcag     1140
```

```
ttcaagcatc tcgtcctcag tgtggtgttt cctgatccct cactctaatc caagtctttc    1200
tgttttatgc acaggtggaa tcttatttcc gtttgcgtcc aatcatgtat tttaatatgc    1260
atgtatatat gtatgtgcat ttgtatgcat gcgattaaga actagaataa ttaataattg    1320
gaaagctcca tgaaagctgg ttggggacta attttgtaac tactttattc ccacatcctg    1380
taatttctct aaataaaccc tggaatcttg ccttatctcc ttcaggttaa aagccaactg    1440
caaggtctaa tgactgcagg atctagctat ccattgtttc tggccgccta tgcgtgcact    1500
gggtgtctgg cagagaggct gggtaaattg tagtttcatt gtagctgtct gacttggatt    1560
tctcacgcct acttcactgg aaacgcaaac tctcacagca ttttctttta gtttcagaat    1620
cagagcaaat tagaagtctg aatttccttc aacacttgga ataatttat ttatttgaaa     1680 tatattcata attaattcgt tataaaaatg tattaaatgc ttatttgagt cagcagagga    1740
agatagaaac tttatgaaag tagaaggtgg atctcctttt tgccttcatt ttcagaacat    1800
ctcgtttaca cccattagtt gaaacattaa tgtcatttta ttttcgtcct gattatctca    1860
taaaacattt cttagaataa cagcaatacc tatcattgaa gttggataag aaatattttg    1920
caattggttt gcaacttaaa aatctgtttg catgactctt tttcagtgaa agtaggcaag    1980
agaaattaaa attcagaaat atgtgaccta atgtcagagg taatattgat aatttgtgtt    2040
ttacaaataa tacatacaac aataatgaaa aataagtcct atctataggc tcgtatctca    2100
tgcctatttt tggatgtatt tttca                                          2125

<210> SEQ ID NO 93
<211> LENGTH: 1896
<212> TYPE: DNA
<213> ORGANISM: Homo sapiens
<220> FEATURE:
<221> NAME/KEY: misc_feature
<222> LOCATION: (634)..(650)
<223> OTHER INFORMATION: n=any nucleotide
<220> FEATURE:
<221> NAME/KEY: misc_feature
<222> LOCATION: (950)..(961)
<223> OTHER INFORMATION: n=any nucleotide
<220> FEATURE:
<221> NAME/KEY: misc_feature
<222> LOCATION: (1045)..(1045)
<223> OTHER INFORMATION: n=any nucleotide
<220> FEATURE:
<221> NAME/KEY: misc_feature
<222> LOCATION: (1103)..(1103)
<223> OTHER INFORMATION: n=any nucleotide
<220> FEATURE:
<221> NAME/KEY: misc_feature
<222> LOCATION: (1362)..(1369)
<223> OTHER INFORMATION: n=any nucleotide
<220> FEATURE:
<221> NAME/KEY: misc_feature
<222> LOCATION: (1533)..(1534)
<223> OTHER INFORMATION: n=any nucleotide
<220> FEATURE:
<221> NAME/KEY: misc_feature
<222> LOCATION: (1616)..(1617)
<223> OTHER INFORMATION: n=any nucleotide
<220> FEATURE:
<221> NAME/KEY: misc_feature
<222> LOCATION: (1783)..(1783)
<223> OTHER INFORMATION: n=any nucleotide

<400> SEQUENCE: 93
tgaaaaatag atgaaaaata ggcatgagat acgagcctat agataggact tattttttat      60
tattgttgta tgtattattt gtaaaacaca aattatcaat attacctctg acattaggtg     120
agatattctg aatttttaatt tctcttgcct actttcactg aaaaagagtc atgcaaacag    180
```

```
attttaagt tgcaaaccaa ttgcaaaata ttttttatc caacttcaat gataggtatt    240
gctgttaatt ctaagatatg cattaattgt ttcaactaat gggtgtcaaa cgagatgttc    300
tgaaaatgaa ggcaaaaagg agatccacct tctactttca taaagtttct atcttcctct    360
gctgactcaa ataagcattt aatacatttt ataacgaatt aattatgaat atatttcaaa    420
taaataaatt atttccaagt gttcaaggaa attcagactt ctaatttgct ctgattctga    480
aactaaaaca aatgctctgt gagagtttgc gtttccagtg aagtagcgtg agaaatccaa    540
gtcagacagc tacatgaaac tacatttacc agctctctgc cagacaccag tgcacgatag    600
cgcagaacat gtagctagat ctcagtcata gctnnnnnnn nnnnnnnnnn agaccttgca    660
gttggctttt aacctgaagg agataaggca agattccagg gtttatttag agaaattaca    720
ggatctggga ataaagtagt tacaaaatta gtccccaacc agctttcatg gagctttcaa    780
ttattaatta ttctagttct taatcgcatg catacaatgc atacatat  atacatgcat    840 attaaaatac atgattggac gcaaacggaa ataacattgg acctgtgcat aaaacagaaa    900
gacttggtta gagtgaggga tcaggaaaca ccacactgag gacgagatgn nnnnnnnnnn    960
ntagtgggtg gggggcggac atcaataaag aactcttctg tgtcagccac tgagcacgga    1020
ataaagggat gagagtgagg gcaantacca gaagaataaa atcctttaa gagatgaaga    1080 ttgttatgag cacagtgtgt ggnttcaaaa atctttttaac aaccccaagg tgaagctagt    1140
tggaagatat ttgaatttgt ttaaacccat ctggtggtag ccctattctt tgaatcccga    1200
aagagggtca agaattccga gcaggagtgg actacctggt gataccttag actagtcctg    1260
tgtattaaag tccaatgagg agtatcttgg taaaataata aataaagtcc cgaaaatccc    1320
agtactctgc taggagattt acatgctata ttatttacta tnnnnhnnnt aatttgcaga    1380
taatattatc ctcatcataa aatagggtaa ctaacgctga gagggactcg gtaacttgtt    1440
caaggccact aagaagtggc aaagtcaaaa ctggaatttt aataaaagag tctagcttgc    1500
ctgtgtggtt ctgcttttct tagaaagttg gannaagtct camatcagta cccaggaaaa    1560
acagcaaaag acccgctggt aaagaccgtgt ccagattgct gacctggttc acacanntcc    1620
aagcttgcct ctgttacttc caaggaacaa agaatgcaca gagaggtaaa aaaacaaaca    1680
aaccaaacaa aacaaaacaa aacaaaacaa aacaaaacaa aagcaaaaaa aaacttcctc    1740
tgtcttgcag ggctccagca cttggaacct tcctacgtcc tantttcagg ttctctcagt    1800
tctaccctca acctgagtga ctgtcctacc agcagcttgt cgagaactca gccctgcacc    1860
gttcccagct accctcctcc taactcgagg ggtgct                              1896
```

<210> SEQ ID NO 94
<211> LENGTH: 1280
<212> TYPE: DNA
<213> ORGANISM: Homo sapiens
<220> FEATURE:
<221> NAME/KEY: misc_feature
<222> LOCATION: (315)..(320)
<223> OTHER INFORMATION: n=any nucleotide
<220> FEATURE:
<221> NAME/KEY: misc_feature
<222> LOCATION: (1038)..(1039)
<223> OTHER INFORMATION: n=any nucleotide
<220> FEATURE:
<221> NAME/KEY: misc_feature
<222> LOCATION: (453)..(453)
<223> OTHER INFORMATION: n=any nucleotide

<400> SEQUENCE: 94

```
ggattctgtt gagccctagc tcattatgat gtcctgttgt cctacccaaa taagactcat      60
cccaactaca tctcaataat taatgaagat ggaaatgagg taaaaaataa ataaataaat     120
aaaagaaaca ttcccccca tttattattt tttcaaatac cttctatgaa ataatgttct     180
atccctctct aaatattaat agaaatcaat attattgcaa ctgtgaatac ctttaatatc     240
tcattatccg gtgtcaacta ctttcctatg atgttgagtt actgggttta gaagtcggga     300
aataatgctg taaannnnnn agttagtcta cacaccaata tcaaatatga tatacttgta     360
aacctccaag cataaaaaga gatactttat aaaagaggtt cttttttct ttttttttt     420 tccagatgga gtttcactcc tgtcaggcag gcngagtgca gtggtgccat ctcggctcac     480
tgcaacctcc acctcccatg ttcaagggat tctccttcct cagtctcctg agtagctggg     540
attacaggtg tgcaccacca cacccagcta atttttgtat ttttaataga cagggtttt     600 catcgatgtt ggccaggcta gtctcgaact cctgacctct aggtgatcca cccgcctcag     660
cctcccaaag ttctacaatt acacgtgtga ggcactgctc tggccaggag atacattttt     720
gataggttta atttataaag acactgcaca gatttggagt tgctgggaaa tcacgatcca     780
gtatgcattt gacccagcaa ttttttattgg tacttaatga ttatatctca attgatcagg     840
ttgaactctg tgcgaagaat ttgtgtgtgg acatttgaga ggacagtttg gaggcaaggt     900
attttagtag atttaaagaa tttgaatctt gtttgcaagt tggggcatat actgagaaag     960
agaagacaat gcagataaat tgatatattt attatgatgt atgttcaata tgaaagatca    1020
caaaatataa catacatnna tcttacttaa catacctcag ttttagagct accgtatgta    1080
gaagagtcca tttctattta ggtaagttcc tttagtcctt ttattactgg gcactcttaa    1140
ttacatgtag cttgaaatat gtccagtttg agcagtgaac tgaaaatgtc atgtgattaa    1200
gtacatatat aattttttt catagtaggt caataacctc cttttattgt ctaatgaatc    1260
agttctctaa tgattatacg                                               1280
```

<210> SEQ ID NO 95
<211> LENGTH: 1242
<212> TYPE: DNA
<213> ORGANISM: Homo sapiens
<220> FEATURE:
<221> NAME/KEY: misc_feature
<222> LOCATION: (381)..(388)
<223> OTHER INFORMATION: n=any nucleotide
<220> FEATURE:
<221> NAME/KEY: misc_feature
<222> LOCATION: (1091)..(1091)
<223> OTHER INFORMATION: n=any nucleotide
<220> FEATURE:
<221> NAME/KEY: misc_feature
<222> LOCATION: (1167)..(1172)
<223> OTHER INFORMATION: n=any nucleotide
<220> FEATURE:
<221> NAME/KEY: misc_feature
<222> LOCATION: (1212)..(1212)
<223> OTHER INFORMATION: n=any nucleotide
<220> FEATURE:
<221> NAME/KEY: misc_feature
<222> LOCATION: (975)..(975)
<223> OTHER INFORMATION: n=any nucleotide
<220> FEATURE:
<221> NAME/KEY: misc_feature
<222> LOCATION: (978)..(978)
<223> OTHER INFORMATION: n=any nucleotide
<220> FEATURE:
<221> NAME/KEY: misc_feature
<222> LOCATION: (982)..(982)
<223> OTHER INFORMATION: n=any nucleotide
<220> FEATURE:
<221> NAME/KEY: misc_feature

```
<222> LOCATION: (676)..(681)
<223> OTHER INFORMATION: n=any nucleotide
<220> FEATURE:
<221> NAME/KEY: misc_feature
<222> LOCATION: (721)..(721)
<223> OTHER INFORMATION: n=any nucleotide

<400> SEQUENCE: 95
```

| | | | | | |
|---|---|---|---|---|---|
| aatcaaaata | aaacagttaa | agtttgatta | ctataatcaa | acacaaaaaa | aatgaatatt | 60 |
| atcttttatg | tcagtagagg | gtgaatgaat | ccttcaggat | tttgatgata | gtatcagata | 120 |
| cccagcacta | tgctagaagt | tgtgaagaat | tcacgagatg | aataaatcac | agattctgtc | 180 |
| ctcaaaatgg | ttagatctat | tcaggaaaca | aagctaaaaa | aaccccacca | ataactaaaa | 240 |
| atcaaccaaa | tgaaaaacaa | caatcataaa | ataagtaagt | acctatagaa | agaaaagctc | 300 |
| agaggaggta | aaagataac | tcttccaaaa | ggaatactat | atactgtaaa | ctgtgtactg | 360 |
| atagaaggaa | gaattagaaa | nnnnnnnntg | taagtggcat | acatactaag | ctagtgtgaa | 420 |
| cacaagccta | aatatgtagt | tgcttcacag | aaggttagaa | gtaaattaac | ctcatgaatt | 480 |
| tcttgagaga | acttgtaagg | actaagcttt | cgattttgga | gaaagatttt | aataccaaat | 540 |
| aaaaagtacc | tttgtttggt | aatctcaatc | attataatag | tgcttagata | atacctagga | 600 |
| acaaattaaa | tattaaattt | actttaaaaa | aagtacatg | attggggaat | cacaacaggc | 660 |
| cttactagat | tctctnnnnn | natatgcact | gaaaagaatg | aaaacactg | aaccaaatat | 720 |
| ntgttttttt | aagtttaaaa | ttaaattgga | aaaaaatagt | aaggaatatc | agaagcaaaa | 780 |
| aaataaaatg | aaagcaagaa | tcctcagagg | tagcacgaaa | tttggctttg | cttagatgga | 840 |
| tctatcaaag | ctatggccca | tgaaaaggat | tcaggagtta | gtttaaagct | ggttcacata | 900 |
| atggaatcta | gcagaagact | gtgcataaag | gtggtctaag | aacaacaata | tcctgaccag | 960 |
| gtgaggggc | tcacnctnaa | tnccagcact | ttgggagccc | aaggtgggtg | gatcacgagg | 1020 |
| tcaggagttt | gagaccagcc | tgaccaacat | ggtgaaaccg | cgtctctact | aaaaatagaa | 1080 |
| aaattagccg | ngcctacgtg | cttctaatcc | cagctgaact | caggagactg | agacaggaga | 1140 |
| ataccttcaa | cccagcatgc | aagcttnnnn | nngccactgc | actccagcct | agggtgcaaa | 1200 |
| aaaaaaaaaa | angacacatt | actcaggtaa | ggtaatcaat | aa | | 1242 |

```
<210> SEQ ID NO 96
<211> LENGTH: 783
<212> TYPE: DNA
<213> ORGANISM: Homo sapiens

<400> SEQUENCE: 96
```

| | | | | | |
|---|---|---|---|---|---|
| aaggtaaaaa | ttatctcttt | ttttctctcc | cccaatgtaa | aaagttatag | tgggttttac | 60 |
| atgtgtagaa | tcattttctt | aaaactttat | gaataccatt | attttcttgt | attctgtgac | 120 |
| atgcccacct | tacagagagg | acacatttac | taggttatat | cccgggggtta | aattcgagga | 180 |
| ttggaatttg | gccagtgtag | atgtttagag | tgaacagaac | aaattttct | gtgcttacag | 240 |
| gttatggctg | tggcctacaa | gaagcatgca | ctgggtttat | tattaacttt | cagtatcttt | 300 |
| gttttaaata | ttttctacaa | aaatgtttac | taaattaaat | tgtagtatga | attgttataa | 360 |
| ataatgaggg | aaaacaattt | acacatagca | aatttaaaaa | ttactgtcat | ttgatttgtt | 420 |
| aatatatttt | tctctttagt | gggaaattaa | attttaaaaa | attcccttc | gactgtagaa | 480 |
| caaataggaa | tttggcctgt | ggggtctact | tgcttattat | atttgtaagc | tagtggtagg | 540 |
| aaatagcaaa | tgctcactac | cactaataag | aacatttcta | aatctgatgt | tctgaggatt | 600 |

```
tttagagctt atagtagcaa aaagaaaagg gaaattctat ccgagatgtc ctttgttgta      660
ggcctaatga gaaaaggttg aagataaagt tctggtactc atttaagtgt aatattgaaa      720
attgatatta ccgaatctgg aacaaccaat ttaaaataag gaaagaaaga cactgtgttt      780
tct                                                                    783
```

```
<210> SEQ ID NO 97
<211> LENGTH: 782
<212> TYPE: DNA
<213> ORGANISM: Homo sapiens
<220> FEATURE:
<221> NAME/KEY: misc_feature
<222> LOCATION: (505)..(505)
<223> OTHER INFORMATION: n=any nucleaotide

<400> SEQUENCE: 97
```

```
agaaaacaca gtgtctttct ttccttattt taaattggtt gttccagatt cggtaatatc       60
aattttcaat attacactta aatgagtacc agaactttat cttcaacctt ttctcattag      120
gcctacaaca aaggacatct cggatagaat ttccctttc tttttgctac tataagctct      180
aaaaatcctc agaacatcag atttagaaat gttcttatta gtggtagtga gcatttgcta      240
tttcctacca ctagcttaca aatataataa gcaagtagac cccacaggcc aaattcctat      300 tgttctaca gtcgaaaggg aattttttaa aatttaattt cccactaaag agaaaaatat      360
attaacaaat caaatgacag taatttttaa atttcgtatg tgtaaattgt tttccctcat      420
tatttataac aattcatact acaatttaat ttagtaaaca ttttttgtaga aaatatttaa      480 aacaaagata ctgaaagtta atatnaaacc cagtgcatgc ttcttgtagg ccacagccat      540
aacctgtaag cacagaaaaa tttgttctgt tactctaaac atctacactg gccaaattcc      600
aatgctcgaa tttaaccccg ggatataacc tagtaaatgt gtcctctctg taaggtggcc      660
atgtcacaga atacaagaaa ataatggtat tcataaagtt ttaagaaaat gattctacac      720
atgtaaaacc cactataact ttttacattg ggggagagaa aaaagagat aattttttacc      780 tt                                                                     782
```

```
<210> SEQ ID NO 98
<211> LENGTH: 1079
<212> TYPE: DNA
<213> ORGANISM: Homo sapiens
<220> FEATURE:
<221> NAME/KEY: misc_feature
<222> LOCATION: (262)..(268)
<223> OTHER INFORMATION: n=any nucelotide
<220> FEATURE:
<221> NAME/KEY: misc_feature
<222> LOCATION: (545)..(550)
<223> OTHER INFORMATION: n=any nucelotide
<220> FEATURE:
<221> NAME/KEY: misc_feature
<222> LOCATION: (900)..(907)
<223> OTHER INFORMATION: n=any nucelotide
<220> FEATURE:
<221> NAME/KEY: misc_feature
<222> LOCATION: (917)..(917)
<223> OTHER INFORMATION: n=any nucelotide
<220> FEATURE:
<221> NAME/KEY: misc_feature
<222> LOCATION: (955)..(955)
<223> OTHER INFORMATION: n=any nucelotide
<220> FEATURE:
<221> NAME/KEY: misc_feature
<222> LOCATION: (1009)..(1009)
<223> OTHER INFORMATION: n=any nucelotide

<400> SEQUENCE: 98
```

```
gatgctattt gggcaatttc ttattgacag ttttgaaatg ttaggctttt atctccattt      60
tttagtactt aaattttcca acatgggtgt tgcttgttat tttgtcagta taaaatagaa     120
gagtggttct gttctggaat ttagtatata catgagtatc tagtgtatgt cagccatgaa     180
aatgaacctt tcagatgttt aacttcaggg aacctaattg agtcattgct ccagacattg     240
ttgctttgaa cccactatat tnnnnnnnct cgggcaatga ctcagtgtgg caaggatact     300
actgcaggcc tgtttctgga aggcactgga ctcctctgat gcaaactttg gccagggact     360
ccttgatagc tgttaaatag atgctgcacc aacactctct ttcttttctc tctttttctt     420
tattcaatat tagactacaa gcagtctaag gacttctcag ggtttctagc tctctctcat     480
ttcacacatg ctttcctagt aatctctact catatatctt actgctacgc tggggccaga     540
taacnnnnnn cttccatttt gtttttatct ctattcttct tccccttctg ctttcattat     600
tgaaactttc tgctttcatt attgaaactt tccagatttt gttctgctta acctggcatt     660
ggaactgttt cctcttccct gtgctgcttt ctcccattgc catgtccttt tttttttttt     720
tttttttttt tgagacagtg tcactctgtt gcccaggctg gagtgcaatg gtgcaatctt     780
ggccactgca accccgcct ccgggttca agtgattctc ctgcctcagc ctcctgagta     840
gctgggatta caggtgccca ccactatgcc cggctgattt ttgtattttt agtagagatn     900 nnnnnnttt caccatngct gatcaggctg gtctcgaact cctgaccgca gtgantccgc     960
cctccttggc ctcccaaagt gctgagatta caggcatgag tcactgcgnc cagccaccat    1020
tattctctag aggtgagaga acactggctc ttctaacaag ttgaaatttg atagagacc     1079
```

<210> SEQ ID NO 99
<211> LENGTH: 1977
<212> TYPE: DNA
<213> ORGANISM: Homo sapiens
<220> FEATURE:
<221> NAME/KEY: misc_feature
<222> LOCATION: (840)..(843)
<223> OTHER INFORMATION: n=any nucleotide
<220> FEATURE:
<221> NAME/KEY: misc_feature
<222> LOCATION: (1294)..(1295)
<223> OTHER INFORMATION: n=any nucleotide
<220> FEATURE:
<221> NAME/KEY: misc_feature
<222> LOCATION: (1338)..(1343)
<223> OTHER INFORMATION: n=any nucleotide
<220> FEATURE:
<221> NAME/KEY: misc_feature
<222> LOCATION: (1965)..(1966)
<223> OTHER INFORMATION: n=any nucleotide
<220> FEATURE:
<221> NAME/KEY: misc_feature
<222> LOCATION: (1096)..(1101)
<223> OTHER INFORMATION: n=any nucleotide

<400> SEQUENCE: 99

```
cacaaaaaaa gattattagc cacaaaaaaa ccttgaagta acgcattaaa atgttaatgg      60 attcactta ttgagcatct gctcataata ctttaatgag tgcaaagtgc tttgaatata     120
atacgtcatt taaaccttac cataattctg aggaattgct acctccactt cacagatggg     180
gcacaggagg cttagataac atgcccaaag tcatgcttct agtaaatgga tataattaag     240
attcaaatta ttgataagaa tttgatctgc cttaccagta tctagtagta aatctaaaag     300
cgctttccag agcatgtgct gttgatagag cttgatgtct aactctctga aattttccat     360
tcttatttgt ctcactggta tatagttatt ttttactact ttcatacacc tactaagaag     420
```

| acaggaggat caaagatagg atttcattta gaatgcctaa agcttcacgt attttaattc | 480 |
| agaataagat tcaggcagac caccagtata tgccatggtc cctggttatc tttcagcagg | 540 |
| tgaccgagaa agaaaacatg gtaatgttta tgaaatggtg ggttcttgta gtttcacttc | 600 |
| aacatatctg cctttactgt attaagatga tggattaact tattcttgat atgggcatgt | 660 |
| aaaacaatat acttttacta aacagctaca gagagacaaa tgtgtttcca gacaaactta | 720 |
| agagactgag tgttcaaact gaataatctc gaccttaatt gtaactatat tttatgaaat | 780 |
| ccagctgtaa ggcaaaaaca gacttctttg ggcctaccac gggcattttg ttcctgttan | 840 |
| nnntactcca aaccttaaac ccacgtccac ttaataatg gcctggaaat aaatgtcaat | 900 |
| atctgatatt atactgagat gtttagttat gaaatcaaaa gtggagaatt tcaatctgtc | 960 |
| ctgtaagctt tctctgcggt cacgaccctc atgcactcag gctgtgcggt gcagcatgct | 1020 |
| ctgtcatgtc tgttttcttc tgcctgtaca cgggtggttg ttcctgtcta cctgtttgag | 1080 |
| gaaatatgaa tacgtnnnnn nctagaatct actgcacatg caataaggaa acaatcagta | 1140 |
| agaatcactt tctcgtggaa aattcattag aattaacatc tcgttttaaa atgctctatc | 1200 |
| aaagtgtaaa taattcctct ctcttttccc tttttcacta aggagtttgt atattaaaca | 1260 |
| gaatttcaag taatgtatta taaatttatt taanntattt acaataaaat gccacgtata | 1320 |
| agcatcaagc aacatgannn nnncattggt agaaagcaca atacatagtc aaaacagcag | 1380 |
| agtattaaat aaacagaaaa tttgcaaaag gcaagtaaag aatatacata tacttaatta | 1440 |
| tacataaaat attgatacag gaggtagaaa gaaatttagt aagcagataa tgggggcaac | 1500 |
| agagtcctca gcagagcttc ccttctaaca aaaagcagcc caataaatta ttttttttt | 1560 |
| ctaacaaaaa gcagcctgaa aaatcgagct gcaaacatag attagcaatc ggctgaaagt | 1620 |
| gcgggagaat gctggcagct gtgccaatag taaagggcta cctggagccg ggcgcgtggc | 1680 |
| tcacgctgta atcccagcac tttgggaggg cgaggcaacg cggatcacct gaggtcggga | 1740 |
| gtttgagatc agcccgacca acatggagaa accccgtctc tactaaaaaa aaaaaaaaaa | 1800 |
| aaaggcaaaa aatgagccgg gcatggtggc acatgccttg cacatcccag ctgaggcagg | 1860 |
| agaattcact tgaacctggg aggtagagat tgcggtgaag cgagatcacg tcattgcact | 1920 |
| ccagcctggg caaaagagc aaaacttagt ctcaaaaaaa aaanncaaa gaaaaaa | 1977 |

<210> SEQ ID NO 100
<211> LENGTH: 2387
<212> TYPE: DNA
<213> ORGANISM: Homo sapiens

<400> SEQUENCE: 100

| ctcaaaaggg gccggatttc cttctcctgg aggcagatgt tgcctctctc tctcgctcgg | 60 |
| attggttcag tgcactctag aaacactgct gtggtggaga aactggaccc cagggtggtt | 120 |
| tataaaatcc tccaatgaag ctactaacat tactccaaag cataatatga aagcattttt | 180 |
| ggatgaattg aaagctgaga acatcaagaa gttcttatat aattttacac agataccaca | 240 |
| tttagcagga acagaacaaa actttcagct tgcaaagcaa attcaatccc agtggaaaga | 300 |
| atttggcctg gattctgttg agctagcaca ttatgatgtc ctgttgtcct acccaaataa | 360 |
| gactcatccc aactacatct caataattaa tgaagatgaa aatgagattt caacacatc | 420 |
| attatttgaa ccacctcctc caggatatga aaatgtttcg gatattgtac cacctttcag | 480 |
| tgctttctct cctcaaggaa tgccagaggg cgatctagtg tatgttaact atgcacgaac | 540 |
| tgaagacttc tttaaattgg aacgggacat gaaaatcaat tgctctggga aaattgtaat | 600 |

| | |
|---|---|
| tgccagatat gggaaagttt tcagaggaaa taaggttaaa aatgcccagc tggcaggggc | 660 |
| caaaggagtc attctctact ccgaccctgc tgactacttt gctcctgggg tgaagtccta | 720 |
| tccagatggt tggaatcttc ctggaggtgg tgtccagcgt ggaaatatcc taaatctgaa | 780 |
| tggtgcagga gaccctctca caccaggtta cccagcaaat gaatatgctt ataggcgtgg | 840 |
| aattgcagag gctgttggtc ttccaagtat tcctgttcat ccaattggat actatgatgc | 900 |
| acagaagctc ctagaaaaaa tgggtggctc agcaccacca gatagcagct ggagaggaag | 960 |
| tctcaaactg ccctacaatg ttggacctgg ctttagtgga aacttttcta cacaaaaact | 1020 |
| caagatgcac atccactcta gcaatgaact gacaagaatt tacaatgtga taggtagtct | 1080 |
| cagaggagca gtgaaccag acagatatgt cattctggga ggtcaccggg actcatgggt | 1140 |
| gtttggtggt attgaccctc agagtggagc agctgttgtt catgaaattg tgaggagctt | 1200 |
| tggaacactg aaaaggaag ggtggagacc tagaagaaca attttgtttg caagctggga | 1260 |
| tgcagaagaa tttggtcttc ttggttctac tgagtgggca gaggagaatt caagactcct | 1320 |
| tcaagagcgt ggcgtggctt atattaatgc tgactcatct atagaaggaa actacactct | 1380 |
| gagacttgat tgtacaccgc tgatgtacag cttggtacac aacctaacaa aagagctgaa | 1440 |
| aagccctgat gaaggctttg aaggcaaatc tctttatgaa agttggacta aaaaagtcc | 1500 |
| ttccccagag ttcagtggca tgcccaggat aagcaaattg ggatctggaa atgattttga | 1560 |
| ggtgttcttc caacgacttg gaattgcttc aggcagagca cggtatagta aaaattggga | 1620 |
| aacaaacaaa ttcagcggct atccactgta tcacagtgtc tatgaaacat atgagttggt | 1680 |
| ggaaaagttt tatgatccaa tgtttaaata tcacctcact gtggcccagg ttcgaggagg | 1740 |
| gatggtgttt gagctagcca attccatact gctcccttt gattgtcgag attatgctgt | 1800 |
| actttaaga agtatgctg acaaaatcta cagtatttct atgaaacatc cacaggaaat | 1860 |
| gaagacatac agtgtatcat tgattcact tttttctgca ctaaagaatt ttacagaaat | 1920 |
| tgcttccaag ttcagtgaga gactccagga ctttgacaaa agcaacccaa tactattaag | 1980 |
| aatgatgaat gatcaactca tgtttctgga aagagcattt attgatccat tagggttacc | 2040 |
| agacaggcct ttttatatagc atgtcatcta tgctccaagc agccacaaca gtatgcagg | 2100 |
| ggagtcattc ccaggaattt atgatgctct gtttgatatt gaaagcaaac tggacccttc | 2160 |
| caaggcctgg ggagaagtga agagacagat ttatgttgca gccttcacag tgcaggcagc | 2220 |
| tgcagagact ttgagtgaag tagcctaaga ggattcttta gagaatccgt attgaatttg | 2280 |
| tgtggtatgt cactcagaaa gaatcgtaat gggtatattg ataaattta aaattggtat | 2340 |
| atttgaaata aagttgaata ttatatataa aaaaaaaaa aaaaaaa | 2387 |

```
<210> SEQ ID NO 101
<211> LENGTH: 693
<212> TYPE: PRT
<213> ORGANISM: Homo Sapiens

<400> SEQUENCE: 101

Met Lys Ala Phe Leu Asp Glu Leu Lys Ala Glu Asn Ile Lys Lys Phe
1               5                   10                  15

Leu Tyr Asn Phe Thr Gln Ile Pro His Leu Ala Gly Thr Glu Gln Asn
                20                  25                  30

Phe Gln Leu Ala Lys Gln Ile Gln Ser Gln Trp Lys Glu Phe Gly Leu
            35                  40                  45

Asp Ser Val Glu Leu Ala His Tyr Asp Val Leu Leu Ser Tyr Pro Asn
```

```
                 50                   55                       60
Lys Thr His Pro Asn Tyr Ile Ser Ile Ile Asn Glu Asp Gly Asn Glu
 65                       70                  75                       80

Ile Phe Asn Thr Ser Leu Phe Glu Pro Pro Pro Gly Tyr Glu Asn
                     85                  90                  95

Val Ser Asp Ile Val Pro Phe Ser Ala Phe Ser Pro Gln Gly Met
                    100                 105                 110

Pro Glu Gly Asp Leu Val Tyr Val Asn Tyr Ala Arg Thr Glu Asp Phe
                        115                 120                 125

Phe Lys Leu Glu Arg Asp Met Lys Ile Asn Cys Ser Gly Lys Ile Val
 130                     135                 140

Ile Ala Arg Tyr Gly Lys Val Phe Arg Gly Asn Lys Val Lys Asn Ala
 145                     150                 155                 160

Gln Leu Ala Gly Ala Lys Ala Val Ile Leu Tyr Ser Asp Pro Ala Asp
                        165                 170                 175

Tyr Phe Ala Pro Gly Val Lys Ser Tyr Pro Asp Gly Trp Asn Leu Pro
                    180                 185                 190

Gly Gly Gly Val Gln Arg Gly Asn Ile Leu Asn Leu Asn Gly Ala Gly
                195                 200                 205

Asp Pro Leu Thr Pro Gly Tyr Pro Ala Asn Glu Tyr Ala Tyr Arg Arg
 210                     215                 220

Gly Ile Ala Glu Ala Val Gly Leu Pro Ser Ile Pro Val His Pro Ile
 225                     230                 235                 240

Gly Tyr Tyr Asp Ala Gln Lys Leu Leu Glu Lys Met Gly Gly Ser Ala
                    245                 250                 255

Pro Pro Asp Ser Ser Trp Arg Gly Ser Leu Lys Val Pro Tyr Asn Val
                260                 265                 270

Gly Pro Gly Phe Thr Gly Asn Phe Ser Thr Gln Lys Val Lys Met His
                275                 280                 285

Ile His Ser Thr Asn Glu Val Thr Arg Ile Tyr Asn Val Ile Gly Thr
             290                 295                 300

Leu Arg Gly Ala Val Glu Pro Asp Arg Tyr Val Ile Leu Gly Gly His
 305                     310                 315                 320

Arg Asp Ser Trp Val Phe Gly Gly Ile Asp Pro Gln Ser Gly Ala Ala
                    325                 330                 335

Val Val His Glu Ile Val Arg Ser Phe Gly Thr Leu Lys Lys Glu Gly
                340                 345                 350

Trp Arg Pro Arg Arg Thr Ile Leu Phe Ala Ser Trp Asp Ala Glu Glu
                355                 360                 365

Phe Gly Leu Leu Gly Ser Thr Glu Trp Ala Glu Glu Asn Ser Arg Leu
 370                     375                 380

Leu Gln Glu Arg Gly Val Ala Tyr Ile Asn Ala Asp Ser Ser Ile Glu
 385                     390                 395                 400

Gly Asn Tyr Thr Leu Arg Val Asp Cys Thr Pro Leu Met Tyr Ser Leu
                    405                 410                 415

Val His Asn Leu Thr Lys Glu Leu Lys Ser Pro Asp Glu Gly Phe Glu
                420                 425                 430

Gly Lys Ser Leu Tyr Glu Ser Trp Thr Lys Lys Ser Pro Ser Pro Glu
             435                 440                 445

Phe Ser Gly Met Pro Arg Ile Ser Lys Leu Gly Ser Gly Asn Asp Phe
 450                     455                 460

Glu Val Phe Phe Gln Arg Leu Gly Ile Ala Ser Gly Arg Ala Arg Tyr
 465                     470                 475                 480
```

```
Thr Lys Asn Trp Glu Thr Asn Lys Phe Ser Gly Tyr Pro Leu Tyr His
                485                 490                 495

Ser Val Tyr Glu Thr Tyr Glu Leu Val Glu Gly Phe Tyr Asp Pro Met
            500                 505                 510

Phe Lys Tyr His Leu Thr Val Ala Gln Val Arg Gly Gly Met Val Phe
        515                 520                 525

Glu Leu Ala Asn Ser Ile Val Leu Pro Phe Asp Cys Arg Asp Tyr Ala
    530                 535                 540

Val Val Leu Arg Lys Tyr Ala Asp Lys Ile Tyr Ser Ile Ser Met Lys
545                 550                 555                 560

His Pro Gln Glu Met Lys Thr Tyr Ser Val Ser Phe Asp Ser Leu Phe
                565                 570                 575

Ser Ala Val Lys Asn Phe Thr Glu Ile Ala Ser Lys Phe Ser Glu Arg
            580                 585                 590

Leu Gln Asp Phe Asp Lys Ser Asn Pro Ile Val Leu Arg Met Met Asn
        595                 600                 605

Asp Gln Leu Met Phe Leu Glu Arg Ala Phe Ile Asp Pro Leu Gly Leu
    610                 615                 620

Pro Asp Arg Pro Phe Tyr Arg His Val Ile Tyr Ala Pro Ser Ser His
625                 630                 635                 640

Asn Lys Tyr Ala Gly Glu Ser Phe Pro Gly Ile Tyr Asp Ala Leu Phe
                645                 650                 655

Asp Ile Glu Ser Lys Val Asp Pro Ser Lys Ala Trp Gly Glu Val Lys
            660                 665                 670

Arg Gln Ile Tyr Val Ala Ala Phe Thr Val Gln Ala Ala Ala Glu Thr
        675                 680                 685

Leu Ser Glu Val Ala
    690

<210> SEQ ID NO 102
<211> LENGTH: 86
<212> TYPE: PRT
<213> ORGANISM: Homo Sapiens

<400> SEQUENCE: 102

Met Trp Asn Leu Leu His Glu Thr Asp Ser Ala Val Ala Ala Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro Ile Leu Ala Gly Thr
                85

<210> SEQ ID NO 103
<211> LENGTH: 7
<212> TYPE: DNA
<213> ORGANISM: Homo sapiens

<400> SEQUENCE: 103 tkagtca                                                                7
```

```
<210> SEQ ID NO 104
<211> LENGTH: 12
<212> TYPE: DNA
<213> ORGANISM: Homo sapiens
<220> FEATURE:
<221> NAME/KEY: misc_feature
<222> LOCATION: (4)..(9)
<223> OTHER INFORMATION: n=any nucleotide

<400> SEQUENCE: 104
accnnnnnng gt                                                              12

<210> SEQ ID NO 105
<211> LENGTH: 11
<212> TYPE: DNA
<213> ORGANISM: Homo sapiens
<220> FEATURE:
<221> NAME/KEY: misc_feature
<222> LOCATION: (1)..(3)
<223> OTHER INFORMATION: n=any nucleotide
<220> FEATURE:
<221> NAME/KEY: misc_feature
<222> LOCATION: (9)..(11)
<223> OTHER INFORMATION: n=any nucleotide

<400> SEQUENCE: 105
nnntaaatnn n                                                               11

<210> SEQ ID NO 106
<211> LENGTH: 8
<212> TYPE: DNA
<213> ORGANISM: Homo sapiens
<220> FEATURE:
<221> NAME/KEY: misc_feature
<222> LOCATION: (4)..(4)
<223> OTHER INFORMATION: n=any nucleotide

<400> SEQUENCE: 106 gggnggrr                                                                    8

<210> SEQ ID NO 107
<211> LENGTH: 10
<212> TYPE: DNA
<213> ORGANISM: Homo sapiens

<400> SEQUENCE: 107 gggrhtyyhc                                                                 10

<210> SEQ ID NO 108
<211> LENGTH: 8
<212> TYPE: DNA
<213> ORGANISM: Homo sapiens

<400> SEQUENCE: 108 ryywsgtg                                                                    8

<210> SEQ ID NO 109
<211> LENGTH: 13
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n=any nucleotide

<400> SEQUENCE: 109
aawaangaaa ggr                                                             13
```

```
<210> SEQ ID NO 110
<211> LENGTH: 61
<212> TYPE: DNA
<213> ORGANISM: Homo sapiens

<400> SEQUENCE: 110 ttttttttttg cctttttgttt tgttttgttt tgttttgttt tgtttgtttg tttgttttt        60 t                                                                         61

<210> SEQ ID NO 111
<211> LENGTH: 69
<212> TYPE: DNA
<213> ORGANISM: Homo sapiens

<400> SEQUENCE: 111 ttttttttttg cttttgtttt gttttgtttt gtttgtttt gtttgtttt gtttgtttgt         60 ttgttttttt                                                                69

<210> SEQ ID NO 112
<211> LENGTH: 52
<212> TYPE: DNA
<213> ORGANISM: Homo sapiens

<400> SEQUENCE: 112 ttttttttttt gcttttgttt tgttttgttt tgttttgttt gtttgttttt tt              52

<210> SEQ ID NO 113
<211> LENGTH: 61
<212> TYPE: DNA
<213> ORGANISM: Homo sapiens

<400> SEQUENCE: 113 ttttttttttt gcttttgttt tgttttgttt tgttttgttt tgtttgtttg tttgttttt        60 t                                                                         61

<210> SEQ ID NO 114
<211> LENGTH: 60
<212> TYPE: DNA
<213> ORGANISM: Homo sapiens

<400> SEQUENCE: 114 ttttttttttg cttttgtttt gttttgtttt gtttgtttt gtttgtttgt ttgttttttt        60

<210> SEQ ID NO 115
<211> LENGTH: 59
<212> TYPE: DNA
<213> ORGANISM: Homo sapiens

<400> SEQUENCE: 115 ttttttttttg cttttgtttt gttttgtttt gtttgtttt gtttgtttgt ttgtttttt         59

<210> SEQ ID NO 116
<211> LENGTH: 21
<212> TYPE: DNA
<213> ORGANISM: Homo sapiens

<400> SEQUENCE: 116
ctcaaaaggg gccggatttc c                                                   21

<210> SEQ ID NO 117
```

```
<211> LENGTH: 21
<212> TYPE: DNA
<213> ORGANISM: Homo sapiens

<400> SEQUENCE: 117
ctctcaatct actaatgcct c                                              21

<210> SEQ ID NO 118
<211> LENGTH: 20
<212> TYPE: DNA
<213> ORGANISM: Homo sapiens

<400> SEQUENCE: 118
tacccactgc atcaggaaca                                                20

<210> SEQ ID NO 119
<211> LENGTH: 20
<212> TYPE: DNA
<213> ORGANISM: Homo sapiens

<400> SEQUENCE: 119
ccttgaagca caccattaca                                                20

<210> SEQ ID NO 120
<211> LENGTH: 20
<212> TYPE: DNA
<213> ORGANISM: Homo sapiens

<400> SEQUENCE: 120
acacaggcca cctatttcag                                                20

<210> SEQ ID NO 121
<211> LENGTH: 20
<212> TYPE: DNA
<213> ORGANISM: Homo sapiens

<400> SEQUENCE: 121
gtccagcgtc cagcacacag                                                20

<210> SEQ ID NO 122
<211> LENGTH: 23
<212> TYPE: DNA
<213> ORGANISM: Homo sapiens

<400> SEQUENCE: 122
cagatatgtc attctgggag gtc                                            23

<210> SEQ ID NO 123
<211> LENGTH: 21
<212> TYPE: DNA
<213> ORGANISM: Homo sapiens

<400> SEQUENCE: 123
aacaccatcc ctcctcgaac c                                              21

<210> SEQ ID NO 124
<211> LENGTH: 24
<212> TYPE: DNA
<213> ORGANISM: Homo sapiens

<400> SEQUENCE: 124
cctaacaaaa gagctgaaaa gccc                                           24
```

<210> SEQ ID NO 125
<211> LENGTH: 24
<212> TYPE: DNA
<213> ORGANISM: Homo sapiens

<400> SEQUENCE: 125
actgtgatac agtggatagc cgct                                            24

<210> SEQ ID NO 126
<211> LENGTH: 21
<212> TYPE: DNA
<213> ORGANISM: Homo sapiens

<400> SEQUENCE: 126
agcagagaat ggaaagtcaa a                                               21

<210> SEQ ID NO 127
<211> LENGTH: 21
<212> TYPE: DNA
<213> ORGANISM: Homo sapiens

<400> SEQUENCE: 127
tgttgatgtt ggataagaga a                                               21

<210> SEQ ID NO 128
<211> LENGTH: 3017
<212> TYPE: DNA
<213> ORGANISM: Homo sapiens

<400> SEQUENCE: 128
gcgccttaaa aaaaaaaaac tttcttggaa aatgtccagc tcttgcttaa atataaaaat      60
gaaaggaaga aagagactct cctctctcca ctcctataat tatgaggaac ttttattcaa     120
ctctgaaatt ctatacaatc tctacaatac tctactgaat aaaagcagag cagaaaaagc     180
tgcgcttttt ttccatagtc gggaatgctt gtcatcagtg taaatcacca ccgcgccctt     240
tttcctaaag aatattattg ttattaataa acatgtaggg tattatcctc cacttacatt     300
acaaaaccat tttttaaagc cgggcgtggt ggctcacgcc tgtaatccca gcactttggg     360
aggcccagac aggcggatca cgaagtcgag aaatcgagac catcctggcc aacatggtga     420
aaccccatct ctactaaaaa tacaaaaatt agctgggcgt ggtggcgggc tcctgtagtc     480
ccagctactc aggaggctga ggcaggagaa tcgcttgaac cggggaggcg aggttgcag      540 tcagccaaga tagcgccact gcactggagc ctggtgacag agtgagactc cctcaagaaa     600
gaaaggaagg gaagggaaag ggaaggaagg ggaggggaag ggaggggagg ggaggggagg     660
aaagaaaaga atactggaac ttgttgaagg cagagacttt attttcatat cccggctatg     720
tctggctact gtcttacgta atagatataa aatcaatctt ggttggatta accagaagaa     780
tgagaagata tattctggta agttgaatac ttagcaccca ggggtaatca gcttggacag     840
gaccaggtcc aaagactgtt aagagtcttc tgactccaaa ctcagtgctc cctccagtgc     900
cacaagcaaa ctccataaag gtatcctgtg ctgaatagag actgtagagt ggtacaaagt     960
aagacagaca ttatattaag tcttagcttt gtgacttcga atgacttacc taatctagct    1020
aaatttcagt tttaccatgt gtaaatcagg aagagtaata gaacaaacct tgaagggtcc    1080
caatggtgat taaatgaggt gatgtacata acatgcatca ctcataataa gtgctcttta    1140
aatattagtc actattatta gccatctctg attagatttg acaataggaa cattaggaaa    1200
gatatagtac attcaggatt tgttagaaa gagatgaaga aattcccttc cttcctgccc    1260

```
taggtcatct aggagttgtc atggttcatt gttgacaaat taattttccc aaattttca    1320
ctttgctcag aaagtctaca tcgaagcacc caagactgta caatctagtc catcttttc    1380
cacttaactc atactgtgct ctcccttct caaagcaaac tgtttgctat tccttgaata    1440
cactctgagt tttctgcctt tgcctactca gctggcccat ggcccctaat gtttcttctc    1500
atctccactg ggtcaaatcc tacctgtacc ttatggttct gttaaaagca gtgcttccat    1560
aaagtactcc tagcaaatgc acggcctctc tcacggatta taagaacaca gtttatttta    1620
taaagcatgt agctattctc tccctcgaaa tacgattatt attattaaga atttatagca    1680
gggatataat tttgtatgat gattcttctg gttaatccaa ccaagattga ttttatatct    1740
attacgtaag acagtagcca gacatagccg ggatatgaaa ataaagtctc tgccttcaac    1800
aagttccagt attcttttct ttcctcccct cccctcccct ccttcccct cccttcctt    1860
ccctttccct tcccttcctt tctttcttga gggagtctca ctctgtcacc aggctccagt    1920
gcagtggcgc tatcttggct gactgcaacc tccgcctccc cggttcaagc gattctcctg    1980
cctcagcctc ctgagtagct gggactacag gagcccgcca ccacgcccag ctaatttttg    2040
tatttttagt agagatgggg tttcaccatg ttggccagga tggtctcgat ttctcgactt    2100
cgtgatccgc ctgtctggc ctcccaaagt gctgggatta caggcgtgag ccaccacgcc    2160
cggctttaaa aaatggtttt gtaatgtaag tggaggataa taccctacat gtttattaat    2220
aacaataata ttctttagga aaagggcgc ggtggtgatt tacactgatg acaagcattc    2280
ccgactatgg aaaaaaagcg cagcttttc tgctctgctt ttattcagta gagtattgta    2340
gagattgtat agaatttcag agttgaataa aagttcctca taattatagg agtggagaga    2400
ggagagtctc tttcttcctt tcatttttat atttaagcaa gagctggaca ttttccaaga    2460
aagttttttt tttttaaggc gcctctcaaa aggggccgga tttccttctc ctggaggcag    2520
atgttgcctc tctctctcgc tcggattggt tcagtgcact ctagaaacac tgctgtggtg    2580
gagaaactgg accccaggtc tggagcgaat tccagcctgc agggctgata agcgaggcat    2640
tagtgagatt gagagagact ttaccccgcc gtggtggttg gagggcgcgc agtagagcag    2700
cagcacaggc gcgggtcccg ggaggccggc tctgctcgcg ccgagatgtg gaatctcctt    2760
cacgaaaccg actcggctgt ggccaccgcg cgccgcccgc gctggctgtg cgctggggcg    2820
ctggtgctgg cgggtggctt cttctcctc ggcttcctct tcggtagggg ggcgcctcgc    2880
ggagcaaacc tcggagtctt ccccgtggtg ccgcggtgct gggactcgcg ggtcagctgc    2940
cgagtgggat cctgttgctg gtcttcccca ggggcggcga ttagggtcgg ggtaatgtgg    3000
ggtgagcacc cctcgag                                                  3017
```

What is claimed is:

1. A method comprising administering methotrexate tri-glutamate to a subject so as to contact cells comprising prostate-specific membrane antigen and thereby inhibit release of glutamate by N-acetylaspartylglutamic acid (NAAG) hydrolysis in the subject.

* * * * *